(12) United States Patent
Pissarntiski et al.

(10) Patent No.: US 7,256,186 B2
(45) Date of Patent: Aug. 14, 2007

(54) GAMMA SECRETASE INHIBITORS

(75) Inventors: Dimitri A. Pissarntiski, Scotch Plains, NJ (US); Hubert B. Josien, Hoboken, NJ (US); Elizabeth M. Smith, Verona, NJ (US); John W. Clader, Cranford, NJ (US); Theodros Asberom, West Orange, NJ (US); Tao Guo, Dayton, NJ (US); Douglas W. Hobbs, Yardley, PA (US)

(73) Assignee: Schering Corporation, Kenilworth, NJ (US)

( * ) Notice: Subject to any disclaimer, the term of this patent is extended or adjusted under 35 U.S.C. 154(b) by 333 days.

(21) Appl. No.: 10/941,440

(22) Filed: Sep. 15, 2004

(65) Prior Publication Data

US 2005/0085506 A1    Apr. 21, 2005

Related U.S. Application Data

(63) Continuation-in-part of application No. 10/663,042, filed on Sep. 16, 2003, which is a continuation-in-part of application No. 10/358,898, filed on Feb. 5, 2003.

(60) Provisional application No. 60/355,618, filed on Feb. 6, 2002.

(51) Int. Cl.
| | | |
|---|---|---|
| *C07D 211/08* | (2006.01) | |
| *C07D 207/46* | (2006.01) | |
| *C07D 205/00* | (2006.01) | |
| *C07D 279/00* | (2006.01) | |
| *A01N 43/00* | (2006.01) | |

(52) U.S. Cl. .................. 514/210.01; 546/1; 546/18; 546/148; 546/186; 546/192; 546/236; 546/339; 548/542; 548/952; 548/950; 540/604; 514/212.01; 514/345; 514/418

(58) Field of Classification Search ............... 546/192, 546/18, 148, 186, 208, 339, 235; 548/542, 548/952; 540/604; 514/210.01, 418, 345, 514/212.01

See application file for complete search history.

(56) References Cited

U.S. PATENT DOCUMENTS

2004/0171614 A1    9/2004   Pissarnitski

FOREIGN PATENT DOCUMENTS

| WO | WO 99/45006 | 9/1999 |
|---|---|---|
| WO | WO 02/02554 | 1/2002 |
| WO | WO 03/066592 | 8/2003 |
| WO | WO 2005/028440 | 3/2005 |

OTHER PUBLICATIONS

International Search Report for PCT/US2004/030191 (CN01538K1) dated Sep. 15, 2004—3 Pages.

*Primary Examiner*—James O. Wilson
*Assistant Examiner*—Paul V. Ward
(74) *Attorney, Agent, or Firm*—Thomas A. Blinka; Henry C. Jeanette

(57) ABSTRACT

This invention discloses novel gamma secretase inhibitors of the formula:

(I)

wherein:
  $R^1$ is a substituted aryl or substituted heteroaryl group;
  $R^2$ is an $R^1$ group, alkyl, —XC(O)Y, alkylene-XC(O)Y, cycloalkylene-X—C(O)—Y, —CH—X—C(O)—NR$^3$—Y or —CH—X—C(O)—Y, wherein X and Y are as defined herein;
  each $R^3$ and each $R^{3A}$ are independently H, or alkyl;
  $R^{11}$ is aryl, heteroaryl, alkyl, cycloalkyl, arylalkyl, arylcycloalkyl, heteroarylalkyl, heteroarylcycloalkyl, arylheterocycloalkyl, or alkoxyalkyl. Also disclosed is a method of treating Alzheimer's Disease using one or more compounds of the invention.

24 Claims, No Drawings

GAMMA SECRETASE INHIBITORS

REFERENCE TO RELATED APPLICATIONS

This application is a continuation-in-part of application Ser. No. 10/663,042, filed Sep. 16, 2003, which is a continuation-in-part of application Ser. No. 10/358,898, filed Feb. 5, 2003, which claims the benefit of provisional Application 60/355,618, filed Feb. 6, 2002.

The disclosures of application Ser. Nos. 10/663,042, 10/358,898, and 60/355,618 are hereby incorporated by reference.

BACKGROUND OF THE INVENTION

WO 00/50391, published Aug. 13, 2000, discloses compounds having a sulfonamide moiety that are useful for the treatment and prevention of Alzheimer's Disease and other diseases relating to the deposition of amyloid protein.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of Gamma Secretase and have the formula:

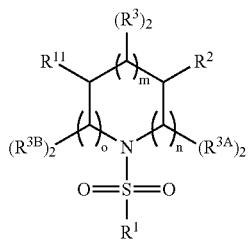

(I)

or a pharmaceutically acceptable salt, solvate or ester thereof, wherein:

wherein:
(A) $R^1$ is selected from the group consisting of:
  (1) unsubstituted aryl;
  (2) aryl substituted with one or more $R^5$ groups;
  (3) unsubstituted heteroaryl; and
  (4) heteroaryl substituted with one or more $R^5$ groups,
(B) $R^2$ is selected from the group consisting of:
  (1) alkyl;
  (2) —XC(O)Y;
  (3) —$(C_1$–$C_6)$alkylene-XC(O)Y;
  (4) —$(C_0$–$C_6)$alkylene-$(C_3$–$C_6)$cycloalkylene-$(C_0$–$C_6)$alkylene-XC(O)Y;
  (5) aryl;
  (6) aryl substituted with one or more $R^5$ groups;
  (7) heteroaryl;
  (8) heteroaryl substituted with one or more $R^5$ groups;
  (9) cycloalkylene-X—C(O)—Y;
  (10) —$CH_2$—X—C(O)—$NR^3$—Y;
  (11) —$CH_2$—X—C(O)—Y; and
  (12) —$CH_2$—X—C(O)—$NR^3$—Y, (C) Each $R^3$ is independently selected from the group consisting of:
  (1) H;
  (2) alkyl:
  (3) —OH;
  (4) —O-alkyl;
  (5) acyl;
  (6) aroyl;
  (7) the moiety $(R^3)_2$, together with the ring carbon atom to which it is shown attached in formula I, defines a carbonyl group, —C(O)—, with the proviso that when m is an integer greater than 1, at most one carbonyl group is present in the ring shown in formula I;
  (8) halo,
(D) Each $R^{3A}$ and $R^{3B}$ is independently selected from the group consisting of:
  (1) H; and
  (2) alkyl;
(E) $R^5$ is independently selected from the group consisting of:
  (1) halo;
  (2) —$CF_3$;
  (3) —OH;
  (4) —O-alkyl;
  (5) —$OCF_3$;
  (6) —CN;
  (7) —$NH_2$;
  (8) —$C(O)_2$alkyl;
  (9) —$C(O)NR^6R^7$;
  (10) -alkylene-$NR^6R^7$;
  (11) —$NR^6C(O)$alkyl;
  (12) —$NR^6C(O)$aryl;
  (13) —$NR^6C(O)$heteroaryl; and
  (14) —$NR^6C(O)NR^6R^7$;
(F) X is selected from the group consisting of:
  (1) —O—;
  (2) —NH—;
  (3) —N-alkyl; and
  (4) —O-alkylene;
(G) Y is selected from the group consisting of:
  (1) —$NR^6R^7$;
  (2) —$N(R^3)(CH_2)_bNR^6R^7$ wherein b is 2–6;
  (3) unsubstituted aryl;
  (4) unsubstituted heteroaryl;
  (5) -alkyl;
  (6) -cycloalkyl,
  (7) unsubstituted arylalkyl;
  (8) unsubstituted arylcycloalkyl;
  (9) unsubstituted heteroarylalkyl;
  (10) unsubstituted heteroarylcycloalkyl;
  (11) unsubstituted arylheterocycloalkyl;
  (12) substituted aryl;
  (13) substituted heteroaryl;
  (14) substituted arylalkyl;
  (15) substituted arylcycloalkyl;
  (16) substituted heteroarylalkyl;
  (17) substituted heteroarylcycloalkyl; and
  (18) substituted arylheterocycloalkyl;
  (19) substituted heterocycloalkyl alkyl;
  (20) unsubstituted heteroaryl alkyl;
  (21) substituted aryl alkyl heterocycloalkyl;
  (22) unsubstituted heterocycloalkyl; and
  (23) unsubstituted cycloalkyl, wherein the aryl moiety in said substituted groups (12), (14), (15), (18), and (21) of said Y group, and the heteroaryl moiety in said substituted groups (13), (16), (17) and (20) of said Y group, are substituted with one or more substituents independently selected from the group consisting of:
(a) halo;
(b) —$CF_3$;
(c) —OH;
(d) —O-alkyl;
(e) —$OCF_3$;
(f) —CN;
(g) —$NH_2$;
(h) —$C(O)_2(C_1-C_6)$alkyl;
(i) —$C(O)NR^6R^7$;
(j) —$(C_1-C_6)$alkylene-$NR^6R^7$;
(k) —$NR^6C(O)$alkyl;
(l) —$NR^6C(O)$aryl;
(m) —$NR^6C(O)$heteroaryl;
(n) —$NR^6C(O)NR^6R^7$; and
(o) alkyl, or Y is selected from the group consisting of:

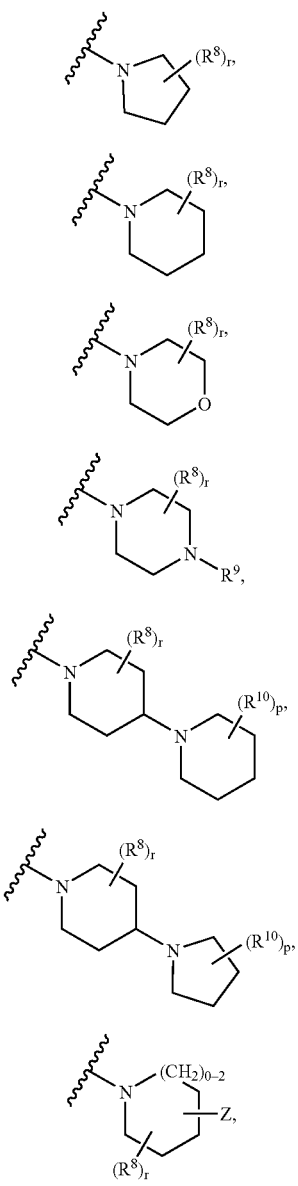

(c)

(d)

(e)

(f)

(g)

(h)

(i)

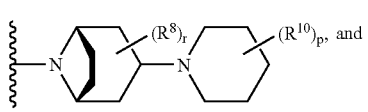

(j)

(k)

(H) $R^6$ and $R^7$ are independently selected from the group consisting of:
(1) H;
(2) alkyl;
(3) alkyl substituted with 1 to 4 hydroxy groups, with the proviso that none of the hydroxy groups are bonded to a carbon to which a nitrogen is also bonded;
(4) cycloalkyl;
(5) arylalkyl;
(6) heteroarylalkyl;
(7)

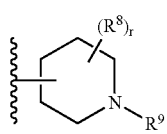

(a)

(8)

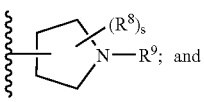

(b)

(9) heterocycloalkyl,
(I) Each $R^8$ is independently selected from the group consisting of:
(1) H;
(2) alkyl;
(3) alkyl substituted with 1 to 4 hydroxy groups;
(4) aryl;
(5) —OH;
(6) —O-alkyl;
(7) —C(O)O-alkyl; or
(8) if r is greater than 1, two $R^8$ groups, together with the ring carbon atom or atoms to which they are attached define a ring, wherein one or more carbon atoms of said ring may be replaced independently of each other by —O— or —C(O)O—, and said ring may be unsubstituted or substituted with 1 to 4 hydroxy groups,
(J) Each $R^9$ is independently selected from the group consisting of:
(1) H;
(2) alkyl;
(3) alkyl substituted with 1 to 4 hydroxy groups;
(4) cycloalkyl;
(5) cycloalkyl substituted with 1 to 4 hydroxy groups;
(6) arylalkyl;
(7) heteroarylalkyl;
(8) —C(O)O-alkyl;

(9) alkylene-O-alkylene-OH;
(10) aryl substituted with one or more $R^5$ groups;
(11) heteroaryl substituted with one or more $R^5$ groups;
(12) unsubstituted heteroaryl;
(13) unsubstituted aryl;
(14) -alkylene-C(O)O-alkyl; and
(15) hydroxyalkyl-O-alkyl,
(K) Each $R^{10}$ is independently selected from the group consisting of:
(1) H; and
(2) alkyl,
(L) $R^{11}$ is selected from the group consisting of:
(1) unsubstituted aryl;
(2) substituted aryl;
(3) unsubstituted heteroaryl,
(4) alkyl;
(5) cycloalkyl;
(6) unsubstituted arylalkyl;
(7) unsubstituted arylcycloalkyl,
(8) unsubstituted heteroarylalkyl;
(9) unsubstituted heteroarylcycloalkyl;
(10) unsubstituted arylheterocycloalkyl;
(11) alkoxyalkyl;
(12) substituted heteroaryl;
(13) substituted arylalkyl;
(14) substituted arylcycloalkyl;
(15) substituted heteroarylalkyl; and
(16) substituted arylheterocycloalkyl, wherein the aryl moiety in said substituted groups (2), (13), (14) and (16) of said $R^{11}$ group, and the heteroaryl moiety in said substituted groups (12) and (15) of said $R^{11}$ group, are substituted with one or more substituents independently selected from the group consisting of:
(a) halo;
(b) —$CF_3$;
(c) —OH;
(d) —O-alkyl;
(e) —$OCF_3$;
(f) —CN;
(g) —$NH_2$;
(h) —$C(O)_2(C_1–C_6)$alkyl;
(i) —$C(O)NR^6R^7$;
(j) —$(C_1–C_6)$alkylene-$NR^6R^7$;
(k) —$NR^6C(O)$alkyl;
(l) —$NR^6C(O)$aryl;
(m) —$NR^6C(O)$heteroaryl; and
(n) —$NR^6C(O)NR\ R$;
(M) (1) m is an integer of from 0 to 3, and if m is greater than 1, m moieties can be the same or different from one another;
(2) n is an integer of from 0 to 3, and if n is greater than 1, n moieties can be the same or different from one another;
(3) o is an integer of from 0 to 3, and if o is greater than 1, o moieties can be the same or different from one another;

such that m+n+o is 1, 2, 3 or 4;
(N) p is an integer of from 0 to 4, and if greater than 1, p moieties can be the same or different from one another;
(O) r is an integer of from 0 to 4, and if greater than 1, r moieties can be the same or different from one another;
(P) s is an integer of from 0 to 3, and if greater than 1, s moieties can be the same or different from one another; and
(Q) Z is selected from the group consisting of:

(1) unsubstituted heterocycloalkyl;
(2) substituted heterocycloalkyl;
(3) —$NH_2$;
(4) —NH(alkyl);
(5) —N(alkyl)$_2$ wherein each alkyl is the same or different;
(6) —NH(unsubstituted cycloalkyl);
(7) —NH(substituted cycloalkyl);
(8) —N(alkyl)(unsubstituted cycloalkyl);
(9) —N(alkyl)(substituted cycloalkyl);
(10) —NH(unsubstituted aralkyl);
(11) —NH(substituted aralkyl);
(12) —N(alkyl)(aralkyl);
(13) —NH(unsubstituted heterocycloalkyl);
(14) —NH(substituted heterocycloalkyl);
(15) —N(alkyl)(unsubstituted heterocycloalkyl),
(16) —N(alkyl)(substituted heterocycloalkyl);
(17) —NH(unsubstituted heteroaralkyl);
(18) —NH(substituted heteroaralkyl);
(19) —NH-alkylene-(unsubstituted cycloalkyl);
(20) —NH-alkylene-(substituted cycloalkyl);
(21) —N(alkyl)alkylene-(unsubstituted cycloalkyl);
(22) —N(alkyl)alkylene-(substituted cycloalkyl);
(23) —NHalkylene-(unsubstituted heterocycloalkyl);
(24) —NHalkylene-(substituted heterocycloalkyl);
(25) —N(alkyl)alkylene-(unsubstituted heterocycloalkyl);
(26) —N(alkyl)alkylene-(substituted heterocycloalkyl);
(27) unsubstituted benzofused heterocycloalkyl; and
(28) substituted benzofused heterocycloalkyl;
(29) H; and
(30) —N(hydroxyalkyl)$_2$, wherein each alkyl may be the same or different, wherein said substituted heterocycloalkyl moiety of substituents (2), (14), (16), (24), (26) and (27) of group Z, and said substituted cycloalkyl moiety of substituents (7), (9), (20) and (22) of group Z, and said substituted aryl moiety of substituent (11) of group Z, and said substituted heteroaryl moiety of substituent (18) of group Z, are substituted with 1 to 3 groups independently selected from the group consisting of:
(a) alkyl;
(b) —OH;
(c) —Oalkyl;
(d) —OC(O)alkyl;
(e) —OC(O)aryl;
(f) —$NH_2$;
(g) —NH(alkyl);
(h) —N(alkyl)$_2$ wherein each alkyl is the same or different;
(i) —NHC(O)alkyl;
(j) —N(alkyl)C(O)alkyl;
(k) —NHC(O)aryl;
(l) —N(alkyl)C(O)aryl;
(m) —C(O)alkyl;
(n) —C(O)aryl;
(o) —C(O)$NH_2$;
(p) —C(O)NH(alkyl);
(q) —C(O)N(alkyl)$_2$ wherein each alkyl is the same or different;
(r) —$C(O)_2$alkyl;
(s) -alkylene-C(O)Oalkyl;
(t) piperidinyl;
(u) pyrrolidinyl;
(v) 1,1-ethylenedioxy;
(w) aryl;

(x) heteroaryl; and (y) —O—CH$_2$CH$_2$—O—wherein both oxygen atoms are bound to the same carbon atom, and provided that the aryl and heteroaryl moieties of said Z group are not substituted with said —O—CH$_2$CH$_2$—O— group.

In (M) through (P), each reference to moieties preceded by an index, e.g., "m moieties", refers to the moieties quantified by that index. Thus, for example, the term "m moieties" refers to the moieties whose quantity is indicated by the index "m".

This invention further provides compounds that are inhibitors of Gamma Secretase selected from the group consisting of:

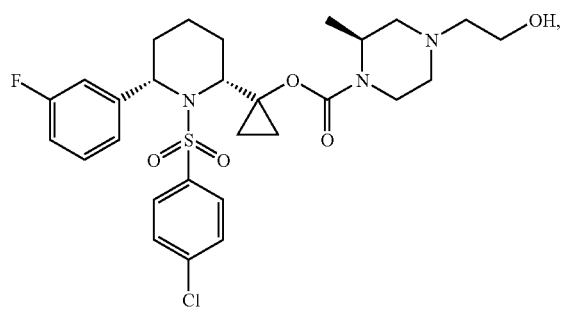

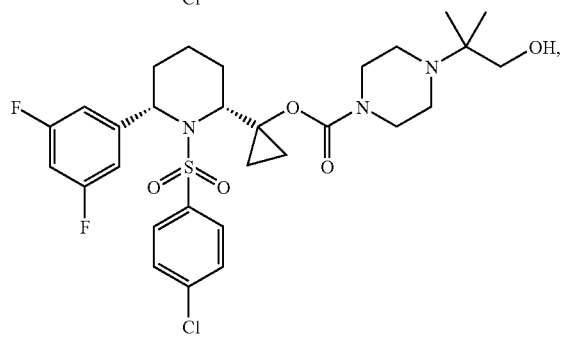

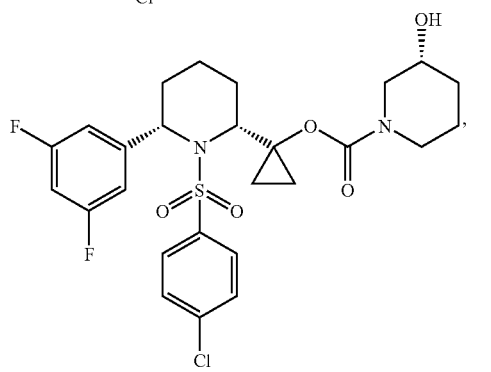

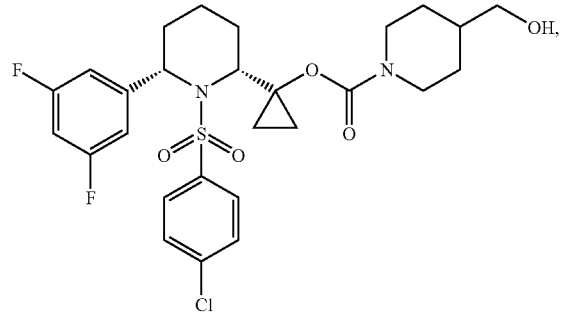

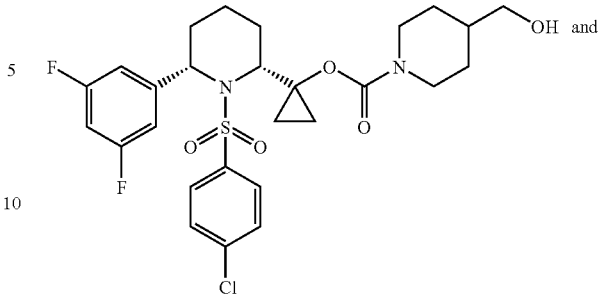

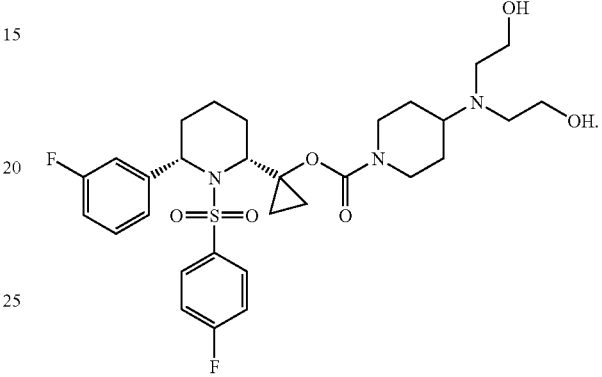

This invention also provides a pharmaceutical composition comprising an effective amount of one or more compounds of the above formulas and at least one pharmaceutically acceptable carrier.

This invention also provides a method for inhibiting gamma-secretase comprising administering an effective (i.e., therapeutically effective) amount of one or more compounds of the above formulas to a patient in need of such inhibition.

This invention also provides a method of treating one or more neurodegenerative diseases comprising administering an effective. (i.e., therapeutically effective) amount of one or more compounds of the above formulas to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of the above formulas to a patient in need of such inhibition.

This invention also provides a method of treating Alzheimer's disease comprising administering an effective (i.e., therapeutically effective) amount of one or more compounds of the above formulas to a patient in need of treatment.

DETAILED DESCRIPTION OF THE INVENTION

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Ring system substituent" means a substituent attached to an aromatic or non-aromatic ring system, which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1–2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

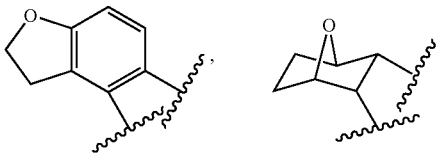

and the like.

"Cycloalkenyl" means a non-aromatic mono or multicyclic ring system comprising about 3 to about 10 carbon atoms, preferably about 5 to about 10 carbon atoms, which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5, 6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different on the carbon(s) and/or heteroatoms(s), and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6, 7-tetrahydrobenzoxazoly, 1H-4-oxa-1,5-diazanaphthalen-2- onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl-group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means an heteroaryl-alkynyl-group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "cycloalkylene" refers to substitution on the same carbon atom in an alkylene group with a cyclic group. Nonlimiting examples include

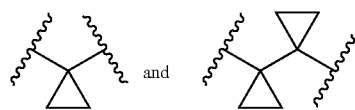

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

The wavy line ∿∿ as a bond generally indicates a mixture of, or either of, the possible isomers, e.g., containing (R)— and (S)— stereochemistry. For example,

means containing both

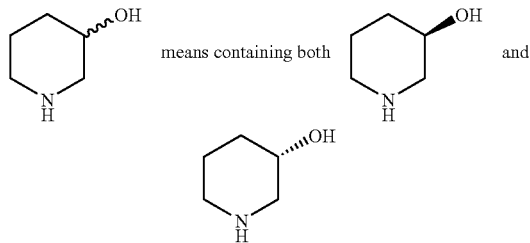

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting gamma-secretase and thus producing the desired therapeutic effect in a suitable patient.

The compounds of formula I form salts that are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates), undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of the invention with a carboxylic acid group can form pharmaceutically acceptable esters with an alcohol. Examples of suitable alcohols include methanol and ethanol.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Any formula, compound, moiety or chemical illustration with otherwise unsatisfied valences in the present specification and/or claims herein is assumed to have the requisite hydrogen atom(s) to satisfy the valences.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems, such as, for example:

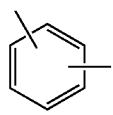

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom. For example:

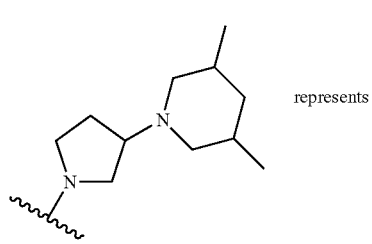 represents

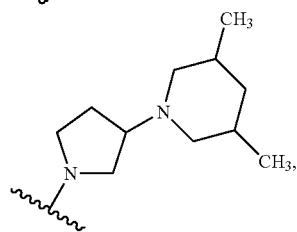

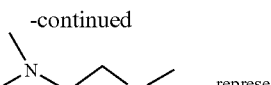 represents

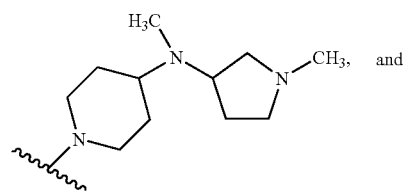 and

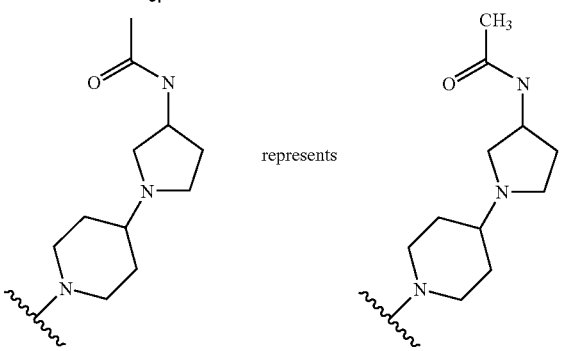 represents

Referring to formula I, examples of Z in the moiety

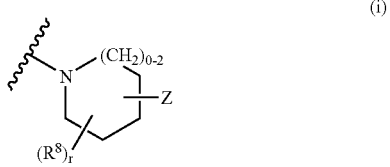 (i)

include, but are not limited to:

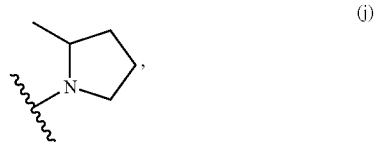 (j)

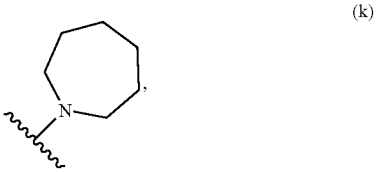 (k)

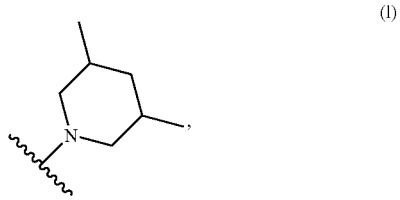 (l)

-continued
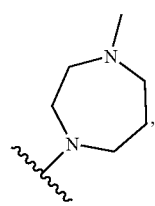 (m)
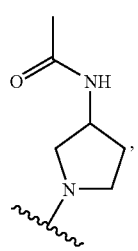 (n)
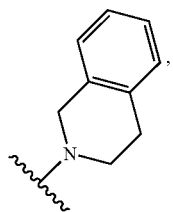 (o)
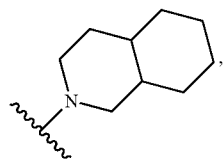 (p)
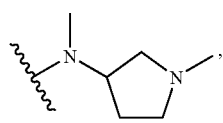 (q)
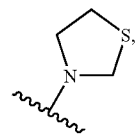 (r)
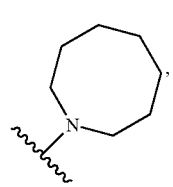 (s)
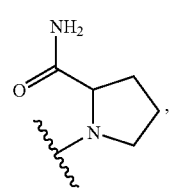 (t)
-continued
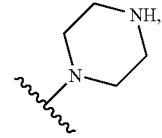 (u)
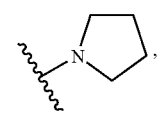 (v)
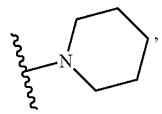 (w)
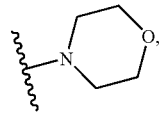 (x0)
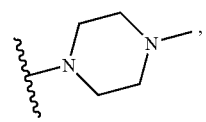 (y)
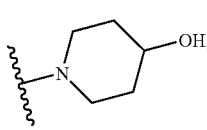 (z)
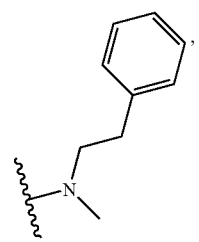 (aa)
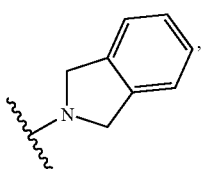 (ab)
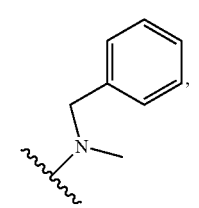 (ac)
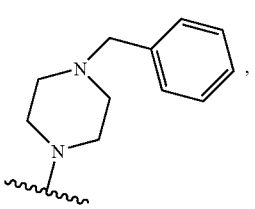 (ad)

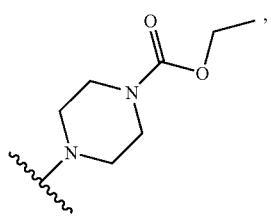
(ae)
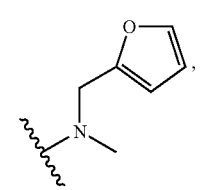
(af)
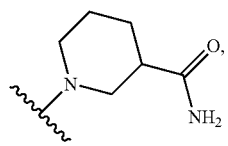
(ag)
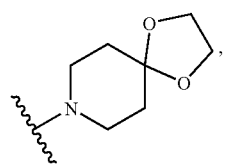
(ah)
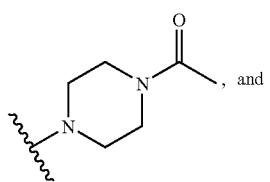
, and (ai)
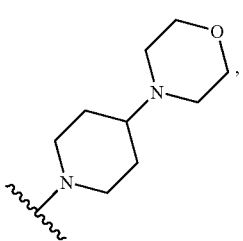
(aj)
Referring to formula I, examples of the Y group in —X—C(O)—Y— or —X—CO—Y— include, but are not limited to:
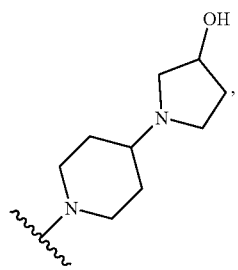
(ak)
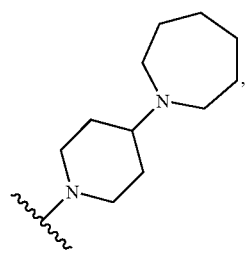
(al)
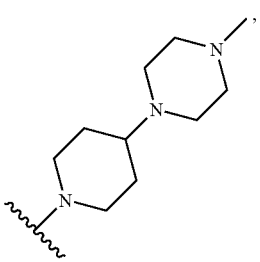
(am)
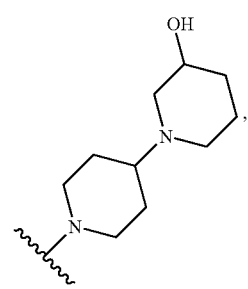
(an)
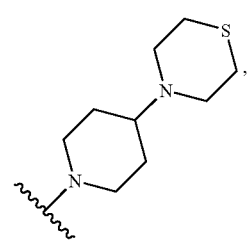
(ao)
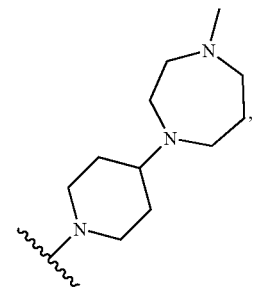
(ap)
(aq)

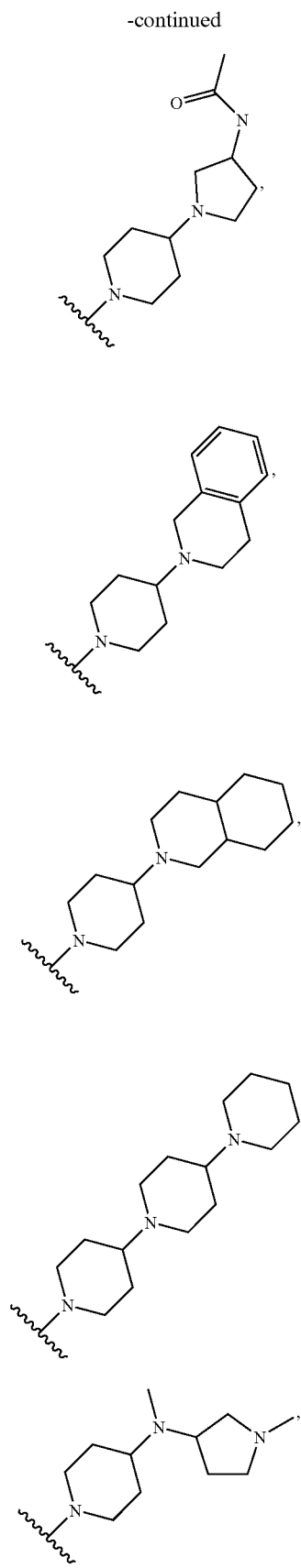

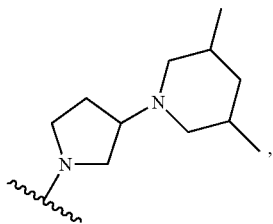 (bg)
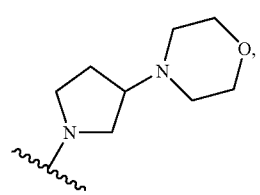 (bh)
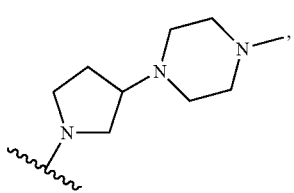 (bi)
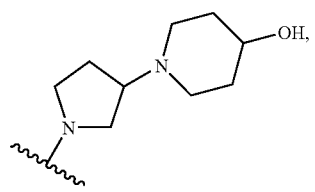 (bj)
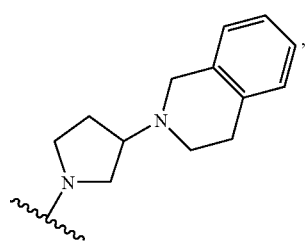 (bk)
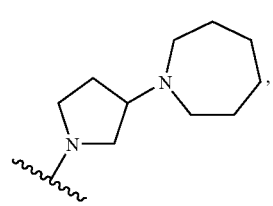 (bl)
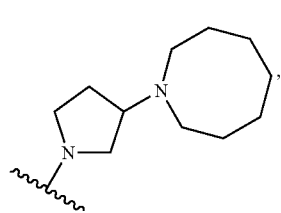 (bm)
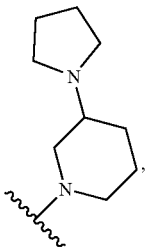 (bn)
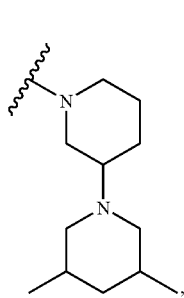 (bo)
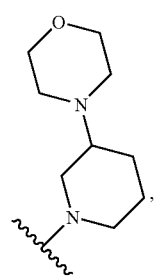 (bp)
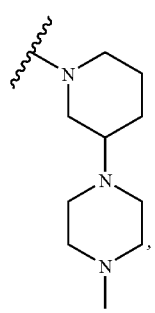 (bq)
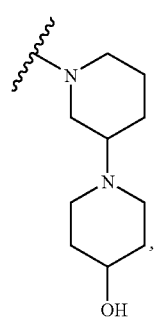 (br)

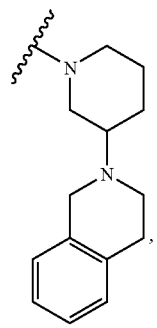 (bs)
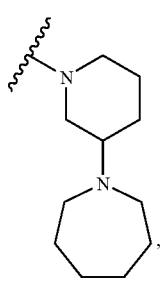 (bt)
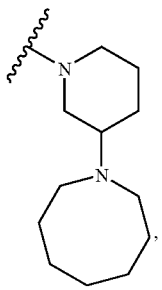 (bu)
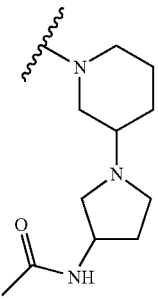 (bv)
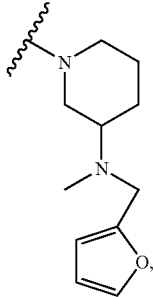 (bw)
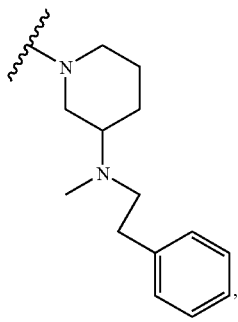 (bx)
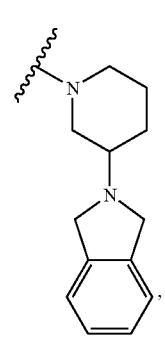 (by)
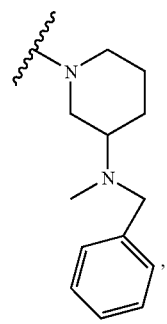 (bz)
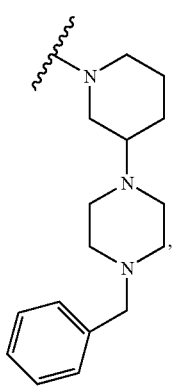 (ca)

(cb)
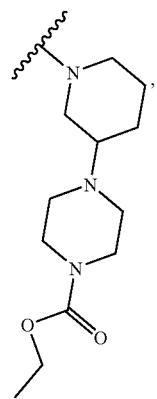

(cc)
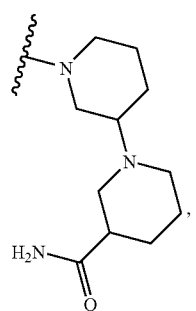

(cd)
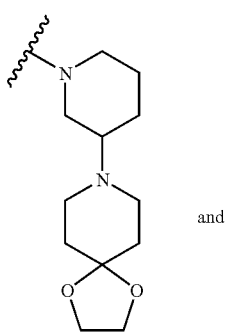
and (ce)
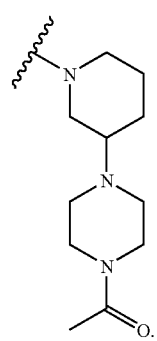

Preferably R¹ is aryl substituted with one or more R⁵ groups, most preferably phenyl substituted with one or more R⁵ groups, and more preferably phenyl substituted with one or more (e.g., 1–3) halo atoms, and still more preferably phenyl substituted with one halo atom, and even still more preferably phenyl substituted with chloro (e.g., p-chlorophenyl).

Preferably n is 0 or 1, o is 0 or 1, and m is 1, 2 or 3, such that m+n+o is 3, and most preferably n and o are independently 0 and m is 3.

Preferably, p is 0 or 1, and most preferably 0.

Preferably, r is 0 or 1, and most preferably 1.

Preferably, s is 0.

Preferably, R² is —XC(O)Y, —(C₁–C₆)alkylene-XC(O)Y, —CH(C₁–C₂alkyl)-X—C(O)—Y (e.g., —CH(CH₃)—X—C(O)—Y), —C(C₁–C₂alkyl)₂—X—C(O)—Y, (spirocyclic-substituted alkyl)-X—C(O)—Y, —CH₂—X—C(O)—NR³—Y, —CH₂—X—C(O)—Y or —CH₂—X—C(O)—NR³—Y, wherein each alkyl is the same or different, —(C₃–C₆)cycloalkylene-XC(O)Y, most preferably —(C₁₋₆)alkylene-XC(O)Y or —(C₃–C₆)cycloalkylene-XC(O)Y, more preferably —(C₁₋C₆)alkylene-XC(O)Y or —(C₃–C₆)cycloalkylene-XC(O)Y wherein X is —O— or —NH—, still more preferably —(C₁–C₆)alkylene-XC(O)Y or —(C₃–C₆)cycloalkylene-XC(O)Y wherein X is —O—, yet more preferably —CH₂—X—C(O)—Y or

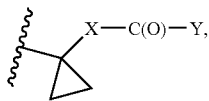

still yet more preferably —CH₂—X—C(O)—Y or

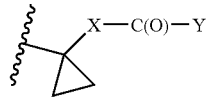

wherein X is —O— or —N(H)—, and even still more preferably —CH₂—X—C(O)—Y or

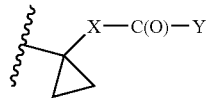

wherein X is —O—.

Preferably, R³ is H.

Preferably, R⁸ is H, —(C₁–C₆)alkyl, or —OH, and most preferably H or methyl.

Preferably, R⁹ is H, —(C₁–C₆)alkyl (e.g., methyl), —(C₁–C₆)alkyl substituted with 1 to 4 —OH groups (e.g., —(CH₂)₂OH), —(C₁–C₆)alkyl-O—(C₁–C₆)alkyl-OH (e.g., 2-(2-hydroxyethoxy)ethyl), (C₃–C₈)cycloalkyl, heteroaryl, or hydroxyalkyl-O-alkyl, and most preferably H, methyl, cyclohexyl, 2-pyridyl, 2-hydroxyethyl or 2-(2-hydroxyethoxy)ethyl;

Preferably, R¹⁰ is H or —(C₁–C₆)alkyl, most preferably H or methyl, more preferably H.

Preferably, R¹¹ is selected from the group consisting of: —(C₁–C₆)alkyl (most preferably methyl or ethyl), (C₃–C₈)-cycloalkyl (most preferably cyclopropyl), aryl (most preferably phenyl), aryl(C₁–C₆)alkyl (most preferably benzyl or —(CH₂)₂phenyl) and —(C₁–C₆)alkoxyalkyl (most preferably —CH₂OCH₃).

Preferably, X is —NH— or —O—, and most preferably —O—.

Preferably Y is —NR⁶R⁷, substituted heterocycloalkyl alkyl, unsubstituted heteroaryl alkyl, unsubstituted aryl alkyl heterocycloalkyl, unsubstituted heterocycloalkyl or unsubstituted cycloalkyl, or Y is selected from the group consisting of:
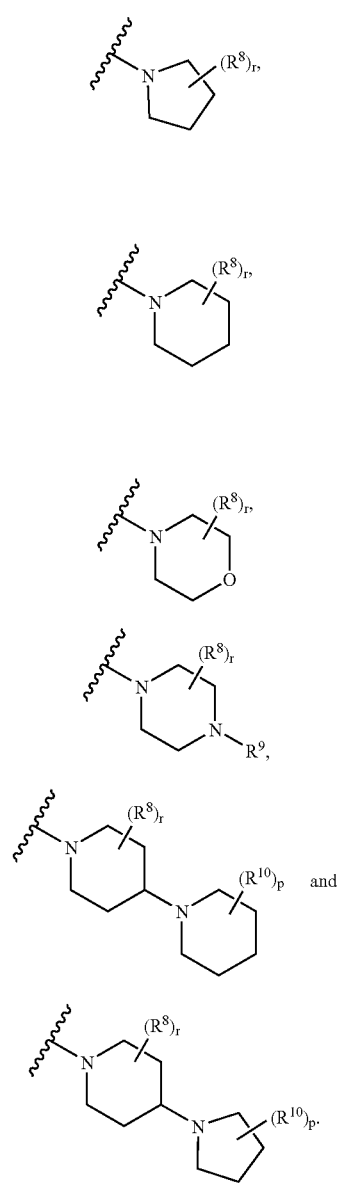
Most preferably, Y is selected from the group consisting of:
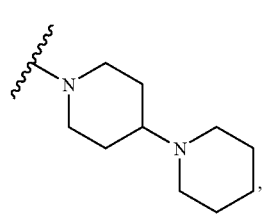
-continued
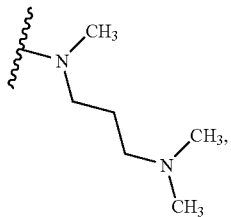
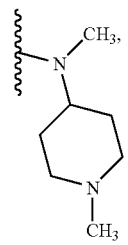
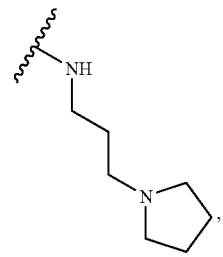
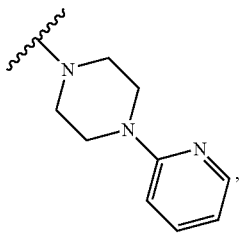
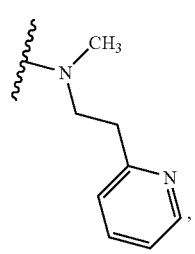
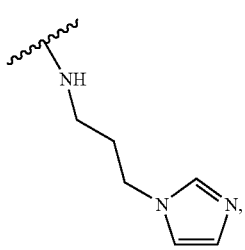

-continued (bk) 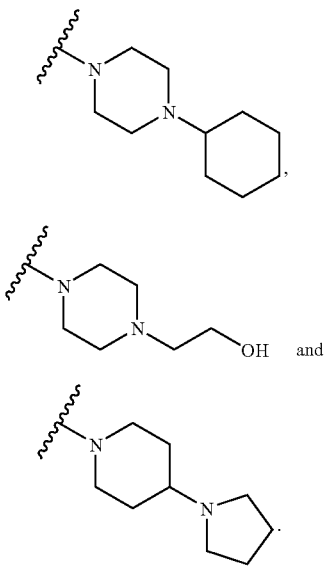

(bl)

and (bm)

Preferably, $R^6$ and $R^7$ are independently selected from the group consisting of: H, methyl, ethyl, —$(C_3$–$C_8)$cycloalkyl, -aryl$(C_1$–$C_6)$alkyl, 4-pyridylmethyl, heterocycloalkyl, (a) 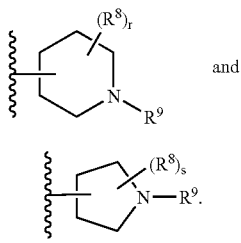

and (b)

is a group of the formula:

(a1) 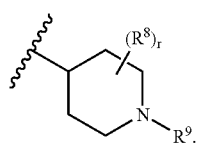

is a group of the formula:

(b1) 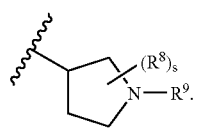

Thus, in one embodiment of the invention:
$R^1$ is aryl substituted with one or more $R^5$ groups, preferably phenyl substituted with one or more $R^5$ groups, and most preferably phenyl substituted with one or more halo atoms, and more preferably phenyl substituted with one halo atom, and still more preferably phenyl substituted with chloro (e.g., p-chlorophenyl);

n and o are 0 or 1, and m is 1, 2 or 3, such that m+n+o is 3, and preferably n and o are 0 and m is 3;
p is 0 or 1, and preferably 0;
r is 0 or 1, and preferably 1;
s is 0;
$R^2$ is —XC(O)Y, —$(C_1$–$C_6)$alkylene-XC(O)Y, —$(C_3$–$C_6)$ cycloalkylene-XC(O)Y—CH$(C_1$–$C_2$alkyl)-X—C(O)—Y (e.g., —CH(CH$_3$)—X—C(O)—Y), or —C$(C_1$–$C_2$alkyl)$_2$—X—C(O)—Y wherein each alkyl is the same or different, preferably —$(C_1$–$C_6)$alkylene-XC(O)Y, or —$(C_3$–$C_6)$cycloalkylene-XC(O), most preferably —$(C_1$–$C_6)$alkylene-XC(O)Y or —$(C_{3-C6})$cycloalkylene-XC(O)Y, wherein X is —O— or —NH—, more preferably —$(C_{1-C6})$alkylene-XC (O)Y or —$(C_3$–$C_6)$cycloalkylene-XC(O)Y, wherein X is —O—, still more preferably —CH$_2$—X—C(O)—Y or

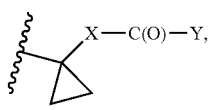

yet still more preferably CH$_2$—X—C(O)—Y or

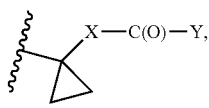

wherein X is —O— or —NH—, and even still more preferably —CH$_2$—X—C(O)—Y or

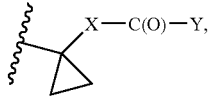

wherein X is —O—;
$R^3$ is H;
$R^8$ is H or —$(C_1$–$C_6)$alkyl, and preferably H or methyl;
$R^9$ is H, —$(C_1$–$C_6)$alkyl (e.g., methyl), —$(C_1$–$C_6)$alkyl substituted with 1 to 4 —OH groups (e.g., —(CH$_2$)$_2$OH), —$(C_1$–$C_6)$alkyl-O—$(C_1$–$C_6)$alkyl-OH (e.g., 2-(2-hydroxyethoxy)ethyl), —$(C_3$–$C_8)$cycloalkyl, or heteroaryl, and preferably H, methyl, cyclohexyl, 2-pyridyl, 2-hydroxyethyl or 2-(2-hydroxyethoxy)ethyl;
$R^{10}$ is H or —$(C_1$–$C_6)$alkyl, preferably H or methyl, and most preferably H; and
$R^{11}$ is selected from the group consisting of: —$(C_1$–$C_6)$ alkyl (most preferably methyl or ethyl), $(C_3$–$C_8)$-cycloalkyl (most preferably cyclopropyl), aryl (most preferably phenyl), aryl$(C_1$–$C_6)$alkyl (most preferably benzyl or —(CH$_2$)$_2$ phenyl) and —$(C_1$–$C_6)$alkoxyalkyl (most preferably —CH$_2$OCH$_3$); and
the remaining substituents are as defined for formula I.
In another embodiment of the invention:
$R^1$ is aryl substituted with one or more $R^5$ groups, preferably phenyl substituted with one or more $R^5$ groups, and most preferably phenyl substituted with one or more halo atoms, and more preferably phenyl substituted with one halo atom, and still more preferably phenyl substituted with chloro (e.g., p-chlorophenyl);

n and o are 0 or 1, and m is 1, 2 or 3, such that m+n+o are 3, and preferably n and o are 0 and m is 3;

p is 0 or 1, and preferably 0;

r is 0 or 1, and preferably 1;

s is 0;

$R^2$ is —XC(O)Y, —($C_1$–$C_6$)alkylene-XC(O)Y, —($C_3$–$C_6$)cycloalkylene-XC(O)Y, —CH($C_1$–$C_2$alkyl)-X—C(O)—Y (e.g., —CH(CH$_3$)—X—C(O)—Y), or —C($C_1$–$C_2$alkyl)$_2$—X—C(O)—Y wherein each alkyl is the same or different, preferably —($C_1$–$C_6$)alkylene-XC(O)Y or —($C_3$–$C_6$)cycloalkylene-XC(O), and most preferably —CH$_2$—X—C(O)—Y or

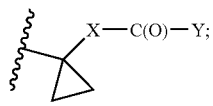

$R^3$ is H;

$R^8$ is H or —($C_1$–$C_6$)alkyl, and preferably H or methyl;

$R^9$ is H, —($C_1$–$C_6$)alkyl (e.g., methyl), —($C_1$–$C_6$)alkyl substituted with 1 to 4 —OH groups (e.g., —(CH$_2$)$_2$OH), —($C_1$–$C_6$)alkyl-O—($C_1$–$C_6$)alkyl-OH (e.g., 2-(2-hydroxyethoxy)ethyl), ($C_3$–$C_8$)cycloalkyl, or heteroaryl, and preferably H, methyl, cyclohexyl, 2-pyridyl, 2-hydroxyethyl or 2-(2-hydroxyethoxy)ethyl;

$R^{10}$ is H or —($C_1$–$C_6$)alkyl, preferably H or methyl, and most preferably H;

X is —O—;

Y is —NR$^6$R$^7$; or

Y is selected from the group consisting of:

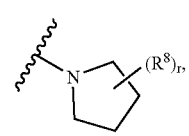 (c)

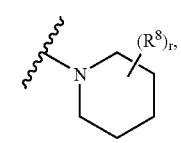 (d)

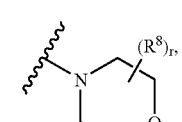 (e)

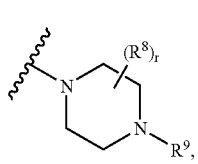 (f)

-continued

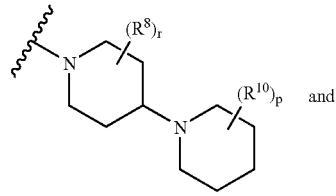 (g)

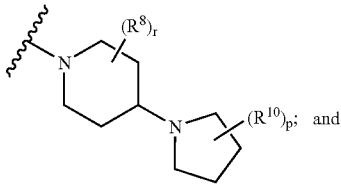 (h)

$R^{11}$ is selected from the group consisting of: —($C_1$–$C_6$)alkyl (most preferably methyl or ethyl), ($C_3$–$C_8$)-cycloalkyl (most preferably cyclopropyl)aryl (most preferably phenyl), aryl($C_1$–$C_6$)alkyl (most preferably benzyl or —(CH$_2$)$_2$phenyl) and —($C_1$–$C_6$)alkoxyalkyl (most preferably —CH$_2$OCH$_3$); and the remaining substituents are as defined for formula I.

In another embodiment of this invention:

$R^1$ is aryl substituted with one or more $R^5$ groups, preferably phenyl substituted with one or more $R^5$ groups, and most preferably phenyl substituted with one or more halo atoms, and more preferably phenyl substituted with one halo atom, and still more preferably phenyl substituted with chloro (e.g., p-chlorophenyl);

n is 0 or 1, o is 0 or 1, and m is 1, 2 or 3, such that m+n+o is 3, and preferably n is 0, o is 0, and m is 3;

p is 0 or 1, and preferably 0;

r is 0 or 1, and preferably 1;

s is 0;

$R^2$ is —XC(O)Y, —($C_1$–$C_6$)alkylene-XC(O)Y, —CH($C_1$–$C_2$alkyl)-X—C(O)—Y (e.g., —CH(CH$_3$)—X—C(O)—Y), or —C($C_1$–$C_2$alkyl)$_2$—X—C(O)—Y wherein each alkyl is the same or different, preferably —($C_1$–$C_6$)alkylene-XC(O)Y, and most preferably —CH$_2$—X—C(O)—Y or —($C_3$–$C_6$)cycloalkylene-X—C(O)—Y—;

$R^3$ is H;

$R^8$ is H or —($C_1$–$C_6$)alkyl, and preferably H or methyl;

$R^9$ is H, —($C_1$–$C_6$)alkyl (e.g., methyl), —($C_1$–$C_6$)alkyl substituted with 1 to 4 —OH groups (e.g., —(CH$_2$)$_2$OH), —($C_1$–$C_6$)alkyl-O—($C_1$–$C_6$)alkyl-OH (e.g., 2-(2-hydroxyethoxy)ethyl), ($C_3$–$C_8$)cycloalkyl, or heteroaryl, and most preferably H, methyl, cyclohexyl, 2-pyridyl, 2-hydroxyethyl or 2-(2-hydroxyethoxy)ethyl;

$R^{10}$ is H or —($C_1$–$C_6$)alkyl, preferably H or methyl, and more preferably H;

X is —O—;

Y is —NR$^6$R$^7$; or

Y is selected from the group consisting of:

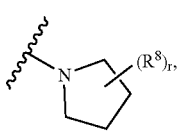 (c)

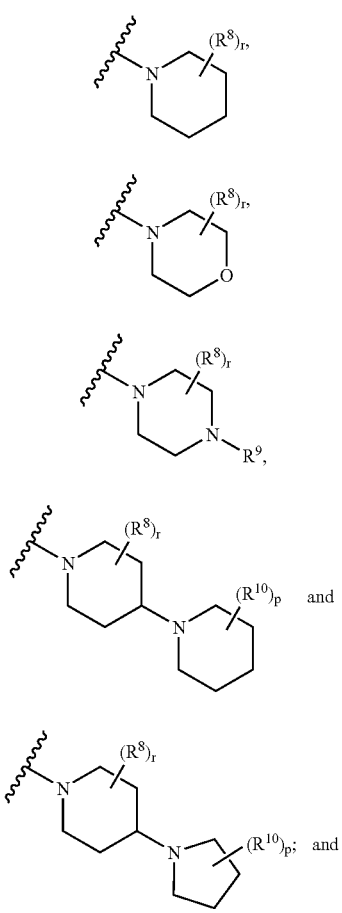

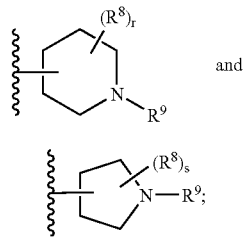

$R^{11}$ is selected from the group consisting of: —$(C_1–C_6)$ alkyl (preferably methyl or ethyl), $(C_3–C_8)$-cycloalkyl (preferably cyclopropyl), aryl (preferably phenyl), aryl$(C_1–C_6)$ alkyl (preferably benzyl or —$(CH_2)_2$phenyl), and —$(C_1–C_6)$ alkoxyalkyl (preferably —$CH_2OCH_3$); and the remaining substituents are as defined for formula I.

Representative compounds of the invention include but are not limited to the compounds of Examples 1–29, 31–33, 35–48, 50–61, 63–67, 67A–67BS 68, 69, 71–74, 74A, 74B, 74C, 75, 76, 78–83, 85–99, 101–159, 159A, 159B, 160, 160A–160AA, 161, 161A–161G, 162, 162A, 162B, 164, 164A, 164B, 164C, 165–167, 167A, 167B, 167C, 168, 168A, 169, 169A–169D, 170, 170A–170AD, 171–173, 173A–173T, 174, and 178.

Preferred compounds of the invention are the compounds of Examples 7, 61, 67B, 67E, 67N, 67P, 67U, 67AG, 67AT, 67AW, 67AY, 67BA, 67BD, 67BE, 67BG, 67BH, 67BL, 73, 160B, 160K, 161, 161A, 161E, 161F, 173, 173A, 173B, 173C, 173E, 173G, 173I, 173J, 173K, 173L, 173N, and 178. Most preferred compounds are the compounds of Examples 7, 61, 67-B, 67-AT, 67-BG, 73, 161-A, 173, 173-A, 173-C, 173-E, 173-J, 173-N, 173-P, 173-Q, 173-R, 173-S, 173-T 173-U, and 178.

Compounds of formula I can be prepared by various methods well known to those skilled in the art, and by the methods described below.

$R^6$ and $R^7$ are independently selected from the group consisting of: H, methyl, ethyl, —$(C_3–C_8)$cycloalkyl, -aryl $(C_1–C_6)$alkyl, 4-pyridylmethyl, Method 1

In Method 1, compounds of formula I having the structure Ia are prepared.

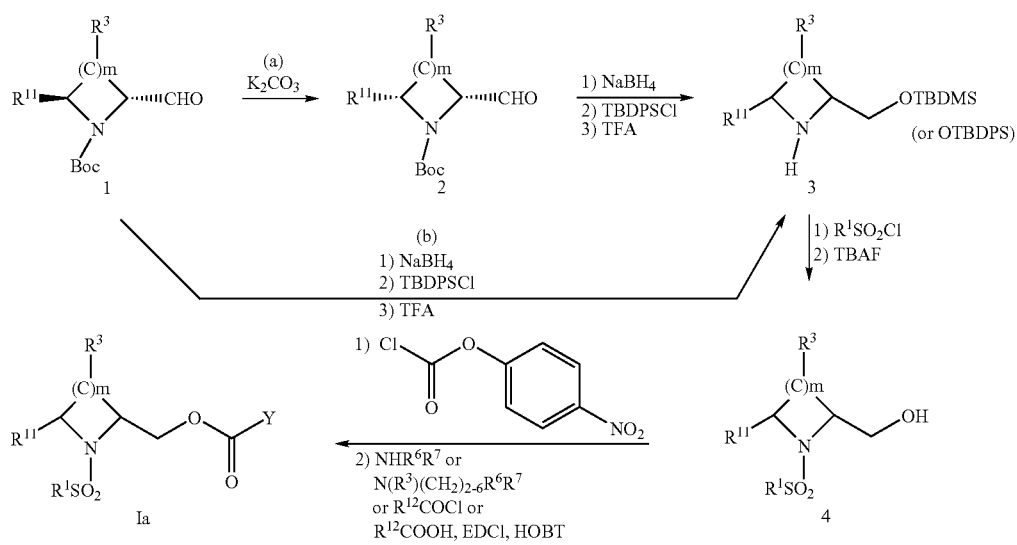

In method 1, $R^{12}$ represents the Y substituents defined above in paragraphs (3) to (18) of the definition of Y. When the reagents $R^{12}COCl$ or $R^{12}COOH$ are used in Method 1, then Y in formula Ia represents $R^{12}$.

In Method 1, a trans-substituted N-Boc-cyclic amine 2-carboxaldehyde 1 is epimerized to the corresponding cis isomer using a mild base such as potassium carbonate (path a). The cis geometry is retained in all subsequent steps. Alternatively, the epimerization step can be omitted to yield trans products (path b). Aldehyde 2 is reduced using a reducing agent such as sodium borohydride. The alcohol is protected using a typical protecting group such as a t-butyldiphenylsilyl ether, and the Boc group is removed under acidic conditions to give 3. The cyclic amine is converted to a sulfonamide by reaction with a sulfonyl halide, and the alcohol protecting group is removed under standard conditions to give 4. Alcohol 4 can be converted to a variety of compounds of type Ia using methods well known to those skilled in the art. For example, carbamates can be prepared by reaction of 4 with 4-nitrophenylchloroformate followed by reaction of the resulting carbonate with a primary or secondary amine. Alternatively, esters can be prepared by reaction of 4 with either an acid halide of a carboxylic acid in the presence of a suitable coupling reagent such as EDCI and HOBT.

Starting material of formula 1 in Method 1 are known in the art or can be prepared as described below.

Method 2

In Method 2, compounds of formula I having the structure Ib are prepared.

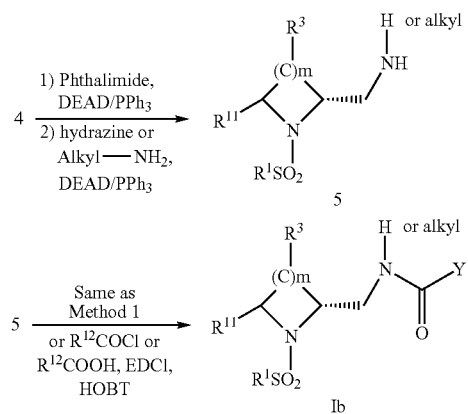

In Method 2, $R^{12}$ is as defined in Method 1.

In Method 2, alcohol 4 from method 1 converted to the corresponding primary or secondary amine under a variety of conditions, such as by reaction with phthalimide under Mitsunobu conditions followed by treatment with hydrazine or by reaction with a primary amine under Mitsunobu conditions. The resulting amine is converted to ureas or to amides Ib using the same procedures described for carbamates and esters in Method 1.

Methods 3-A and 3-B

In Methods 3-A and 3-B, compounds of formula I having the structure Ic are prepared.

Method 3-A

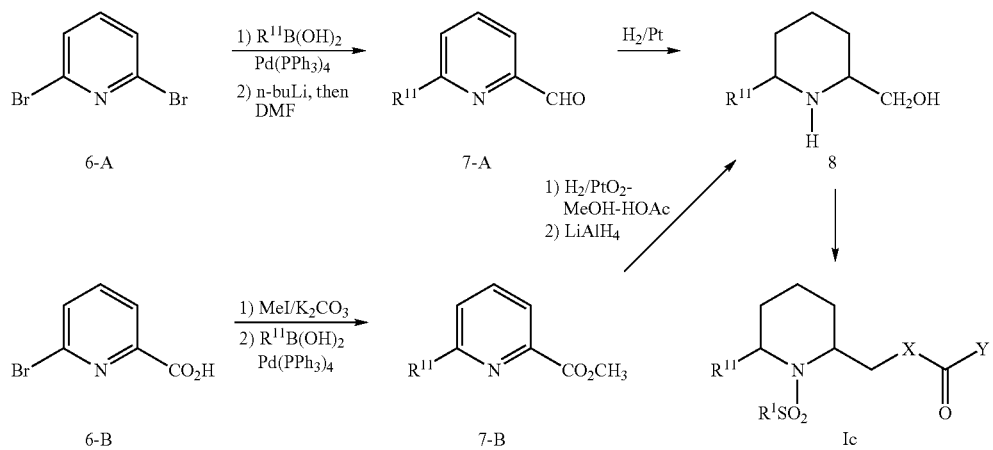

In Method 3-A, 2,6-dibromopyridine is reacted with a boronic acid derivative $R^{11}B(OH)_2$ (most preferably an aryl or vinyl boronic acid) in the presence of a palladium catalyst. The resulting 6-substituted 2-bromopyridine is formylated by treatment with an alkyl lithium such as n-butyllithium followed by treatment with a formylating agent such as dimethylformamide to give 7-A. This product is hydrogenated to give alcohol 8 (where any unsaturation in $R^{11}$ may also have been reduced). Alcohol 8 can be converted to compounds of formula Ic using the procedures previously described.

Method 3-B

In Method 3-B, 6-bromopicolinic acid 6-B is converted to its methyl ester under standard conditions followed by reaction with a boronic acid derivative $R^{11}B(OH)_2$ (most preferably an aryl or vinyl boronic acid) in the presence of a palladium catalyst to give 7-B. This is then hydrogenated using a suitable catalyst such as platinum oxide, preferably in the presence of acetic acid, then reduced with a hydride reagent such as lithium aluminum hydride to give alcohol 8. Alcohol 8 can be converted to compounds of formula Ic using the procedures previously described.

Method 4

In Method 4, compounds of formula I having the structure Id are prepared wherein $R^{11}$ in 9 and Id represents alkyl having at least two carbons, arylalkyl, or heteroarylalkyl.

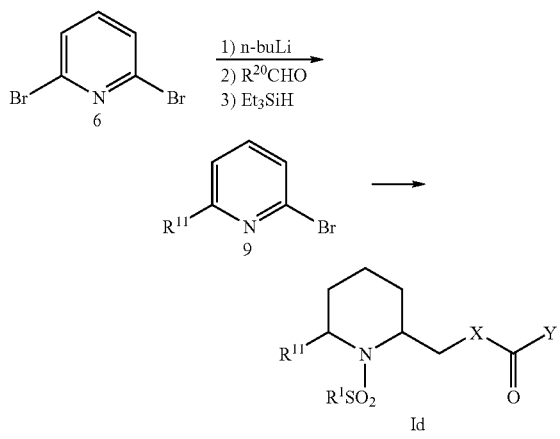

In Method 4, R[20] represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for R[11] above.

In Method 4, 2,6-dibromopyridine is mono-metallated under a variety of conditions, such as treatment with an alkyllithium at about −78° C. or by treatment with a lithium trialkylmagnesiumate complex at −10 to 0° C. The resulting organometallic derivative is reacted with an aldehyde R[20]CHO, and the product is deoxygenated under a variety of conditions, such as by treatment with triethylsilane, to give 9. Compound 9 is formylated and the resulting formyl derivative converted compounds of type Id using the procedures previously described.

Method 5

In Method 5, compounds of formula I having the structure Ie are prepared wherein R[11] in Ie represents alkyl having at least three carbons, arylalkyl wherein said alkyl moiety has at least two carbons, or heteroarylalkyl wherein said alkyl moiety has at least two carbons.

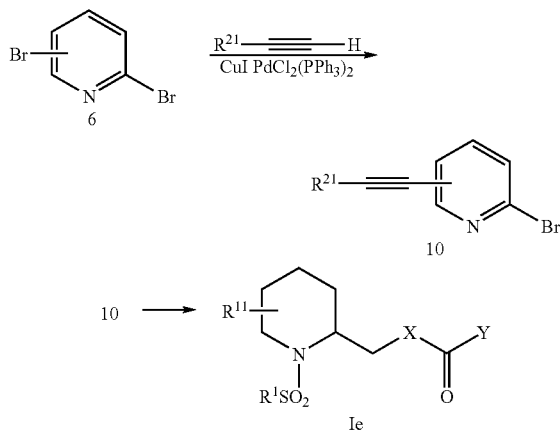

In Method 5, R[21] represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for R[11] above.

In Method 5, 2,6-dibromopyridine is coupled with a mono-substituted alkyne in the presence of a catalyst such as $PdCl_2(PPh_3)_4$/CuI. The resulting product is formylated, hydrogenated, and converted to compounds Ie using the procedures previously described.

Method 6

In Method 6, compounds of formula I having the structure If are prepared wherein R[11] in 12 and If represents alkyl having at least three carbons, arylalkyl wherein said alkyl moiety has at least two carbons, or heteroarylalkyl wherein said alkyl moiety has at least two carbons.

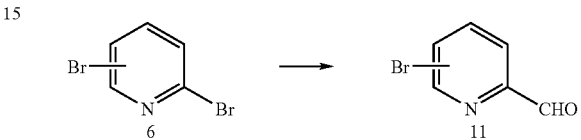

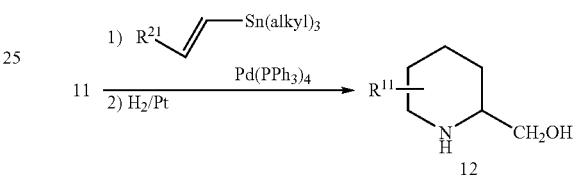

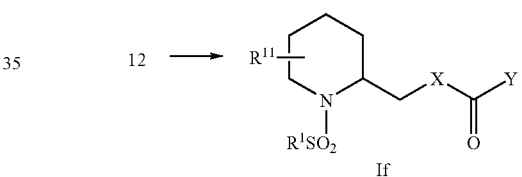

In Method 6, R[21] represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for R[11] above.

In Method 6, 2,6-dibromopyridine is mono-metallated as previously described and the resulting organometallic is reacted with a formylating agent such as DMF to give 11. This compound is reacted with a vinyl tin reagent in the presence of a catalyst such as $Pd(PPh_3)_4$, and the resulting product is hydrogenated to give 12. Compound 12 is converted to compounds If as previously described.

Method 7

In Method 7, compounds of formula I having the structure Ig are prepared.

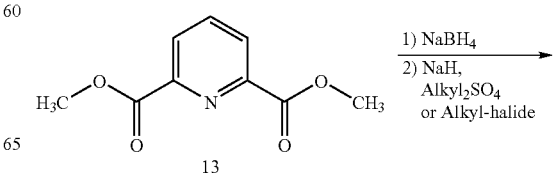

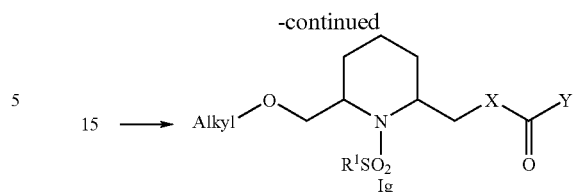

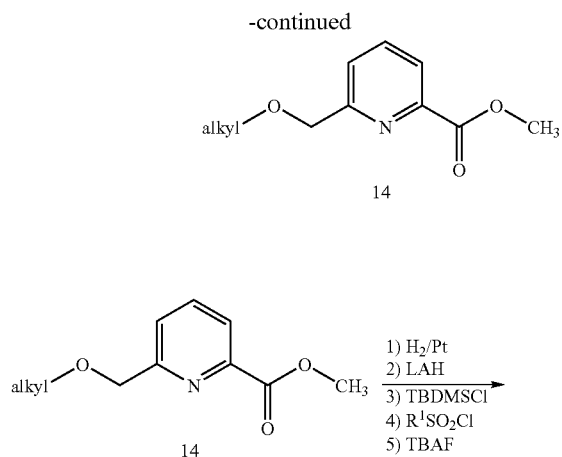

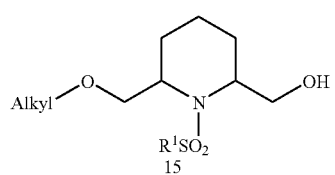

In Method 7, pyridine-2,6-dicarboxylic acid dimethyl ester is reacted with a reducing agent such as sodium borohydride, and the resulting monohydroxymethyl derivative is treated with an alkylating agent such as an alkyl halide or alkylsulfonate to give 14. This is hydrogenated over a catalyst such as platinum oxide, and then reacted with a reducing agent such as lithium aluminum hydride to provide an intermediate cyclic amino alcohol. The alcohol function is protected using a typical protecting group such as a t-butyldimethylsilyl ether, the cyclic amine is converted to a sulfonamide by reaction with a sulfonyl halide, and the alcohol protecting group is removed under standard conditions to give 15. Compound 15 is converted to compounds of type Ig using the methods previously described.

Method 8

In Method 8, compounds of formula I having the structure Ih are prepared.

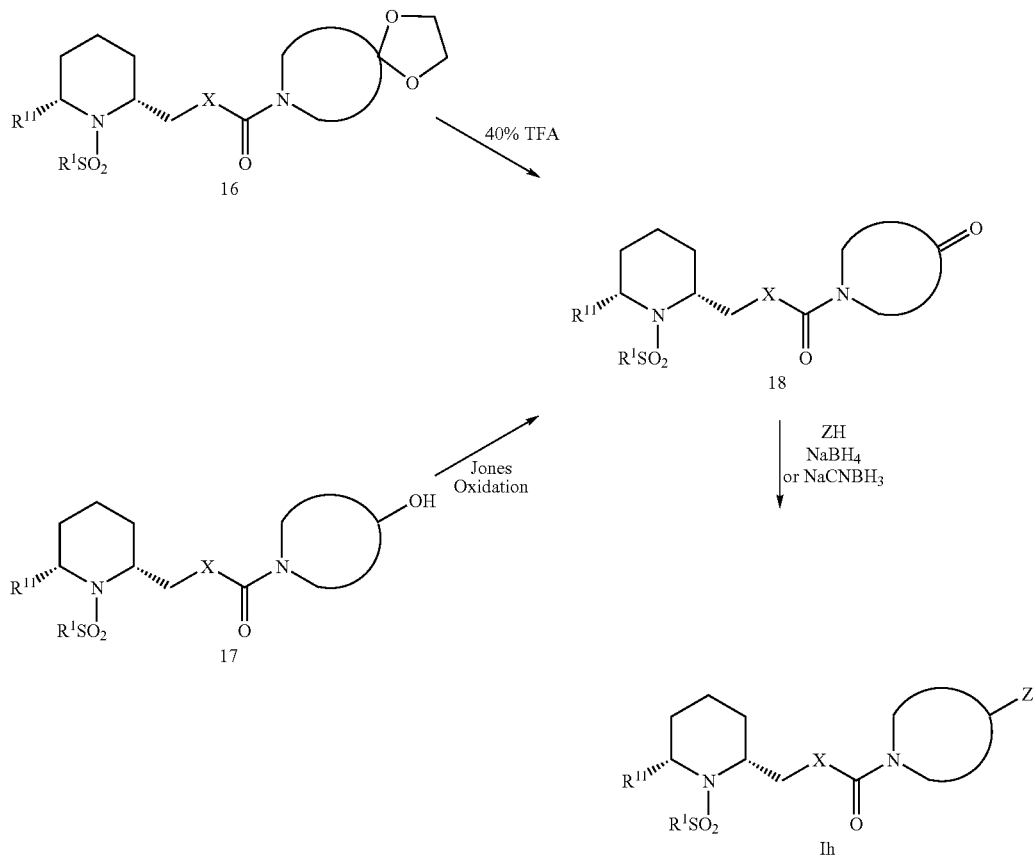

In Method 8, ketal 16 or alcohol 17 are prepared using the procedures described in Method 1 and Method 2. These are converted to the corresponding ketone by either acid hydrolysis of 16 or by oxidation of 17. The ketone is converted to compounds of type Ih by reaction with a primary or secondary amine in the presence of a reducing agent such as sodium borohydride, sodium cyanoborohydride, sodium triacetoxyborohydride, or polymer-bound derivatives thereof.

Method 9

In Method 9, compounds of formula I having the structure Ii and Ij are prepared.

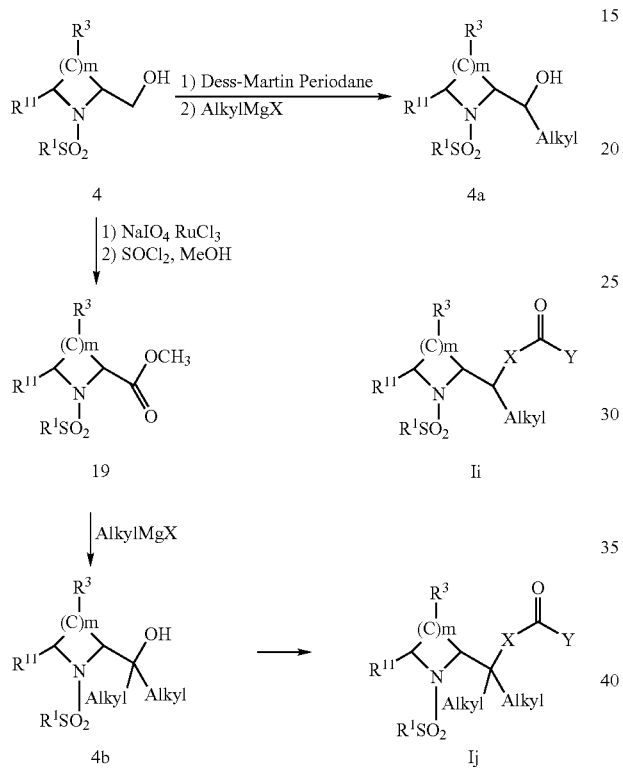

In Method 9, intermediate 4 prepared via any of the methods previously described can be oxidized to an aldehyde using a variety of well-known reagents such as Dess-Martin Periodane. The aldehyde is then treated with an alkylmetal reagent such as a Grignard reagent, an alkyllithium reagent, or an alkylzinc reagent to give alcohol 4a. Intermediate 4a can be converted to compounds of type Ii using the procedures described in Methods 1 through 8. Alternatively, 4 can be converted to ester 19 and then treated with a Grignard reagent to give 4b. This is converted to compounds of type Ij as previously described.

Compounds of type Ik are prepared according to Method 10.

Method 10:

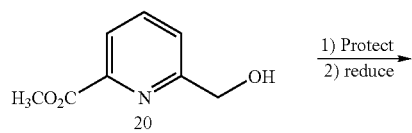

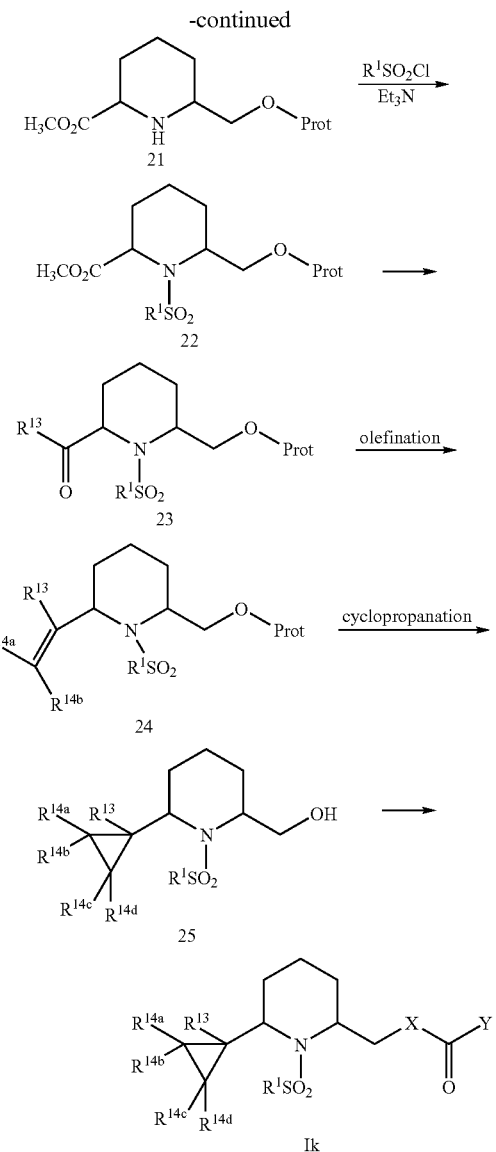

Ester 20 is protected with a suitable protecting group (Prot) such as t-butyldimethylsilyl ether, and the pyridine is reduced by well-known methods such as by treatment with hydrogen gas in the presence of a catalyst such as platinum oxide in a solvent such as ethanol or ether, to give piperidine 21. This is sulfonylated by treatment with a sulfonyl halide in the presence of a base such as triethylamine to give 22. Using well-known methods, the ester of 22 can be converted to 23, where $R^{13}$ is H or alkyl. For instance, 22 can be reduced to the corresponding aldehyde (23, $R^{13}$=H) by treatment with DIBAL. The aldehyde can be treated with a Grignard reagent followed by oxidation to give a ketone (23, $R^{13} \neq H$). Compound 23 can be converted to olefin 24 using well-known methods such as by treatment with a alkyl phosphonium ylide. Olefin 24 can be converted to cyclopropane 25 by well-known methods, for instance, by treatment with a dihalomethane such as diiodomethane in the presence of dialkylzinc and optionally in the presence of trifluoroacetic acid, by treatment with an alkyl or substituted alkyldiazo compound in the presence of a metal such as rhodium chloride, or by treatment of an alkyl halide or substituted alkyl halide with a base such as potassium hydroxide. In the above example, $R^{14a}$, $R^{14b}$, and $R^{14c}$=H, alkyl, aryl, halo, —OH, —O(alkyl), —NH$_2$, —N(H)alkyl, N(alkyl)$_2$, or C(O)Oalkyl. Compound 25 can be converted to compounds of type Ik using the methods previously described.

Compounds of type 1l are prepared as described in method 11.

Method 11:

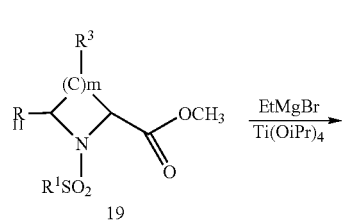

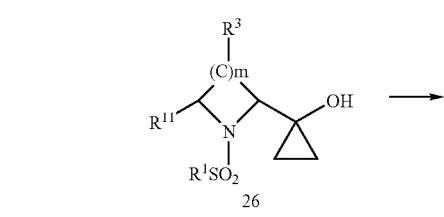

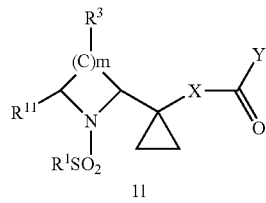

Intermediate 19 of method 9 is treated with ethylmagnesium bromide in the presence of Ti(OiPr)$_4$ to give cyclopropanol 26, which is converted to compounds of type 1l as previously described.

Compounds of type 1m, wherein $R^{11}$ is a heteroaryl moiety can be made by several methods as shown below.

Method 12:

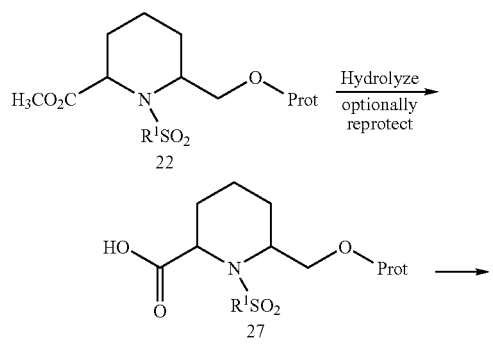

-continued

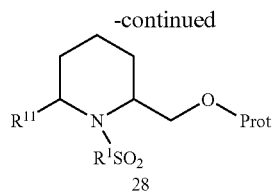

$R^{11}$ = heteroaryl or substituted heteroaryl

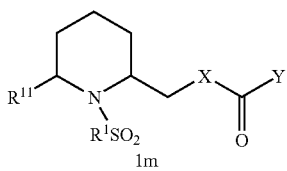

$R^{11}$ = heteroaryl or substituted heteroaryl

Intermediate 22 from method 10 can be hydrolyzed and, optionally as needed, reprotected to give acid 27. This acid can be transformed to a variety of heteroaryl moieties using methods well known to those skilled in the art. For instance, coupling with 2-aminoethanol followed by oxidation and dehydrative cyclization according to the method of Morwick et al (*Organic Letters* 2002, 2665) gives 28 where $R^{11}$=2-oxazolyl. Compounds of type 28 can be transformed into compounds of type 1 m using the methods described earlier.

Method 13:

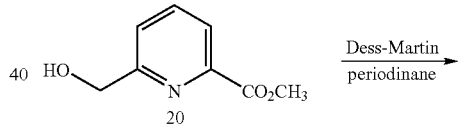

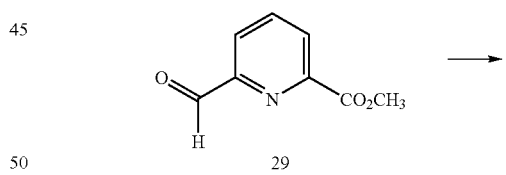

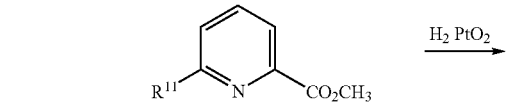

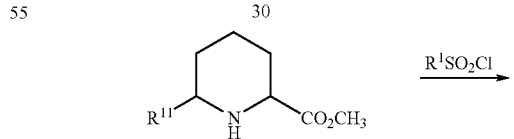

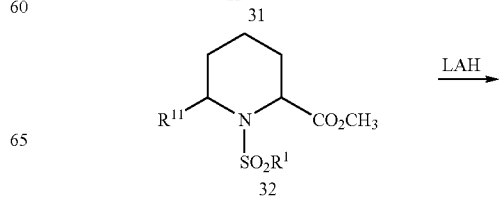

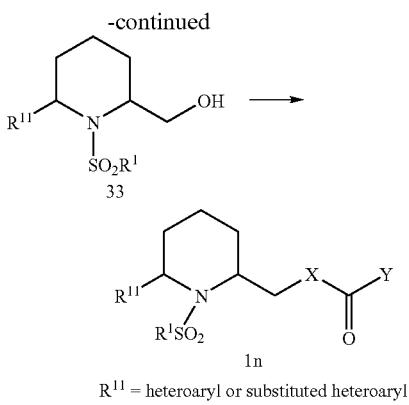

$R^{11}$ = heteroaryl or substituted heteroaryl

Intermediate 20 from method 10 can be oxidized to aldehyde 29 using, for instance, Dess-Martin periodinane. Aldeyde 29 can be transformed into a variety of intermediates 30 where $R^{11}$ is heteroaryl using well-known methods. For instance, treatment of 29 with glyoxal and ammonia gives 30 where $R^{11}$ is 2-imidazolyl. Intermediate 30 can be reduced to piperidine 31 and sulfonylated to give 32 as previously described, and the ester of 32 can be reduced to alcohol 33 using, for instance, lithium aluminum hydride. Intermediate 33 can be transformed to compounds 1n as previously described.

Compounds of this invention of type 1o can be prepared according to method 14:

Method 14:

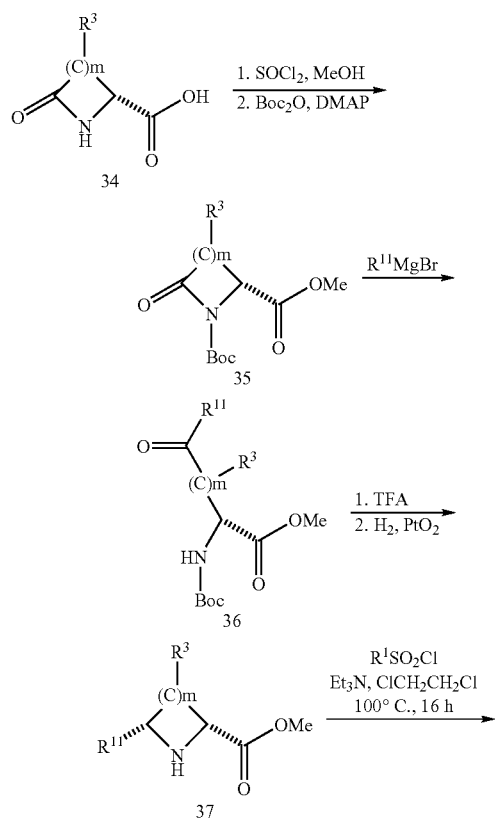

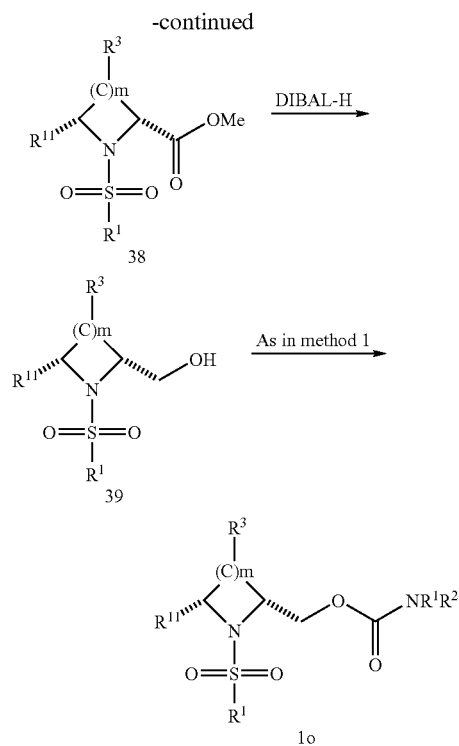

Carboxylactam 34, where m and $R^3$ are as previously defined, is converted to Boc-protected ester 35 by standard procedures. This is reacted with an organometallic reagent such as a Grignard reagent or organolithium to give ketone 36. The Boc group is removed by treatment with an acid such as trifluoroacetic acid and the resulting compound undergoes reductive cyclization in the presence of a suitable reducing agent such as by treatment with hydrogren and a catalyst such as $PtO_2$, to give 37. This is converted to the corresponding sulfonamide by treatment with a sulfonyl halide in the presence of a base such as triethylamine. The ester is reduced to give alcohol 39, which is converted to compounds of type 1o by the methods previously described.

Method 15

Compounds of type 1f can be prepared according to Method 15:

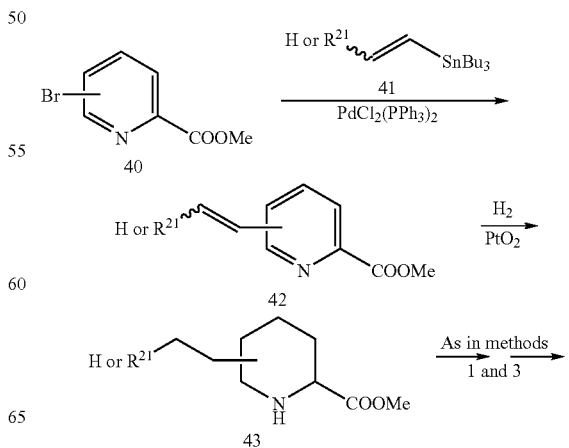

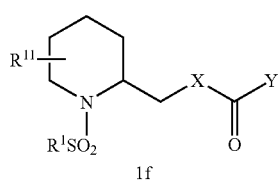

1f

Bromopyridyl ester 40, prepared by well-known methods as described subsequently, is treated with vinyl organometallic compounds such as a vinylstannane 41, where $R^{21}$ is as previously described, in the presence of a suitable catalyst such as palladium chloride bis-triphenylphosphine to give coupled product 42. This is reduced by well-known methods, such as by treatment with hydrogen gas at a suitable pressure such as 10 atmospheres in the presence of a catalyst such as platinum oxide to give piperidine ester 43. This is converted to products 1f using previously described methods.

Compounds of type 1p and 1q, where Z and X(CO)Y together constitute a group $R^2$ as previously defined, can be prepared as in Method 16.

Method 16

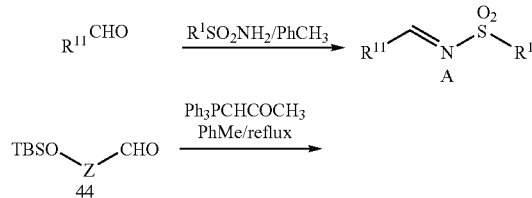

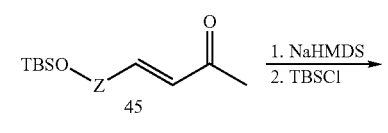
45

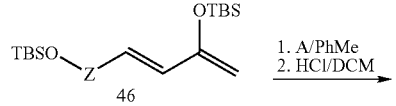
46

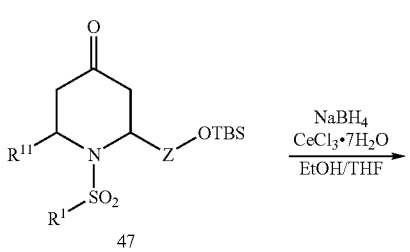
47

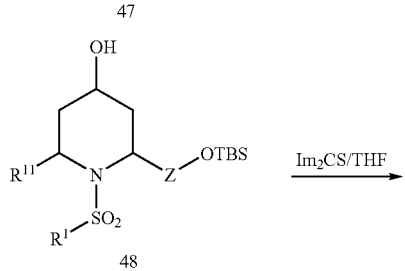
48

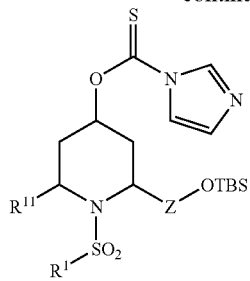
49

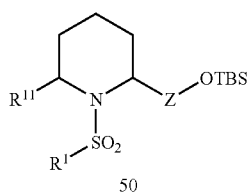
50

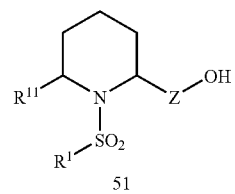
51

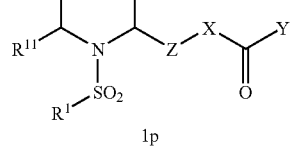
1p

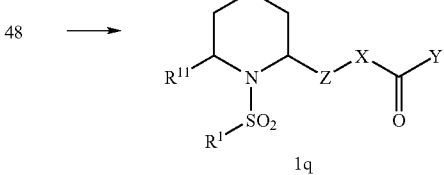
1q

An aldehyde $R^{11}CHO$ is treated with a sulfonamide in the presence of a suitable dehydrating agent such as molecular sieves to give an N-sulfonylimine A. A protected hydroxaldehyde 44, where the protecting group is for example a silyl ether, is converted to an unsaturated ketone 45 by treatment with an appropriate olefinating reagent, such as 1-triphenyl phosphoranylidene-2-propanone. This is converted to a diene by treatment with base followed by treatment with an alkylating or silylating agent such as t-butyldimethylsilylchloride to give 46. The diene undergoes Diels-Alder reaction with N-sulfonylimine A at a suitable temperature, typically room temperature to 150° C., to give a tetrahydropyridine derivative which is hydrolyzed with an acid such as aqueous HCl to give the piperidinone derivative 47. The carbonyl group of 47 can be removed by a variety of methods. For instance, the carbonyl group can be reduced to alcohol 48 using hydride reagents such as sodium borohydride, optionally in the presence of cerium trichloride. The resulting alcohol can be deoxygenated by conversion to xanthate 49 followed by treatment with tri-nbutyltin hydride to give 50. The protecting group of 50 is removed, for instance by treatment with an acid or with fluoride to remove the silyl protecting group, and the resulting alcohol 51 can be converted to compounds of type 1p using the methods previously described. Alternatively, alcohol 48 can be converted to compounds of type Iq (where G=OH or O-alkyl) using similar methods. Chiral compounds of this invention can be resolved by chromatography over a chiral stationary phase as described in the examples.

EXAMPLES

The invention disclosed herein is exemplified by the following examples, which should not be construed as limiting the scope of the invention. Alternative mechanistic pathways and analogous structures within the scope of the invention may be apparent to those skilled in the art.

Abbreviations Used:
AcOEt represents: ethyl acetate;
AcOH represents: acetic acid;
Boc represents: t-butoxycarbonyl;
DCM represents: dichloromethane;
DEAD represents: diethylazodicarboxylate;
DMAP represents: 4-dimethylaminopyridine;
DMF: represents dimethylformamide;
EDCI represents: 1-(3-dimethylaminopropyl)-3-ethylcarbodiimide;
Et$_2$O represents: diethyl ether;
EtOAc represents: ethyl acetate;
MCPBA represents: m-chloroperoxybenzoic acid;
MeOH represents: methanol;
NaHMDS represents: sodium 1,1,1,3,3,3-hexamethyldisilazide;
OTBDMS represents: t-butyldimethylsilyloxy (or t-butyldimethylsilyl ether);
OTBDPS represents: t-butyldiphenylsilyloxy (or t-butyldiphenylsilyl ether);
Ph represents: phenyl;
PyBrop represents: bromo-tris-pyrrolidino-phosphonium hexafluorophosphate;
SEM represents: 2-(trimethylsilyl)ethoxymethyl;
HOBT represents: 1-hydroxybenzotriazole;
TBAF represents: tetrabutylammonium fluoride;
TBDMSCl represents: t-butyldimethylsilyl chloride
TBDPSCl: represents t-butyidiphenylsilylchloride;
TFA: represents trifluroacetic acid;
THF: represents tetrahydrofuran;
TMS represents: trimethylsilane.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

Example 1

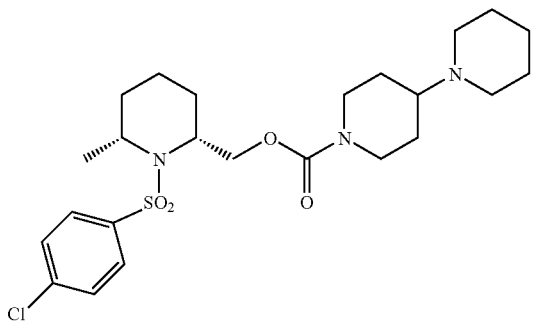

Step 1

Racemic trans 1-(tert-butoxycarbonyl)-2-formyl-6-methyl-piperidine was obtained as described in S. Chackalamannil, R. J. Davies, Y. Wang, T. Asberom, D. Doller, J. Wong, D. Leone and A. T. McPhail, *J. Org. Chem.* 1999, 64, 1932–1940, which is incorporated herein by reference in its entirety. A solution of 5.44 g of this aldehyde was stirred in 100 mL of methanol with 6.0 g of K$_2$CO$_3$ overnight. Solids were filtered out, and the residue was concentrated. The mixture was redissolved in DCM, washed with water, dried over Na$_2$SO$_4$, concentrated and purified chromatographically using 7% ethyl acetate in hexanes as solvent to furnish 3.2 g of product.

Step 2 a) To a solution of 3.21 g (14.1 mmol) of the product of Step 1 in 20.0 mL of THF at 0° C. was added 534 mg (14.1 mmol) of sodium borohydride. The mixture was stirred for 1.5 h, quenched with saturated NaHCO$_3$, extracted with ether, dried over Na$_2$SO$_4$ and freed from solvent under vacuum to give 3.08 g of crude alcohol.

b) The crude alcohol from step 2 was dissolved in 20.0 mL of DMF and treated with 1.83 g (27 mmol) of imidazole and 4.79 g (17.5 mmol) of TBDPSCl. The mixture was stirred overnight, diluted with DCM, washed with water, dried over Na$_2$SO$_4$, and solvent was evaporated. The product was purified by chromatography to furnish 4.67 g of TBDPS ether.

c) A solution of 4.67 g of TBDPS ether in 15 mL of DCM was cooled to 0° C. and treated with a mixture containing 30 mL of 99% TFA and 70 mL of DCM. Cooling was removed and the mixture was stirred for 1.5 h. Volatiles were evaporated, the residue was re-evaporated with DCM, re-dissolved in DCM, washed with saturated NaHCO$_3$, dried over Na$_2$SO$_4$, concentrated and passed through a silica gel plug using 5% MeOH in DCM as solvent to yield 3.50 g of product.

Step 3 a) A mixture of 3.50 g (9.53 mmol) of the product of Step 2, 3.02 g (13.84 mmol) of 4-chlorobenzenesulfonyl chloride and 1.92 g (19.06 mmol) of triethylamine in 20.0 mL of DCM was stirred over a period of 48 h. The reaction mixture was washed with saturated NaHCO$_3$, dried over Na$_2$SO$_4$, concentrated and purified by chromatography using 10% ethyl acetate in hexanes as the eluent to yield 4.66 g of sulfonamide.

b) The resulting sulfonamide (4.66 g, 8.61 mmol) was dissolved in 50.0 mL of THF and treated with 17.2 mL (17.2 mmol) of 1M TBAF/THF solution. The mixture was stirred over 1.5 h, poured into water, extracted with ethyl acetate and DCM. The combined organic phases were dried over Na$_2$SO$_4$, concentrated and purified by chromatography using gradient of 10–30% ethyl acetate in hexanes as solvent to furnish 2.39 g of product.

Step 4 a) To a mixture of 712 mg (2.3 mmol) of the product of step 3, and 370 mg (4.6 mmol) of pyridine in 10 mL of DCM at 0° C. was added a solution of 927 mg (4.6 mmol) of 4-nitrophenylchlorocarbonate in 5 mL of DCM. The mixture was stirred overnight at ambient temperature, treated with an additional 0.17 mL of pyridine and 100 mg of 4-nitrophenylchlorocarbonate and stirred for additional 5 h. The mixture was diluted with DCM, washed with water, dried over Na$_2$SO$_4$, purified by chromatography using 20% ethyl acetate in hexanes as solvent to furnish 860 mg of 4-nitrophenylcarbonate.

b) To a solution of 20 mg of the above product in 0.5 mL of DMF was added 20 mg of 4-(1-piperidino)piperidine. The mixture was allowed to stand overnight, diluted with DCM, washed with 1M NaOH, dried over Na$_2$SO$_4$ and purified by prep. TLC (5% MeOH/DCM) to furnish 17 mg of the desired product. $^1$H NMR (CDCl$_3$, 300 MHz) δ 7.75 (2H, d, J=8.5 Hz), 7.45 (2H, d, J=8.5 Hz), 4.33–4.20 (4H, m), 4.11–4.00 (2H, m), 2.74 (2H, wide), 2.48–2.34 (5H, ser.m.), 1.80–1.22 (16H, ser.m.), 1.30 (3H, d, J=7.1 Hz); MS (ES) m/e 498.1 (M+H)$^+$.

Following procedures similar to those in Example 1, the compounds in Table 1 were prepared.

TABLE 1

| EX. No. | COMPOUND | Mass Spec |
|---|---|---|
| 2 | | 401.1 |
| 3 | | 455.1 |
| 4 | | 401.1 |

TABLE 1-continued
| EX. No. | COMPOUND | Mass Spec |
|---|---|---|
| 5 | 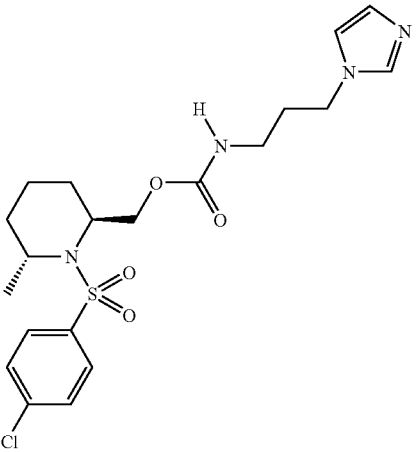 | 455.1 |
| 6 | 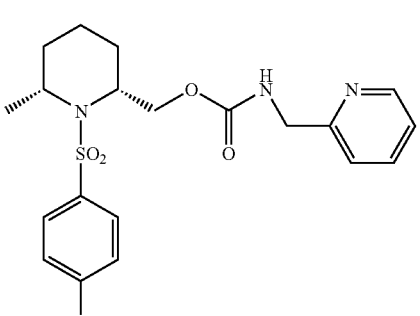 | 438.1 |
| 7 | 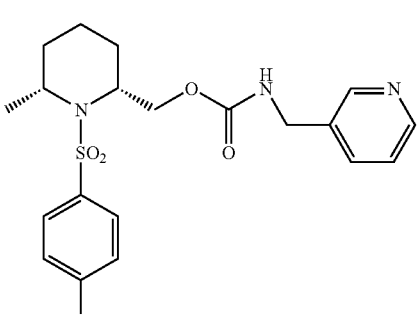 | 438.1 |
| 8 | 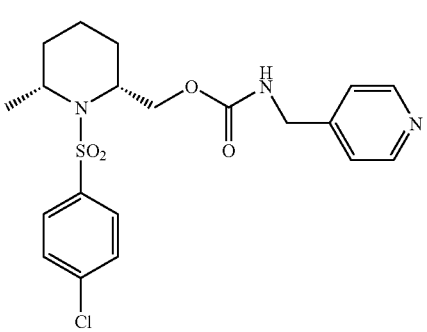 | 438.1 |

TABLE 1-continued
| EX. No. | COMPOUND | Mass Spec |
|---|---|---|
| 9 | 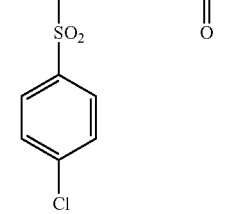 | 466.1 |
| 10 | 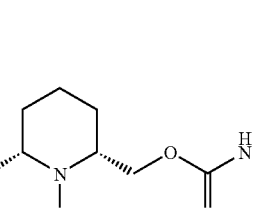 | 452.1 |
| 11 | 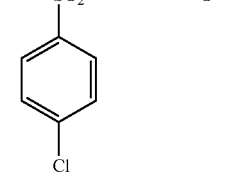 | 452.1 |
| 12 | 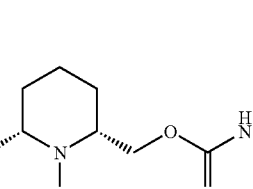 | 452.1 |

TABLE 1-continued
| EX. No. | COMPOUND | Mass Spec |
|---|---|---|
| 13 | 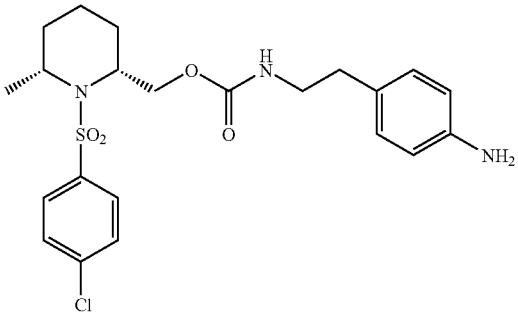 | 466.1 |
| 14 | 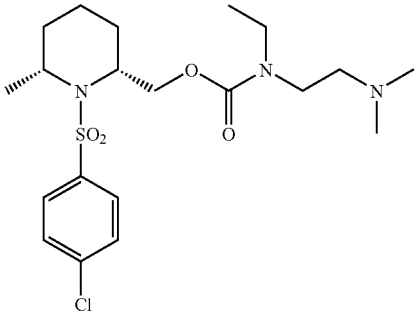 | 446.1 |
| 15 | 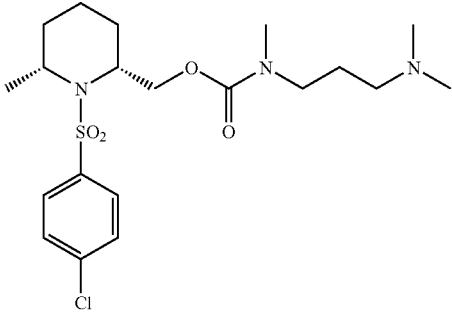 | 446.1 |
| 16 | 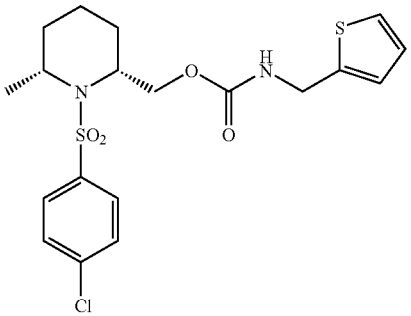 | 443.1 |

TABLE 1-continued
| EX. No. | COMPOUND | Mass Spec |
|---|---|---|
| 17 | 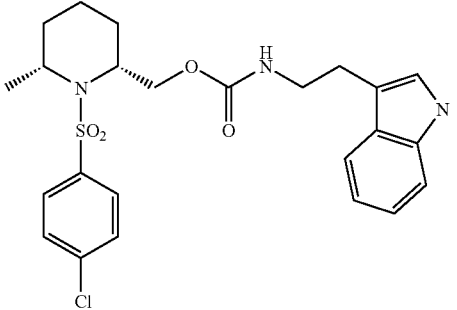 | 490.1 |
| 18 | 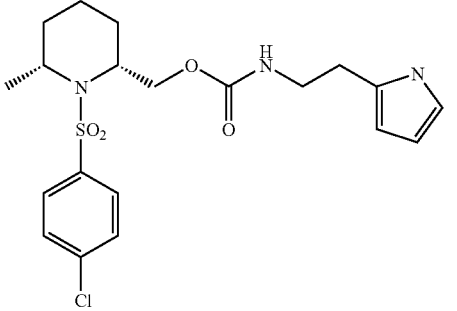 | 441.1 |
| 19 | 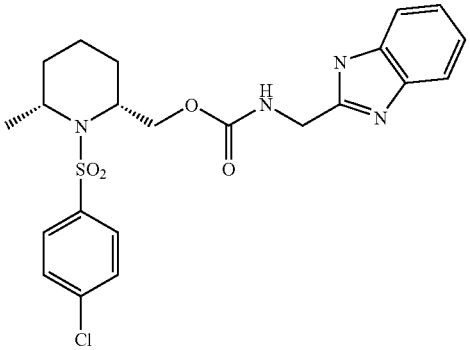 | 477.1 |
| 20 | 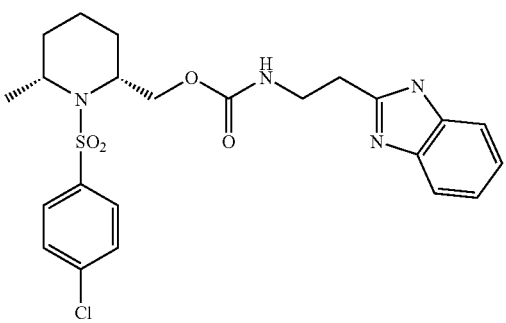 | 491.1 |

TABLE 1-continued

| EX. No. | COMPOUND | Mass Spec |
|---|---|---|
| 21 | (structure) | 405.1 |
| 22 | (structure) | 491.1 |
| 23 | (structure) | 458.1 |
| 24 | (structure) | 466.1 |
| 25 | (structure) | 460.1 |

TABLE 1-continued
| EX. No. | COMPOUND | Mass Spec |
|---|---|---|
| 26 | 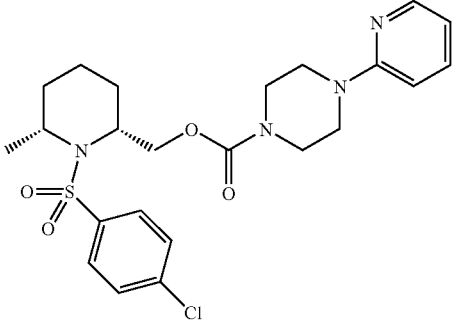 | 493.1 |
| 27 | 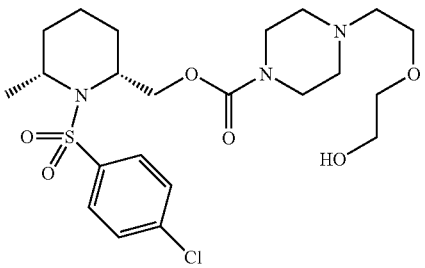 | 504.1 |
| 28 | 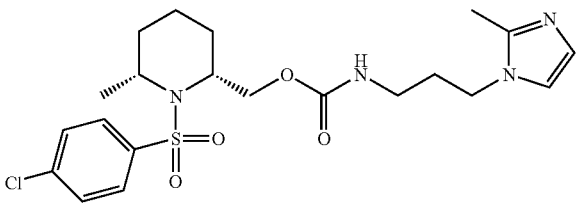 | 469.1 |
| 29 | 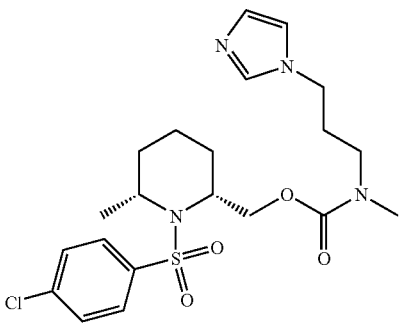 | 469.1 |

Example 31

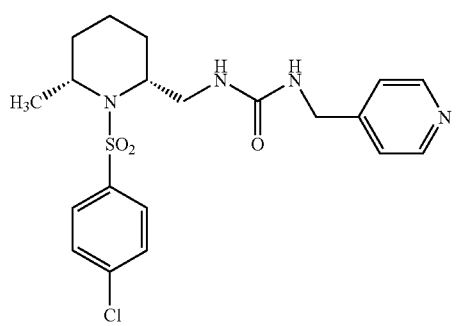

Step 1 a) To a stirred mixture of the product of Example 1, step 3 (425 mg, 1.40 mmol), 308 mg (2.09 mmol) of phthalimide, and 917 mg (3.49 mmol) of triphenylphosphine, was added 609 mg (3.49 mmol) of DEAD. The mixture was stirred overnight, concentrated under vacuum and purified by column chromatography using 20% ethyl acetate in hexanes as the eluent. The resulting material was dissolved in 15.0 ml of a 1:1 mixture of methanol and DCM and treated with 2 mL of hydrazine. The mixture was stirred over 48 h, partitioned between 1M NaOH solution and DCM, and the organic phase was washed with 1M NaOH solution to furnish 475 mg of amine.

Step 2

The product of step 1 was transformed to the desired product as described in Example 1, Step 4, using 4-aminomethylpyridine as the amine. $^1$H NMR (CDCl$_3$ 300 MHz) δ 8.56 (2H, d, J=5.5 Hz), 7.71 (2H, d, J=8.2 Hz), 7.48 (2H, d, J=8.2 Hz), 7.29 (2H, d, J=5.5 Hz), 5.14 (2H, m), 4.45 (2H, d, J=6.0 Hz), 4.13 (1H, m), 3.97 (1H, m), 3.53 (1H, m), 3.33 (1H, m), 1.85–1.19 (6H, ser.m.), 1.33 (3H, d, J=7.1 Hz); MS (ES) m/e 437.1 (M+H)$^+$.

Following procedures similar to those in Example 31, the compounds in Table 2 were prepared.

TABLE 2

| EX. No. | COMPOUND | Mass Spec |
|---|---|---|
| 32 | | 437.1 |
| 33 | | 437.1 |
| 35 | | 465.1 |

TABLE 2-continued
| EX. No. | COMPOUND | Mass Spec |
|---|---|---|
| 36 | 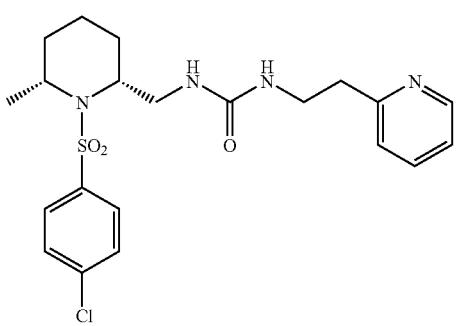 | 451.1 |
| 37 | 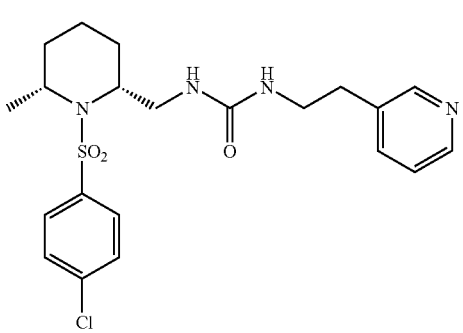 | 451.1 |
| 38 | 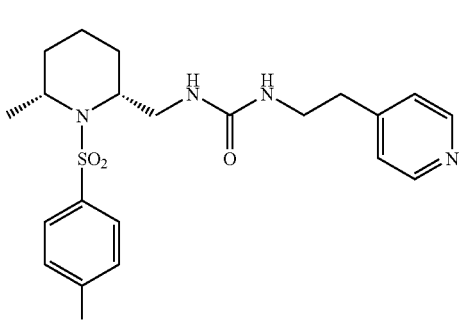 | 451.1 |
| 39 | 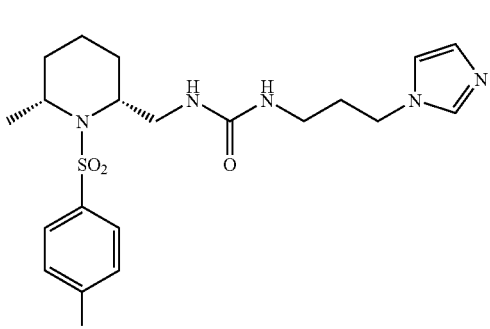 | 454.1 |

TABLE 2-continued
| EX. No. | COMPOUND | Mass Spec |
|---|---|---|
| 40 | 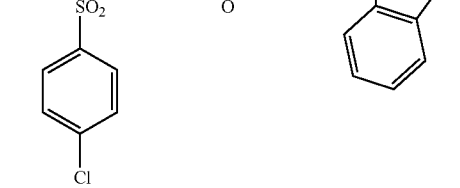 | 489.1 |
| 41 | 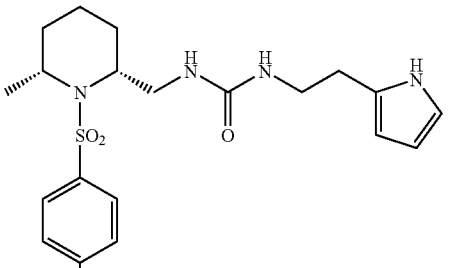 | 440.1 |
| 42 | 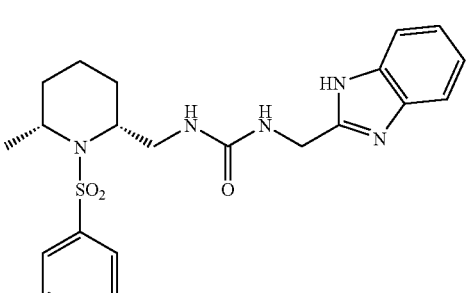 | 476.1 |
| 43 | 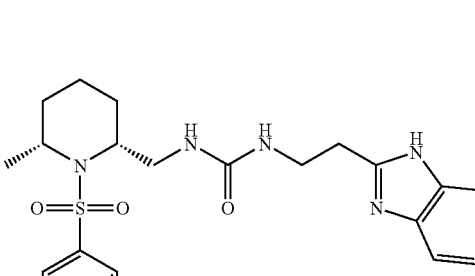 | 490.1 |

Example 44

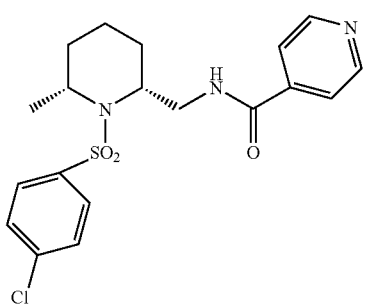

The product of Example 31, step 1 was converted to the title compound by reaction with isonicotinic acid using EDCI and HOBT as coupling reagents, according to a method known in the art. $^1$H NMR (CDCl$_3$ 300 MHz) δ 8.75 (2H, d, J=5.8 Hz), 7.78–7.74 (4H, m), 7.50 (2H, d, J=8.7 Hz), 4.27–4.13 (2H, ser.m), 3.89 (1H, m), 3.39 (1H, dt, J=13.0, 4.3 Hz), 1.81–1.22 (7H, ser.m), 1.35 (3H, d, J=7.3 Hz), MS (ES) m/e 408.1 (M+H)$^+$.

Following procedures similar to those in Example 44, the compounds in Table 3 were prepared.

TABLE 3

| EX. No. | COMPOUND | Mass Spec |
|---|---|---|
| 45 | | 422.1 |
| 46 | | 422.1 |
| 47 | | 416.1 |
| 48 | | 450.1 |
| 50 | | 446.1 |
| 51 | | 474.1 |

TABLE 3-continued

| EX. No. | COMPOUND | Mass Spec |
|---|---|---|
| 52 | | 458.1 |

Example 53

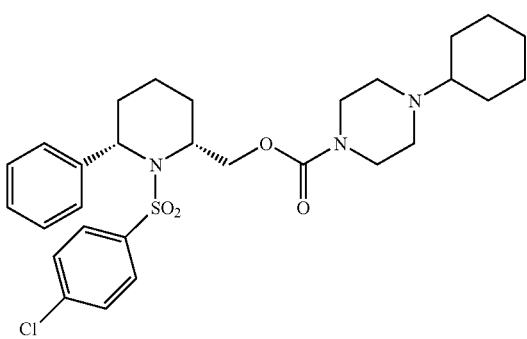

Preparation A: cis(6-Phenyl-piperidin-2-yl)-methanol

Step 1

(a) To a mixture of 600 mg (2.5 mmol) of 2,6-dibromopyridine in 15 mL of toluene was added a mixture of 150 mg (1.27 mmol) of phenylboronic acid in 5 mL of methanol, 86 mg (0.075 mmol) of Pd(PPh$_3$)$_4$ and 15 mL of 2 M Na$_2$CO$_3$. The mixture was refluxed overnight, cooled, extracted with ethyl acetate, dried and 2-bromo-6-phenylpyridine isolated chromatographically from unreacted 2,6-dibromopyridine and 2,6-diphenylpyridine.

(b) To a solution of 7.2 g (31.03 mmol) of 2-bromo-6-phenylpyridine in 50 mL of THF at −78° C. was added drop-wise 13.5 mL (31 mmol) of 2.3 M n-BuLi in hexanes followed by 10 mL of DMF. The mixture was stirred in the cold for 30 min, quenched with saturated NaHCO$_3$, extracted with ethyl acetate, dried, concentrated, and purified by chromatography using a gradient of 3–5% of ethyl acetate in hexanes to provide 2.02 g of product.

Step 2

To a solution of 2 g of the product of step 1 in 20 mL of MeOH was added 5 mL of AcOH and 300 mg of PtO$_2$. The mixture was hydrogenated under a balloon. The progress of the reaction was followed by taking NMR spectra of worked-up portions. After overnight stirring another portion of 300 mg of PtO$_2$ was added and hydrogenation continued for additional 24 h. Catalyst was filtered out, volatiles evaporated, residue re-dissolved in DCM and washed with 1M NaOH solution, saturated NaHCO$_3$, dried, and evaporated. Column chromatography yielded 1.30 g of cis(6-phenyl-piperidin-2-yl)-methanol and 200 mg of cis(6-cyclohexyl-piperidin-2-yl)-methanol.

Preparation B: Alternate Synthesis of cis(6-phenyl-piperidin-2-yl)-methanol

Step 1

6-bromopicolinic acid (1.99 g) in DMF (10 mL) was treated with potassium carbonate (1.40 g) and then methyl iodide (4 mL) at room temperature for 20 h. The reaction mixture was diluted with dichloromethane (60 mL) and filtered. The filtrate was extracted with brine (twice), dried (MgSO$_4$), and concentrated under vacuum to give methyl 6-bromopicolinate as a pale yellow solid (1.75 g).

Step 2

Methyl 6-bromopicolinate (0.75 g), phenylboronic acid (0.61 g), tetrakis(triphenylphosphine)palladium (0.19 g) and potassium carbonate (0.75 g) in toluene (20 mL) and methanol (4.5 mL) were heated at reflux for 1 hr. The reaction mixture was then cooled, diluted with dichloromethane, and filtered. The filtrate was washed with water, and the dried (K$_2$CO$_3$) organic solution was concentrated under vacuum to give an amber residue (0.81 g). The residue was purified by chromatography on silica gel plates (8, 1000 μm) using hexane:ethyl acetate 3:1 as the eluent, to give methyl 6-phenylpicolinate as a colorless oil (0.55 g).

Step 3

Under a hydrogen atmosphere, a solution of methyl 6-phenylpicolinate (0.55 g) in MeOH (30 mL) and glacial acetic acid (15 mL) was stirred in the presence of platinum oxide (0.150 g) for 5 hr. The reaction mixture was purged with nitrogen. The reaction mixture was filtered and concentrated under vacuum to give a yellow oil (0.77 g). The oil was purified by chromatography on silica gel plates (8, 1000 μm) using hexane:ethyl acetate 3:1 as the eluent, to give methyl 6-phenylpipecolinate as a colorless oil (0.23 g).

Step 4

A solution of methyl 6-phenylpipecolinate (0.23 g) in THF (15 mL) was treated with 1M lithium aluminum hydride in ether (10 mL) at room temperature for 2 h. The reaction mixture was quenched with EtOAc, then MgSO$_4$ was added and the mixture was filtered. The filtrate was concentrated to give a residue, which was purified by chromatography on silica gel plates (2, 1000 μm) using EtOAc:hexane 1:1 as the eluent, to give (6-phenyl-piperidin-2-yl)-methanol as a white solid (0.06 g).

Preparation C:

Step 1

(a) At 0° C., to a solution of 1.29 g (6.77 mmol) of cis(6-phenyl-piperidin-2-yl)-methanol (prepared by the method of Preparation A or Preparation B) in 20.0 mL of DCM was added 1.90 mL (13.6 mmol) of triethylamine and 1.84 mL (10.1 mL) of trimethylsilyl trifluoromethanesulfonate. The mixture was stirred for 1 h at ambient temperature, washed with saturated NaHCO$_3$, dried over Na$_2$SO$_4$ and volatiles were evaporated.

(b) The residue was re-dissolved in DCM, treated with 1.90 mL (13.5 mmol) of triethylamine and 2.11 g (10.0 mmol) of 4-chlorobenzenesulfonylchloride. The mixture was stirred for 24 h, washed with 1M HCl, saturated NaHCO₃, and concentrated.

(c) To insure cleavage of TMS ether, the material was dissolved in methanol (5 mL), treated with 1 mL of 1M HCl, stirred for 30 min, and concentrated. The residue was chromatographed using 10–20% ethyl acetate in hexanes to furnish 1.45 g of 1-(4-chloro-benzenesulfonyl)-6-phenyl-piperidin-2-yl]-methanol.

Step 2

The product of Step 1 was converted to the title compound according to Step 4 of Example 1, using N-cyclohexylpiperazine at the last stage as the amine. $^1$H NMR (CDCl$_3$ 300 MHz) δ 7.86 (2H, d, J=8.2 Hz), 7.57–7.49 (4H, m), 7.36–7.24 (3H, m), 5.24 (1H, d, J=4.9 Hz), 4.34 (1H, q, J=6.2 Hz), 3.68 (1H, dd, J=11.0, 6.5 Hz), 3.58–3.40 (5H, ser.m.), 2.55 (4H, m), 2.37–2.24 (2H, ser.m.), 1.90–1.58 (6H, ser.m.), 1.53–1.36 (3H, ser.m.), 1.30–1.13 (6H, ser.m.); MS (ES) m/e 560.1 (M+H)$^+$.

Following procedures similar to those in Example 53, the compounds in Table 4 were prepared. Cis-(6-cyclohexyl-piperidin-2-yl)-methanol, obtained in Preparation A, step 2, was used in Examples 63–66.

TABLE 4

| EX. No. | COMPOUND | Mass Spec |
|---|---|---|
| 54 | | 517.1 |
| 55 | | 560.1 |
| 56 | | 555.1 |

TABLE 4-continued

| EX. No. | COMPOUND | Mass Spec |
|---|---|---|
| 57 | | 520.1 |
| 58 | | 508.1 |
| 59 | | 528.1 |
| 60 | | 528.1 |
| 61 | | 520.1 |

TABLE 4-continued

| EX. No. | COMPOUND | Mass Spec |
|---|---|---|
| 63 | | 523.1 |
| 64 | | 566.1 |
| 65 | | 526.1 |
| 66 | | 514.1 |

TABLE 4-continued

| EX. No. | COMPOUND | Mass Spec |
|---|---|---|
| 67 | (structure: 6-phenyl-piperidine N-sulfonyl(4-chlorophenyl), 2-CH2-O-C(O)-N-piperazine-CH2CH2-OH) | 522.1 |

NMR data are given in Table 5 below for compounds in Table 4:

TABLE 5

| EX. No. | COMPOUND | NMR |
|---|---|---|
| 54 | (structure with imidazolyl-propyl carbamate) | $^1$H NMR (CDCl$_3$, 300 MHz) δ 7.84 (2H, d, J=8.8 Hz), 7.58–7.51 (5H, ser.m.), 7.37–7.24 (3H, ser.m.), 7.07 (1H, br), 6.96 (1H, br), 5.22 (1H, d, J=5.5 Hz), 4.91 (1H, m), 4.33 (1H, m), 4.03 (2H, t, J=7.0 Hz), 3.75 (1H, dd, J=6.0, 11.5 Hz), 3.42 (1H, dd, J=6.0, 11.5 Hz), 3.27–3.17 (1H, m), 3.13–3.05 (1H, m), 2.34 (1H, d, J=14.8 Hz), 1.88 (2H, m), 1.68–1.19 (5H, ser.m.) |
| 55 | (structure with 4-piperidinopiperidine carbamate) | $^1$H NMR (CDCl$_3$, 300 MHz) δ 7.85 (2H, d, J=8.8 Hz), 7.57–7.50 (4H, ser.m.), 7.36–7.23 (3H, ser.m.), 5.24 (1H, d, J=4.5 Hz), 4.38–4.13 (3H, ser.m.), 3.70 (1H, dd, J=6.0, 11.0 Hz), 3.47 (1H, s), 3.42 (1H, dd, J=9.0, 11.0 Hz), 2.73 (1H, br), 2.53–2.30 (5H, ser.m.), 1.94–1.17 (16H, ser.m.) |
| 57 | (structure with N-methyl-N-(1-methylpiperidin-4-yl) carbamate) | $^1$H NMR (CDCl$_3$, 300 MHz) δ 7.84 (2H, d, J=8 Hz), 7.59–7.50 (4H, m), 7.34–7.26 (3H, ser.m.), 5.23 (0.5H, br), 5.12 (0.5H, br), 4.59 (0.5H, br), 4.47–4.32 (1H, m), 4.11 (0.5H, br), 3.71 (1H, d, J=10.2 Hz), 3.43 (2H, t, J=10.5 Hz), 3.24 (1H, br) |

TABLE 5-continued
| EX. No. | COMPOUND | NMR |
|---|---|---|
| 58 | 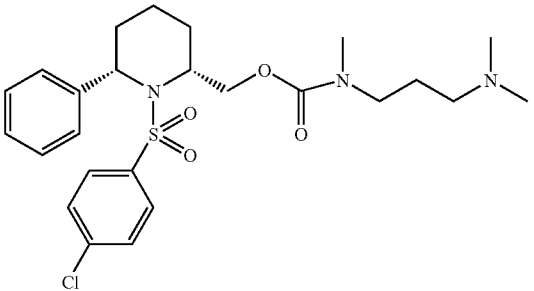 | $^1$H NMR (CDCl$_3$ 300 MHz) δ 7.83 (2H, d, J=8 Hz), 7.63–7.53 (4H, ser.m.), 7.38–7.27 (3H, ser.m.), 5.18 (1H, m), 4.44 (1H, m), 3.86–3.62 (3H, ser.m), 3.56–3.30 (2H, ser.m.), 3.00 (3H, s), 2.78 (3H, s), 2.73 (3H, s) |
| 61 | 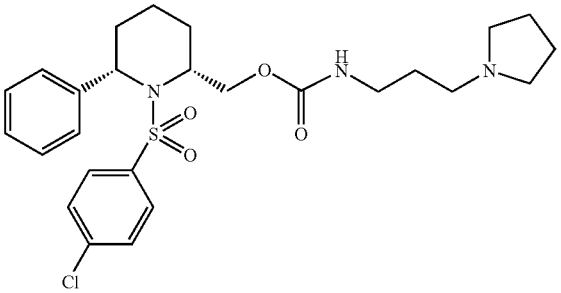 | $^1$H NMR (CDCl$_3$ 300 MHz) δ 7.84 (2H, d, J=8.7 Hz), 7.56–7.51 (4H, ser.m), 7.38 (2H, 1, J=7.3 Hz), 7.29 (1H, d, J=7.3 Hz), 5.66 (1H, m), 5.20 (1H, d, J=5.1 Hz), 4.35 (1H, m), 3.70 (1H, dd, J=11.2, 7.0 Hz), 3.45–3.0 (3H, ser.m), 3.27–2.96 (5H, ser.m), 2.30 (1H, d, J=14.0 Hz), 2.04–1.2 (12H, ser.m) |
| 64 | 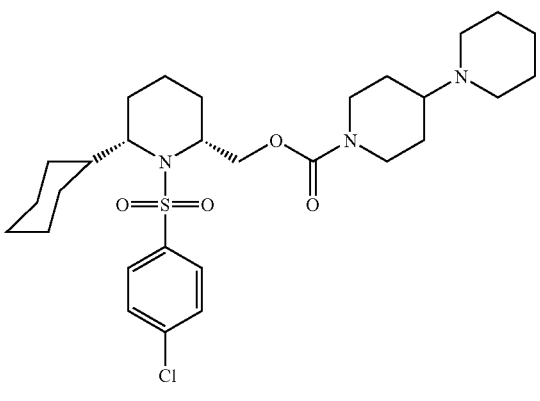 | $^1$H NMR (CDCl$_3$ 300 MHz) δ 7.78 (2H, d, J=8.5 Hz), 7.47 (2H, d, J=8.5 Hz), 4.29–4.08 (5H, ser.m.), 3.68 (1H, m), 2.76 (2H, m), 2.5–2.35 (5H, ser.m.), 2.10 (1H, d, J=12.6 Hz), 1.85–0.77 (26H, ser.m.) |
| 67 | 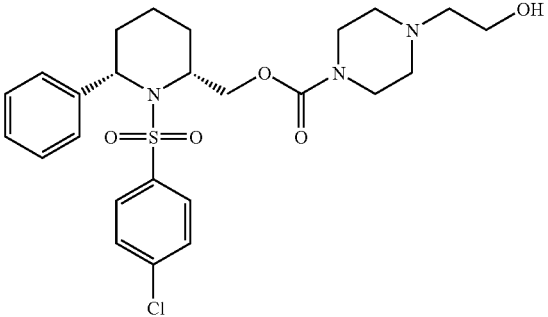 | $^1$H NMR (CDCl$_3$ 300 MHz) δ 7.85 (2H, d), 7.57–7.50 (4H, ser.m.), 7.37–7.24 (3H, ser.m.), 5.24 (1H, d, J=4.5 Hz), 4.35 (1H, m), 3.72 (1H, dd, J=11.0, 6.0 Hz), 3.64 (2H, t, J=5.2 Hz), 3.60–3.45 (4H, ser.m.), 3.43 (1H, dd, J=11.0, 9.3 Hz), 2.61–2.46 (6H, ser.m.), 2.35 (1 H, d, J=14.3 Hz), 1.73–1.18 (6H, ser. m.) |

Also prepared were the following compounds:

TABLE 5-A

| Compound No. | Structure | Retention Time (minutes) | Observed Mass |
|---|---|---|---|
| 67-A | [Alpha]$^{20}$$_D$ = +51.40 | 5.38 | 578.1 |
| 67-B | [Alpha]$^{20}$$_D$ = +56.95 | 5.38 | 578.1 |
| 67-C | 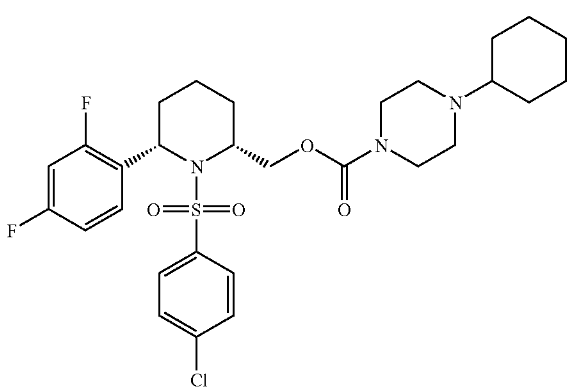 | 5.52 | 596.1 |

TABLE 5-A-continued

| Compound No. | Structure | Retention Time (minutes) | Observed Mass |
|---|---|---|---|
| 67-D | 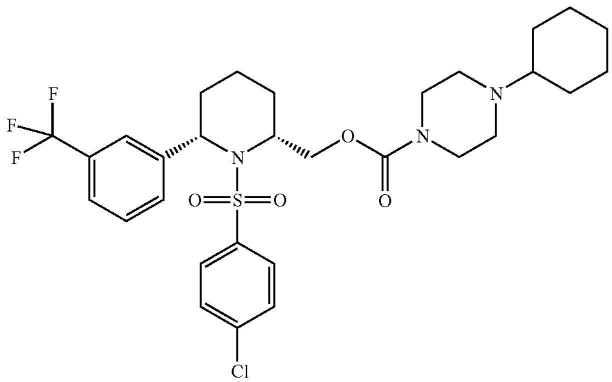 | 5.68 | 628.1 |
| 67-E | 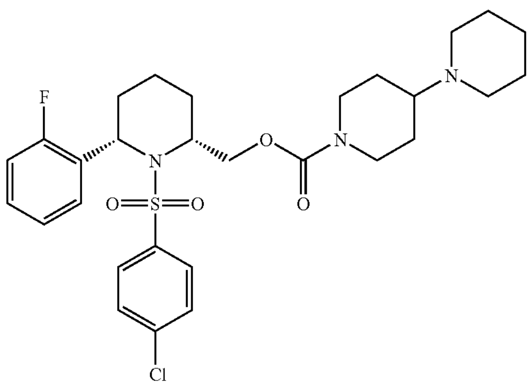 | 5.42 | 578.1 |
| 67-F | 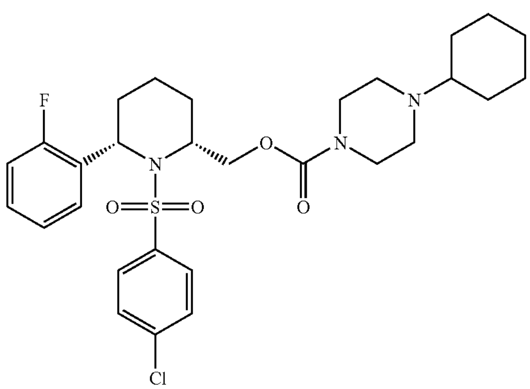 | 5.48 | 578.1 |
| 67-G | 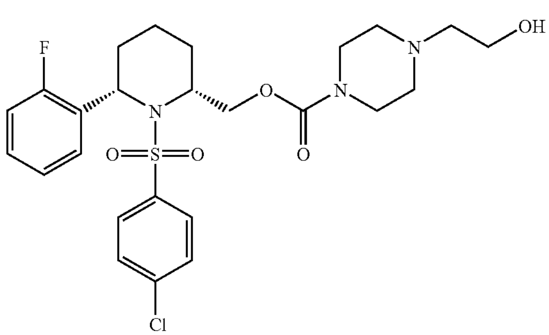 | 4.83 | 540.1 |

TABLE 5-A-continued

| Compound No. | Structure | Retention Time (minutes) | Observed Mass |
|---|---|---|---|
| 67-H | 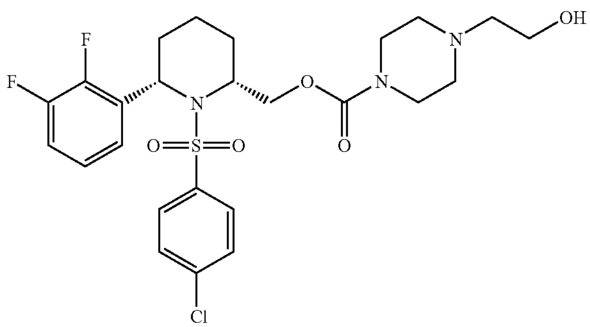 | 4.75 | 558.1 |
| 67-I | 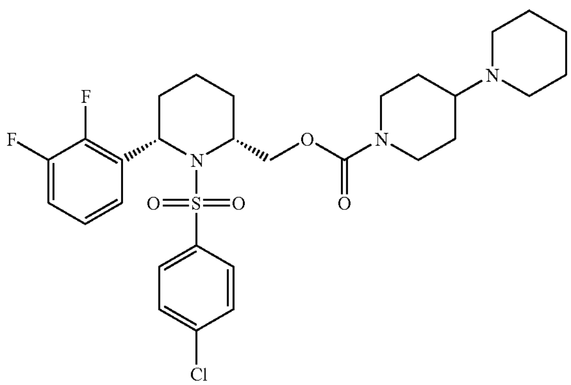 | 5.42 | 596.1 |
| 67-J | 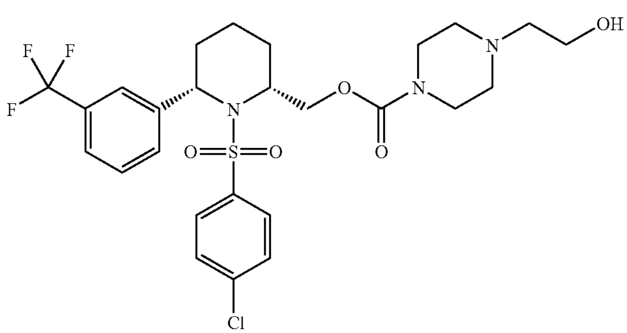 | 5.18 | 590.1 |
| 67-K | 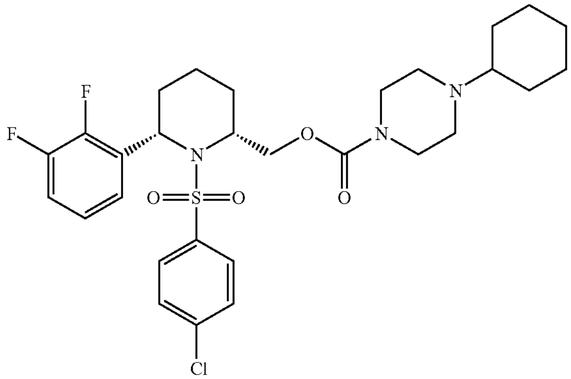 | 5.48 | 596.1 |

TABLE 5-A-continued

| Compound No. | Structure | Retention Time (minutes) | Observed Mass |
|---|---|---|---|
| 67-L | 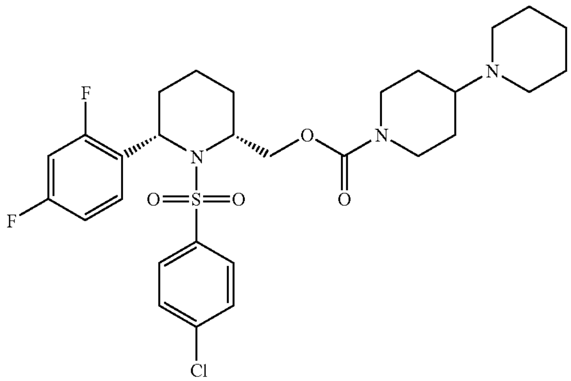 | 5.62 | 596.1 |
| 67-M | 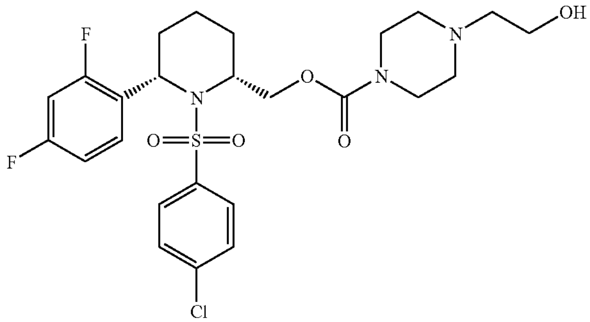 | 4.85 | 558.1 |
| 67-N | 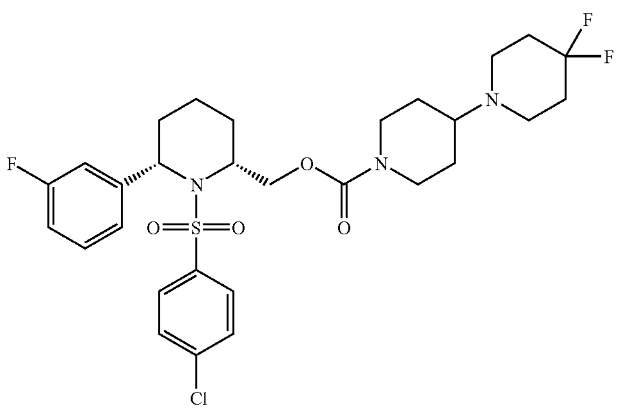 | 5.51 | 614.3 |
| 67-O | 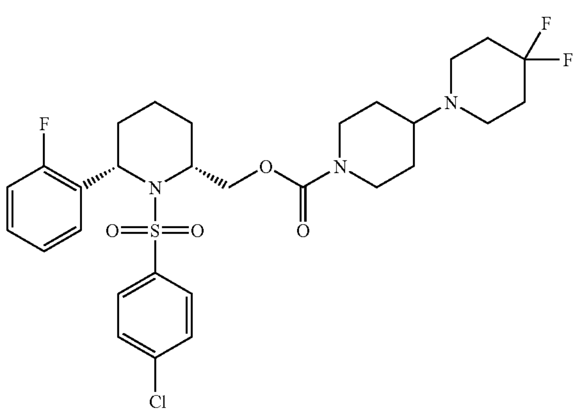 | 5.48 | 614.3 |

TABLE 5-A-continued

| Compound No. | Structure | Retention Time (minutes) | Observed Mass |
|---|---|---|---|
| 67-P | 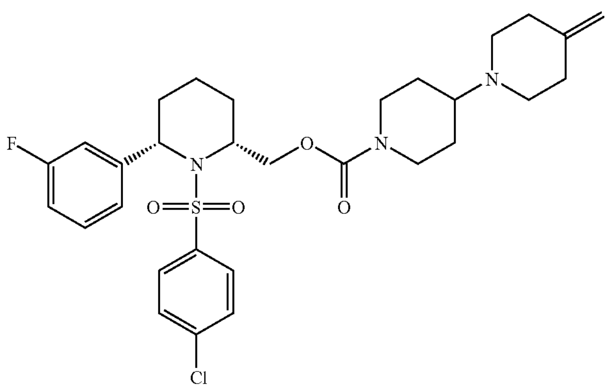 | 5.55 | 590.1 |
| 67-Q | 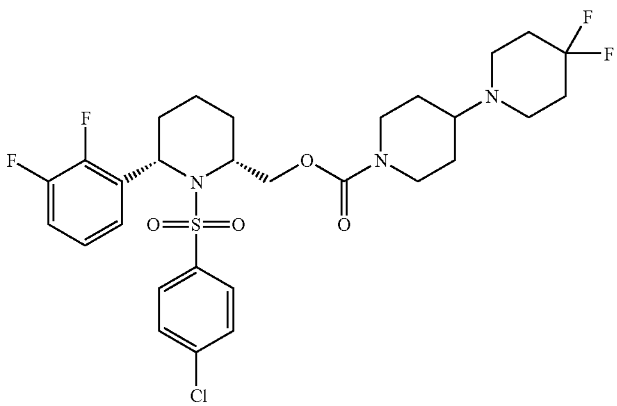 | 5.48 | 632.1 |
| 67-R | 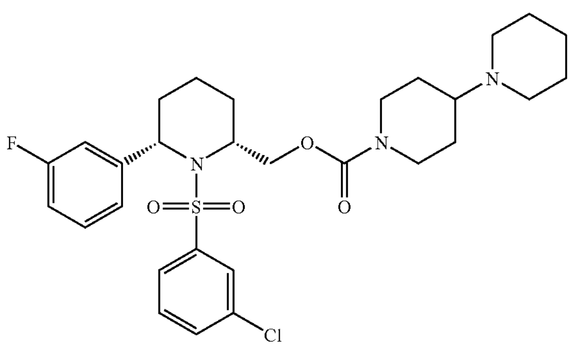 | 5.82 | 578.1 |
| 67-S | 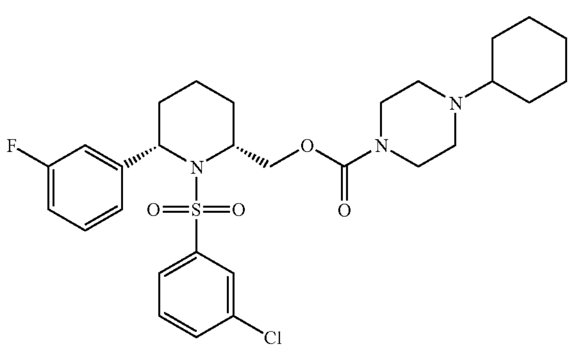 | 5.85 | 578.1 |

TABLE 5-A-continued

| Compound No. | Structure | Retention Time (minutes) | Observed Mass |
|---|---|---|---|
| 67-T | 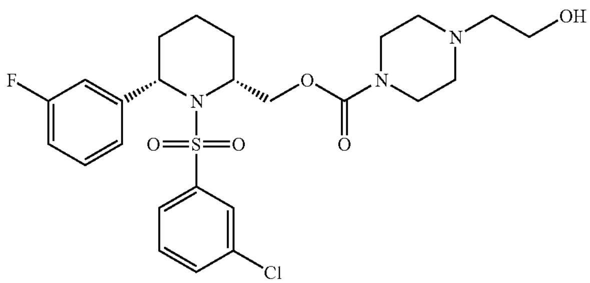 | 5.35 | 540.1 |
| 67-U | 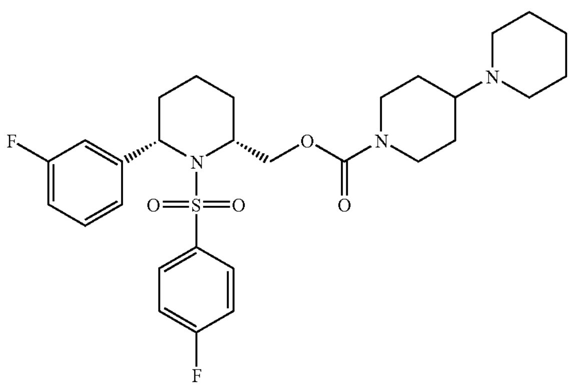 | 5.65 | 562.1 |
| 67-V | 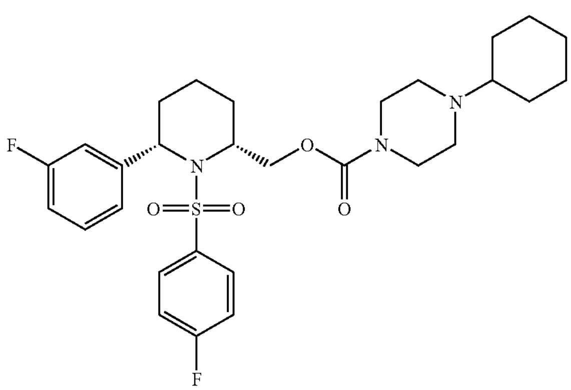 | 5.68 | 562.1 |
| 67-W | 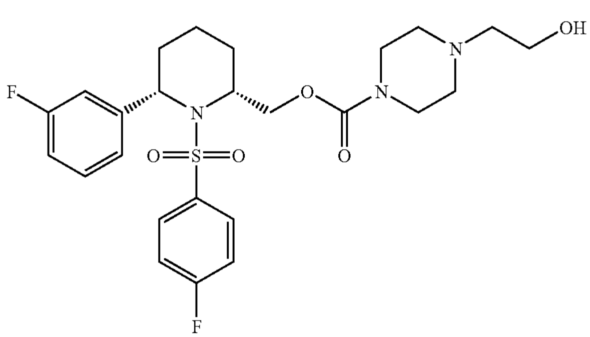 | 5.18 | 524.1 |

TABLE 5-A-continued

| Compound No. | Structure | Retention Time (minutes) | Observed Mass |
|---|---|---|---|
| 67-X | 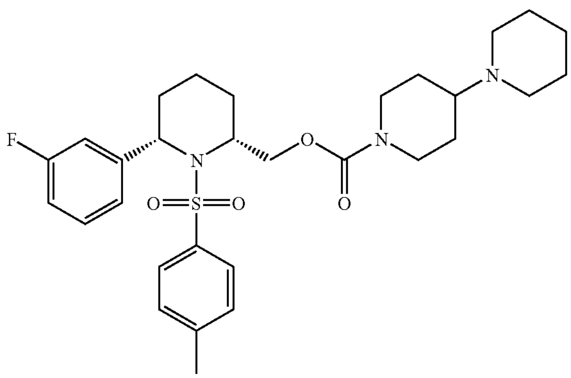 | 5.08 | 558.3 |
| 67-Y | 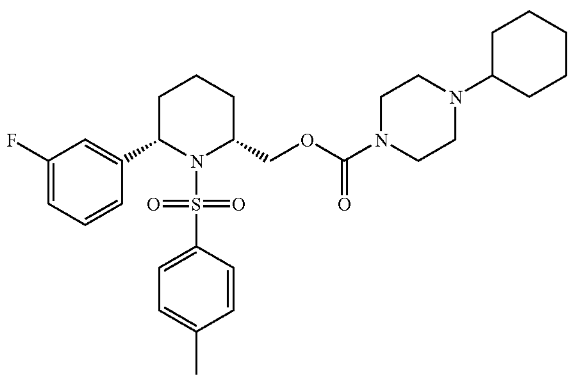 | 5.18 | 558.3 |
| 67-Z | 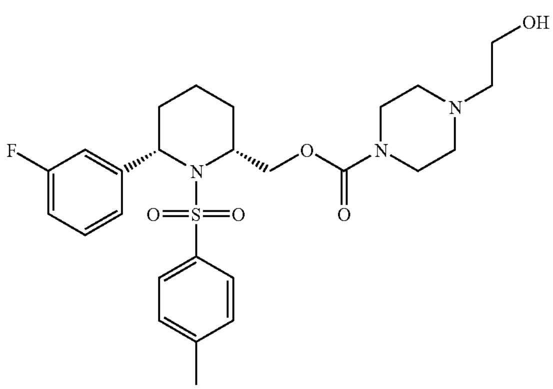 | 4.38 | 520.3 |
| 67-AA | 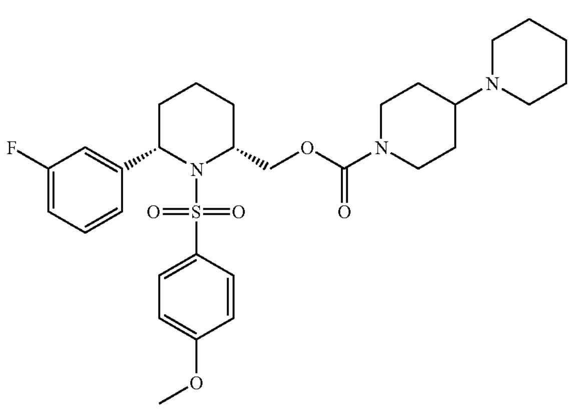 | 5.32 | 574.1 |

TABLE 5-A-continued

| Compound No. | Structure | Retention Time (minutes) | Observed Mass |
|---|---|---|---|
| 67-AB | 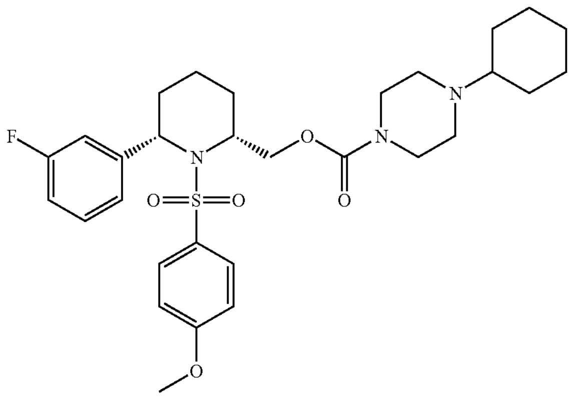 | 5.55 | 574.1 |
| 67-AC | 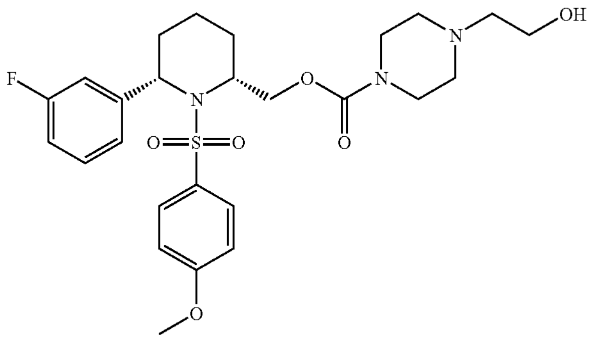 | 4.68 | 536.1 |
| 67-AD | 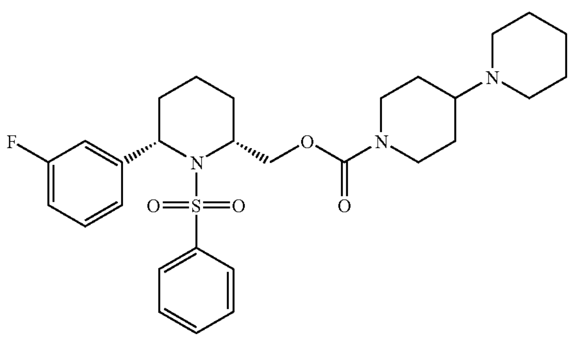 | 5.25 | 544.1 |
| 67-AE | 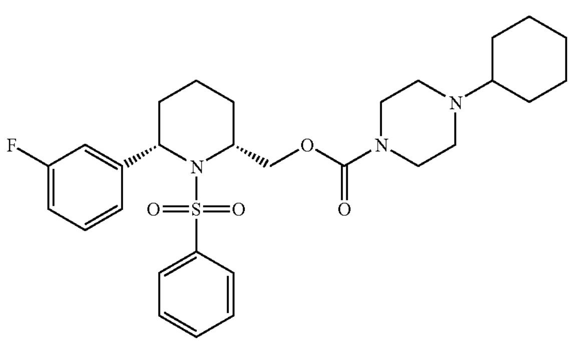 | 5.55 | 544.1 |

TABLE 5-A-continued

| Compound No. | Structure | Retention Time (minutes) | Observed Mass |
|---|---|---|---|
| 67-AF | 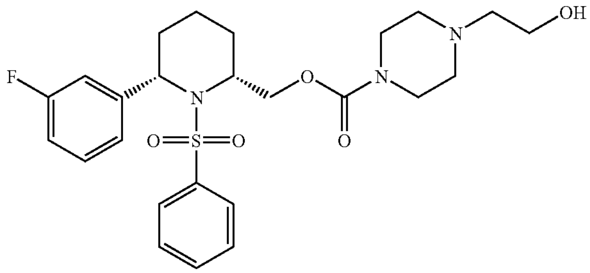 | 4.61 | 506.1 |
| 67-AG | 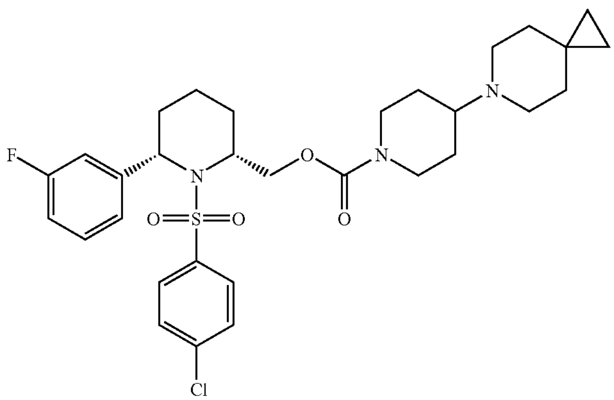 | 5.65 | 608.1 |
| 67-AH | 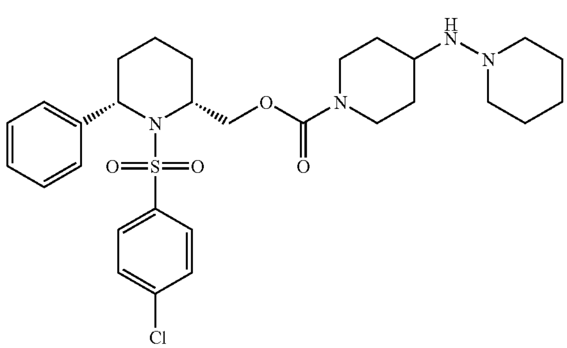 | 5.38 | 575.1 |
| 67-AI | 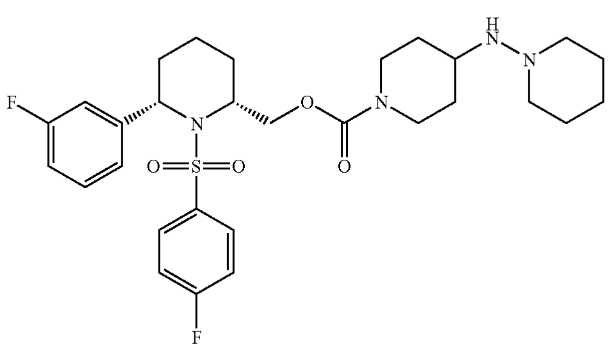 | 5.25 | 577.1 |

TABLE 5-A-continued

| Compound No. | Structure | Retention Time (minutes) | Observed Mass |
|---|---|---|---|
| 67-AJ | 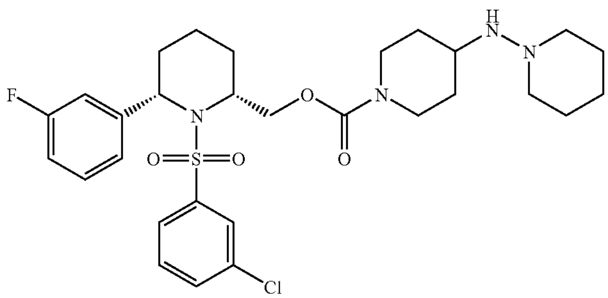 | 5.38 | 593.1 |
| 67-AK | 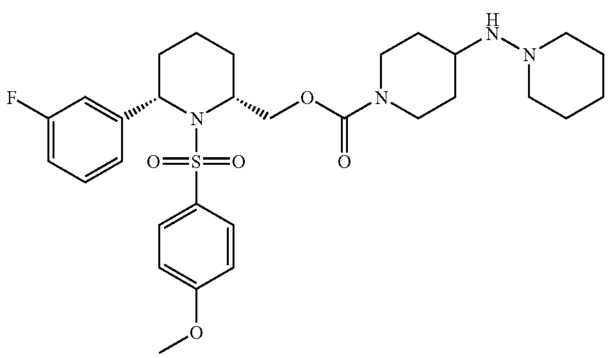 | 5.22 | 589.1 |
| 67-AL | 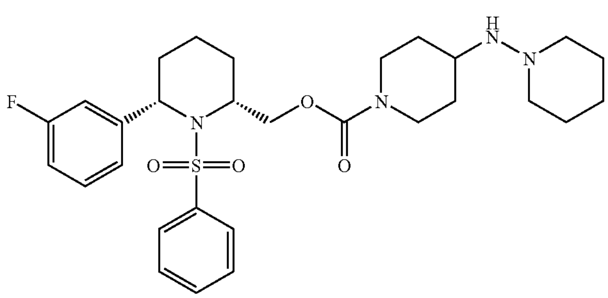 | 5.15 | 559.1 |
| 67-AM | 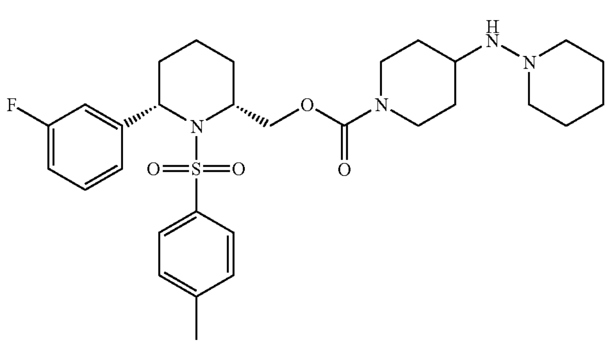 | 5.35 | 573.1 |

TABLE 5-A-continued

| Compound No. | Structure | Retention Time (minutes) | Observed Mass |
|---|---|---|---|
| 67-AN | 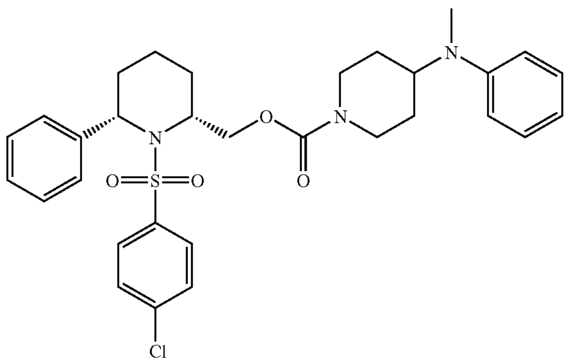 | 5.01 | 582.3 |
| 67-AO | 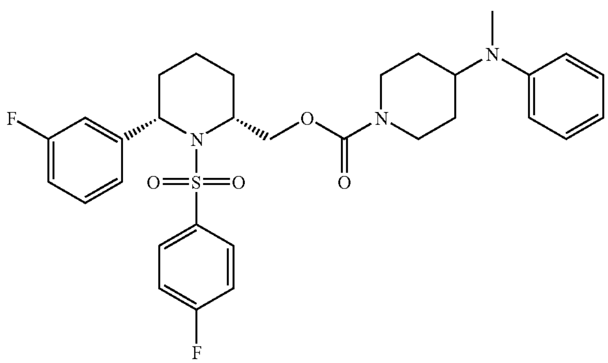 | 4.85 | 584.3 |
| 67-AP | 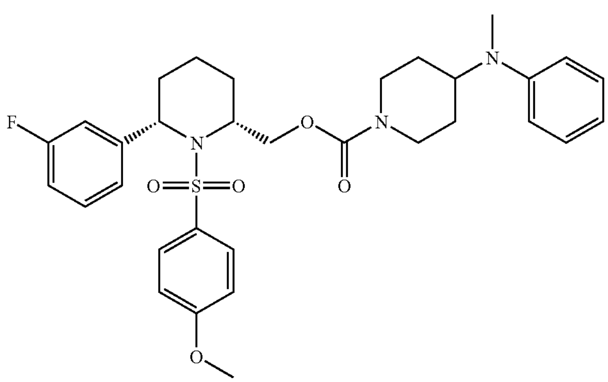 | 4.85 | 596.3 |
| 67-AQ | 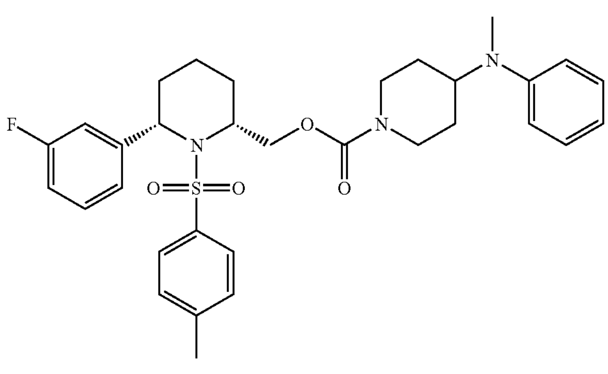 | 5.01 | 580.3 |

TABLE 5-A-continued

| Compound No. | Structure | Retention Time (minutes) | Observed Mass |
|---|---|---|---|
| 67-AR | 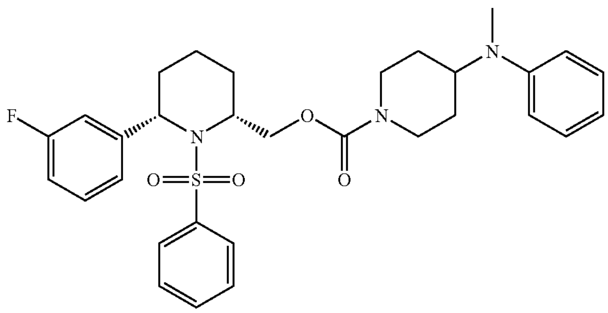 | 4.78 | 566.3 |
| 67-AS | 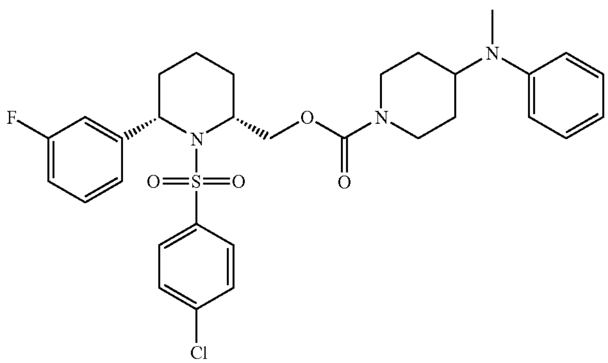 | 5.52 | 600.1 |
| 67-AT | 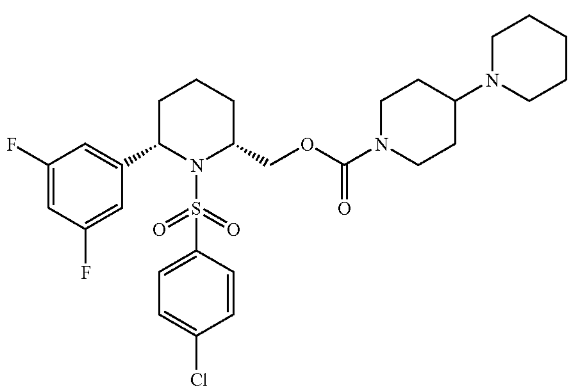 | 5.52 | 696.1 |
| 67-AV | 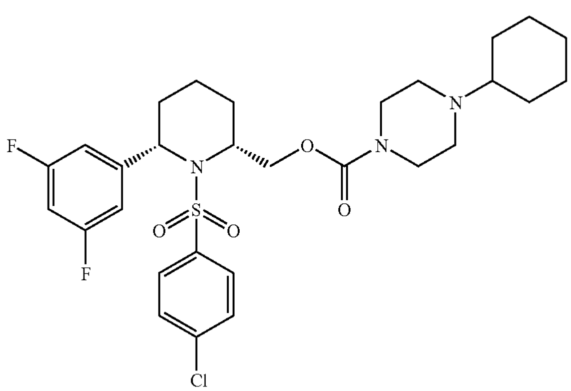 | 5.52 | 596.1 |

TABLE 5-A-continued

| Compound No. | Structure | Retention Time (minutes) | Observed Mass |
|---|---|---|---|
| 67-AW | 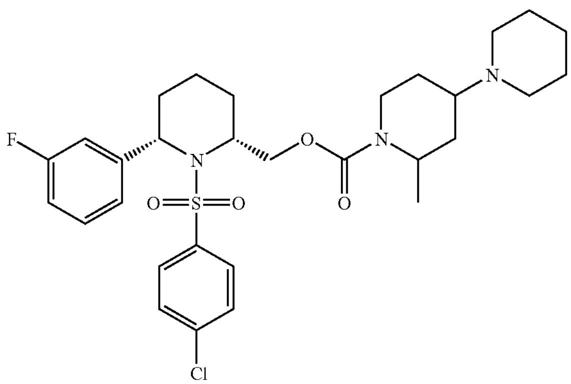 | 5.85 | 578.1 |
| 67-AX | 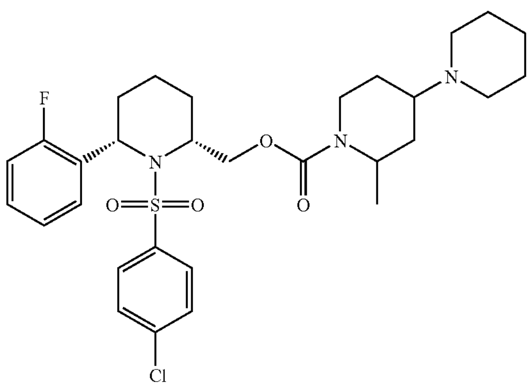 | 5.85 | 578.1 |
| 67-AY | 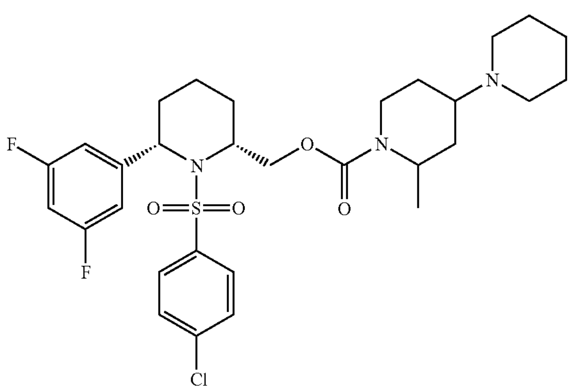 | 5.82 | 596.1 |
| 67-AZ | 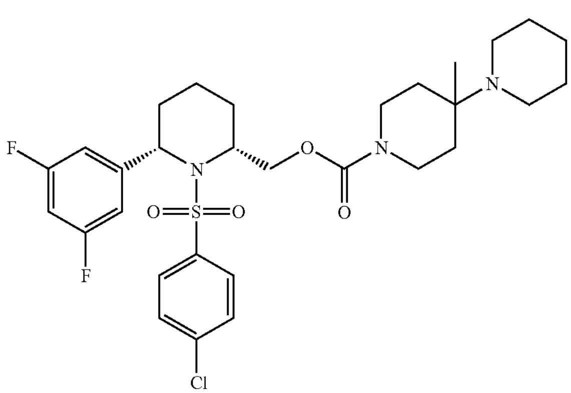 | 5.45 | 610.1 |

TABLE 5-A-continued

| Compound No. | Structure | Retention Time (minutes) | Observed Mass |
|---|---|---|---|
| 67-BA | 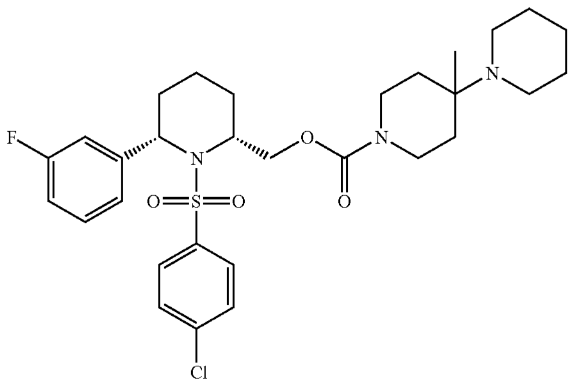 | 5.92 | 592.1 |
| 67-BB | 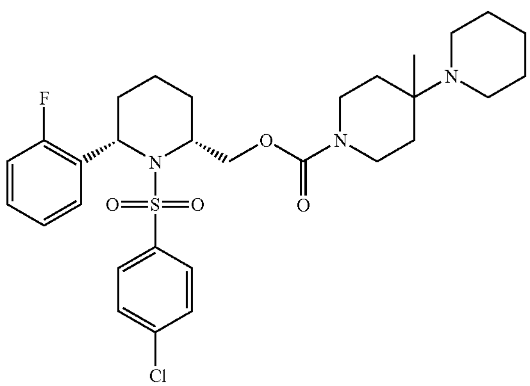 | 5.88 | 592.1 |
| 67-BC | 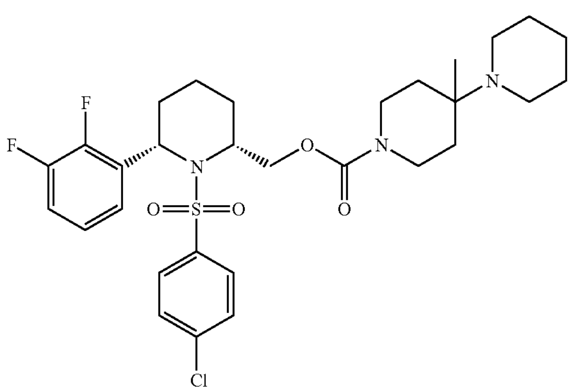 | 5.92 | 610.1 |

TABLE 5-A-continued

| Compound No. | Structure | Retention Time (minutes) | Observed Mass |
| --- | --- | --- | --- |
| 67-BD | 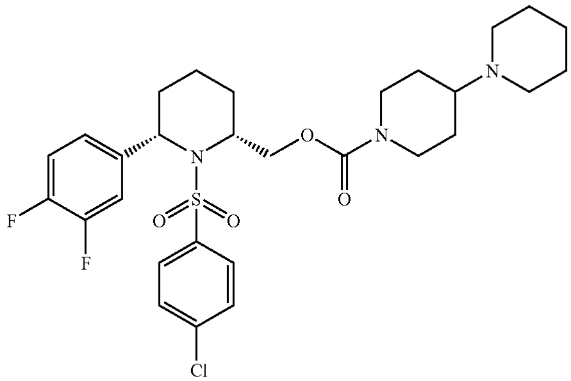 | 5.72 | 596.1 |
| 67-BE | 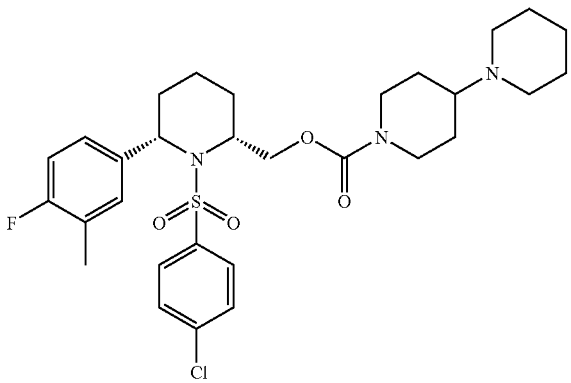 | 5.92 | 592.1 |
| 67-BF | 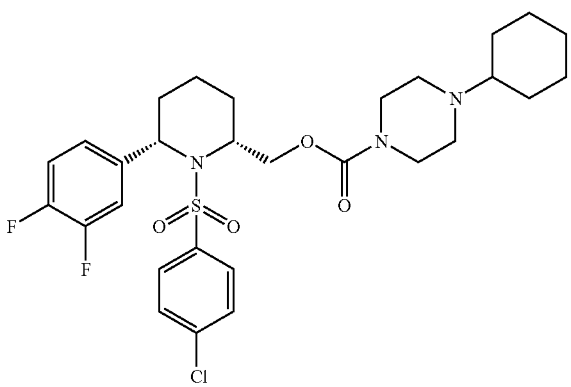 | 5.78 | 596.1 |
| 67-BG | 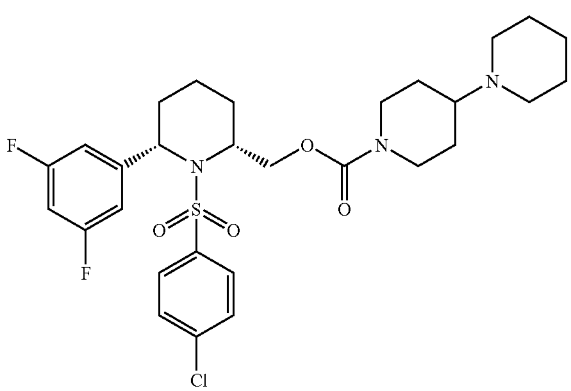 | 5.42 | 596.1 |

TABLE 5-A-continued

| Compound No. | Structure | Retention Time (minutes) | Observed Mass |
| --- | --- | --- | --- |
| 67-BH | 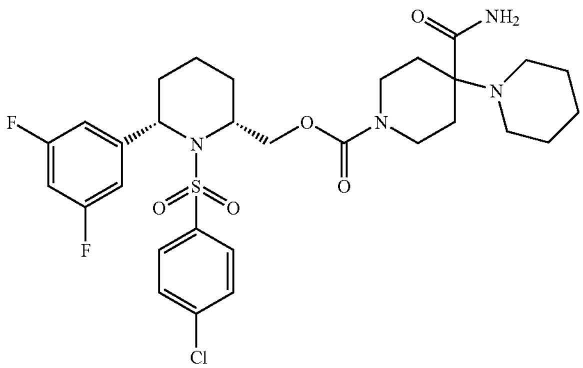 | 5.35 | 639.0 |
| 67-BI | 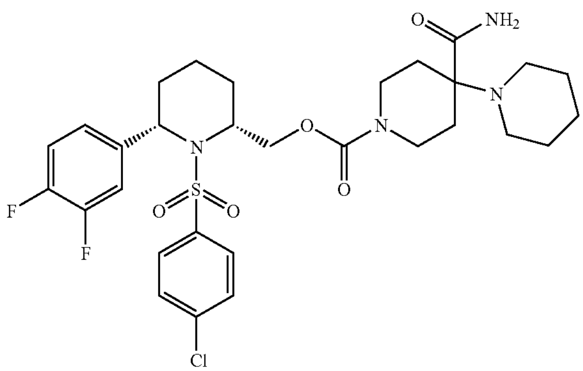 | 5.15 | 639.2 |
| 67-BJ | 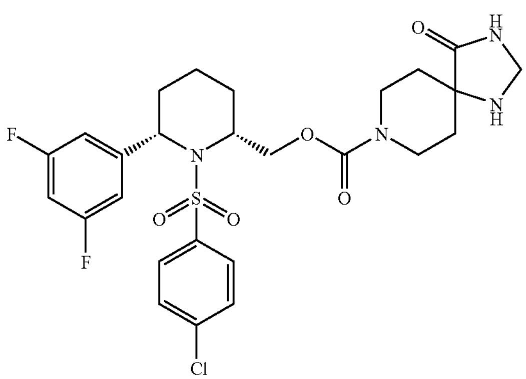 | 4.65 | 583.1 |
| 67-BK | 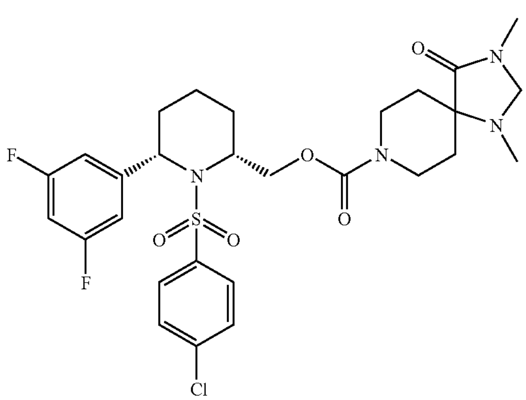 | 5.22 | 611.1 |

TABLE 5-A-continued

| Compound No. | Structure | Retention Time (minutes) | Observed Mass |
|---|---|---|---|
| 67-BL | 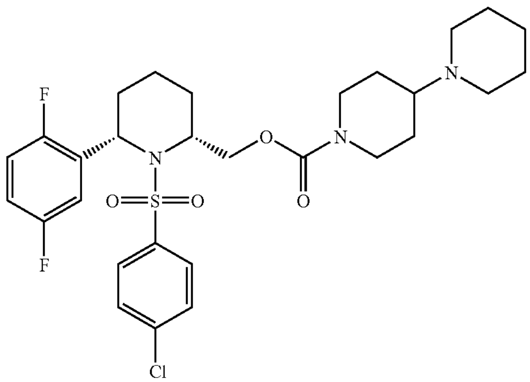 | 5.00 | 596.1 |
| 67-BM | 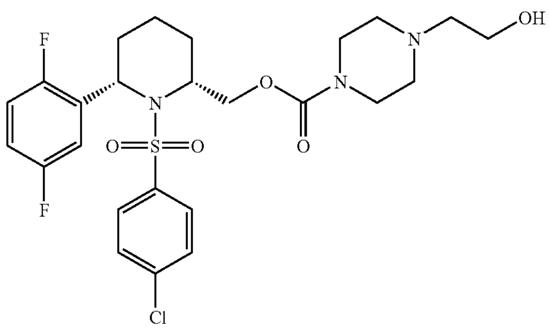 | 4.50 | 558.1 |
| 67-BN | 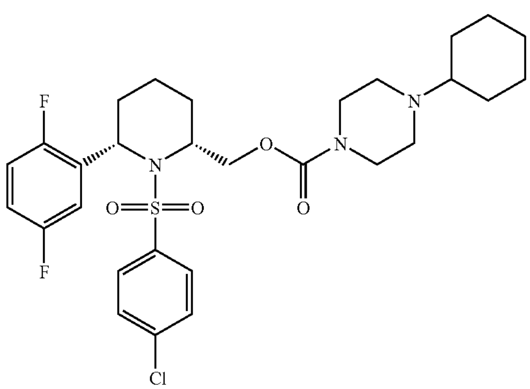 | 5.30 | 596.1 |
| 67-BO | 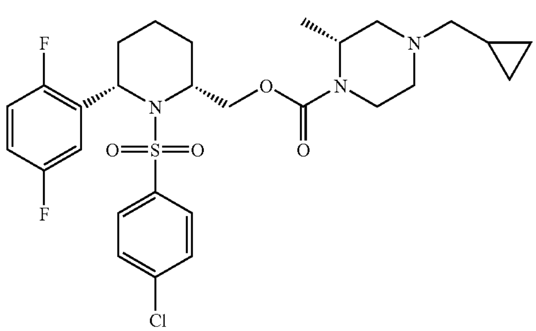 | 5.00 | 582.1 |

TABLE 5-A-continued

| Compound No. | Structure | Retention Time (minutes) | Observed Mass |
|---|---|---|---|
| 67-BP | 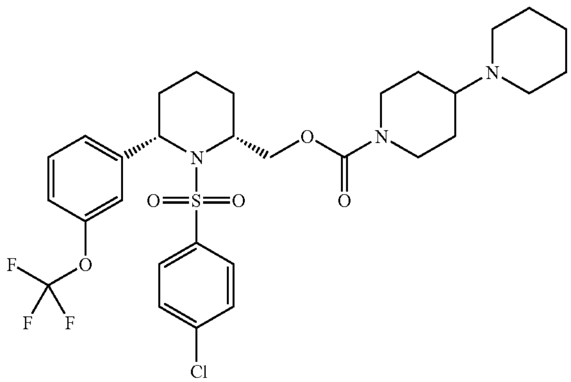 | 5.50 | 644.2 |
| 67-BQ | 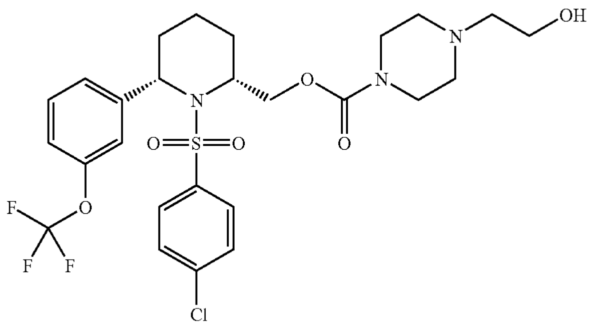 | 5.00 | 606.1 |
| 67-BR | 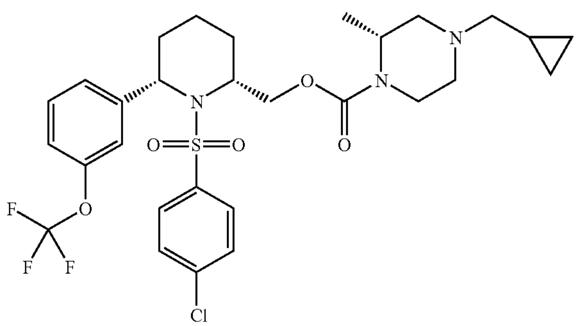 | 5.30 | 631.1 |
| 67-BS | 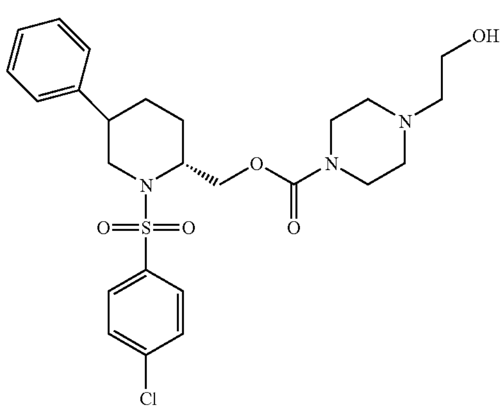 | 4.85 | 522.1 |

Example 68

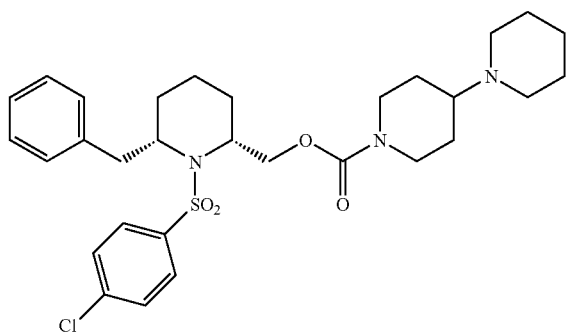

Step 1

(a) A solution of 1.00 g (4.29 mmol) of 2,6-dibromopyridine in a mixture of 20 mL of ether and 20 mL of THF was cooled to −78° C. (the solution became turbid due to partial precipitation). To this was added drop-wise 1.86 mL (4.29 mmol) of 2.3 M BuLi, and the reaction mixture was stirred for 5 min.

(b) Benzaldehyde (456 mg, 4.3 mmol) was added dropwise to the above mixture, and the reaction mixture was stirred in the cold for 15 min, quenched with saturated NaHCO$_3$, extracted with ethyl acetate, dried, and concentrated. The residue was purified by chromatography using a gradient of 10–30% of ethyl acetate in hexane as the eluent, to give 0.85 g of oily product.

(c) A mixture of the above product, 5 ml of triethylsilane, 5 mL of TFA and 5 mL of DCM was heated at reflux over a period of 36 h. After evaporating most of the volatiles, the residue was redissolved in DCM, washed with 1M NaOH, dried, concentrated, and purified by chromatography using 5% ethyl acetate in hexanes, to yield 0.55 g of the product.

Step 2

The product of step 1 was converted to the target compound using the conditions described in Example 53, Preparations A and C. $^1$H NMR (CDCl$_3$ 300 MHz) δ 7.75 (2H, d, J=8.8 Hz), 7.44 (2H, d, J=8.8 Hz), 7.33–7.19 (5H, ser.m.), 4.42–4.22 (4H, ser.m.), 4.14 (1H, m), 3.98 (1H, m), 3.09 (1H, dd, J=12.0, 2.7 Hz), 2.90 (1H, t, J=12.0 Hz), 2.78 (2H, br), 2.51–2.37 (5H, ser.m.), 1.84–1.27 (16H, ser.m.); MS (ES) m/e 574.1 (M+H)$^+$.

Following procedures similar to Example 68, the compounds in Table 6 were prepared.

TABLE 6

| Ex No. | COMPOUND | Mass Spec |
|---|---|---|
| 69 | 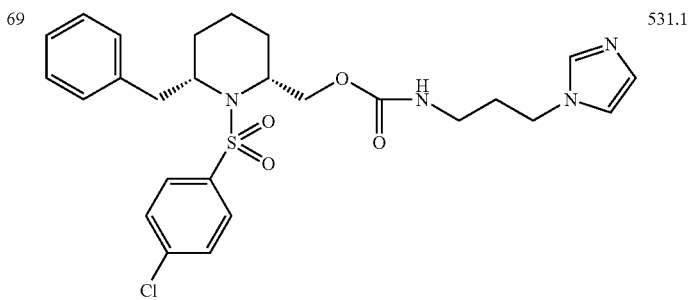 | 531.1 |
| 71 | 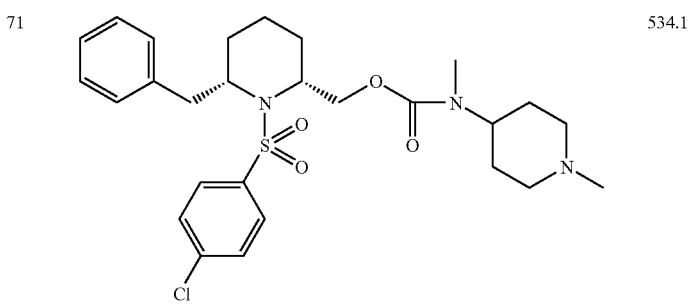 | 534.1 |

TABLE 6-continued

| Ex No. | COMPOUND | Mass Spec |
|---|---|---|
| 72 | (structure) | 522.1 |
| 73 | (structure) | 534.1 |
| 74 | (structure) | 574.1 |

Also prepared were the following compounds:

TABLE 6-A

| EXAMPLE NO. | STRUCTURE | RETENTION TIME (minutes) | OBSERVED MASS |
|---|---|---|---|
| 74-A | (structure) | 5.35 | 574.3 |

TABLE 6-A-continued

| EXAMPLE NO. | STRUCTURE | RETENTION TIME (minutes) | OBSERVED MASS |
|---|---|---|---|
| 74-B | 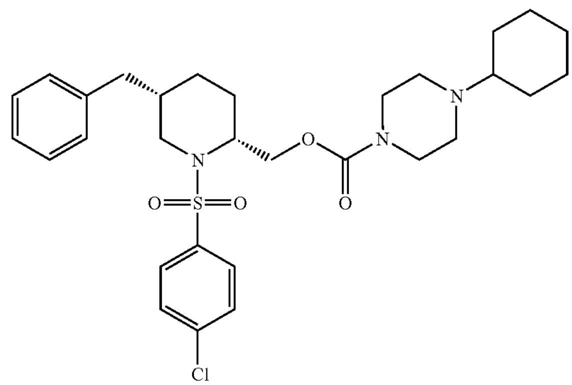 | 5.38 | 574.3 |
| 74-C | 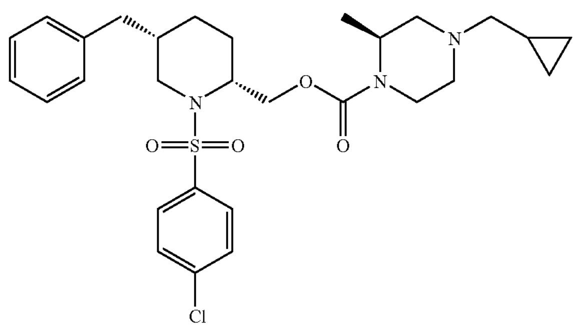 | 5.05 | 560.3 |

Example 75

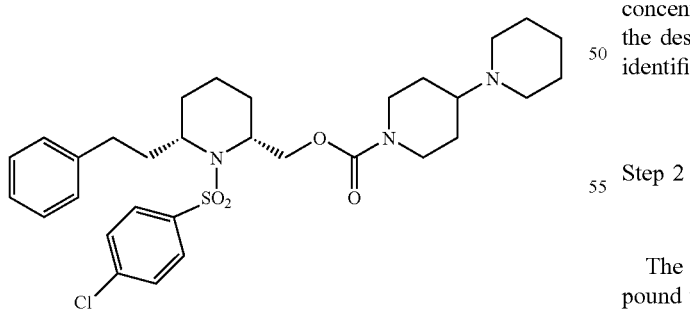

Step 1

To a solution of 5.0 g (21.4 mmol) of 2,6-dibromopyridine in 50.0 mL of DCM was added 5.6 mL (40 mmol) of triethylamine, 701 mg (1 mmol) of Pd(PPh$_3$)$_4$Cl$_2$, 95 mg (0.5 mmol) of CuI, and a mixture of phenylacetylene in 20.0 mL of DCM. The dark mixture was stirred overnight, washed with concentrated ammonium hydroxide, dried, concentrated, and chromatographed. Fractions containing the desired product of mono-substitution of bromine were identified by MS (m/z=258.1), yield 2.41 g.

Step 2

The product of step 1 was converted to the target compound using conditions described in Example 53, Preparations A and C. $^1$H NMR (CDCl$_3$ 300 MHz) δ 7.73 (2H, d, J=8.8 Hz), 7.45 (2H, d, J=8.8 Hz), 7.31–7.16 (5H, ser.m.), 4.30 (4H, m), 4.13 (1H, m), 3.97 (1H, m), 2.73 (4H, m), 2.42 (5H, m), 2.04 (1H, m), 1.78–1.15 (17H, ser.m.); MS (ES) m/e 588.1 (M+H)$^+$.

Following procedures similar to those of Example 75 the compounds in Table 7 were prepared.

TABLE 7

| EX No. | COMPOUND | Mass Spec |
|---|---|---|
| 76 | | 545.1 |
| 78 | | 548.1 |
| 79 | | 536.1 |
| 80 | | 548.1 |

TABLE 7-continued

| EX No. | COMPOUND | Mass Spec |
|---|---|---|
| 81 | | 588.1 |

Example 82

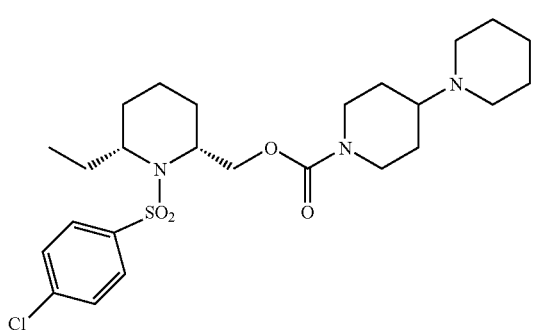

Step 1

To a solution of 5.0 g (21.2 mmol) of 2,6-dibromopyridine in THF at −78° C. was added 9.2 mL (21 mmol) of 2.3 M solution of n-BuLi in hexanes, followed by 2.3 mL (30 mmol) of DMF. The mixture was stirred for 45 min in the cold, quenched with saturated $NaHCO_3$, extracted with ethyl acetate and the product purified by column chromatography (3% ethyl acetate in hexanes) to furnish 1.13 g of 2-bromo-6-formylpyridine.

Step 2

(a) A mixture containing 750 mg (4.05 mmol) of product of step 1, 1.41 g (4.46 mmol) of vinyltributyltin, 231 mg (0.2 mmol) of $Pd(PPh_3)_4$, and 5.0 mL of DMF was heated for 12 h at 90° C. The volatiles were evaporated, and the residue purified by chromatography (3–5% ethyl acetate in hexanes) to furnish 360 mg of 2-formyl-6-vilylpyridine.

(b) The above product was hydrogenated at 50 psi over catalytic $PtO_2$ using 1:3 mixture of AcOH and MeOH as solvent to furnish 87 mg of reduced product.

Step 3

The product of step 2 was converted to the target compound using conditions described in Example 53, Preparations C. $^1H$ NMR (CDCl3 300 MHz) δ 7.77 (2H, d, J=8 Hz), 7.47 (2H, d, J=8 Hz), 4.29–4.22 (4H, ser.m.), 4.05 (1H, m), 3.79 (1H, m), 2.77 (2H, br), 2.50–2.37 (5H, ser.m.), 1.83–1.70 (6H, ser.m.), 1.62–1.10 (12H, ser.m.), 0.96 (3H, t, J=7.3 Hz); MS (ES) m/e 512.1 (M+H)+.

Following procedures similar to those of Example 82 the compounds in Table 8 were prepared.

TABLE 8

| EX No. | COMPOUND | Mass Spec |
|---|---|---|
| 83 | | 469.1 |
| 85 | | 472.1 |
| 86 | | 472.1 |

TABLE 8-continued

| EX No. | COMPOUND | Mass Spec |
|---|---|---|
| 87 | | 512.1 |

Example 88

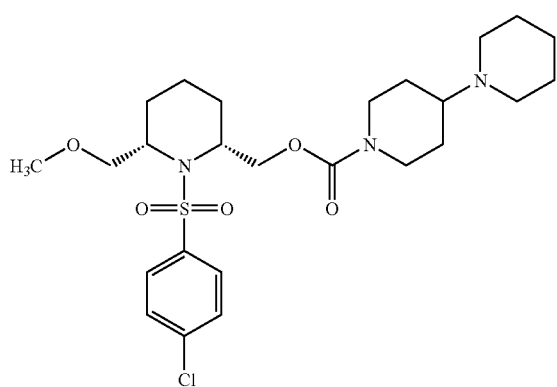

Step 1
To a solution of 2,6-pyridinedicarboxylate methyl ester (19.52 g; 100 mmol) in ice-cooled anhydrous methanol (300 ml) was added sodium borohydride (3.03 g; 80 mmol) portion-wise, then the reaction mixture was stirred 30 min at room temperature. Another 1.0 g of sodium borohydride was added to the mixture and the reaction mixture was stirred an additional 30 minutes. After concentration, the crude product was diluted with water and $CH_2Cl_2$ and extracted with $CH_2Cl_2$. The combined organic layers were dried over $Na_2SO_4$, concentrated, and the residue was subjected to flash-chromatography over silica gel (eluting with $CH_2Cl_2$/MeOH 95:5) to give 11.09 g (66%) of alcohol, as a white solid.

Step 2
To a solution of alcohol (9.00 g; 53.8 mmol) in anhydrous THF (200 mL) at 0° C. was added NaH 60% in mineral oil (2.60 g; 64.6 mmol) followed by dimethylsulfate (6.60 ml; 70 mmol) and the reaction mixture was stirred 2 h at 35° C. After concentration, the crude product was diluted with water and extracted with $CH_2Cl_2$. The combined organic layers were dried over $Na_2SO_4$, concentrated, and the residue was subjected to flash-chromatography over silica gel (eluting with $CH_2Cl_2$/MeOH 95:5). The purified product was dissolved in $CH_2Cl_2$/MeOH, treated with an excess of 1 N HCl in Et2O and concentrated to provide 11.5 g (98%) of pyridine intermediate, as a hydrochloride salt.

Step 3
A mixture of pyridine intermediate (11.50 g; 52.8 mmol) and platinum (IV) oxide (1 g) in ethanol was hydrogenated 16 h at 40 psi, filtered over CELITE and concentrated to provide 11.60 g of crude piperidine amine, as a white solid.

Step 4
To a suspension of piperidine amine (11.60 g; 52.1 mmol) in anhydrous THF (50 ml) at 0° C. was slowly added lithium aluminum hydride 1 N in THF (200 ml; 200 mmol), then the reaction mixture was allowed to warm to room temperature and was stirred an additional 1 h. The reaction mixture was quenched with an excess of AcOEt, diluted with 0.5 N aqueous NaOH solution, and extracted with AcOEt and $CH_2Cl_2$. The combined organic layers were dried over $Na_2SO_4$ and concentrated to provide 8.3 g of crude piperidine alcohol, as an oil.

Step 5
A solution of piperidine alcohol (8.3 g; 52.1 mmol), tert-butyldimethylsilyl chloride (8.6 g; 57.3 mmol) and triethylamine (8.7 ml; 62.5 mmol) in anhydrous 1,2-dichloroethane (100 ml) was stirred 16 h at 60° C. The reaction mixture was diluted with 0.5 N aqueous NaOH solution and extracted with $CH_2Cl_2$. The combined organic layers were dried over $Na_2SO_4$, concentrated, and the residue was subjected to flash-chromatography over silica gel (eluting with $CH_2Cl_2$/AcOEt 95:5 to 70:30) to provide 5.0 g (35%) of O-protected piperidine, as an oil.

Step 6
A solution of O-protected piperidine (2.50 g; 9.14 mmol), 4-chlorobenzenesulfonyl chloride (2.90 g; 13.7 mmol) and triethylamine (1.53 ml; 11 mmol) in anhydrous 1,2-dichloroethane (25 ml) was stirred 3 h at 60° C. then overnight at room temperature. The reaction mixture was diluted with a 0.5 N aqueous NaOH solution and extracted with $CH_2Cl_2$. The combined organic layers were dried over $Na_2SO_4$, concentrated, and the residue was subjected to flash-chromatography over silica gel (eluting with $CH_2Cl_2$) to provide 3.72 g (90%) of O-protected sulfonamide, as an oil.

Step 7
To a solution of O-protected sulfonamide (3.70 g; 8.3 mmol) in anhydrous THF (50 ml) was added TBAF 1 N in THF (16.6 ml; 16.6 mmol) and the reaction mixture was stirred overnight at room temperature. After concentration, the crude product was diluted with a 5% $NaHCO_3$ aqueous solution and extracted with $CH_2Cl_2$. The combined organic layers were dried over $Na_2SO_4$, concentrated, and the residue was subjected to flash-chromatography over silica gel (eluting with $CH_2Cl_2$) to give 2.50 g (93%) of sulfonamide alcohol, as an oil: $^1$H-NMR (300 MHz, $CDCl_3$) δ 7.79 (d, J=8.8 Hz, 2H), 7.47 (d, J=8.8 Hz, 2H), 4.24 (m, 1H), 4.09 (m, 1H), 3.40–3.70 (m, 4H), 3.37 (s, 3H), 1.40–1.70 (m, 3H), 1.20–1.40 (m, 3H); HRMS (MH+) 334.0883.

Step 8
To a solution of sulfonamide alcohol (2.50 g; 7.50 mmol) and p-nitrophenyl chloroformate (1.70 g; 8.25 mmol) in anhydrous THF (30 ml) was slowly added triethylamine (1.20 ml; 8.25 mmol) and the reaction was stirred overnight at room temperature. After concentration, the residue was subjected to flash-chromatography over silica gel (eluting with hexanes/AcOEt 90:10) to give 3.70 g (99%) of sulfonamide p-nitrophenylcarbonate, as a foam.

Step 9
A solution of sulfonamide p-nitrophenylcarbonate (50 mg; 0.10 mmol) and 4-piperidinopiperidine (84 mg; 0.50 mmol) in 1,2-dichloroethane (1 ml) was stirred overnight at room temperature. The reaction mixture was diluted with 0.5 N aqueous NaOH solution and $CH_2Cl_2$ and the organic layer was directly subjected to preparative chromatography over silica gel (eluting with $CH_2Cl_2$) then treated with dry 1 N HCl in $Et_2O$ to provide 7 mg of product: $^1$H-NMR (300 MHz, $CDCl_3$) δ 7.76 (d, J=8.8 Hz, 2H), 7.46 (d, J=8.8 Hz, 2H), 4.15–4.35 (m, 4H), 3.85–4.00 (m, 2H), 3.40–3.55 (m, 3H), 3.34 (s, 3H), 2.65–2.90 (m, 2H), 2.10–2.60 (m, 6H), 1.80–1.90 (br d, 2H), 1.00–1.80 (m, 12H); HRMS (MH$^+$) 528.2305.

Following the procedures similar to those in Example 88, the compounds in Table 9 were prepared.

TABLE 9

| EX No. | COMPOUND | High Res. Mass Spec |
|---|---|---|
| 89 | | 476.1985 |
| 90 | | 490.1776 |
| 91 | | 485.1630 |
| 92 | | 523.1792 |

TABLE 9-continued

| EX No. | COMPOUND | High Res. Mass Spec |
|---|---|---|
| 93 | | 460.1440 |
| 94 | | 462.1656 |
| 95 | | 488.1989 |
| 96 | | 528.2304 |

TABLE 9-continued

| EX No. | COMPOUND | High Res. Mass Spec |
|---|---|---|
| 97 | (structure) | 431.1413 |
| 98 | (structure) | 475.1661 |
| 99 | (structure) | 445.1568 |
| 101 | (structure) | 496.1679 |

TABLE 9-continued
| EX No. | COMPOUND | High Res. Mass Spec |
|---|---|---|
| 102 | 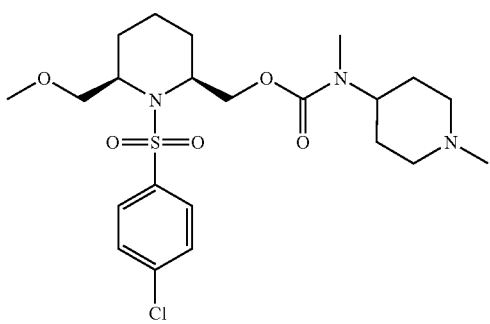 | 488.1986 |
| 103 | 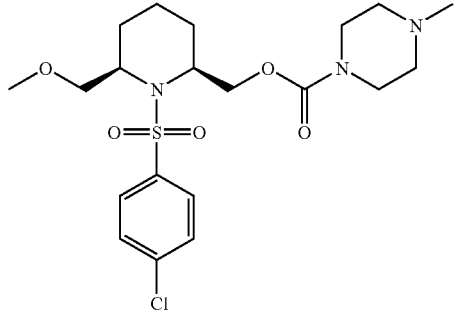 | 460.1677 |
| 104 | 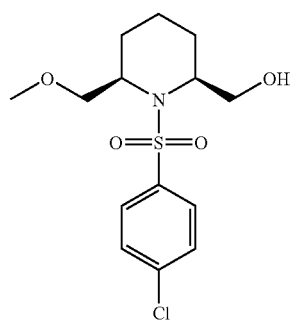 | 334.0883 |

NMR data for compounds in Table 9 are given in Table 10.

TABLE 10

| EX No. | COMPOUND | NMR (δ) |
|---|---|---|
| 92 | | 8.19 (d, J=3.9 Hz, 1H), 7.77 (d, J=8.8 Hz, 2H), 7.40–7.55 (m, 3H), 6.60–6.75 (m, 2H), 4.20–4.35 (m, 2H), 3.95–4.05 (m, 2H), 3.40–3.75 (m, 10H), 3.35 (s, 3H), 1.50–1.80 (m, 3H), 1.05–1.40 (m, 3H) |
| 94 | | 7.78 (d, J=8.8 Hz, 2H), 7.46 (d, J=8.8 Hz, 2H), 4.15–4.35 (m, 2H), 3.90–4.05 (m, 2H), 3.35–3.60 (m, 4H), 3.35 (s, 3H), 2.96 (s, 3H), 2.45–2.60 (m, 2H), 2.31 (s, 3H), 2.28 (s, 3H), 1.45–1.80 (m, 3H), 1.20–1.40 (m, 2H), 1.13 (m, 1H) |
| 96 | | 7.76 (d, J=8.8 Hz, 2H), 7.46 (d, J=8.8 Hz, 2H), 4.15–4.35 (m, 2H), 3.90–4.00 (m, 2H), 3.40–3.60 (m, 6H), 3.34 (s, 3H), 2.45–2.65 (m, 4H), 2.29 (m, 1H), 1.45–1.90 (m, 6H), 1.00–1.40 (m, 10H) |
| 100 | | 7.76 (d, J=8.8 Hz, 2H), 7.46 (d, J=8.8 Hz, 2H), 4.15–4.35 (m, 4H), 3.85–4.00 (m, 2H), 3.40–3.55 (m, 3H), 3.34 (s, 3H), 2.65–2.90 (m, 2H), 2.10–2.60 (m, 6H), 1.80–1.90 (br d, 2H), 1.00–1.80 (m, 12H) |

TABLE 10-continued

| EX No. | COMPOUND | NMR (δ) |
|---|---|---|
| 104 | (structure) | 7.79 (d, J=8.8 Hz, 2H), 7.47 (d, J=8.8 Hz, 2H), 4.24 (m, 1H), 4.09 (m, 1H), 3.40–3.70 (m, 4H), 3.37 (s, 3H), 1.40–1.70 (m, 3H), 1.20–1.40 (m, 3H) |

Example 105

Preparation A

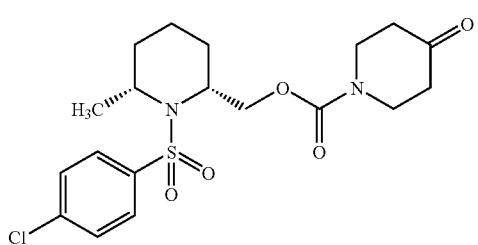

Step 1

A solution of the 4-nitrophenylcarbonate product of Example 1, step 4-a (1.26 g) in methanol (50 mL) was treated with 1,4-dioxa-8-azaspiro[4.5]decane (0.76 mL) and the resulting mixture was stirred at room temperature for 66 h. The reaction mixture was concentrated under vacuum and the residue was partitioned between ethyl acetate/10% sodium hydroxide solution. The ethyl acetate (EtOAc) solution was extracted with water and then brine. The dried (MgSO$_4$) EtOAc solution was concentrated under vacuum to give a pale yellow oil (1.26 g). The oil was purified by chromatography on silica gel plates (8, 1000μ) using EtOAc:hexane 1:3 as the eluent (two elutions) to give the title compound, as a colorless oil (1.11 g).

Step 2

To the product of step 1 (1.10 g) in dichloromethane (20 mL), 40% trifluoroacetic acid (TFA) in water (8 mL) was added, and the resulting mixture was stirred for 4 hr. An additional portion of 40% TFA in water (6 mL) was then added. After 2 h, a third portion of 40% TFA in water (3 ml) was added. The resulting mixture was stirred at room temperature for 18 hr. The reaction mixture was then separated and the dichloromethane washed with water and then sodium bicarbonate solution. The dried (MgSO$_4$) dichloromethane solution was concentrated under vacuum to give a colorless foam. The foam was purified by chromatography on silica gel plates (8, 1000μ) using EtOAc:hexane (1:3) as the eluent to give the title compound (0.80 g).

Preparation B (structure)

Step 1

The 4-nitrophenylcarbonate product of Example 1, step 4-a (0.100 g) in methanol (55 mL) was treated with 3-hydroxypiperidine (0.060 g, liberated from the hydrochloride salt) and the resulting mixture was stirred at room temperature for 24 h. The reaction mixture was concentrated under vacuum and the residue was partitioned between an ethyl acetate/10% sodium hydroxide solution. The ethyl acetate (EtOAc) solution was extracted with water, and then brine. The dried (MgSO$_4$) EtOAc solution was concentrated under vacuum to give the title compound, as a colorless oil (0.10 g).

Step 2

The product from step 1 in acetone (5 mL) was treated with Jones Reagent (0.40 mL) for 40 min at room temperature. The reaction mixture was quenched with MeOH (2 mL), filtered, and diluted with dichloromethane. The organic mixture was extracted with brine. The dried (MgSO$_4$) solution was concentrated under vacuum to give a residue (0.070 g). This residue was purified by chromatography on silica gel plates (1, 1000μ) using EtOAc:hexane 1:3 as the eluent to give the title compound (0.040 g).

Preparation C

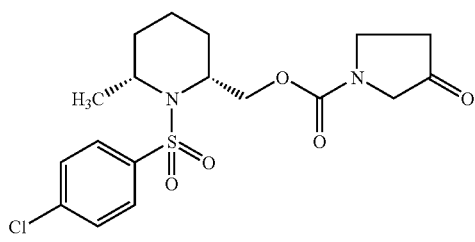

Essentially the same procedure as in Preparation B where followed, except that 3-hydroxypyrrolidine (0.060 g) was used to give the title compound (0.030 g).

Preparation D

Following the procedure described below, the compounds in Table 11 were prepared from the appropriate ketones and amines. The ketones and amines used would be apparent to those skilled in the art from the structure of the compounds in Table 11.

Using BOHDAN Miniblocks (6 mL cartridge), ketones from Preparation A, B or C (0.010 g) in MeOH:AcOH 9:1 (1 mL) were dispensed. Amines (1.2 equiv) were then added, followed by MP-cyanoborohydride resin (~2 equiv, 20 to 30 mg, 2.37 mmol/g, Argonaut). The resulting mixture was shaken at room temperature for 20 hr. PS-isocyanate resin (50–60 mg, 4 equiv. 1.44 mmol/1 g, Argonaut) was then added. After 4 h, additional PS-isocyanate resin (90–100 mg) was added, and the mixture was shaken overnight. The mixture was filtered from BOHDAN block to block and the residue was washed with MeOH (1 mL). MP-TsOH resin (~4 equiv., 1.46 mmol/mg, Argonaut) was added to the filtrate followed by dichloroethane (1 mL), and the mixture was shaken for 2–4 hr. The mixture was then drained and washed with MeOH (1 mL, 3 times). 2M NH$_3$/MeOH (1.5 mL) was added, and the mixture was shaken for 30 min, then drained into vials. 2M NH$_3$/MeOH (2 mL) was added and the mixture was shaken for 10 min. and drained. The solvent was then removed to give the products in Table 11.

TABLE 11

| EX No. | COMPOUND | Mass Spec |
|---|---|---|
| 106 | | 498 |
| 107 | | 500 |

TABLE 11-continued

| EX No. | COMPOUND | Mass Spec |
|---|---|---|
| 108 | (structure) | 500 |
| 109 | (structure) | 512 |
| 110 | (structure) | 513 |

TABLE 11-continued

| EX No. | COMPOUND | Mass Spec |
|---|---|---|
| 111 | | 514 |
| 112 | | 516 |
| 113 | | 526 |

TABLE 11-continued

| EX No. | COMPOUND | Mass Spec |
|---|---|---|
| 114 | | 527 |
| 115 | | 541 |
| 116 | | 546 |

TABLE 11-continued

| EX No. | COMPOUND | Mass Spec |
|---|---|---|
| 117 | | 552 |
| 118 | | 581 |
| 119 | | 527 |
| 120 | | 541 |

TABLE 11-continued
| EX No. | COMPOUND | Mass Spec |
|---|---|---|
| 121 | 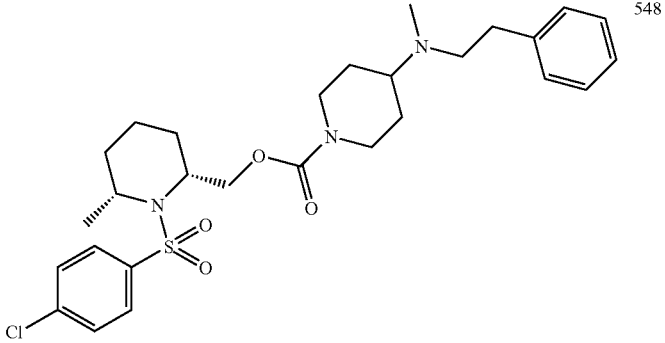 | 548 |
| 122 | 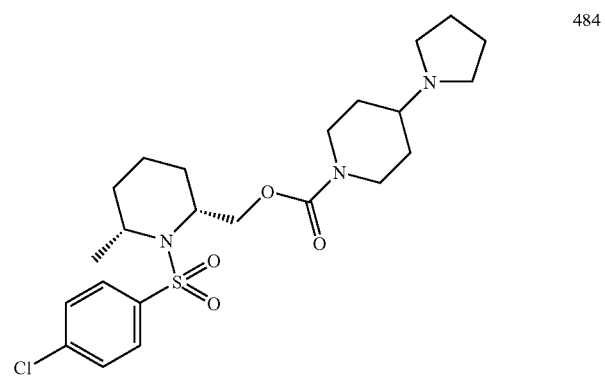 | 484 |
| 123 | 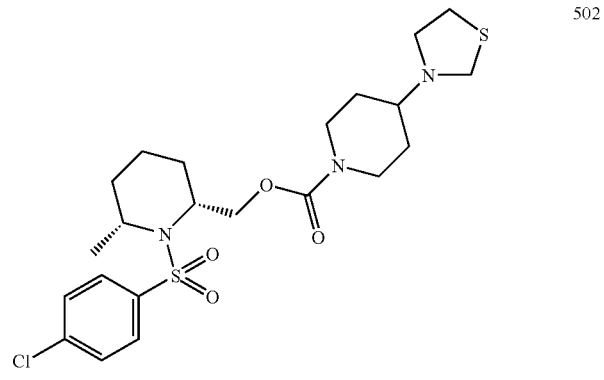 | 502 |
| 124 | 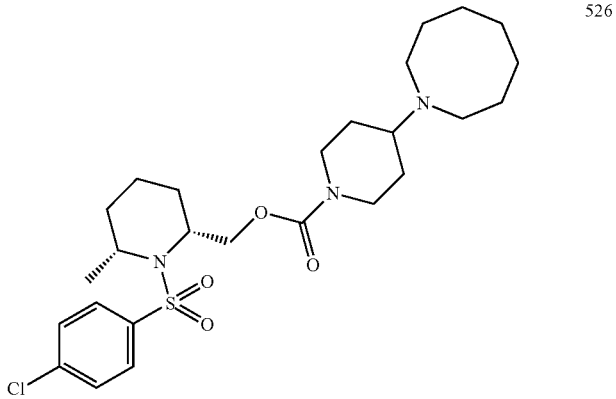 | 526 |

TABLE 11-continued

| EX No. | COMPOUND | Mass Spec |
|---|---|---|
| 125 | | 527 |
| 126 | | 585 |
| 127 | | 576 |

TABLE 11-continued
| EX No. | COMPOUND | Mass Spec |
|---|---|---|
| 128 | 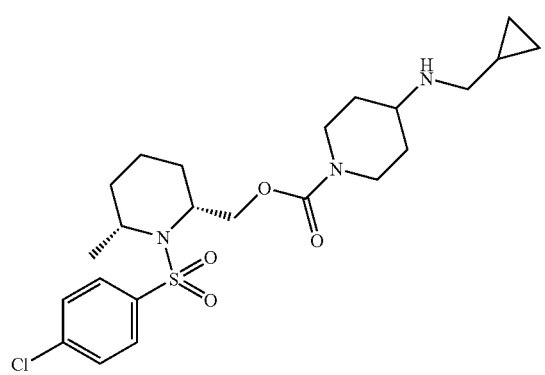 | 484 |
| 129 | 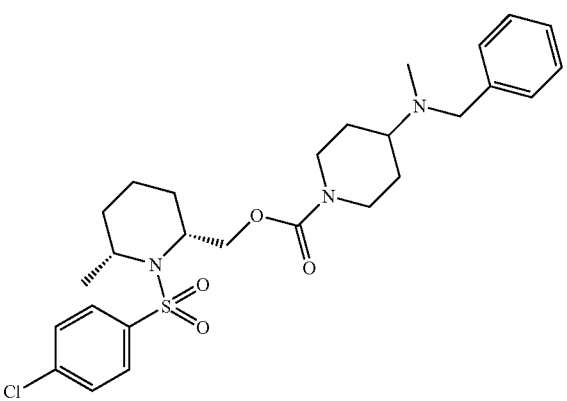 | 534 |
| 130 | 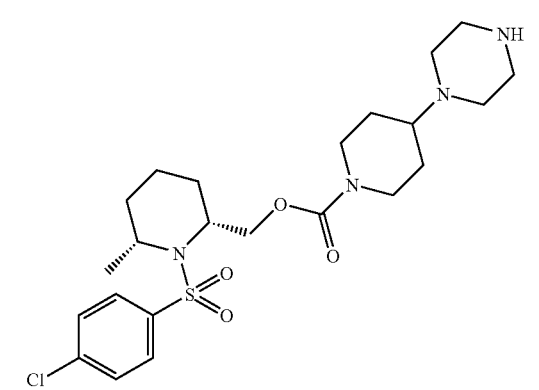 | 498 |
| 131 | 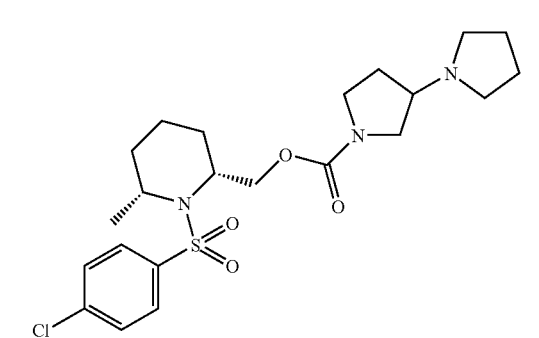 | 470 |

TABLE 11-continued
| EX No. | COMPOUND | Mass Spec |
|---|---|---|
| 132 | 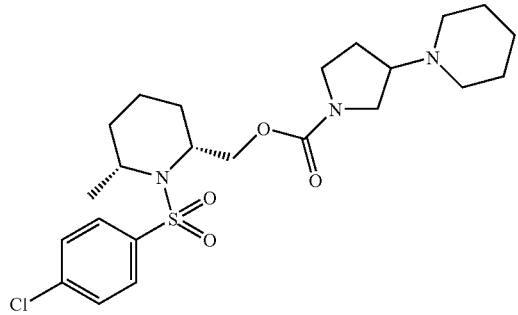 | 484 |
| 133 | 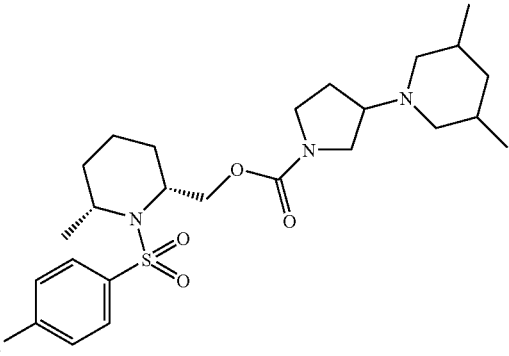 | 512 |
| 134 | 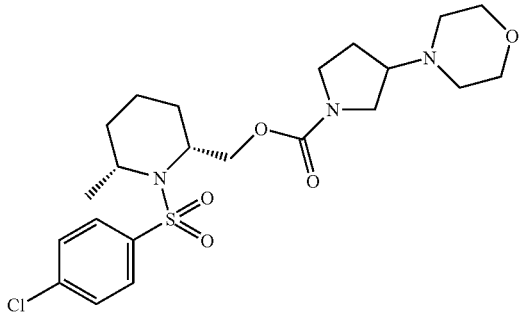 | 486 |
| 135 | 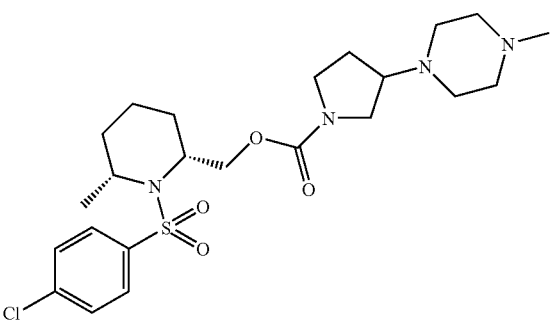 | 499 |

TABLE 11-continued

| EX No. | COMPOUND | Mass Spec |
|---|---|---|
| 136 | | 500 |
| 137 | | 532 |
| 138 | | 498 |
| 139 | | 512 |

TABLE 11-continued

| EX No. | COMPOUND | Mass Spec |
|---|---|---|
| 140 | | 464 |
| 141 | | 526 |
| 142 | | 500 |
| 143 | | 513 |

TABLE 11-continued
| EX No. | COMPOUND | Mass Spec |
|---|---|---|
| 144 | 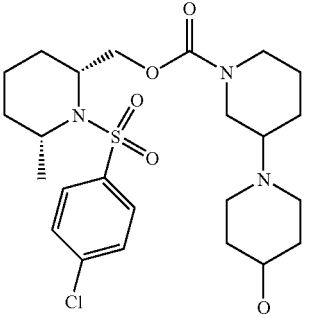 | 514 |
| 145 | 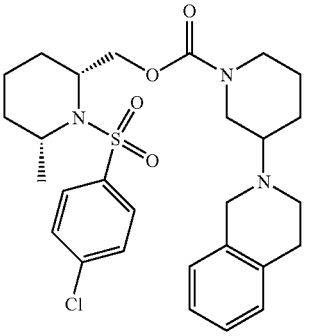 | 546 |
| 146 | 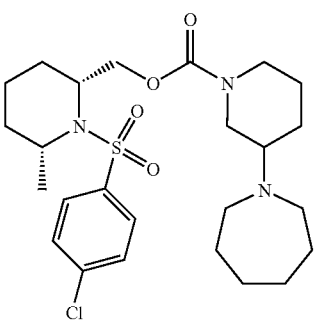 | 512 |
| 147 | 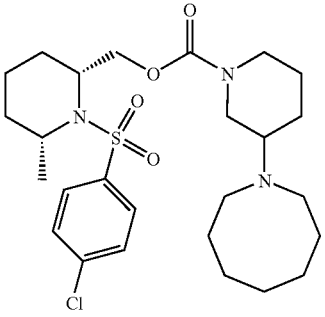 | 526 |

TABLE 11-continued
| EX No. | COMPOUND | Mass Spec |
|---|---|---|
| 148 | 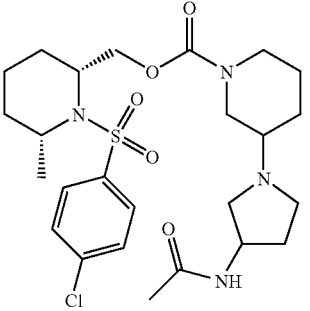 | 541 |
| 149 | 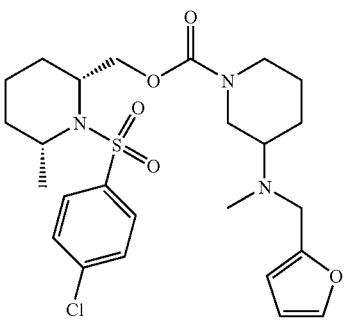 | 524 |
| 150 | 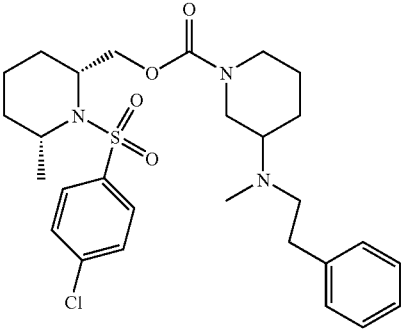 | 548 |
| 151 | 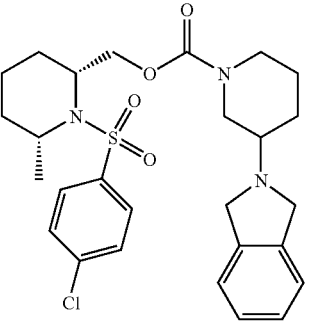 | 532 |

TABLE 11-continued
| EX No. | COMPOUND | Mass Spec |
|---|---|---|
| 152 | 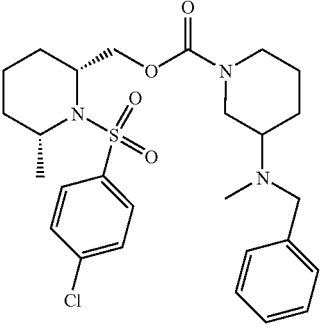 | 534 |
| 153 | 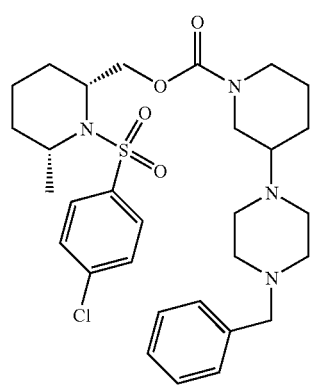 | 589 |
| 154 | 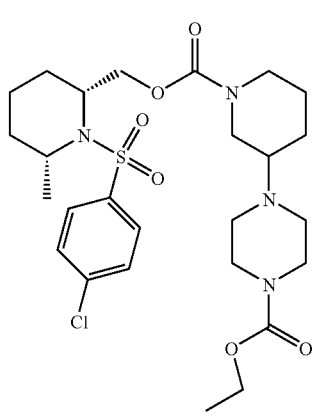 | 571 |
| 155 | 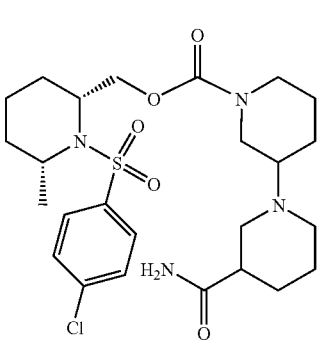 | 541 |

TABLE 11-continued

| EX No. | COMPOUND | Mass Spec |
|---|---|---|
| 156 | | 556 |
| 157 | | 541 |
| 158 | | 541 |

Example 159

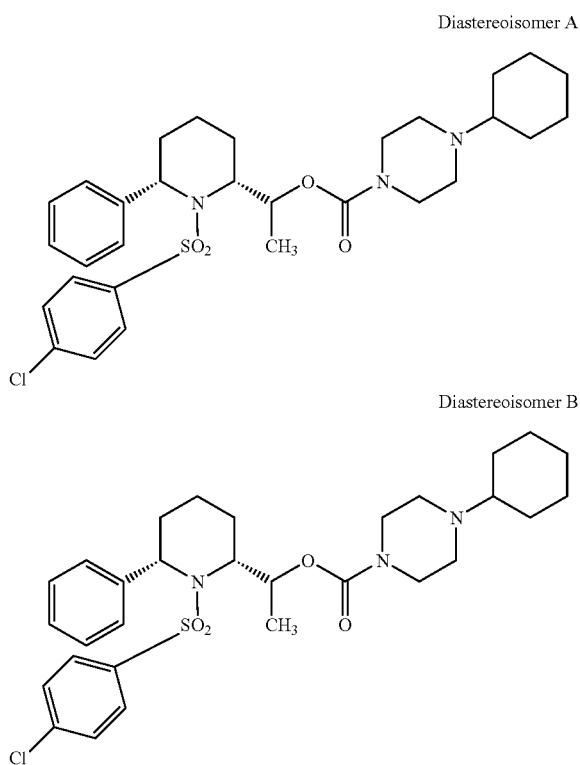

Diastereoisomer A

Diastereoisomer B

Step 1

To a solution of the 1-(4-chloro-benzenesulfonyl)-6-phenyl-piperidin-2-yl-methanol prepared according to Example 53 Preparation C Step 1 (300 mg; 0.82 mmol) in DCM (8 ml) was added Dess-Martin periodinane (850 mg; 2.0 mmol) followed by sodium bicarbonate (100 mg) and two drops of water. The mixture was stirred overnight at room temperature, then quenched with $Et_2O$ (20 mL), saturated $NaHCO_3$ and sodium thiosulfite (2.0 g) for 20 minutes. The reaction was extracted with $Et_2O$, dried over $Na_2SO_4$ and concentrated to provide 232 mg (78%) of 1-(4-chloro-benzenesulfonyl)-6-phenyl-piperidine-2-carbaldehyde as an oil.

Step 2

To a solution of the product of step 1 (232 mg; 0.64 mmol) in THF (6 mL) at 0° C. was added methyl magnesium bromide solution 3 N in $Et_2O$ (0.27 mL; 0.83 mmol) and the reaction was allowed to warm to room temperature for 1 h. The mixture was poured into saturated ammonium chloride, extracted with DCM, and dried over $Na_2SO_4$. After concentration of the solvents, the residue was purified by chromatography over silica gel (eluting Hexanes/EtOAc 8:2) to give 240 mg (100%) of 1-[1-(4-chloro-benzenesulfonyl)-6-phenyl-piperidin-2-yl]-ethanol as a ca 4.5:1 mixture of diastereoisomers.

Step 3

The product of Step 2 was converted to the title compounds according to Step 4 of Example 1, using N-cyclohexylpiperazine at the last stage as the amine. The diastereoisomers were separated at the last stage by chromatography on silica gel (eluting Hexanes/EtOAc 8:2) to provide, in order of elution:

(i) Diastereoisomer A: $^1$H-NMR (300 MHz, $CDCl_3$) δ 7.86 (d, J=6.0 Hz, 2H), 7.60 (d, J=6.0 Hz, 2H), 7.53 (d, J=6.0 Hz, 2H), 7.30–7.45 (m, 2H), 7.20–7.30 (m, 1H), 5.25 (d, J=4.5 Hz, 2H), 4.35–4.50 (m, 1H), 3.90–4.00 (m, 1H), 3.20–3.50 (m, 4H), 2.15–2.60 (m, 5H), 1.70–2.05 (m, 5H), 1.50–1.65 (m, 2H), 1.00–1.45 (m, 9H), 0.99 (d, J=4.5 Hz, 2H); HRMS ($MH^+$) 574.2500.

(ii) Diastereoisomer B: $^1$H-NMR (300 MHz, $CDCl_3$) δ 7.84 (d, J=6.0 Hz, 2H), 7.45–7.60 (m, 4H), 7.25–7.40 (m, 3H), 5.23 (m, 1H), 4.30–4.45 (m, 1H), 4.05–4.20 (m, 1H), 3.30–3.70 (m, 4H), 2.20–2.70 (m, 5H), 1.75–2.00 (m, 5H), 1.05–1.70 (m, 14H); HRMS ($MH^+$) 574.2512.

Some compounds prepared are shown below:

TABLE 12

| Compound No. | Structure | Retention Time (minutes) | Observed Mass |
| --- | --- | --- | --- |
| 159-A | 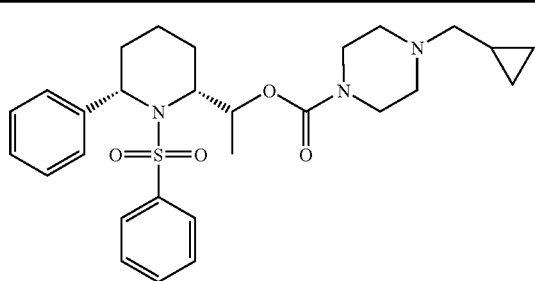 isomer A | 5.10 | 546.1 |

TABLE 12-continued

| Compound No. | Structure | Retention Time (minutes) | Observed Mass |
|---|---|---|---|
| 159-B | 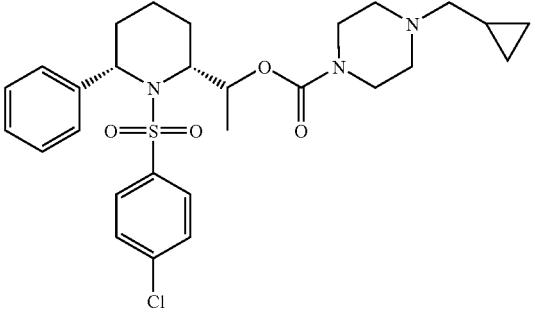<br>isomer B | 5.10 | 546.1 |

Preparations P-1 to P-4 describe the preparation of intermediates used in several procedures.

Preparation P-1: Preparation of 4-[1-(4,4-ethylenedioxypiperidino)]piperidine Step 1:

A solution of 1-tert-butoxycarbonyl-4-piperidone (3.98 g, 20 mmol), 4-piperidoneethyleneketal (3.15 g, 22 mmol), sodium triacetoxyborohydride (4.66 g, 22 mmol), sodium sulfate (15 g) and acetic acid (300 µL) in DCE (15 mL) was stirred 2 days at RT. The solution was quenched with an excess of MeOH for 15 min then treated with diluted NaOH and extracted with DCM and AcOEt. The combined organic layers were dried over Na2SO4 and concentrated, and the crude was purified by flash-chromatography over silica gel (eluting DCM/AcOEt 7:3 to 1:1) to afford 4.72 g (72%) of 1-tert-butoxycarbonyl-4-[1-(4,4-ethylenedioxypiperidino)]piperidine.

Step 2:

To 1-tert-butoxycarbonyl-4-[1-(4,4-ethylenedioxy)piperidino]piperidine (200 mg, 061 mmol) in DCM (10 mL) was added TFA (1.5 mL), and the reaction was stirred 1 h 30. The reaction was treated with 1 N NaOH until pH>12 and extracted with DCM and AcOEt. The combined organic layers were dried over Na2SO4 and concentrated to provide 100 mg (75%) of 4-[1-(4,4-ethylenedioxypiperidino)]piperidine.

Preparation P-2: Preparation of 4-[1-(4-methoxyiminopiperidino)]piperidine:

Step 1:

To a solution of 4-piperidonemethoxime (150 mg, 1.17 mmol) in DCE (5 mL) was added 1-tert-butoxycarbonyl-4-piperidone (350 mg, 1.75 mmol) and the reaction was stirred 1 h at RT. Sodium triacetoxyborohydride (500 mg, 2.34 mmol) was added, followed by AcOH (20 µl), and the reaction was stirred 2 days at RT. The solution was quenched with an excess of MeOH for 15 min then treated with 5% NaHCO3 and extracted with DCM and AcOEt. The combined organic layers were dried over Na2SO4 and concentrated to provide 500 mg of crude 1-tert-butoxycarbonyl-4-[1-(4-methoxyiminopiperidino)]piperidine.

Step 2:

A solution of 1-tert-butoxycarbonyl-4-[1-(4-methoxyiminopiperidino)]piperidine (50 mg, 0.16 mmol) in DCM (2 mL) was treated with TFA (0.2 mL) and stirred at RT for 30 min. The reaction was concentrated, diluted with 1 N NaOH, and extracted with DCM and AcOEt. The combined organic layers were dried over Na2SO4 and concentrated to provide 50 mg (100%) of crude 4-[1-(4-methoxyiminopiperidino)]piperidine that could be used without purification in the next step.

Preparation P-3: Preparation of cis-3-methyl-4-(1-piperidino)piperidine

Step 1:

To a solution of 1-benzyl-3-methylpiperidone (5.0 g, 24.6 mmol) in DCE was added piperidine (2.6 ml, 27.06 mmol) followed by Ti(OiPr)4 (8.8 ml, 29.52 mmol). The reaction was stirred at RT for 8 h, NaBH3(CN) was added slowly and the mixture was then stirred 2 days at RT. The solution was quenched with an excess of MeOH for 15 min, treated with diluted NaOH, extracted with DCM and AcOEt, and the combined organic layers were dried over Na2SO4 and concentrated. Purification of a sample by flash-chromatography over silica gel (eluting hexanes/AcOEt 9:1 to 1:1) afforded 1.7 g of cis-1-benzyl-3-methyl-4-(1-piperidino)piperidine.

Step 2:

A solution of cis-1-benzyl-3-methyl-4-(1-piperidino)piperidine (1.7 g, 6.2 mmol), ammonium formate (6.3 g, 100 mmol) and palladium hydroxide on charcoal (1 g, 7.1 mmol) in MeOH (20 mL) was heated at reflux for 4 h. The final solution was filtered over CELITE, rinsing with MeOH then concentrated. The residue was diluted with saturated NaHCO3, extracted with DCM and AcOEt, and combined organic layers were dried over Na2SO4 and concentrated to give 580 mg (52%) of cis-3-methyl-4-(1-piperidino)piperidine.

183

Preparation P-4: Preparation of 2'-Methyl-[1,4']bipiperidine

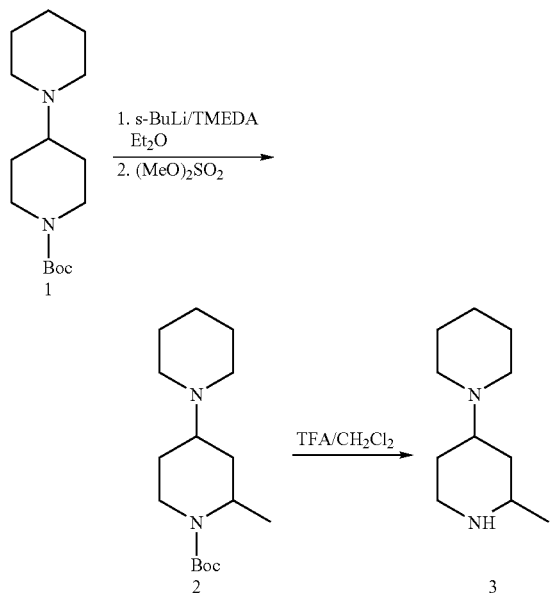

Compound 2: To a solution of 1'-tert-Butoxycarbonyl-[1, 4']-Bipiperidine 1 (5.1 g, 19.0 mmol), TMEDA (19 mL) in dry Et$_2$O (40 ml) at −78° C. is slowly added a solution of sec-butyllithium (19.0 mL, 24.7 mmol, 1.3 M in cyclohexanes) over a period of 30 min. The mixture is stirred at −78° C. for 3 hr, and then is treated with a solution of dimethylsulfate (3.6 g, 28.5 mmol) in Et$_2$O (5 mL). The cooling bath is removed and the reaction mixture is stirred at ambient temperature for 16 hr. After cooling to 0° C., the reaction mixture is quenched with water, extracted with Et$_2$O (5×100 mL), and the combined ether layers is dried over K$_2$CO$_3$. The solvent is removed under vacuum and the residue is purified by silica gel chromatography (eluting with 40% ethyl acetate in hexane) to give 2.51 g of 1'-tert-butoxycarbonyl-2'-methyl-[1,4']-bipiperidine, 2.

Compound 3: To a stirring solution of compound 2 (1.5 g, 5.3 mmol) in DCM (10 ml) is added TFA, and the mixture is stirred at room temperature for 2 hr. After removing the volatiles, the residue is diluted with DCM, basified with 30% NH$_4$OH to pH 8 and the layers are separated. The organic phase is dried over MgSO$_4$ and concentrated to give 730 mg of 2'-methyl-[1,4']bipiperidine.

Specific examples are shown below:

Example 160

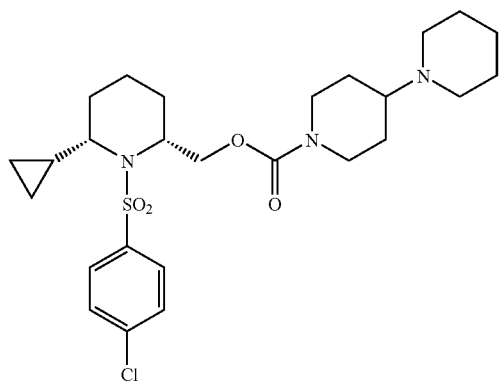

184

Step 1:

a) To a solution of 2-hydroxymethyl-6-(methoxycarbonyl)pyridine (44.5 g, 0.266 mol) in DCE (500 mL) was added triethylamine (44 mL, 0.31 mol) followed by TBSCI (44 g, 0.29 mol) and the reaction was heated at 70° C. for 4 h, then concentrated. The residue was directly purified by flash chromatography over silica gel (eluting hexane to hexane/AcOEt 1:1) to give 68.8 g (92%) of O-protected pyridine ester.

b) A solution of O-protected pyridine ester (68 g, 0.241 mmol) and platinum(IV) oxide (6 g, 0.026 mol) in MeOH (500 mL) and AcOH (50 ml) was hydrogenated 2 h at 40 psi. The final solution was filtered over CELITE, rinsed with MeOH then concentrated. The residue was diluted with 1 N NaOH, extracted with DCM and AcOEt, and combined organic layers were dried over Na$_2$SO$_4$ and concentrated to provide 66 g (97%) of O-protected piperidine ester.

Step 2:

To a solution of O-protected piperidine ester (63 g, 0.22 mol) in DCE (500 mL) was added triethylamine (100 mL, 0.66 mol) then, slowly, 4-chlorobenzenesulfonyl chloride (93 g, 0.44 mol) and the reaction was heated at 40° C. overnight. The final mixture was concentrated and directly purified by flash chromatography over silica gel (eluting hexane to hexane/AcOEt 9:1) to afford 89 g (88%) of O-protected sulfonamide ester.

Step 3:

a) To a solution of O-protected sulfonamide ester (20.0 g, 43.3 mmol) in DCM (200 mL) at −78° C. was slowly added DIBAH 1 N in THF (45 ml, 45 mmol) and the reaction was stirred 1 h at this temperature. The reaction was then quenched with saturated sodium tartrate in water, warmed to room temperature, and diluted with DCM. CELITE was added, the mixture was stirred 30 min and filtered. The solution was extracted with DCM and AcOEt and combined organic layers were dried over Na$_2$SO$_4$ and concentrated. The residue was purified by flash chromatography over silica gel (eluting hexane to hexane/AcOEt 1:1) to afford 15 g (80%) of O-protected sulfonamide aldehyde.

b) To a suspension of methyltriphenylphosphonium bromide (2.6 g, 7.2 mmol) in THF (25 mL) at −78° C. was added n-BuLi 2.5 N in hexanes (2.7 ml, 6.9 mmol). The solution was warmed to −20° C. for 30 min then treated with O-protected sulfonamide aldehyde (2.6 g, 6.0 mmol) dissolved in THF (25 mL). The reaction was allowed to warm to room temperature for 1 h then concentrated. The residue was taken up in saturated NaHCO3, extracted with DCM and AcOEt and combined organic layers were dried over Na$_2$SO$_4$ and concentrated. The residue was purified by flash chromatography over silica gel (eluting hexane to hexane/AcOEt 8:2) to give 2.1 g (85%) of O-protected sulfonamide alkene.

Step 4 a) To diethylzinc 1 N in hexanes (48.4 ml, 48.4 mmol) at 0° C. was added DCM (20 mL) followed by TFA (3.7 ml, 48.4 mmol) and the solution was stirred 5 min at this temperature. Diiodomethane (3.9 ml, 48.4 mmol) was then added followed 5 min later, by O-protected sulfonamide alkene (5.2 g, 12.1 mmol) in DCM (40 mL). The reaction was allowed to warm to room temperature for 2 h, diluted with water and extracted with DCM and AcOEt. The combined organic layers were dried over Na₂SO₄ and concentrated to give 5.7 g (100%) of O-protected cyclopropyl sulfonamide.

b) O-protected cyclopropyl sulfonamide (5.4 g, 12.1 mmol) was treated with TBAF following the conditions described in Example 1 Step 3-b to afford, after flash chromatography over silica gel (eluting with hexane/AcOEt 9:1 to hexane/AcOEt 4:6), 4.0 g (100%) of cyclopropyl sulfonamide alcohol.

Optional Step 4-R: Optional Resolution of Cyclopropyl Sulfonamide Alcohol:

Cyclopropyl sulfonamide alcohol (0.75 g) was resolved by HPLC on CHIRACEL OJ column (eluting with hexane/isopropanol 95:5) to afford, in order of elution, 276 mg of enantiomer A and 296 mg of enantiomer B, both as oils.

Step 5

The product of step 4 was converted to the title compound according to conditions similar to the ones described in Step 4 of Example 1, using 4-(1-piperidino)piperidine at the last stage as the amine. ¹H-NMR (300 MHz, CDCl₃) δ 7.74 (d, J=8.4 Hz, 2H), 7.45 (d, J=8.4 Hz, 2H), 4.10–4.40 (m, 5H), 3.24 (m, 1H), 2.40–2.90 (m, 7H), 1.05–1.90 (m, 17H), 0.70 (m, 1H), 0.59 (m, 2H), 0.25 (m, 1H); HRMS (MH⁺) 524.2356.

Following procedures similar to those in Example 160, the following compounds were prepared:

TABLE 13

| Compound No. | Structure | Retention Time (minutes) | Observed Mass |
|---|---|---|---|
| 160-A | 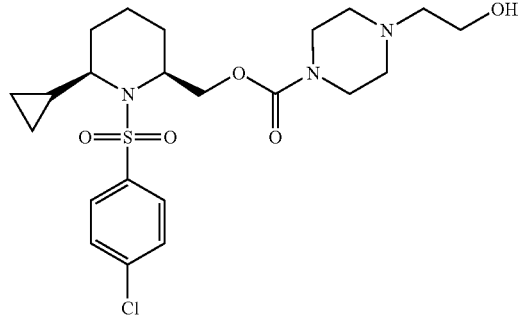 | 4.60 | 486.1 |
| 160-B | 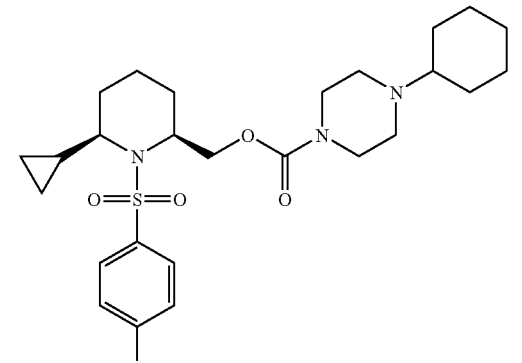 | 5.00 | 524.1 |
| 160-C | 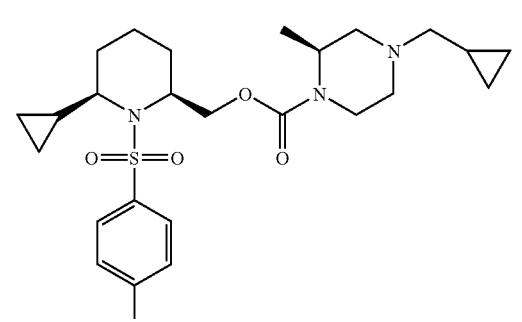 | 5.30 | 510.1 |

TABLE 13-continued

| Compound No. | Structure | Retention Time (minutes) | Observed Mass |
|---|---|---|---|
| 160-D | 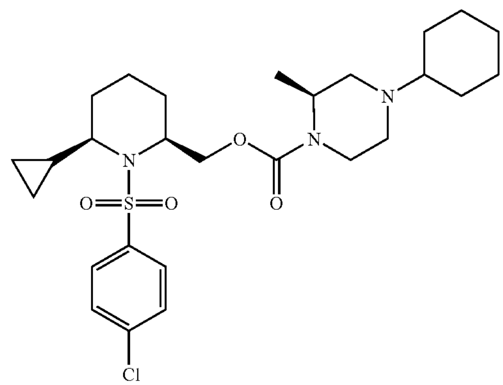 | 5.40 | 538.1 |
| 160-E | 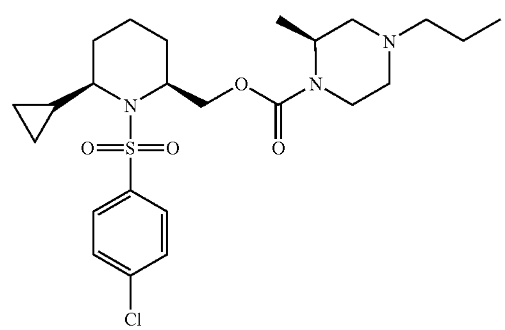 | 5.30 | 498.1 |
| 160-F | 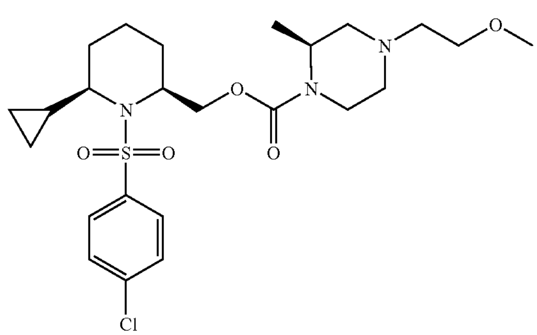 | 5.40 | 514.1 |
| 160-G | 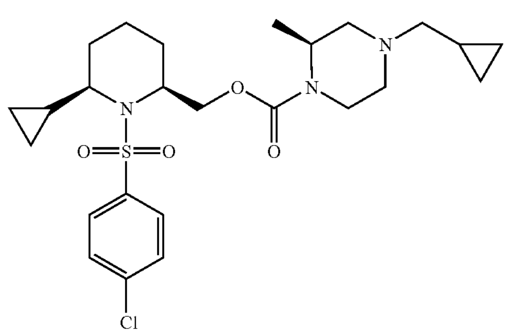 | 5.30 | 510.1 |

TABLE 13-continued

| Compound No. | Structure | Retention Time (minutes) | Observed Mass |
|---|---|---|---|
| 160-H | 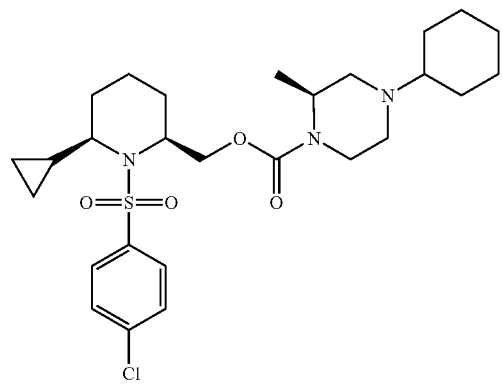 | 5.50 | 538.1 |
| 160-I | 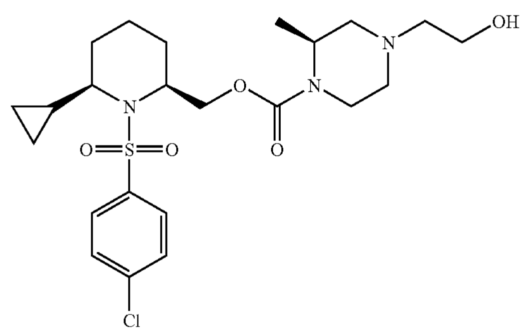 | 5.00 | 500.1 |
| 160-J | 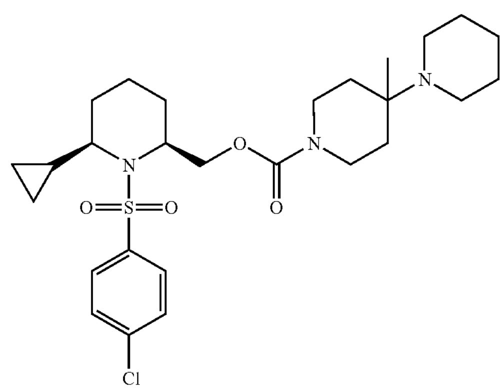 | 5.70 | 538.1 |
| 160-K | 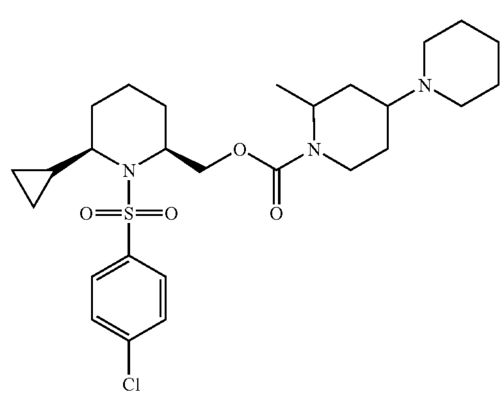 | 5.90 | 538.1 |

TABLE 13-continued

| Compound No. | Structure | Retention Time (minutes) | Observed Mass |
|---|---|---|---|
| 160-L | 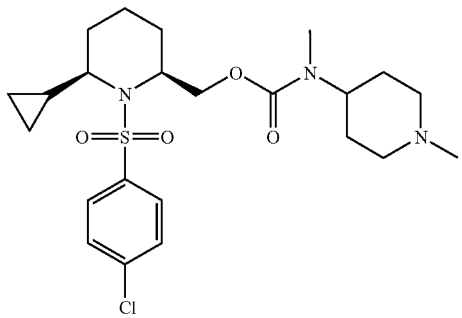 | 4.50 | 484.1 |
| 160-M | 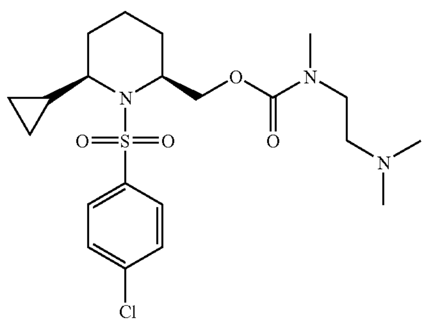 | 4.70 | 458.3 |
| 160-N | 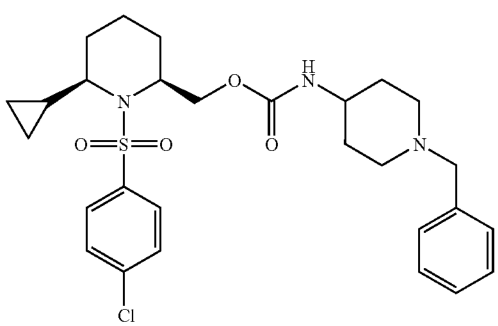 | 4.80 | 546.3 |
| 160-O | 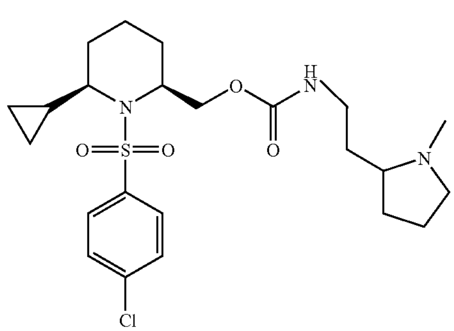 | 4.60 | 484.3 |

TABLE 13-continued

| Compound No. | Structure | Retention Time (minutes) | Observed Mass |
|---|---|---|---|
| 160-P | 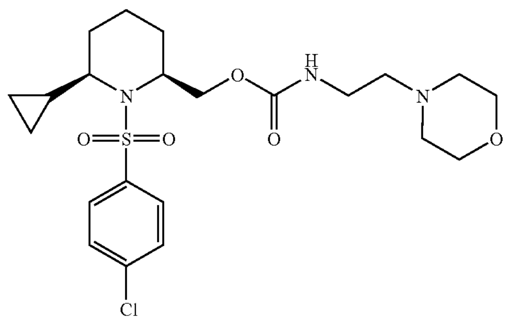 | 4.30 | 486.3 |
| 160-Q | 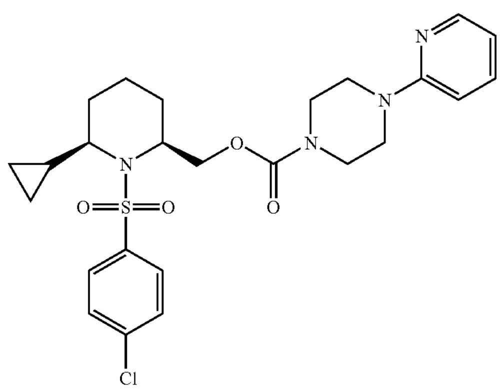 | 4.80 | 519.3 |
| 160-R | 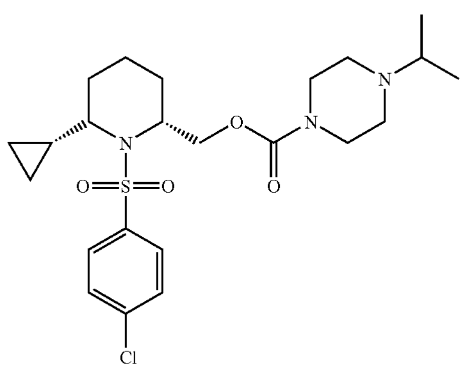 | 5.00 | 484.1 |
| 160-S | 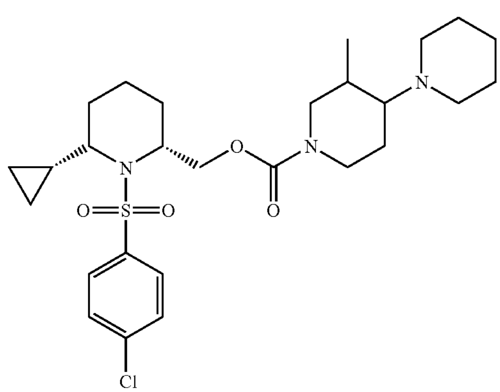 | 5.30 | 538.1 |

TABLE 13-continued
| Compound No. | Structure | Retention Time (minutes) | Observed Mass |
|---|---|---|---|
| 160-T | 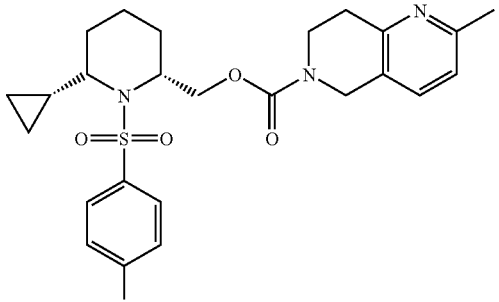 | 5.10 | 504.1 |
| 160-U | 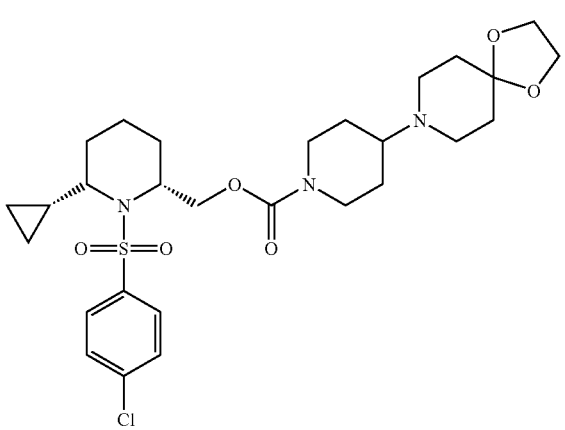 | 5.60 | 582.1 |
| 160-V | 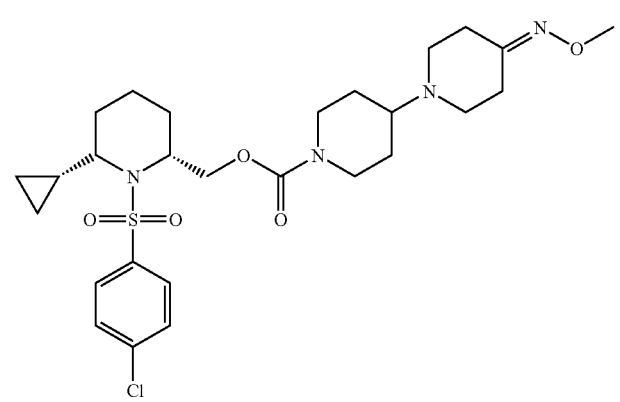 | 4.90 | 567.1 |
| 160-W | 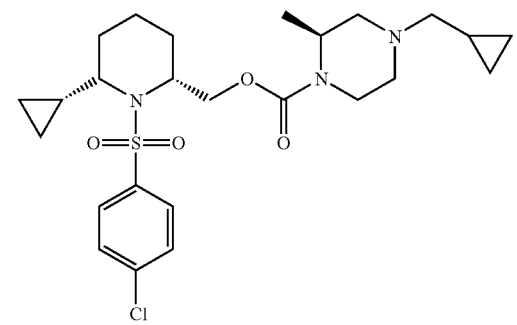 | 4.70 | 510.3 |

TABLE 13-continued

| Compound No. | Structure | Retention Time (minutes) | Observed Mass |
|---|---|---|---|
| 160-X | 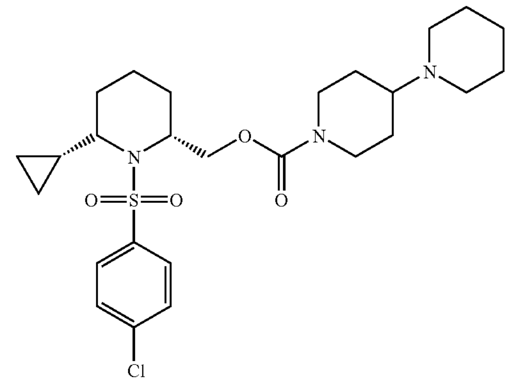 | 5.10 | 526.1 |
| 160-Y | 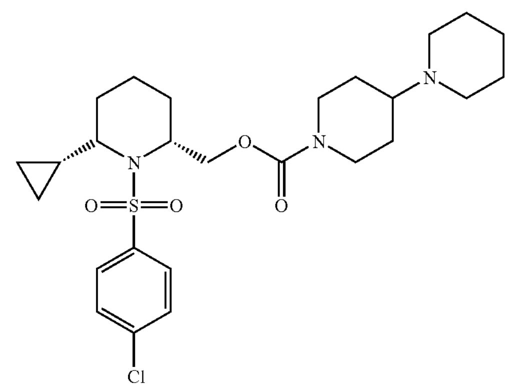 | 5.00 | 526.1 |
| 160-Z | 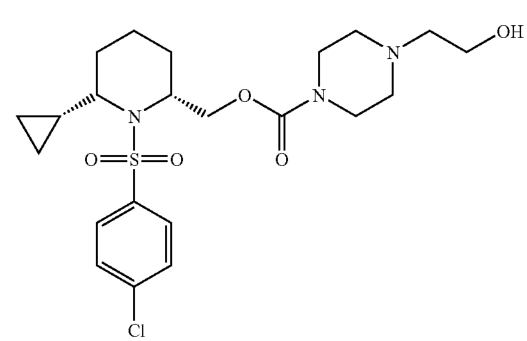 | 4.50 | 486.1 |

TABLE 13-continued

| Compound No. | Structure | Retention Time (minutes) | Observed Mass |
|---|---|---|---|
| 160-AA | 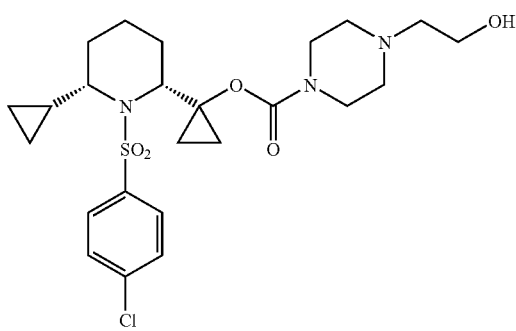 | 4.60 | 510.3 |

Example 161

Step 1:

a) To a solution of cyclopropyl sulfonamide alcohol product of Example 160 Step 4-b (4.8 g, 14.5 mmol) in AcOEt (25 mL), acetonitrile (25 mL) and water (50 mL) was added sodium periodate (9.3 g, 43.5 mmol) followed by RuCl$_3$.nH$_2$O (100 mg). The reaction mixture was stirred at RT for 2 hr, filtered over CELITE, and extracted with AcOEt. The combined organic layers were dried over Na$_2$SO$_4$ and concentrated to provide 4.55 g (90%) of cyclopropyl sulfonamide acid.

b) A solution of cyclopropyl sulfonamide acid (4.55 g, 13.2 mmol) in MeOH (100 mL) was treated with thionyl chloride (2 ml, 26.5 mmol) at RT slowly then the solution was heated to reflux for 2 hr. The reaction was concentrated, diluted with saturated NaHCO$_3$, extracted with DCM and AcOEt and the combined organic layers were dried over Na$_2$SO$_4$ and concentrated. The residue was purified by flash chromatography over silica gel (eluting with hexane to hexane/AcOEt 1:1) to afford 3.0 g (64%) of cyclopropyl sulfonamide ester.

Step 2:

To a solution of cyclopropyl sulfonamide ester (600 mg, 1.7 mmol) in THF (10 mL) was added Ti(OiPr)$_4$ (0.1 ml, 0.34 mmol), then the reaction was cooled to 10° C. and slowly treated with EtMgBr (3 N in ether, 1.7 ml, 5.1 mmol) over 30–40 min. The mixture was stirred another 30 min at 10° C., then treated with saturated aqueous NH$_4$Cl at this temperature, and extracted with DCM and AcOEt. The combined organic layers were dried over Na$_2$SO$_4$, concentrated, and the residue was purified by flash chromatography over silica gel (eluting with hexane to hexane/AcOEt 1:1) to yield 370 mg (61%) of cyclopropyl sulfonamide cyclopropylalcohol.

Step 3:

The product of step 2 was converted to the title compound according to conditions similar to the ones described in Step 4 of Example 1, using 1-(2-hydroxyethyl)piperazine at the last stage as the amine. $^1$H-NMR (300 MHz, CDCl$_3$) δ 7.69 (d, J=8.8 Hz, 2H), 7.42 (d, J=8.8 Hz, 2H), 4.56 (d, J=6.6 Hz, 1H), 3.30–3.75 (m, 6H), 3.01 (m, 1H), 2.30–2.65 (m, 6H), 1.40–1.70 (m, 4H), 0.95–1.25 (m, 8H), 0.73 (m, 1H), 0.58 (m, 2H), 0.23 (m, 1H); HRMS (MH$^+$) 512.1992.

Following procedures similar to those in Example 161 the following compounds were prepared:

TABLE 14

| Compound No. | Structure | Retention Time (minutes) | Observed Mass |
|---|---|---|---|
| 161-A | 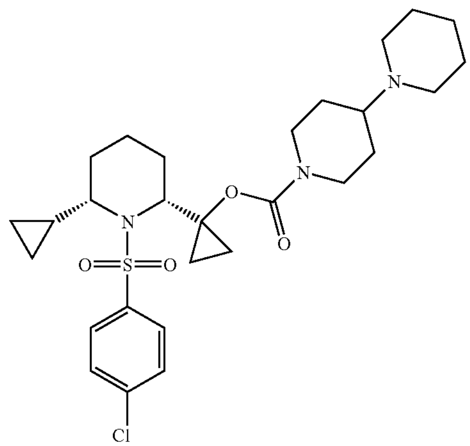 | 4.60 | 550.3 |
| 161-B | 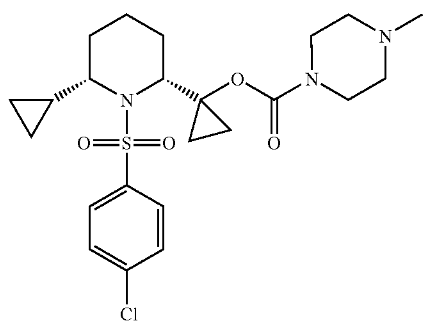 | 4.40 | 482.3 |
| 161-C | 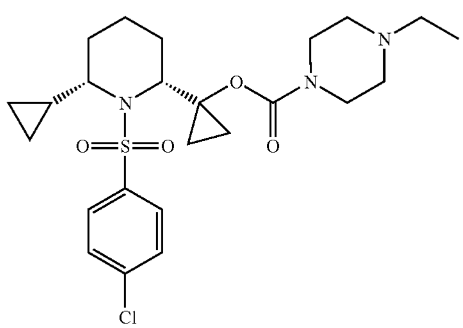 | 4.40 | 496.3 |
| 161-D | 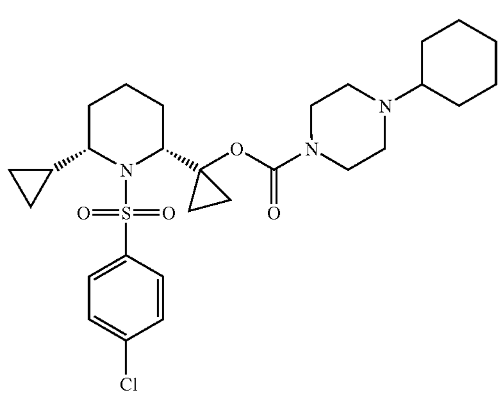 | 4.90 | 550.3 |

TABLE 14-continued

| Compound No. | Structure | Retention Time (minutes) | Observed Mass |
|---|---|---|---|
| 161-E | 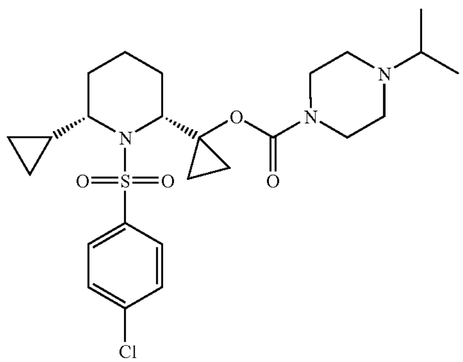 | 4.60 | 510.3 |
| 161-F | 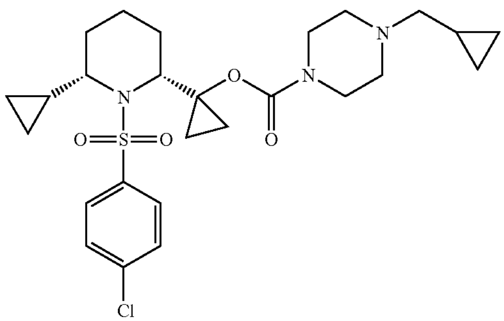 | 4.90 | 522.1 |
| 161-G | 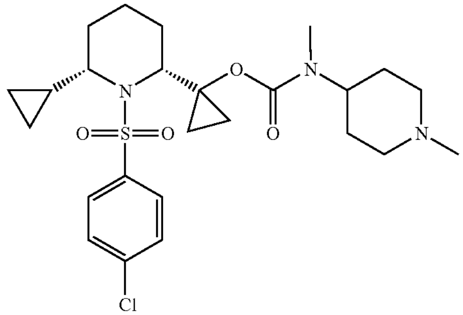 | 4.80 | 510.3 |

Example 162

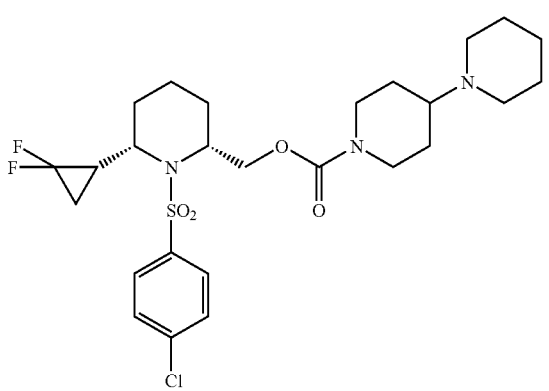

Step 1:

To a solution of the O-protected sulfonamide alkene product of Example 160 Step 3-b (480 mg, 1.12 mmol) and sodium fluoride (1 mg) in toluene (0.2 mL) at 100° C. was added $FSO_2CF_2COOTMS$ (700 mg, 2.8 mmol) over 1 h and the reaction was stirred an additional 2 h at this temperature. The final mixture was concentrated and purified over silica gel (eluting with hexane/AcOEt 9:1) to afford 338 mg of starting material and 65 mg (41% based on recovery) of O-protected difluorocyclopropyl sulfonamide.

Step 2:

The product of step 1 was converted to the title compound according to conditions similar to the ones described in Example 1 Step 3-b and Step 4, using 4-(1-piperidino)piperidine at the last stage as the amine. $^1$H-NMR (300 MHz, $CDCl_3$) δ 7.78 (d, J=8.4 Hz, 2H), 7.46 (d, J=8.4 Hz, 2H), 3.90–4.35 (m, 6H), 3.47 (s, 1H), 2.60–2.80 (m, 2H), 2.35–2.60 (m, 5H), 1.70–2.05 (m, 5H), 1.20–1.70 (m, 12H), 1.06 (m, 1H); HRMS ($MH^+$) 560.2153.

Following procedures similar to those in Example 162 the following compounds were prepared.

TABLE 15

| Compound No. | Structure | Retention Time (minutes) | Observed Mass |
|---|---|---|---|
| 162-A | 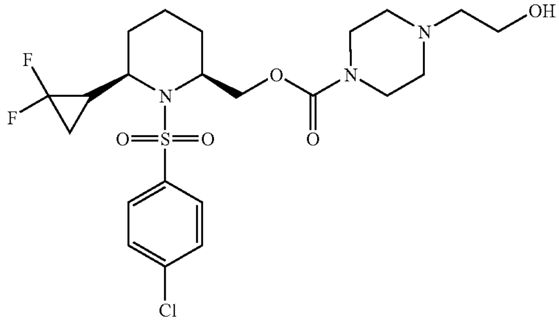 | 4.10 | 522.3 |
| 162-B | 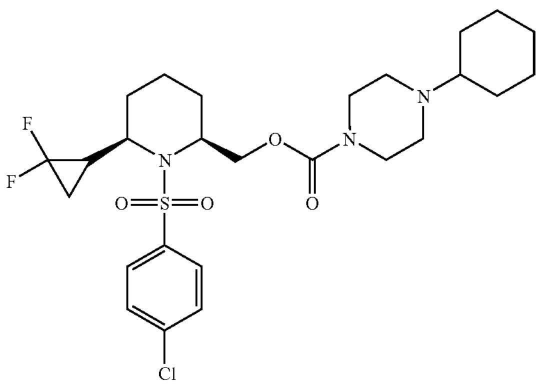 | 4.90 | 560.3 |

Example 163

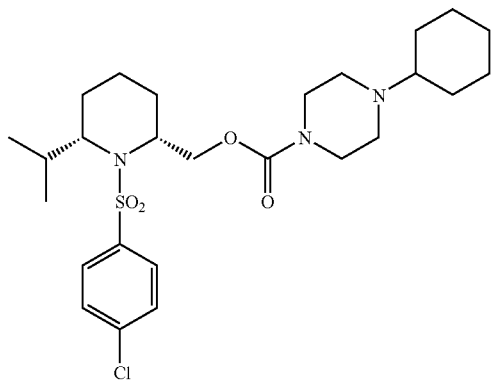

Step 1:

a) To a solution of O-protected pyridine ester product from Example 160 Step 1-a (10.0 g, 36 mmol) in THF (140 mL) at 0° C. was slowly added MeMgBr (3 N in ether, 30 ml, 90 mmol), and the reaction was warmed to RT and stirred 1 h. The final mixture was poured into 1 N NaOH and DCM to which was added CELITE, and the mixture was then stirred and filtered. The aqueous layer was extracted with DCM and AcOEt, the combined organic layers were dried over $Na_2SO_4$ and concentrated, and the residue was purified by flash chromatography over silica gel (eluting with hexane/AcOEt 8:2) to give 3.0 g (30%) of O-protected pyridine dimethylcarbinol.

b) To a solution of O-protected pyridine dimethylcarbinol (3.0 g, 10.6 mmol) in THF (50 mL) at −78° C. was added n-BuLi 2.5 N in hexanes (4.7 ml, 11.7 mmol) followed, 1 min later, by phenylthionochloroformate (2.76 g, 16.0 mmol). The reaction was stirred at −78° C. for 40 min, then allowed to warm to RT and stirred 4 h. The final mixture was treated with saturated $NaHCO_3$, extracted with DCM and AcOEt and the combined organic layers were dried over $Na_2SO_4$ and concentrated. Purification of the residue by flash chromatography over silica gel (eluting with hexane to DCM) afforded 1.5 g of O-protected pyridine propene as well as 1.8 g of starting O-protected pyridine dimethylcarbinol.

Step 2:

a) A solution of O-protected pyridine propene (1.5 g, 5.7 mmol) and platinum(IV) oxide (258 mg) in MeOH (20 mL) and AcOH (4 ml) was hydrogenated 6 h at 40 psi. The final solution was filtered over CELITE, rinsed with MeOH then concentrated. The residue was diluted with 1 N NaOH, extracted with DCM and AcOEt, and the combined organic layers were dried over $Na_2SO_4$ and concentrated. The residue was quickly passed through a plug of silica gel (eluting hexanes/AcOEt 8:2) to provide 1.0 g (65%) of O-protected isopropyl piperidine.

b) A solution of O-protected isopropyl piperidine (0.82 g, 3.0 mmol), 4-chlorobenzenesulfonyl chloride (1.2 g, 6.0 mmol) and pyridine (10 mL) in DCE (10 mL) was heated at 60° C. overnight. The final mixture was concentrated and directly purified by flash chromatography over silica gel (eluting hexane to DCM) to afford 0.42 g (32%) of O-protected isopropyl sulfonamide.

Step 3:

The product of step 2 was converted to the title compound according to conditions similar to the ones described in Example 1 Step 3-b and Step 4, using 1-cyclohexylpiperazine at the last stage as the amine. $^1$H-NMR (300 MHz, CDCl$_3$) δ 7.77 (d, J=8.8 Hz, 2H), 7.47 (d, J=8.8 Hz, 2H), 4.05–4.30 (m, 3H), 3.40–3.70 (m, 5H), 2.53 (br s, 4H), 2.27 (m, 1H), 1.35–2.00 (m, 10H), 0.95–1.35 (m, 10H), 0.91 (dm J=6.6 Hz, 3H); HRMS (MH$^+$) 526.2501.

Following procedures similar to those in Example 163 the following compounds were prepared.

TABLE 16

| Compound No. | Structure | Retention Time (minutes) | Observed Mass |
|---|---|---|---|
| 163-A | 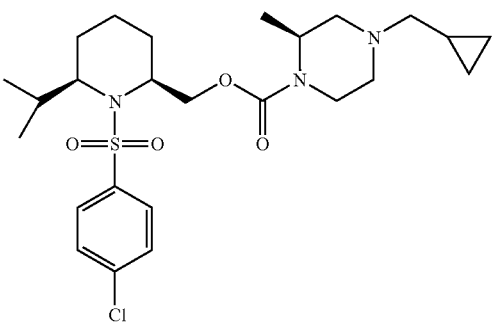 | 5.40 | 512.1 |
| 163-B | 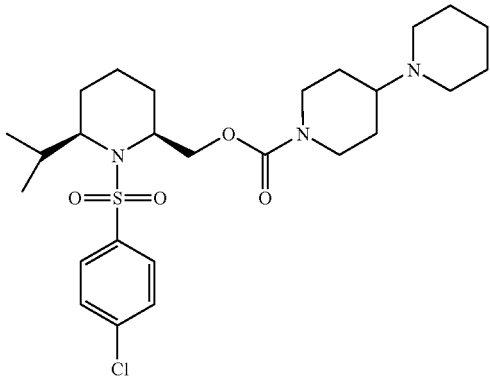 | 5.60 | 526.1 |
| 163-C | 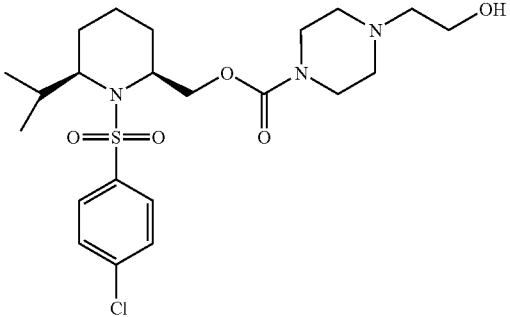 | 5.10 | 488.1 |

Example 164

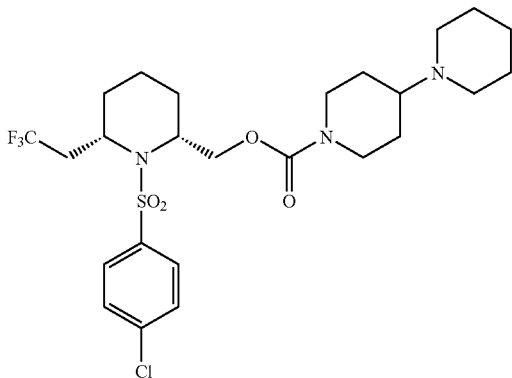

Step 1:

a) To a solution of O-protected pyridine ester product from Example 160 Step 1-a (45.75 g, 0.16 mol) in DCM (500 mL) at −40° C. was slowly added DIBAH 1 N in hexane (211 ml, 0.21 mmol) and the reaction mixture was stirred 1 h at this temperature. The reaction was then quenched with an excess of acetone, and treated with sodium fluoride (25 g) solution in water (100 mL) for 30 min. The final mixture was filtered over CELITE, extracted with DCM and AcOEt and the combined organic layers were dried over $Na_2SO_4$ and concentrated. The residue was purified by flash chromatography over silica gel (eluting with hexane/AcOEt 8:2) to afford 27.2 g (68%) of O-protected pyridine aldehyde.

b) To a solution of O-protected pyridine aldehyde (5.0 g, 19.9 mmol) and TBAF 1 N in THF (1.5 mL, 1.5 mmol) in THF (60 mL) at 0° C. was slowly added trifluoromethyltrimethylsilane (3.4 mL, 20.9 mmol) and the reaction mixture was allowed to warm to RT overnight. The reaction mixture was diluted with water and DCM, extracted with DCM, dried over $Na_2SO_4$ and concentrated. The residue was purified by flash chromatography over silica gel (eluting with hexane/AcOEt 8:2) to afford 1.5 g (24%) of b-protected pyridine trifluoroethyl alcohol.

Step 2:

a) To a solution of O-protected pyridine trifluoroethyl alcohol (1.8 g, 5.6 mmol) in THF (30 mL) at −78° C. was added n-BuLi 2.5 N in hexanes (2.5 ml, 6.2 mmol) followed, 1 min later, by phenylthionochloroformate (1.45 g, 8.4 mmol). The reaction was stirred at −78° C. for 40 min, then allowed to warm to RT and stirred an additional 1 h. The final mixture was then diluted with saturated aqueous $NaHCO_3$, extracted with DCM and AcOEt and the combined organic layers were dried over $Na_2SO_4$ and concentrated. Purification of the residue by flash chromatography over silica gel (eluting with DCM/hexane 1:1) afforded 2.3 g (92%) of O-protected pyridine trifluoroethyl thionocarbonate.

b) To a solution of O-protected pyridine trifluoroethyl thionocarbonate (2.3 g, 5.0 mmol) in toluene (60 mL) was added tributyltin hydride (3.0 mL, 10.5 mmol) followed by 2,2'-azobisisobutyronitrile (265 mg, 1.6 mmol) and the reaction mixture was heated under reflux for 5 h. After concentration of the solvent, the residue was purified by flash chromatography over silica gel (eluting with hexane to DCM/hexane 1:1) to give 1.3 g (86%) of O-protected trifluoroethyl pyridine.

Step 3:

a) A solution of O-protected trifluoroethyl pyridine (1.3 g, 4.3 mmol) and platinum(IV) oxide (100 mg) in MeOH (50 mL) and AcOH (5 ml) was hydrogenated overnight at 50 psi. The final solution was filtered over CELITE, rinsed with MeOH then concentrated. The residue was diluted with 1 N NaOH, extracted with DCM and AcOEt, and the combined organic layers were dried over $Na_2SO_4$ and concentrated to provide 1.13 g (84%) of O-protected trifluoroethyl piperidine.

b) To a solution of O-protected trifluoroethyl piperidine (1.13 g, 3.6 mmol) in DCE (15 mL) was added triethylamine (0.6 mL, 4.3 mmol) then 4-chlorobenzenesulfonyl chloride (1.13 g, 5.4 mmol) and the reaction mixture was heated at reflux overnight. The final mixture was concentrated and directly purified by flash chromatography over silica gel (eluting with hexane to DCM) to afford 0.67 g (38%) of O-protected trifluoroethyl sulfonamide.

Step 4:

The product of step 3 was converted to the title compound according to conditions similar to the ones described in Example 1 Step 3-b and Step 4, using 4-(1-piperidino)piperidine at the last stage as the amine. $^1$H-NMR (300 MHz, $CDCl_3$) δ 7.77 (d, J=8.3 Hz, 2H), 7.48 (d, J=8.3 Hz, 2H), 4.10–4.45 (m, 5H), 3.99 (m, 1H), 2.40–2.95 (m, 9H), 1.20–2.00 (m, 16H); HRMS ($MH^+$) 566.2075.

Following procedures similar to those in Example 164, the following compounds were prepared.

TABLE 17

| Compound No. | Structure | Retention Time (minutes) | Observed Mass |
|---|---|---|---|
| 164-A | 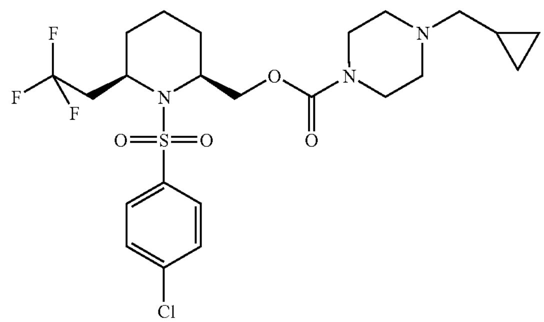 | 5.00 | 538.1 |
| 164-B | 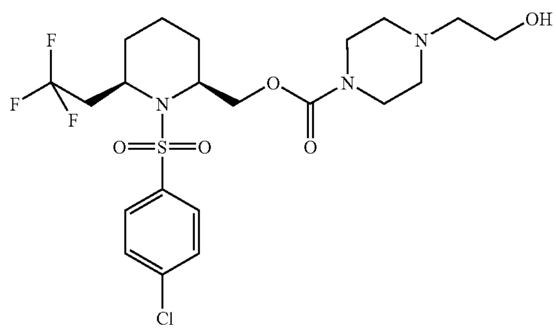 | 4.60 | 528.1 |
| 164-C | 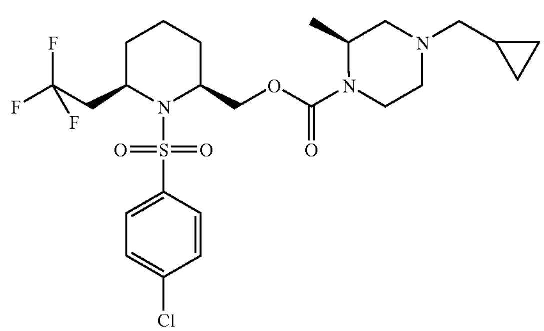 | 4.90 | 552.1 |

Example 165
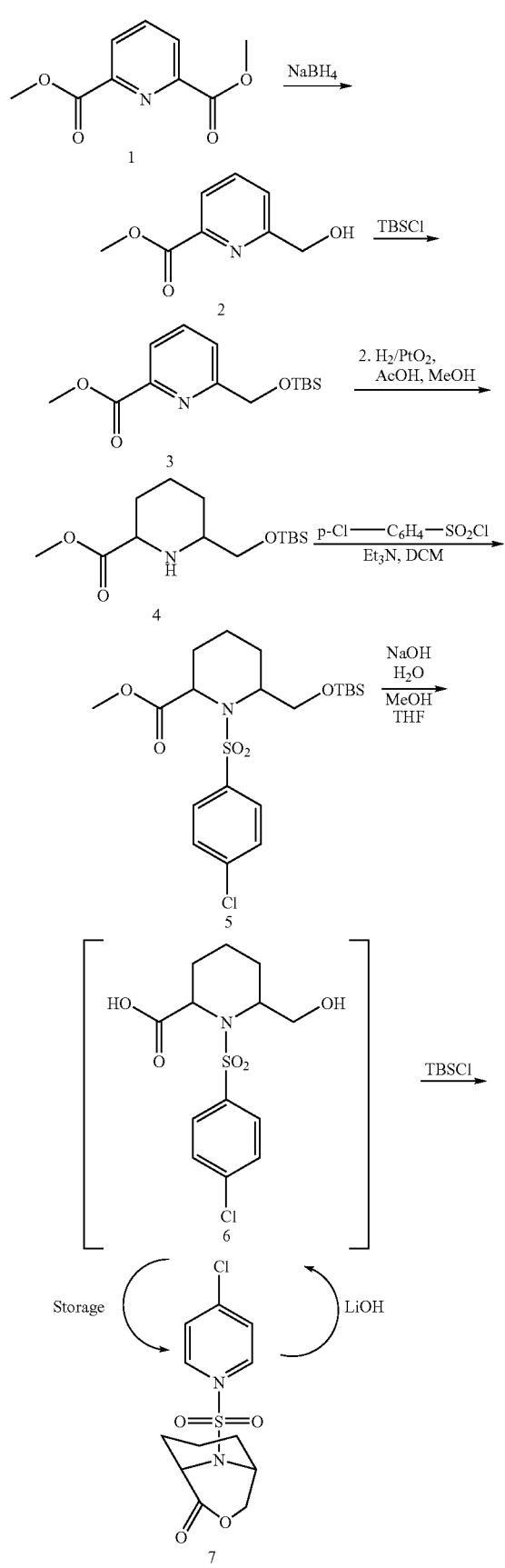
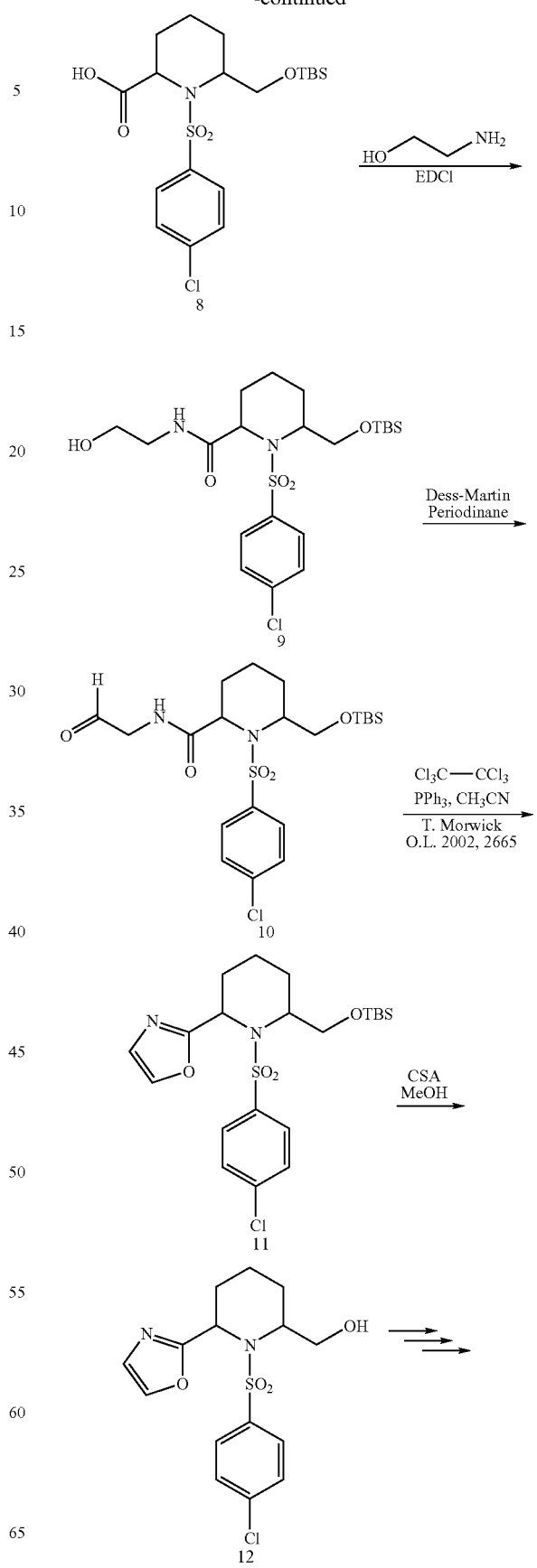

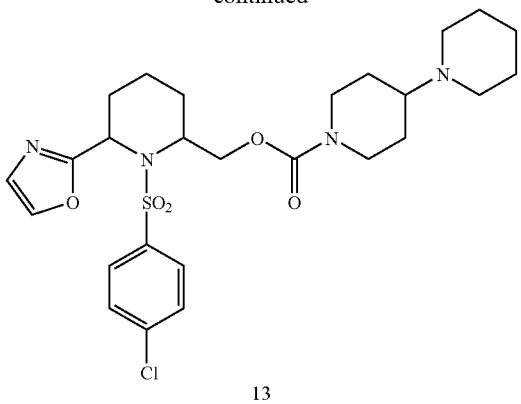

13

Step 1:

Compound 2 was prepared as described in Example 88, Step 1.

Step 2:

A mixture of 1.396 g (8.35 mmol) of Compound 2 and 1.137 g (19.71 mmol) of imidazole in 10 ml of DMF was treated with 1.210 g (9.18 mmol) of TBSCI. After overnight stirring, the mixture was diluted with DCM, washed with water, dried over sodium sulfate and concentrated. The product was purified by chromatography using 10% ethyl acetate in hexanes as solvent to furnish 1.65 g of Compound 3.

Step 3:

Compound 3 (4.0 g) was hydrogenated at 50 psi using 200 mg of $PtO_2$ as catalyst and a mixture of 20 mL of methanol and 20 mL of acetic acid as solvent over a period of 12 h. The reaction vessel was flushed with nitrogen, catalyst was filtered out and volatiles were evaporated. The residue was re-dissolved in DCM, washed with sat. $NaHCO_3$, aqueous phase was re-extracted with DCM, and the combined organic phase was dried over sodium sulfate and concentrated to furnish 3.77 g of Compound 4.

Step 4:

A mixture of 3.77 g (13.13 mmol) of Compound 4, 7.4 mL (52.6 mmol) of triethylamine and 5.54 g (26.26 mmol) of 4-chlorobenzenesulfonyl chloride in 60 ml of DCM was stirred over 7 days. The mixture was diluted with DCM, washed with water, dried over sodium sulfate and concentrated. The product was purified by chromatography using 5–15% of ethyl acetate in hexanes as the eluent to furnish 4.99 g of Compound 5.

Step 5:

A mixture of 150 mg of Compound 5, 5 mL of methanol, 5 mL of THF and 5.0 mL of 1 M aqueous NaOH was refluxed overnight. The mixture was cooled, DCM (100 mL) and 1 M HCl were added so that the pH was adjusted to ~3. The organic layer was separated and the aqueous phase was extracted with DCM. The combined organic phase was dried over sodium sulfate and concentrated to furnish 90 mg of unstable Compound 6, which had a tendency to dehydrate on storage to provide Compound 7. In order to regenerate Compound 6 from Compound 7, the following procedure was used:

A mixture of 500 mg of Compound 7, 4.0 ml of THF, 0.7 mL of water and 72 mg of LiOH was vigorously stirred overnight. The reaction mixture was diluted with ethyl acetate and the pH was adjusted to ~3 with 1 M HCl. The organic layer was separated and the aqueous phase was extracted with DCM. The combined organic phase was dried over sodium sulfate and concentrated to furnish 310 mg of unstable Compound 6.

Step 6:

A mixture of 310 mg (0.931 mmol) of freshly prepared Compound 6, 349 mg (2.33 mmol) of TBSCI, 272 mg (4 mmol) of imidazole and 5 mL of DMF was stirred overnight. The mixture was diluted with DCM, partitioned with citric acid, and the aqueous phase was re-extracted with DCM. The combined organic phase was dried over sodium sulfate and concentrated. The product was purified by chromatography using 30% of ethyl acetate in hexanes as the eluent to furnish 350 mg of Compound 8.

Step 7:

To a mixture of 350 mg (0.783 mmol) of Compound 8, 95 mg (1.56 mmol) of ethanolamine in 5 ml of DMF was added 211 mg (1.56 mmol) of HOBt, 300 mg (1.56 mmol) of EDCI, and 0.218 ml (1.56 mmol) of triethylamine. The turbid mixture was stirred overnight, diluted with DCM, washed with water, dried over sodium sulfate and concentrated. The product was purified by chromatography using 40% of ethyl acetate in hexanes as the eluent to furnish 138 mg of Compound 9.

Step 8:

To a solution of 138 mg (0.2816 mmol) of Compound 9 in 2 mL of DCM was added 238 mg (0.563 mmol) of Dess-Martin periodinane. The mixture was stirred over a period of 1 h, diluted with DCM, washed with sat. $NaHCO_3$, dried over sodium sulfate and concentrated. The product was purified by chromatography using 40% of ethyl acetate in hexanes as the eluent to furnish 110 mg of Compound 10.

Step 9:

To a mixture of 80 mg (0.1638 mmol) of Compound 1–0 in 3 mL of acetonitrile was added 194 mg (0.82 mmol) of hexachloroethane, 0.23 mL (1.64 mmol) of triethylamine followed by 215 mg (0.82 mmol) of triphenylphosphine. (The latter reagent dissolved gradually, then a new precipitate formed after 10 min of stirring). The mixture was stirred overnight and Compound 11 (56 mg) was isolated by prep. TLC chromatography using 20% ethyl acetate in hexanes as the eluent.

Step 10:

A mixture of 56 mg (0.119 mmol) of Compound 11 in 1.5 mL of THF was treated with 0.24 mL (0.24 mmol) of 1M TBAF solution in THF. The reaction mixture was stirred for 1 h, poured into water, extracted with DCM, and the organic phase was dried over sodium sulfate and concentrated to furnish 50 mg of crude Compound 12, which was used without further purification.

Step 11:

Compound 13 was prepared from Compound 12 using procedures similar to Example 1, Step 4(a) and 4(b), except that step 4(a) was modified so that a 2:1 mixture of THF and acetonitrile was used as solvent instead of DCM.

$^1$H NMR ($CDCl_3$, 400 MHz) δ 7.86 (2H, d, J=8.8 Hz), 7.63 (1H, s), 7.51 (2H, d, J=8.8 Hz), 7.09 (1H, s), 5.32 (1H, d, J=5.0 Hz), 4.25 (1H, m), 4.14 (1H, br), 3.73 (1H, t, J=9.0 Hz), 3.58 (1H, t, J=9.0 Hz), 2.70 (2H, m), 2.52–2.33 (6H, ser. m.), 2.0–1.2 (16H, ser. m.); MS (ES) m/e 552.1 (M+H)[+].

Example 166

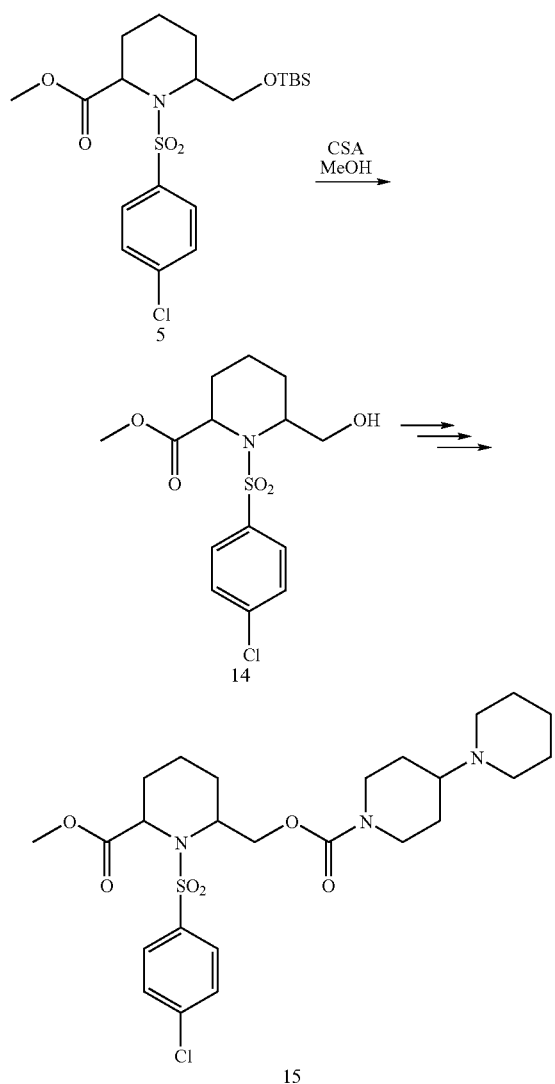

Example 167

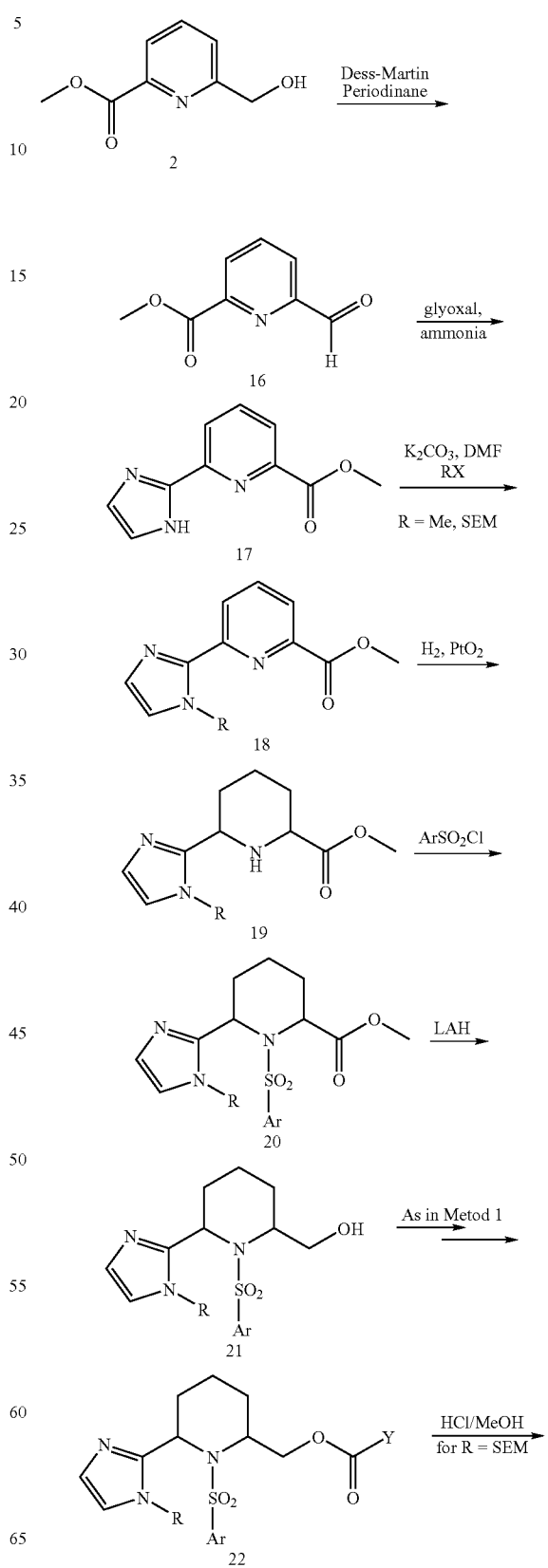

Step 1:

A mixture of 480 mg (1.04 mmol) of Compound 5, 10 mL of MeOH and 1 mL of DCM was warmed with a heat gun until dissolution was complete. The mixture was cooled to RT and 48 mg of CSA was added. The mixture was stirred for 1.5 h, diluted with DCM, washed with sat. NaHCO$_3$, dried over sodium sulfate and concentrated. The product was purified by chromatography using 30% of ethyl acetate in hexanes as the eluent to furnish 320 mg of Compound 14.

Step 2:

Compound 15 was prepared from Compound 14 using procedures similar to Example 1, Step 4(a) and 4(b), except that step 4(a) was modified so that a 2:1 mixture of THF and acetonitrile was used as solvent instead of DCM.

$^1$H NMR (CDCl$_3$ 400 MHz) δ 7.86 (2H, d, J=8.8 Hz), 7.63 (1H, s), 7.51 (2H, d, J=8.8 Hz), 7.09 (1H, s), 5.32 (1H, d, J=5.0 Hz), 4.25 (1H, m), 4.14 (1H, br), 3.73 (1H, t, J=9.0 Hz), 3.58 (1H, t, J=9.0 Hz), 2.70 (2H, m), 2.52–2.33 (6H, ser. m.), 2.0–1.2 (16H, ser. m.); MS (ES) m/e 542.3 (M$^+$).

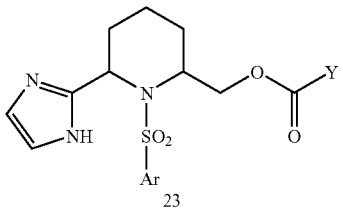

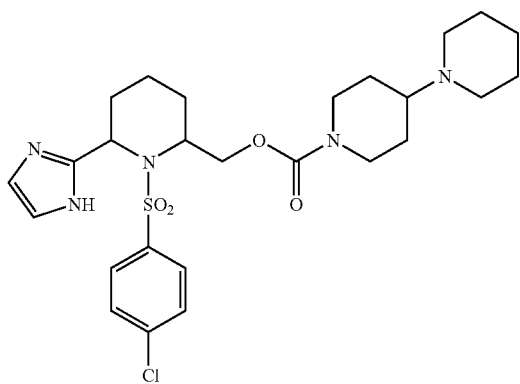

Step 1:
Compound 2 was oxidized with Dess-Martin Periodinane using procedure similar to the one used in preparation of Compound 10.

Step 2:
To a solution of 3.1 g (18.8 mmol) of Compound 16 in 95 mL of MeOH was added 7.9 g (37.5 mmol) of glyoxal trimer dihydrate followed by slow addition of 24.1 mL of a 7 N ammonia/methanol solution. The reaction mixture was worked-up by evaporating the volatiles and partitioning the residue between water and DCM. The aqueous phase was extracted with DCM and the combined organic phase was dried to yield 81.6 g of compound 17.

Step 3:
To a solution of 250 mg (1.19 mmol) of Compound 17 in 7 mL of DMF was added 412.8 mg (2.99 mmol) of $K_2CO_3$ followed by 0.422 mL (2.4 mmol) of SEMCl. The mixture was stirred overnight, partitioned between water and DCM, the aqueous phase was re-extracted with DCM, and the combined organic phase was dried over sodium sulfate, concentrated and purified chromatographically to furnish 230 mg of Compound 18.

Step 4:
A mixture of 230 mg (0.69 mmol) of Compound 18, 40 mg of $PtO_2$, 10 mL of MeOH and 5 mL of AcOH was hydrogenated at 55 psi over a period of 15 hrs. The catalyst was filtered out, volatiles evaporated, the residue dissolved in DCM and washed with sat. $NaHCO_3$, the aqueous phase was re-extracted with DCM, and the combined organic phase was dried over sodium sulfate and concentrated to furnish Compound 19.

Step 5:
Compound 20 was prepared from compound 19 using the procedure similar to the procedure used for the preparation of compound 5 in step 4 of example 165.

Step 6:
Compound 21 was prepared from Compound 20 by reduction with LAH using the procedure described in Example 53, Preparation B, Step 4

Step 7:
Compound 22 was prepared from Compound 21 using procedures similar to Example 1, Step 4(a) and 4(b), except that step 4(a) was modified so that a 2:1 mixture of THF and acetonitrile was used as solvent instead of DCM.

Step 8:
A solution of compound 22 in 3M HCl/EtOH was refluxed for 3 hours, concentrated, partitioned between DCM and 15% aq. NaOH, the aqueous phase was re-extracted with DCM, and the combined organic phase was dried over sodium sulfate, concentrated and purified chromatographically using 8% MeOH in DCM to furnish Compound 23. $^1$H NMR (CDCl$_3$ 300 MHz) δ 10 (1H, s), 7.81 (2H, d, J=8.8 Hz), 7.53 (2H, d, J=8.8 Hz), 7.02 (2H, s), 4.48 (1H, d, J=4.8 Hz), 4.49 (1H, m), 4.20 (2H, d, J=12.0 Hz), 3.85 (1H, s), 3.38 (1H, t, J=10.4 Hz), 2.92–2.48 (7H, ser. m.), 2.06–1.17 (16H, ser. m.); MS (ES) m/e 550.1 (M+H)$^+$.

Other compounds were prepared by this method as shown in Table 18:

TABLE 18

| Compound No. | Structure | Retention Time (minutes) | Observed Mass |
|---|---|---|---|
| 167-A | 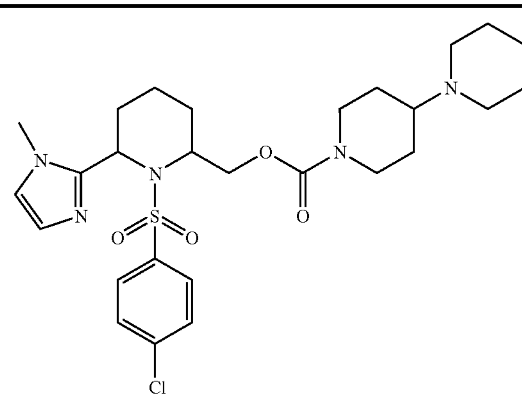 | 3.91 | 564.3 |

TABLE 18-continued

| Compound No. | Structure | Retention Time (minutes) | Observed Mass |
|---|---|---|---|
| 167-B | 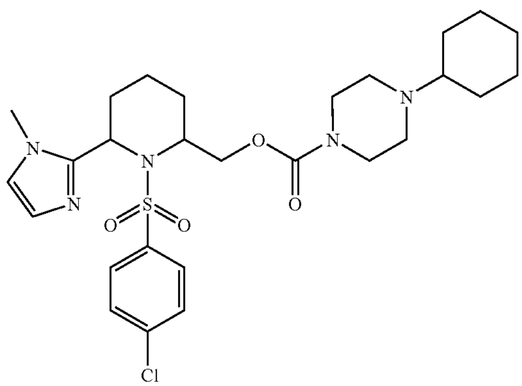 | 4.68 | 564.1 |
| 167-C | 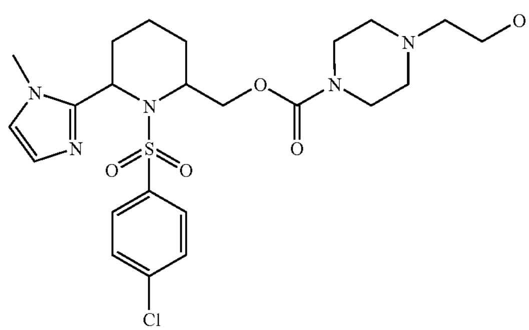 | N/A | N/A |

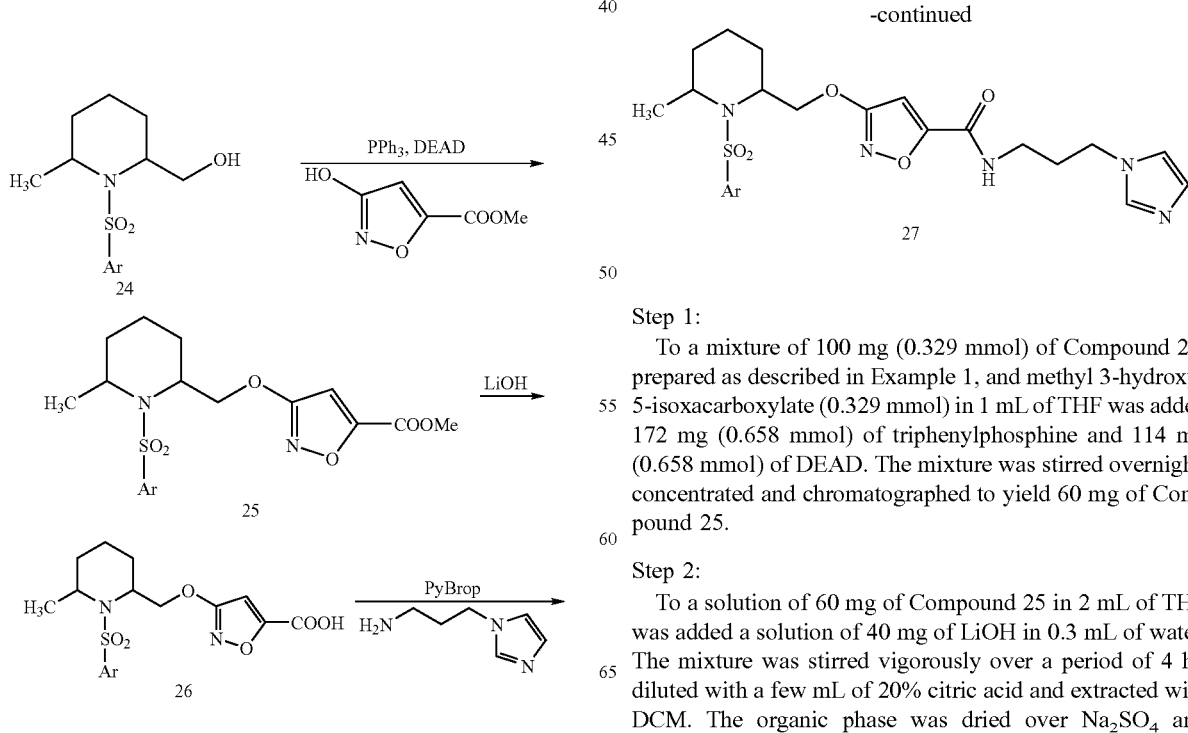

Example 168

Step 1:

To a mixture of 100 mg (0.329 mmol) of Compound 24, prepared as described in Example 1, and methyl 3-hydroxy-5-isoxacarboxylate (0.329 mmol) in 1 mL of THF was added 172 mg (0.658 mmol) of triphenylphosphine and 114 mg (0.658 mmol) of DEAD. The mixture was stirred overnight, concentrated and chromatographed to yield 60 mg of Compound 25.

Step 2:

To a solution of 60 mg of Compound 25 in 2 mL of THF was added a solution of 40 mg of LiOH in 0.3 mL of water. The mixture was stirred vigorously over a period of 4 hr, diluted with a few mL of 20% citric acid and extracted with DCM. The organic phase was dried over $Na_2SO_4$ and concentrated, the residue was passed through a silica gel plug using 10% of MeOH in DCM as solvent to yield 40 mg of Compound 26.

Step 3:

A solution of 20 mg of Compound 26 in a mixture of 1 mL of DCM and 0.5 mL of DMF was treated with 20 mg of N-(3-aminopropyl)imidazole and 25 mg of PyBrop. The mixture was stirred overnight, washed with water, dried, concentrated and purified chromatographically using 10% of MeOH in DCM to furnish 12 mg of Compound 27.

$^1$H NMR (CDCl$_3$ 300 MHz) δ 7.78 (2H, d, J=8.8 Hz), 7.53 (1H, s), 7.47 (2H, d, J=8.8 Hz), 7.10–6.98 (2H, ser.m.), 6.52 (1H, s), 4.43–4.34 (3H, ser.m.), 4.14 (1H, m), 4.05 (2H, t, J=7.0 Hz), 3.44 (2H, m), 2.12 (3H, m), 1.90–1.20 (6H, ser.m.), 1.28 (3H, d, J=7.1 Hz); MS (ES) m/e 522.1 (M+H)$^+$.

Other compounds prepared by this method:

-continued

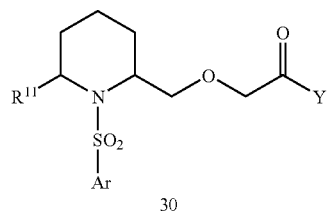

TABLE 19

| Compound No. | Structure | Retention Time (minutes) | Observed Mass |
|---|---|---|---|
| 168-A | 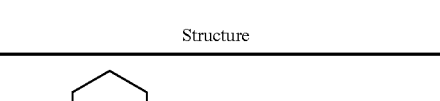 | 5.31 | 429.1 |

Example 169

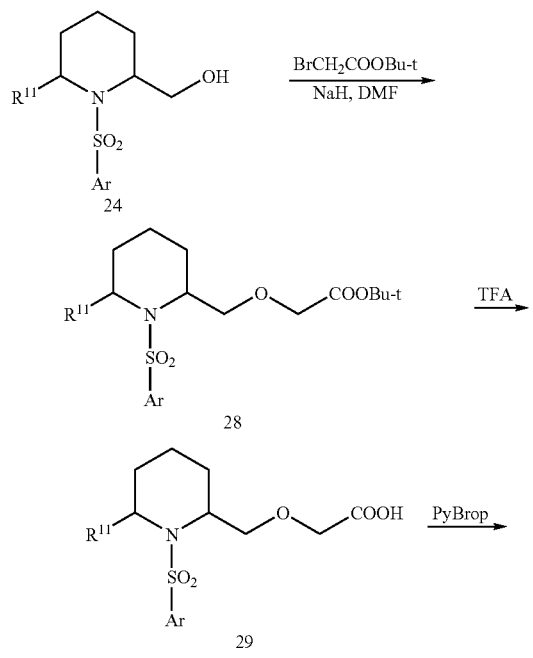

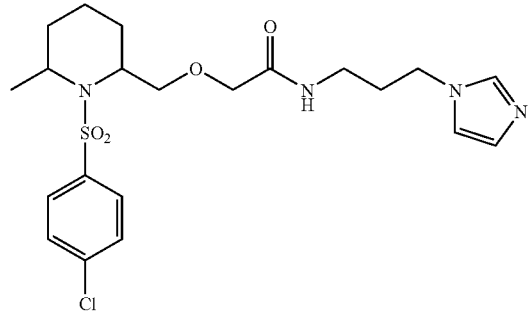

-continued

Step 1:

To a solution of 100 mg (0.329 mmol) of Compound 24 in 1 mL of DMF was added 26 mg (0.658 mmol) of a 60% dispersion of NaH in mineral oil. The mixture was sonicated for 15 min. 137 mg (0.9 mmol) of t-butyl bromoacetate was added and the mixture was stirred overnight. The reaction mixture was quenched with water, extracted with DCM, concentrated, passed through a silica gel plug using 10% of ethyl acetates in hexanes as solvent to furnish 130 mg of Compound 28.

225

Step 2:

120 mg of compound 28 was dissolved in 2 mL of DCM. 2 mL of TFA wasn added, and the mixture was stirred for 30 min, and then the volatiles were evaporated. 120 mg of crude acid 29 was obtained.

Step 3:

For the preparation of amide 30, the procedure described in Example 168 (synthesis of Compound 27) was used.

$^1$H NMR (CDCl$_3$ 300 MHz) δ 7.76 (2H, d, J=8.8 Hz), 7.66 (1H, s), 7.48 (2H, d, J=8.8 Hz), 7.03 (2H, d, J=10.5 Hz), 4.40 (1H, m), 4.12–3.93 (4H, ser. m.), 3.83 (1H, m), 3.71 (1H, m), 3.52 (1H, m), 3.36 (2H, m), 2.65 (1H, br), 2.07 (2H, m), 1.66–1.26 (6H, ser. m.), 1.33 (3H, d, J=7.1 Hz); MS (ES) m/e 469.1 (M+H)$^+$.

Other compounds prepared by this method:

226

Example 170

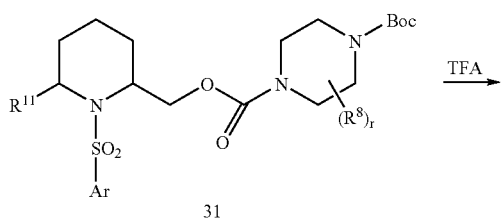

31

TABLE 20

| Compound No. | Structure | Retention Time (minutes) | Observed Mass |
|---|---|---|---|
| 169-A | 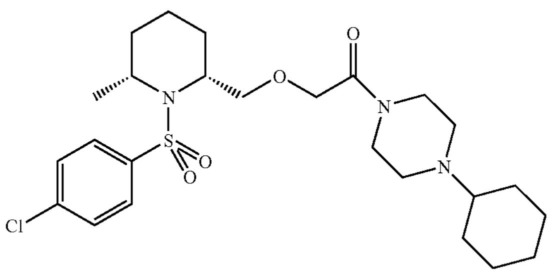 | 4.81 | 512.1 |
| 169-B | 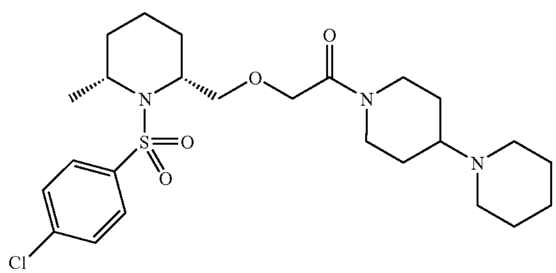 | 4.57 | 512.1 |
| 169-C | 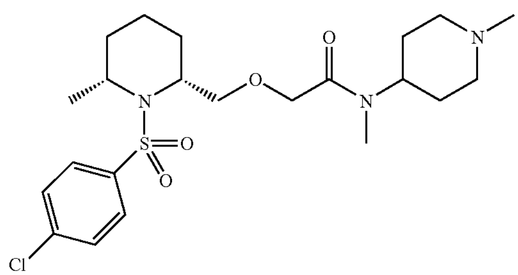 | 4.56 | 472.1 |
| 169-D | 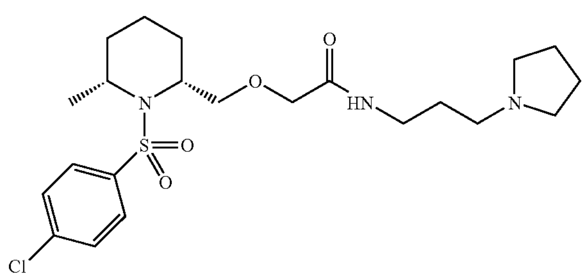 | 4.81 | 472.1 |

-continued

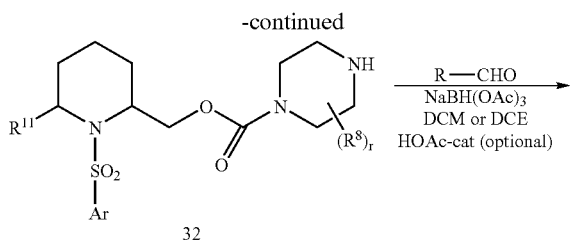

More Specifically

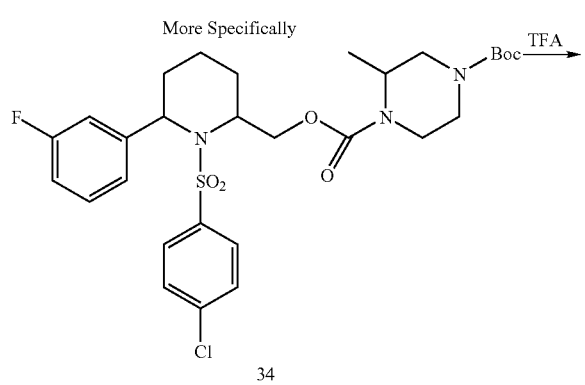

-continued

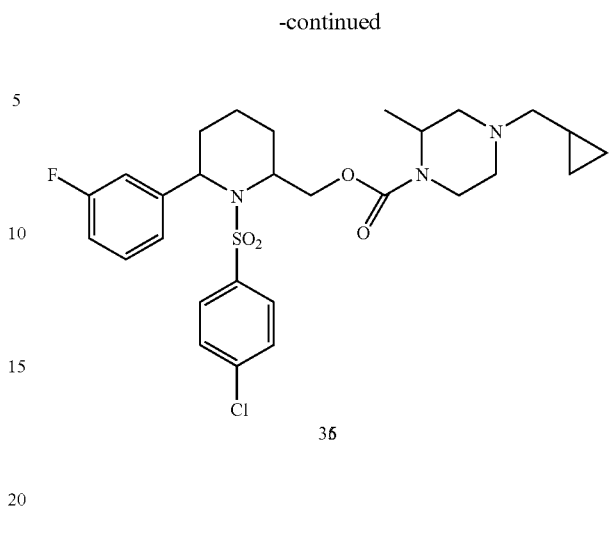

Step 1:

120 mg of Compound 34, prepared using procedures described in Example 53, was dissolved in 20 mL of DCM and treated with a pre-mixture of 10 mL of TFA and 1 mL of water. The reaction mixture was stirred over a period of 1 hr, the volatiles were evaporated, and the residue was re-dissolved in DCM and washed with 1M sodium hydroxide. The organic phase was dried over sodium sulfate and concentrated to furnish 90 mg of Compound 35.

Step 2:

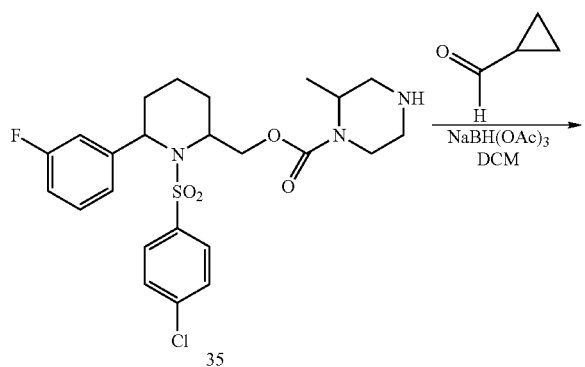

To a solution of 44 mg (0.0864 mmol) of compound 35 in 2 mL of DCM was added 100 mg of cyclopropylcarboxaldehyde, 55 mg (0.259 mmol) of sodium triacetoxyborohydrate and one drop of acetic acid. The mixture was stirred overnight, diluted with DCM, washed with 1 M sodium hydroxide, dried over sodium sulfate and concentrated. The residue was purified by chromatography using 5% of MeOH in DCM as the eluent. $^1$H NMR (CDCl$_3$ 400 MHz) δ 7.85 (2H, m), 7.53 (2H, m), 7.38–7.27 (3H, m), 7.00–6.94 (1H, m), 5.19 (1H, m), 4.42–4.24 (2H, ser. m.), 3.91 (1H, m), 3.76 (1H, m), 3.50–3.38 (1H, m), 3.21 (1H, m), 2.89 (2H, m), 2.33–1.95 (4H, ser. m.), 1.64–1.20 (9H, ser. m., J=7.1 Hz), 0.85 (1H, ser. m.), 0.52 (2H, s), 0.11 (2H, s); MS (ES) m/e 564.1 (M+H)$^+$.

Other compounds prepared are shown below:
TABLE 21
| Compound No. | Structure | Retention Time (minutes) | Observed Mass |
|---|---|---|---|
| 170-A | 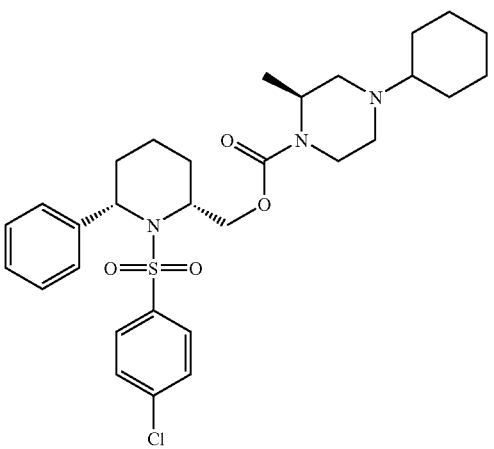 | 5.56 | 574.1 |
| 170-B | 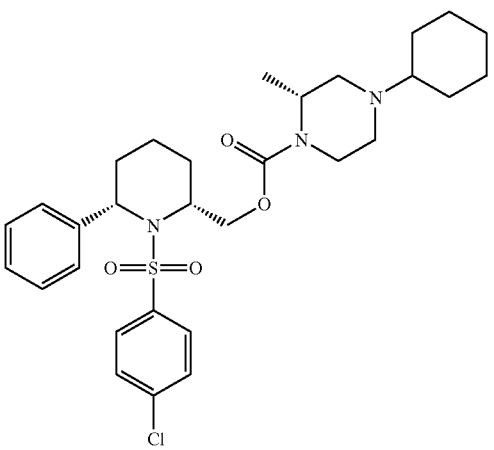 | 5.41 | 575.1 |
| 170-C | 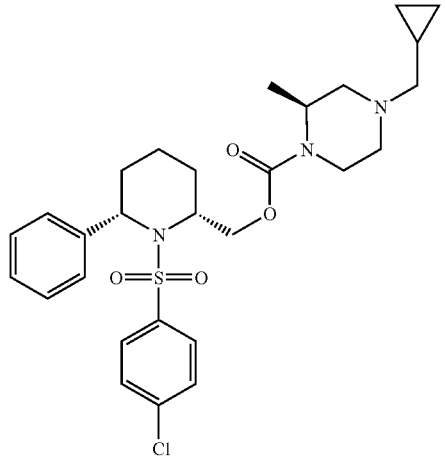 | 5.21 | 546.1 |

TABLE 21-continued
| Compound No. | Structure | Retention Time (minutes) | Observed Mass |
|---|---|---|---|
| 170-D | 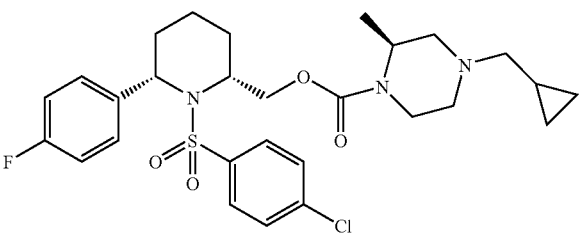 | 5.36 | 564.1 |
| 170-E | 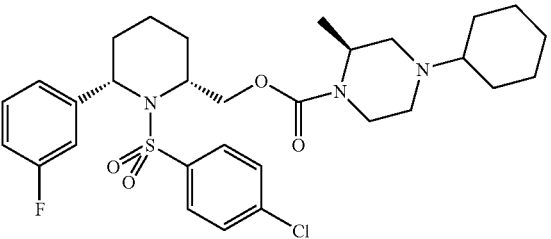 | 5.21 | 592.3 |
| 170-F | 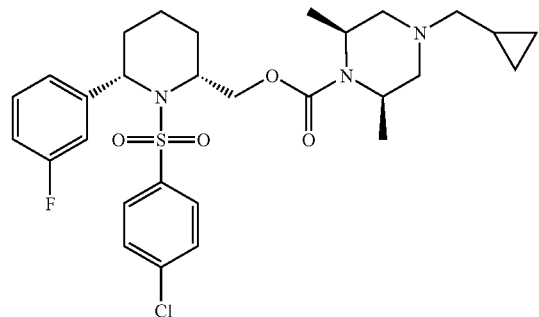 | 5.18 | 578.1 |
| 170-G | 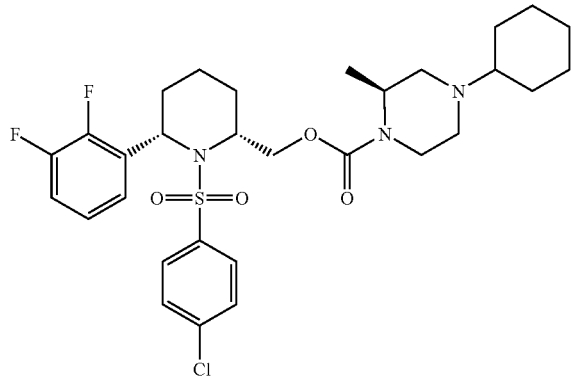 | 5.55 | 610.1 |
| 170-H | 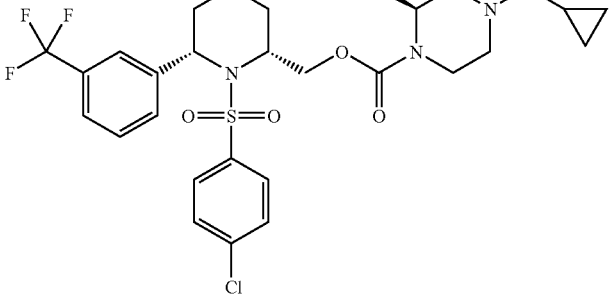 | 5.72 | 614.1 |

TABLE 21-continued

| Compound No. | Structure | Retention Time (minutes) | Observed Mass |
|---|---|---|---|
| 170-I | 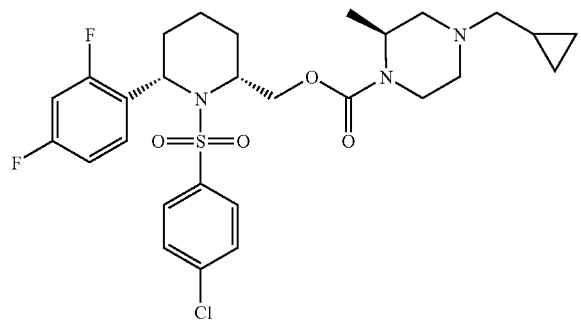 | 5.55 | 582.1 |
| 170-J | 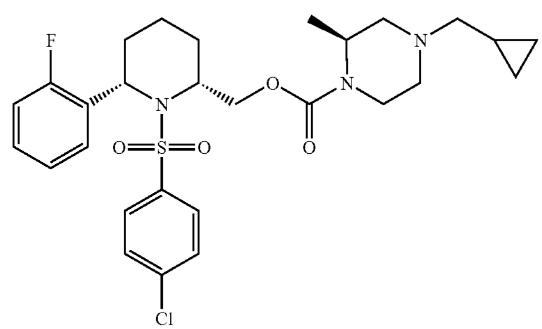 | 5.58 | 564.1 |
| 170-K | 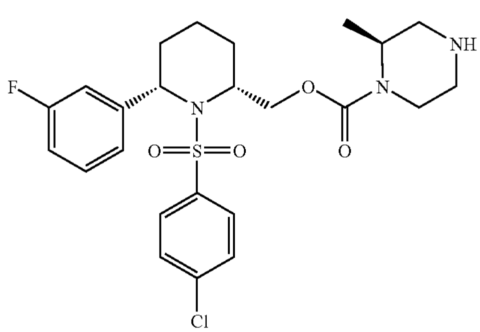 | 5.12 | 510.1 |
| 170-L | 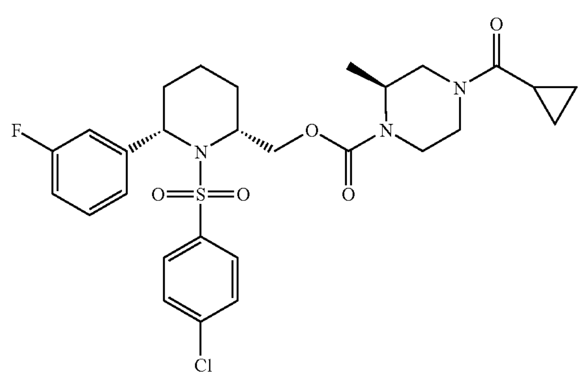 | 5.58 | 578.1 |

TABLE 21-continued

| Compound No. | Structure | Retention Time (minutes) | Observed Mass |
|---|---|---|---|
| 170-M | 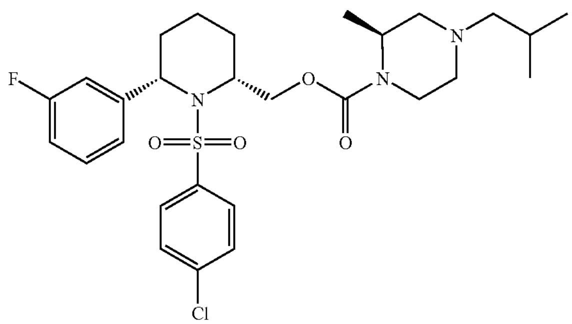 | 5.72 | 566.1 |
| 170-N | 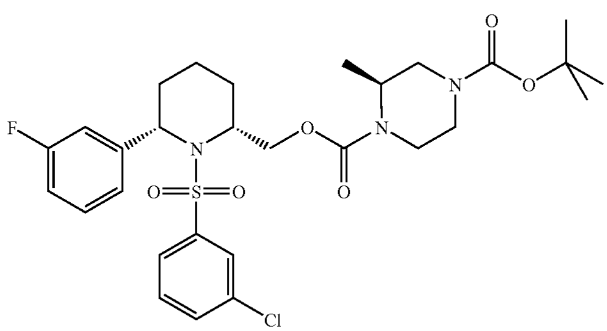 | 6.05 | 610.1 |
| 170-O | 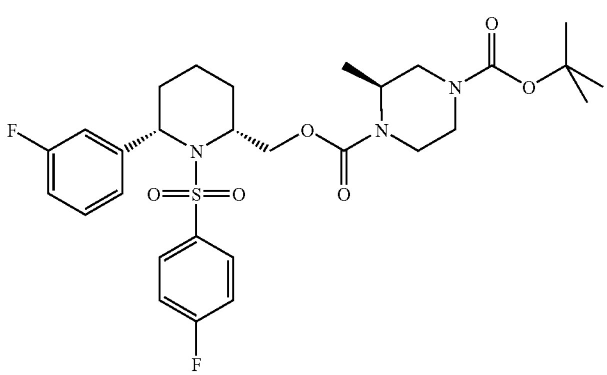 | 6.05 | 594.1 |
| 170-P | 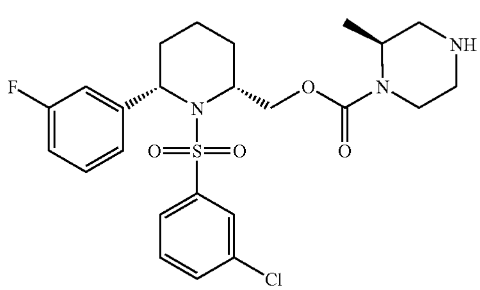 | 5.22 | 510.1 |

TABLE 21-continued
| Compound No. | Structure | Retention Time (minutes) | Observed Mass |
|---|---|---|---|
| 170-Q | 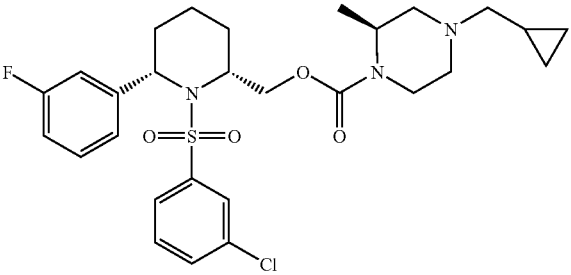 | 4.87 | 564.3 |
| 170-R | 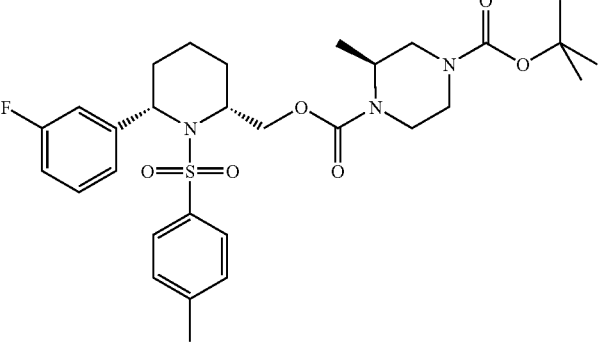 | 5.48 | 590.3 |
| 170-S | 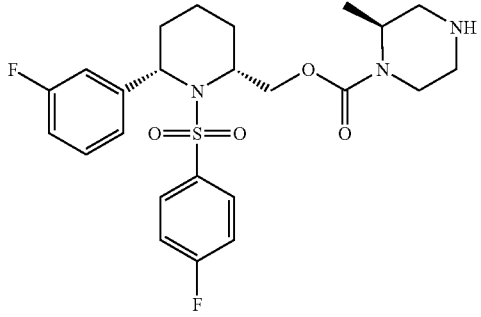 | 4.41 | 494.3 |
| 170-T | 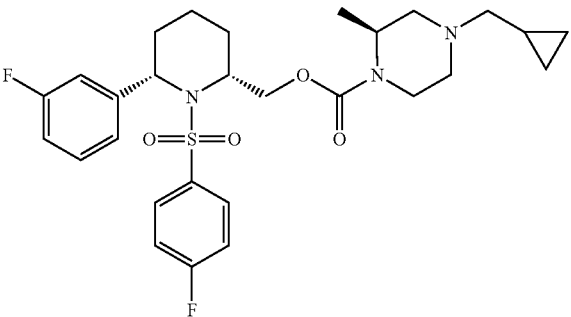 | 4.78 | 548.3 |

TABLE 21-continued

| Compound No. | Structure | Retention Time (minutes) | Observed Mass |
|---|---|---|---|
| 170-U | 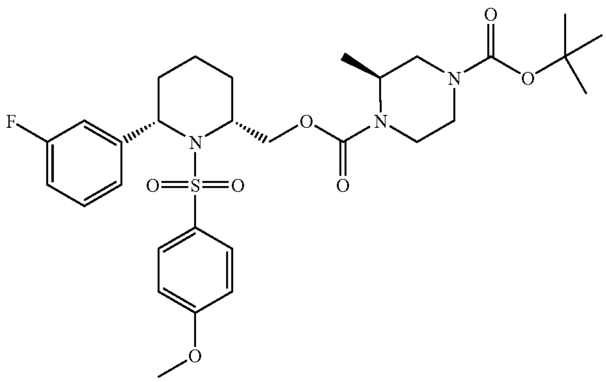 | 5.98 | 606.1 |
| 170-V | 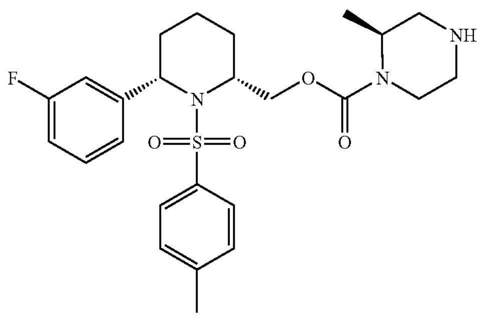 | 4.75 | 490.1 |
| 170-W | 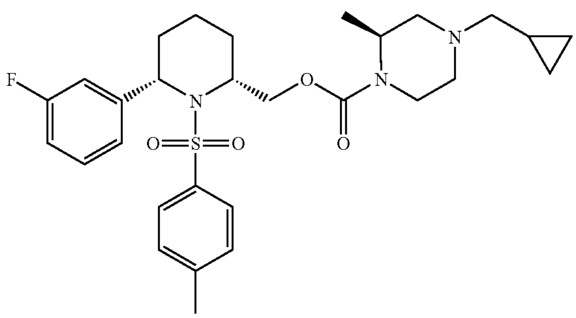 | 5.38 | 544.1 |
| 170-X | 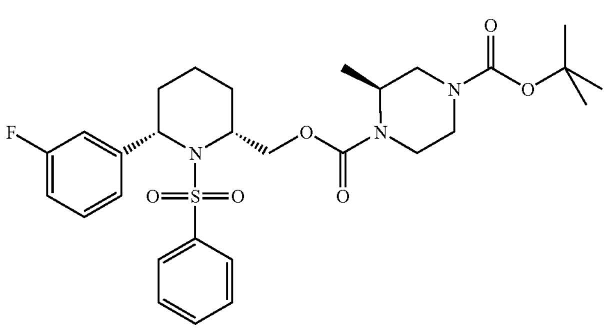 | 5.92 | 576.1 |

TABLE 21-continued
| Compound No. | Structure | Retention Time (minutes) | Observed Mass |
|---|---|---|---|
| 170-Y | 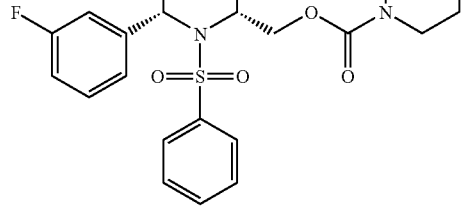 | 4.61 | 476.1 |
| 170-Z | 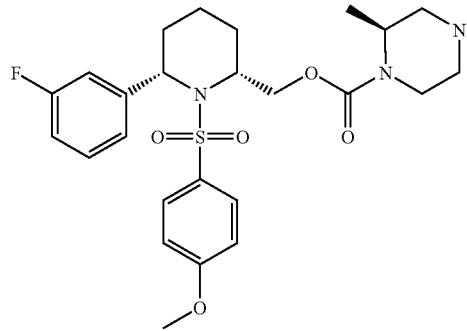 | 4.51 | 506.1 |
| 170-AA | 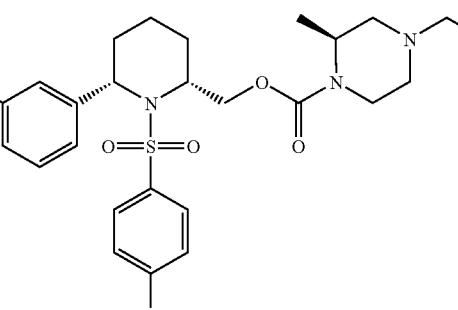 | 5.28 | 560.1 |
| 170-AB | 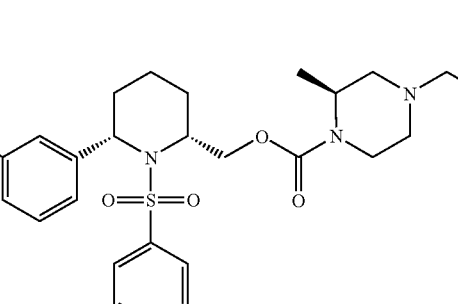 | 5.12 | 531.1 |

TABLE 21-continued
| Compound No. | Structure | Retention Time (minutes) | Observed Mass |
|---|---|---|---|
| 170-AC | 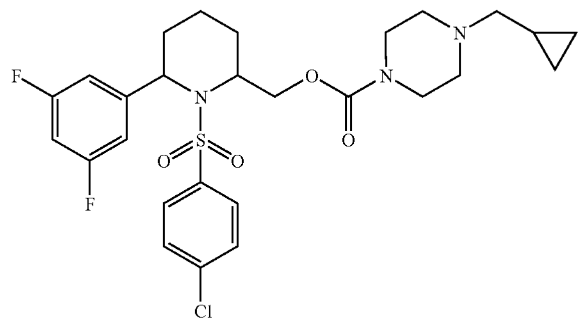 | 5.55 | 568.3 |
| 170-AD | 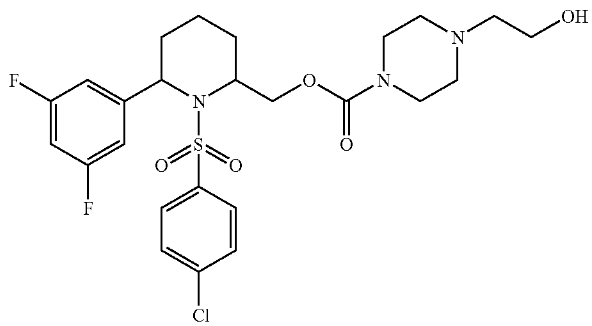 | 5.01 | 558.3 |
Example 171
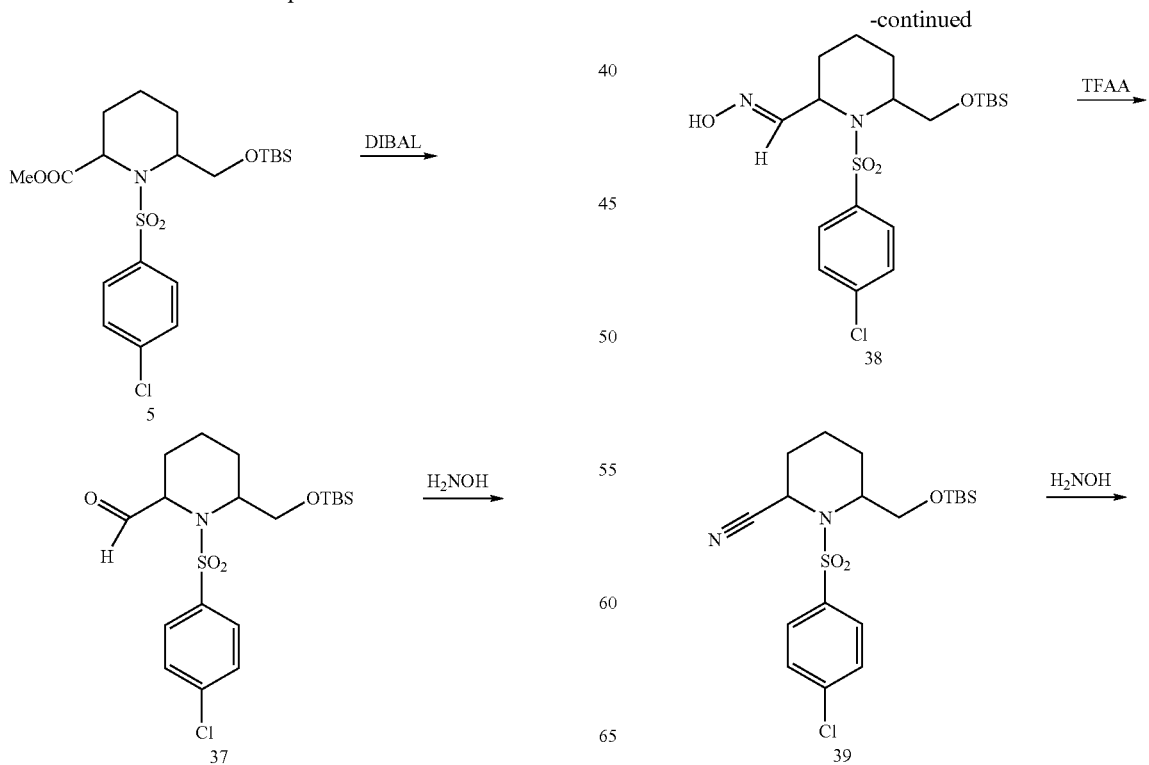

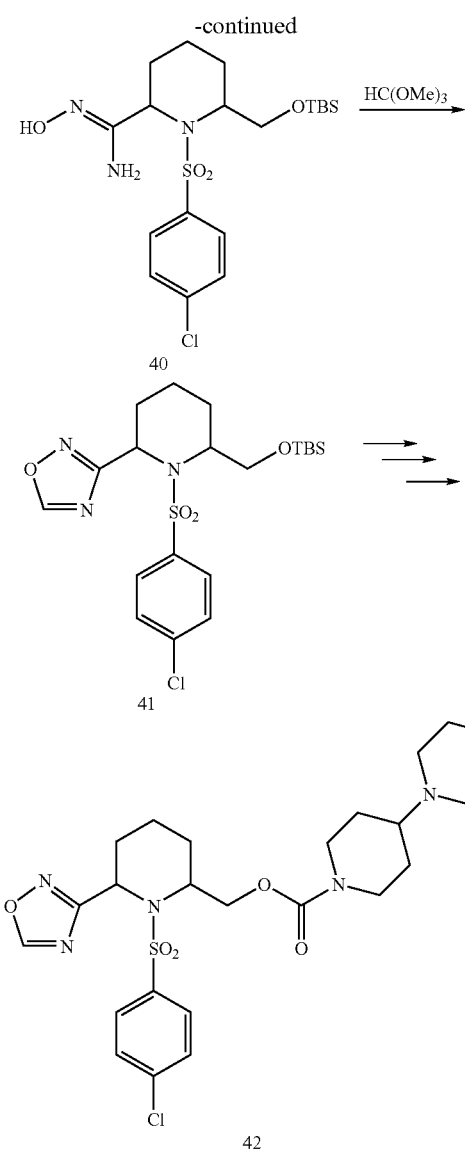

Step 1:

To a solution of 1.35 g (2.92 mmol) of Compound 5 in 20.0 mL of DCM at −78° C. was added 3.2 mL (3.2 mmol) of 1 M solution of DIBAL in toluene. The mixture was stirred for 5 min, quenched with a 20% aq. sodium potassium tartrate solution, warmed up to room temperature, extracted with DCM, dried over sodium sulfate and concentrated. The product was purified chromatographically using DCM as the eluent to furnish 1.06 g of aldehyde 37.

Step 2:

A mixture of 3.21 g of aldehyde 37, 3.21 g of hydroxylamine hydrochloride, 8 mL of triethylamine and 50 mL of ethanol was heated briefly with a heat gun to boiling until all components dissolved. The reaction mixture was stirred overnight at RT, the volatiles were evaporated, the residue was partitioned between DCM and water, and the aqueous phase was re-extracted with DCM. The combined organic phase was dried over sodium sulfate and concentrated. The product was purified chromatographically using gradient 5 to 20% of ethyl acetate in hexanes as the eluent to furnish 1.546 g of oxime 38.

Step 3:

To a solution of 1.21 g (2.71 mmol) of oxime 38 in 12 mL of DCM was added 2.18 mL (27 mmol) of pyridine followed by 1.14 g (5.42 mmol) of trifluoroacetic acid anhydride. The reaction mixture was stirred for 1 h, washed with water, dried over sodium sulfate and concentrated. The product was purified chromatographically using 10% of ethyl acetate in hexanes as the eluent to furnish 1.09 g of nitrile 39.

Step 4:

A mixture of 100 mg of nitrile 39, 100 mg of hydroxylamine hydrochloride, 0.1 ml of Hunig's base and 1.0 ml of ethanol was heated at 80° C. for 10 min. The heat was removed and the mixture was stirred over 24 h. The reaction mixture was partitioned between water and DCM and the organic phase was dried over sodium sulfate and concentrated. The product was purified chromatographically using 30% of ethyl acetate in hexanes as the eluent to furnish 90 mg of amidoxime 40.

Step 5:

A mixture of 90 mg of amidoxime 40, 3.0 mL of triethylorthoformate, 5 mg of tosic acid hydrate and 0.5 mL of DCM was heated at 100° C. over a period of 40 min. The reaction mixture was partitioned between DCM and sat. sodium bicarbonate, and the organic phase was dried over sodium sulfate and concentrated. The product was purified chromatographically using 20% of ethyl acetate in hexanes as the eluent to furnish 70 mg of oxadiazole 41.

Step 6:

The conversion of oxadiazole 41 to compound 42 was carried out according to Steps 1 and 2 of example 166. $^1$H NMR (CDCl$_3$ 300 MHz) δ 8.67 (1H, s), 7.89 (2H, d, J=8.05 Hz), 7.50 (2H, d, J=8.05 Hz), 5.42 (1H, d, J=5.8 Hz), 4.26 (1H, m), 4.12 (2H, m), 3.83 (2H, m), 2.69 (2H, m), 2.48 (4H, m), 2.37 (2H, m), 1.84–1.36 (15H, ser. m.), MS (ES) m/e 552.1 (M+H)$^+$.

Example 172

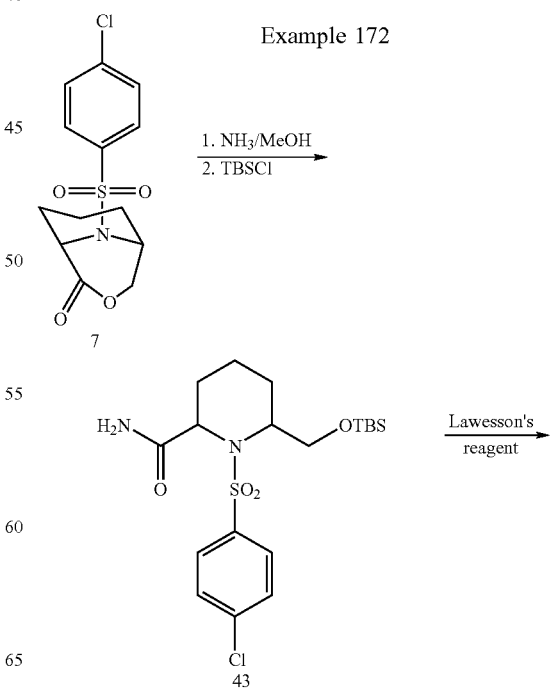

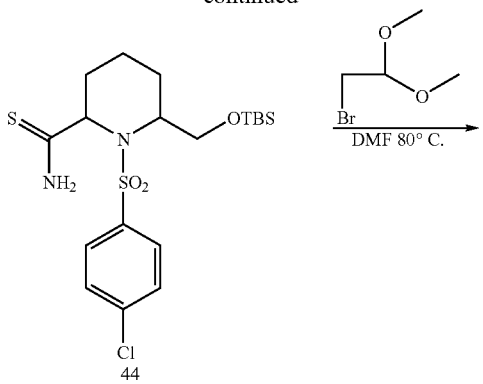

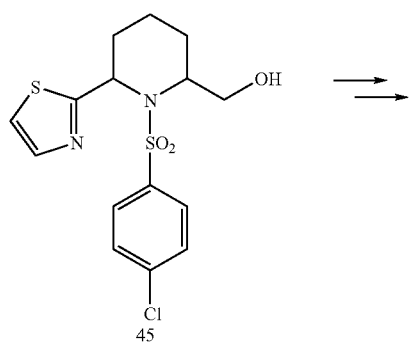

product purified by prep. TLC using 30% of ethyl acetate in hexanes as the eluent to furnish 70 mg of thioamide 44.

Step 3:

A mixture of 70 mg (0.151 mmol) of thioamide 44, 0.5 mL of dimethylacetal of bromoaldehyde in 1 mL of DMF was heated at 80° C. over a period of 5 h. The reaction mixture was partitioned between DCM and sat. NaHCO$_3$, dried and concentrated. The product was purified chromatographically using 30% of ethyl acetate in hexanes as the eluent to furnish 25 mg of thiazole 45.

Step 4:

Transformation of alcohol 45 to compound 46 was carried out according to Example 1 steps A and B. LCMS m/z=567.1, retention 4.88 min.

$^1$H NMR (CDCl$_3$ 300 MHz) δ 7.86 (2H, d, J=8.8 Hz), 7.68 (1H, d, J=3.3 Hz), 7.52 (2H, d, J=8.8 Hz), 7.37 (1H, d, J=3.3 Hz), 5.35 (1H, d, J=5.5 Hz), 4.36 (1H, m), 4.20 (2H, m), 3.83 (1H, dd, J=6.6, 11.0 Hz), 3.63 (1H, dd, J=8.7, 11.0 Hz), 2.82–2.33 (8H, ser. m.), 1.88–1.20 (15H, ser. m.), MS (ES) m/e 567.1 (M+H)$^+$.

Example 173

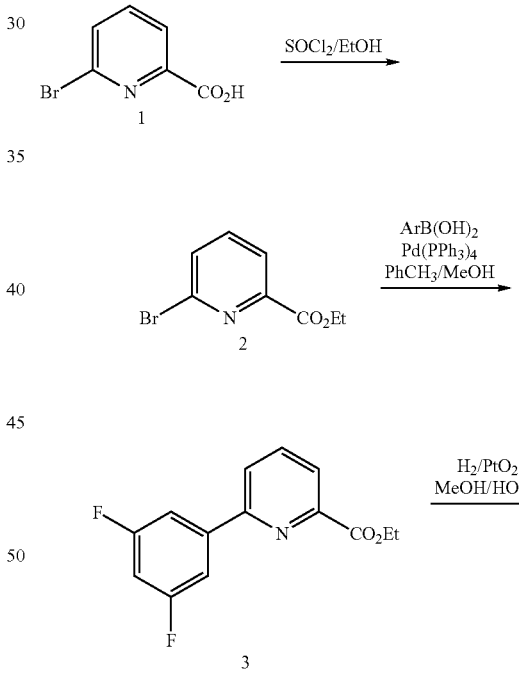

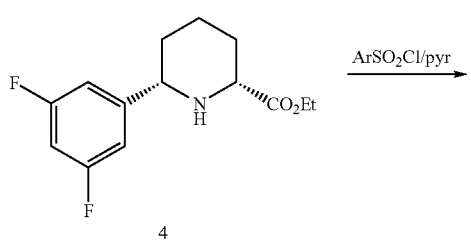

Step 1:

A mixture of 1.0 g of compound 7 in 10 mL of a 7 M solution of ammonia in methanol was stirred over a period of 3 h and then the volatiles were evaporated. 500 mg of the resulting product were dissolved in 5 mL of DMF and treated with 152 mg (2.24 mmol) of imidazole and 218 mg (1.456 mmol) of TBSCl. The reaction mixture was stirred overnight, diluted with DCM, washed with sat. NaHCO$_3$, dried and concentrated. The product was purified chromatographically using 20% of ethyl acetate in hexanes as the eluent to furnish 500 mg of amide 43.

Step 2:

A mixture of 250 mg (0.56 mmol) of amide 43 and 226 mg (0.56 mmol) of Lawesson's reagent was refluxed in 3 mL of DCM over 8 h. The solvent was evaporated and the

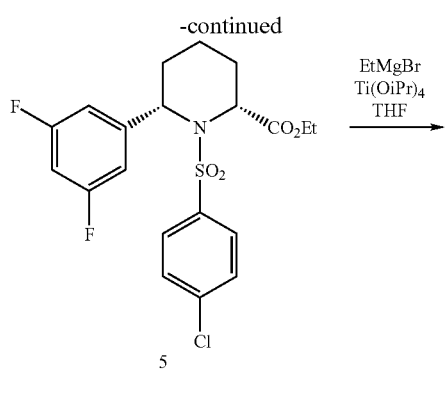

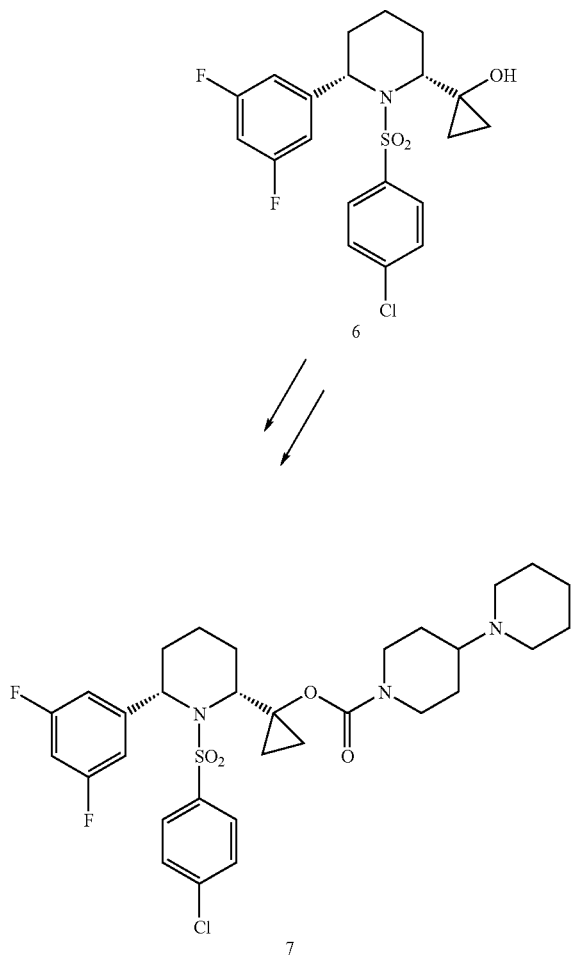

Step 1:

To a stirring solution of 6-bromopicolinic acid (14.25 g, 70.3 mmol) in anhydrous ethanol (250 ml) was slowly added thionyl chloride (60 ml) at 5° C. After the addition was completed, the ice-bath was removed and the mixture was stirred at 25° C. for 3 hr. The solvent was evaporated under vacuum, the aqueous residue basified with saturated sodium carbonate, and extracted with DCM. The organic phase was dried over $Na_2SO_4$ and concentrated to give ethyl 6-bromopicolinate as a white solid (15.75 g).

Step 2:

Ethyl 6-bromopicolinate (15.75 g, 68.5 mmol), 3,5-difluorophenylboronic acid (12.98 g, 82.2 mmol), tetrakis(triphenylphsphine)palladium (7.9 g, 6.85 mmol) and sodium carbonate (18 g) in toluene (160 mL) and methanol (80 mL) was heated under reflux for 16 hr, then cooled to room temperature, diluted with DCM, and filtered. The filtrate was washed with water and the dried ($Na_2SO_4$) organic solution was concentrated, and the residue purified chromatographically using 5% ethyl acetate in hexanes as eluent to give 10.6 g of the product, as a white solid.

Step 3:

Under a hydrogen atmosphere, a solution of Compound 3 (10.5 g, 39.9 mmol) in methanol (400 mL) and glacial acetic acid (40 mL) was stirred in the presence of platinum oxide (1.81 g) for 72 hr. The reaction mixture was purged with nitrogen, filtered and then concentrated under vacuum. The residue was taken up in water, basified with saturated sodium carbonate, and extracted with DCM. The organic phase was dried over $Na_2SO_4$ and concentrated under vacuum to give a light yellow foam (10.7 g).

Step 4:

A solution of Compound 4 (10.7 g, 39.7 mmol) in pyridine (100 mL) was treated with 4-chlorobenzenesulfonylchloride (16.8 g, 79.5 mmol). The mixture was heated at 60° C. for 4 hr, cooled to room temperature, concentrated under vacuum, and the residue was subjected to flash-chromatography over silica gel (eluting with 10% ethyl acetate in hexanes) to provide 14 g of product, as a white powder.

Step 5:

To a stirring solution of Compound 5 (2.0 g, 4.5 mmol) and titanium isopropoxide (0.41 ml, 1.35 mmol) in terahydrofuran (15 mL) was added a solution of ethylmagnesium bromide (4.5 mL, 13.5 ml, 3M in $Et_2O$) slowly over a period of 1 hr at 5° C., and the stirring was continued for 10 min. The mixture was then poured into cooled (5° C.) 10% aq HCl (45 mL) and the products were extracted with DCM (3×25 mL). The combined DCM extracts were washed with water (25 mL), dried ($Na_2SO_4$), and the solvent was removed. The product was obtained by flash-chromatography (eluting with 13% ethyl acetate in hexanes) as a light yellow oil (1.5 g).

Step 6:

The compound was prepared from Compound 6 using procedures similar to Example 1, Step 4(a) and 4(b), except that step 4(a) was modified so that a 2:1 mixture of THF and acetonitrile was used as solvent instead of DCM, and the mixture was heated at 78° C. for 16 hr.

$^1$H NMR ($CDCl_3$, 400 MHz) δ 7.81 (2H, d, J=8.3 Hz), 7.79 (2H, d, J=7.9 Hz), 7.49 (2H, d, J=8.1 Hz), 6.75–6.62 (1H, m), 5.50–4.60 (2H, m), 4.35–3.62 (2H, m), 2.90–2.20 (7H, m), 2.10–0.86 (16H, m), 0.85–0.63 (2H, m), 0.50–0.10 (2H, m); MS (ES) m/e 623.1 (M+H)$^+$.

Compounds prepared via a similar method:

TABLE 22

| Compound No. | Structure | Time (minutes) | Observed Mass |
|---|---|---|---|
| 173-A | 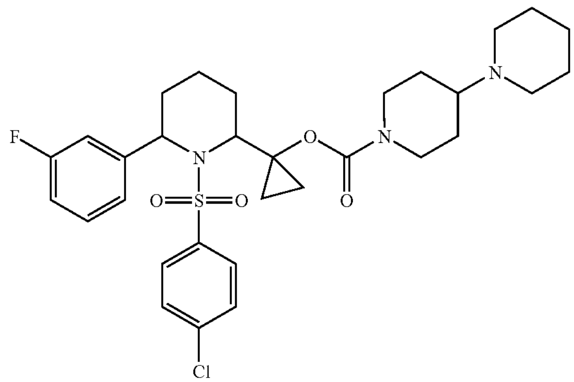 | 5.45 | 604.1 |
| 173-B | 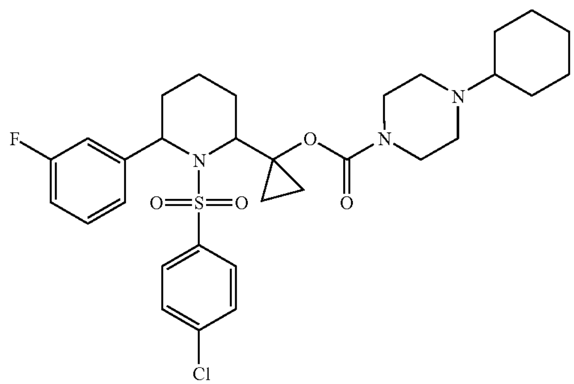 | 5.55 | 604.1 |
| 173-C | 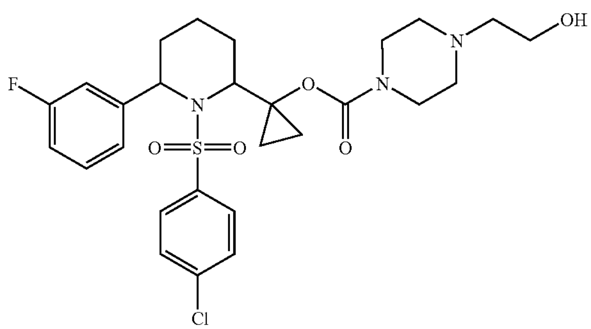 | 4.95 | 566.1 |
| 173-D | 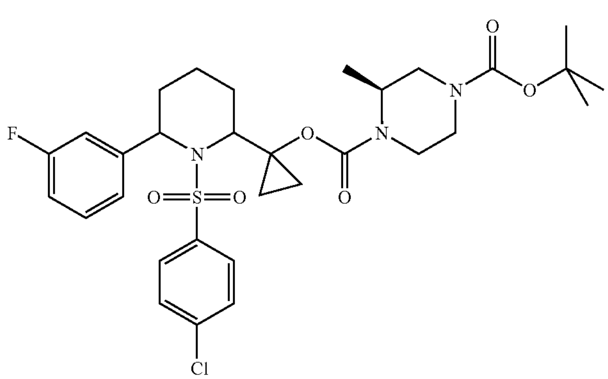 | 5.62 | 636.2 |

TABLE 22-continued
| Compound No. | Structure | Time (minutes) | Observed Mass |
|---|---|---|---|
| 173-E | 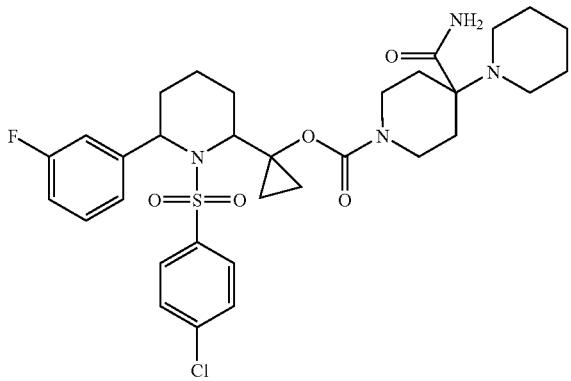 | 4.65 | 647.4 |
| 173-F | 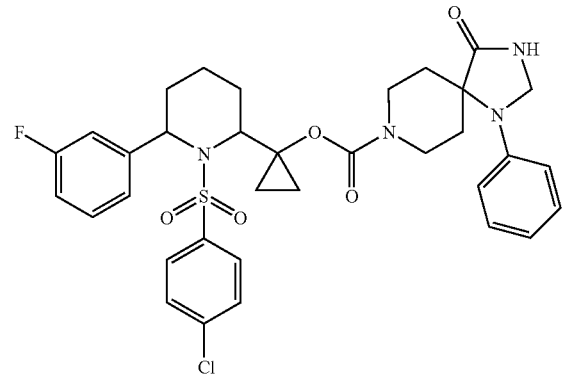 | 5.08 | 667.4 |
| 173-G | 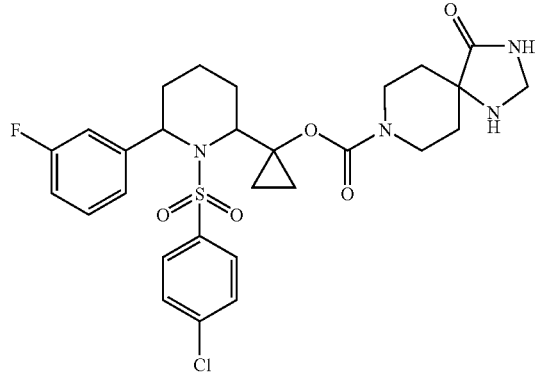 | 4.24 | 591.3 |

TABLE 22-continued

| Compound No. | Structure | Time (minutes) | Observed Mass |
|---|---|---|---|
| 173-I | 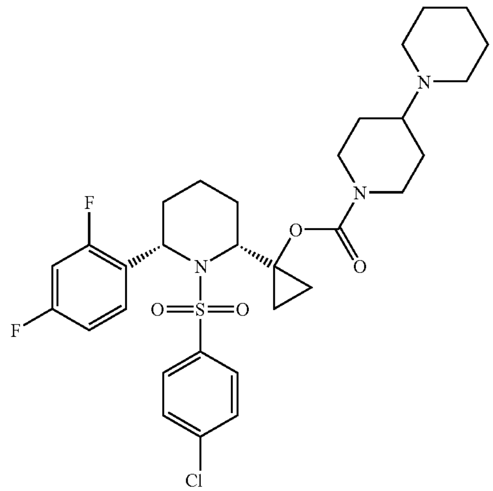 | 5.75 | 622.1 |
| 173-J | 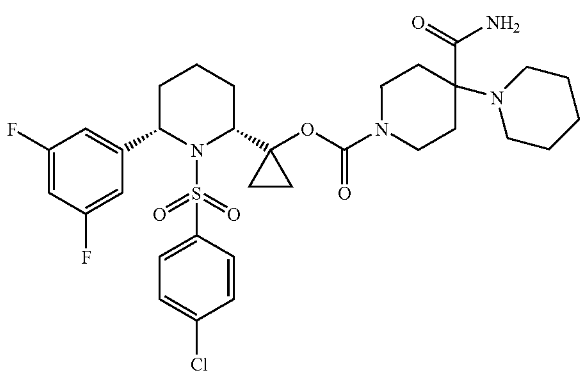 | 5.12 | 665.2 |
| 173-K | 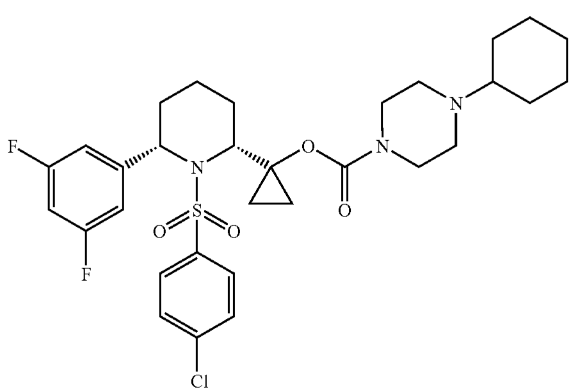 | 5.45 | 622.1 |

TABLE 22-continued

| Compound No. | Structure | Time (minutes) | Observed Mass |
|---|---|---|---|
| 173-L | 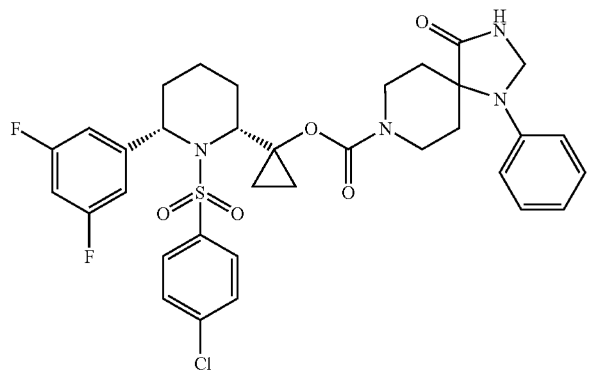 | 5.42 | 685.2 |
| 173-M | 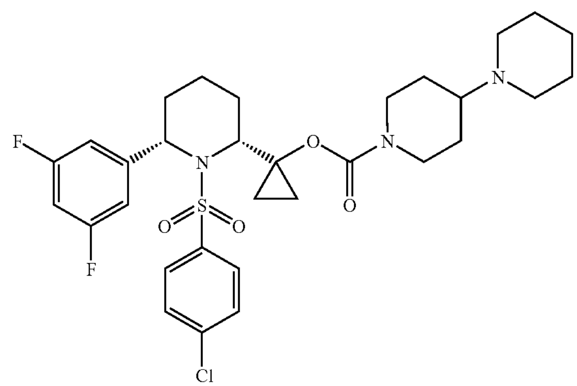 | 5.55 | 622.1 |
| 173-N | 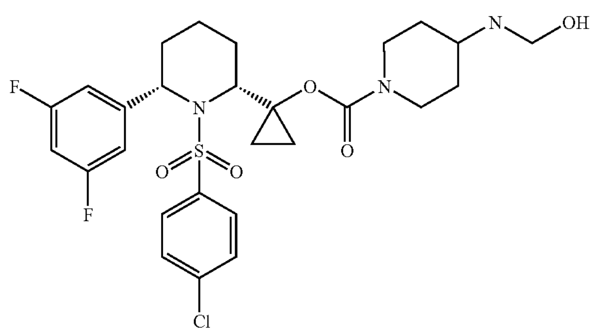 | 5.02 | 584.1 |
| 173-O | 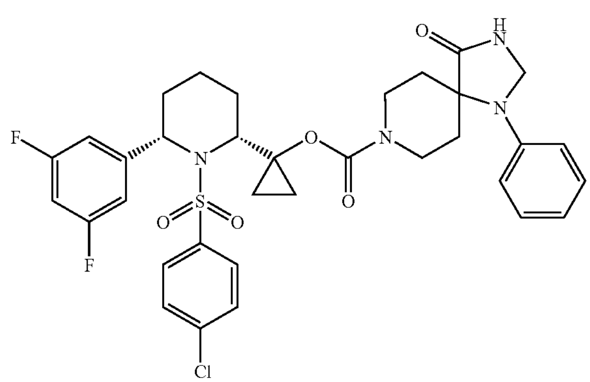 | 5.42 | 685.2 |

TABLE 22-continued

| Compound No. | Structure | Time (minutes) | Observed Mass |
|---|---|---|---|
| 173-P | 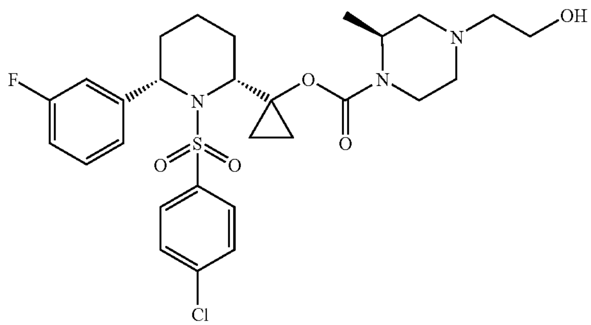 | 4.91 | 580.1 |
| 173-Q | 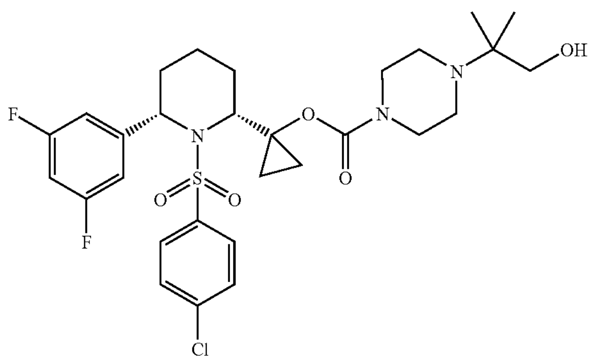 | 5.08 | 612.1 |
| 173-R | 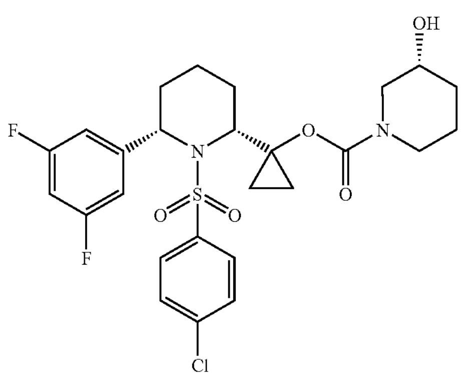 | 4.68 | 555.1 |
| 173-S | 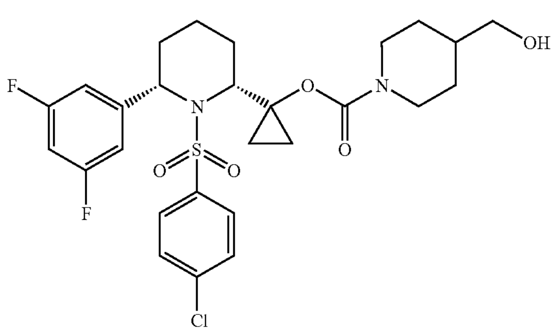 | 4.69 | 569.1 |

TABLE 22-continued
| Compound No. | Structure | Time (minutes) | Observed Mass |
|---|---|---|---|
| 173-T | 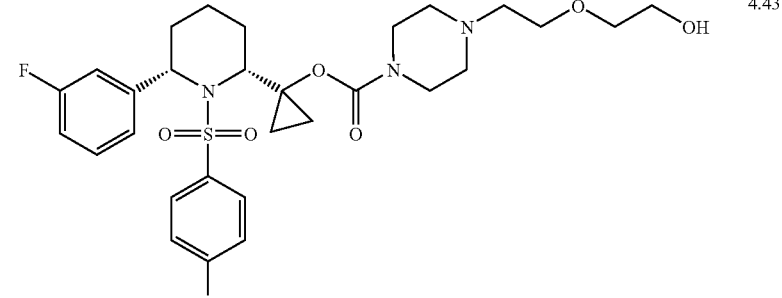 | 4.43 | 494.1 |
| 173-U | 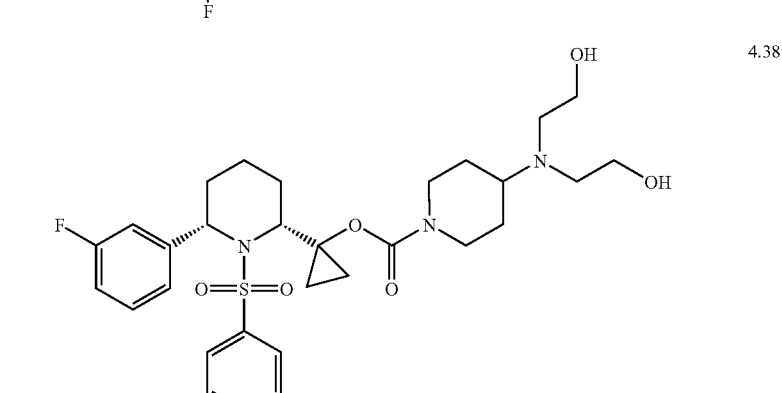 | 4.38 | 608.1 |
Example 174
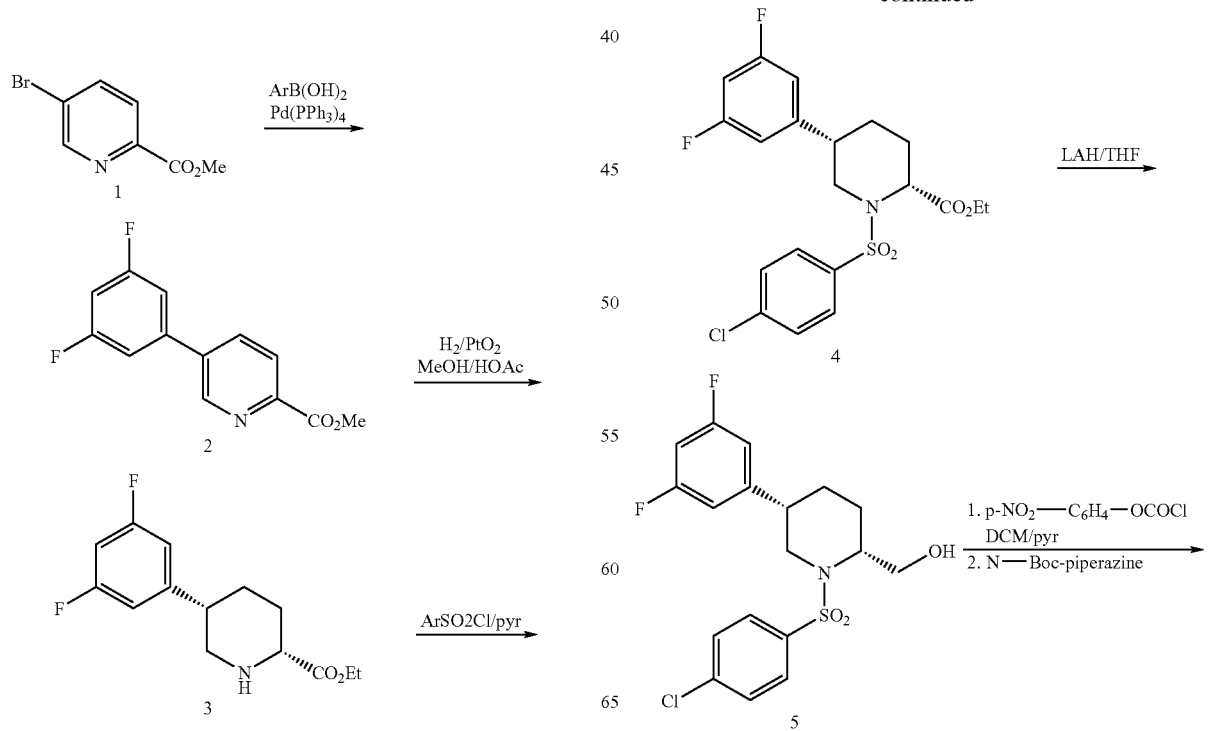

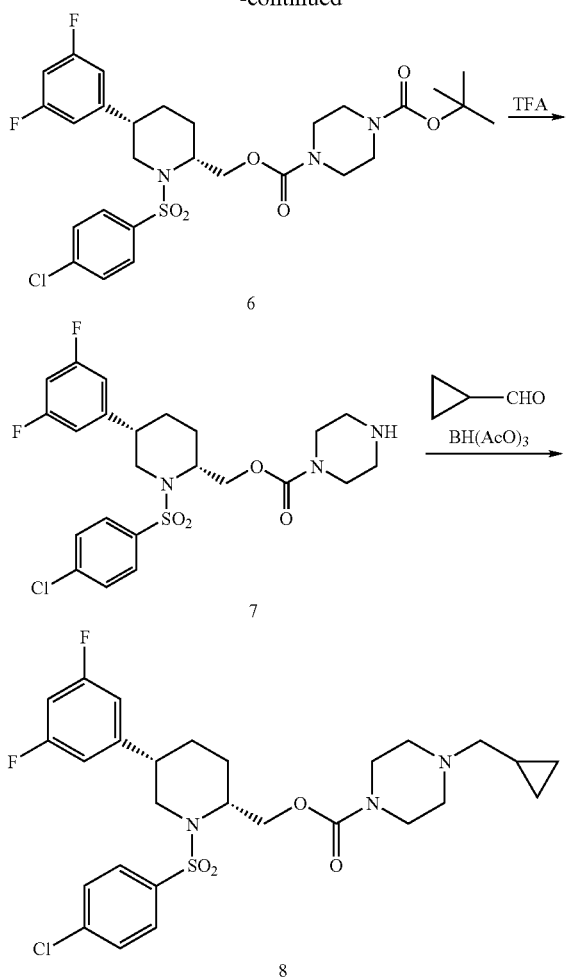

Step 1:

Methyl 5-Bromopicolinate 1 was obtained as described in J. J. Song and N. K. Yee, *J. Org. Chem.* 2001, 66, 605–608, which is incorporated by reference in its entirety. A solution of this ester (2.5 g, 11.6 mmol) in a mixture of toluene (160 ml) and ethanol (80 ml) was treated with 3,5-difluorobenzeneboronic acid (2.19 g, 13.9 mmol), tetrakis(triphenylphosphine)palladium (1.34 g, 1.16 mmol) and sodium carbonate (2.5 g). The mixture was heated at reflux for 16 hr. The solvent was removed at reduced pressure. The residue was redissolved in DCM, washed with water, dried over $Na_2SO_4$, concentrated and purified chromatographically using 30% ethyl acetate in hexanes as the eluent to furnish 2.17 g of the product.

Step 2:

Under a hydrogen atmosphere, a solution of Compound 2 (2.3 g, 9.2 mmol) in methanol (90 mL) and glacial acetic acid (10 mL) was stirred in the presence of platinum oxide (0.42 g) for 8 hr. The reaction mixture was purged with nitrogen, filtered and then concentrateed under vacuum. The residue was taken up in water, basified with saturated sodium carbonate, and extracted with DCM. The organic phase was dried over $Na_2SO_4$ and concentrated under vacuum to give a light yellow foam (2.3 g).

Step 3:

A solution of Compound 3 (2.3 g, 9.2 mmol) in pyridine (20 ml) was treated with 4-chlorobenzenesulfonylchloride (3.8 g, 18.5 mmol). The mixture was heated at 60° C. for 16 hr, cooled to room temperature, concentrated under vacuum, and the residue subjected to flash-chromatography over silica gel (eluting 10% ethyl acetate in hexanes) to provide 2.1 g of product, as a white powder.

Step 4:

To an ice-cold solution of Compound 4 (2.1 g, 4.9 mmol) in THF (15 mL) was slowly added a solution of lithium aluminum hydride (9.8 mL, 1 M THF). The cooling bath was removed and the reaction was stirred at ambient temperature for 2 hr. The mixture was quenched sequentially with water (0.4 mL), 15% NaOH (0.4 mL), and water (1.2 mL). The mixture was stirred for 1 hr, filtered, the filtrate dried over $Na_2SO_4$, and concentrated to give 1.8 g of the product as yellow solid.

Step 5:

This was prepared according to Step 4 of Example 1, using N-Boc piperazine at the last stage as the amine.

Step 6:

A solution of Compound 6 (100.0 mg, 0.163 mmol) in DCM (3 mL) was treated with TFA, and the mixture was stirred at ambient temperature for 2 hr. The mixture was basified with saturated sodium carbonate, extracted with DCM, dried over $Na_2SO_4$, and concentrated to afford 72.3 mg of the product, as a white powder.

Step 7:

To a solution of Compound 7 (50.0 mg, 0.097 mmol) in dichloroethane (2.0 ml) was added cyclopropanecarboxaldehyde (20.0 mg, 0.28 mmol) followed by sodium triacetoxyborohydride (60.0 mg, 0.28 mmol) and one drop of acetic acid. After stirring at ambient temperature for 16 hr, the mixture was diluted with water and basified with saturated sodium carbonate. The crude product was extracted with DCM, washed with water, dried over $Na_2SO_4$, and concentrated. The crude product was purified by preparative TLC (eluting with 95:5:0.5; $DCM:MeOH:NH_4OH$) to furnish 30.0 mg of the product, as a white powder. $^1H$ NMR ($CDCl_3$, 400 MHz) δ 7.78 (2H, d, J=7.8 Hz), 7.49 (2H, d, J=7.8 Hz), 6.75–6.62 (3H, m), 4.50–4.36 (2H, m), 4.18–4.02 (1H, m), 3.89–3.71 (1H, m), 3.52 (4H, s. br.), 3.08 (1H, t, J=9.0 Hz)), 2.65–2.34 (4H, m), 2.34 (2H, d, J=6.6 Hz), 1.84–1.56 (4H, m), 0.95–0.74 (1H, m), 0.53 (2H, d, J=7.8 Hz), 0.11 (2H, d, J=4.5 Hz); MS (ES) m/e 569.1 $(M+H)^+$.

Example 175

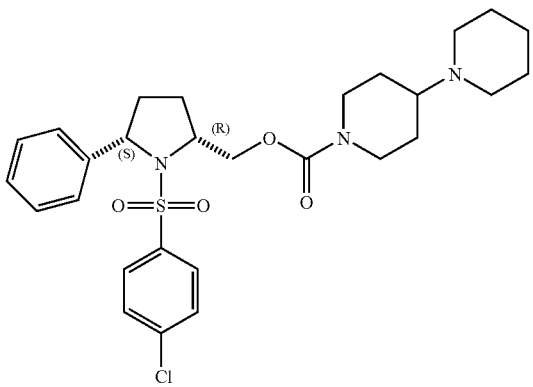

Step 1

(2R,5S)-Boc-5-phenyl-pyrrolidine-2-carboxylic acid (1.3 g, 4.5 mmol, obtained from SNPE North America LLC, 5 Vaughn Drive—Suite 111, Princeton, N.J. 08540, USA) was added to 10 mL of 4N HCl in dioxane and the mixture was stirred at room temperature for 2 hr. The mixture was concentrated under vacuum to give 1.0 g (100%) of (2R,5S)-5-phenyl-pyrrolidine-2-carboxylic acid HCl salt as a white solid. The solid was dissolved in 7 mL of anhydrous THF and the solution was added slowly into a stirred solution of 1 M LiAlH$_4$ in THF (10.3 mL, 10.3 mmol, 3 eq) at room temperature. The mixture was then heated at reflux for 4 hr. After cooling to room temperature, the reaction mixture was treated sequentially with 0.42 mL of water, 0.85 mL of 1 N NaOH, and 1.26 mL of water. The mixture was stirred for 1 hr and the white precipitate was filtered off. The filtrate was dried (Na$_2$SO$_4$) and concentrated under vacuum to give 0.78 g (98%) of (2R,5S)-(5-phenyl-pyrrolidin-2-yl)-methanol as a yellow oil. 1H NMR (CDCl$_3$, 300 MHz) δ7.60–7.30 (5H, m), 4.40 (1H, m), 3.78 (1H, m), 3.60 (2H, m), 2.60 (2H, br.s), 2.25 (1H, m), 2.10 (1H, m), 1.80 (2H, m).

Step 2

To a solution of (2R,5S)-(5-phenyl-pyrrolidin-2-yl)-methanol (0.78 g, 4.4 mmol) in CH$_2$Cl$_2$ (7 mL) at 0° C. was added 0.72 mL (5.2 mmol, 1.2 eq) of Et$_3$N followed by a slow addition of 0.66 mL (5.2 mmol, 1.2 eq) of TMSCl. The mixture was stirred at 0° C. for 45 min. Water (3 mL) was added to quench the reaction. The organic layer was separated and the aqueous layer was extracted with CH$_2$Cl$_2$ (2 mL×2). The combined organic layer was dried (Na$_2$SO$_4$) and concentrated under vacuum to give 0.98 g (89%) of (2R,5S)-2-phenyl-5-trimethylsilanyloxymethyl-pyrrolidine as a yellow oil. 1H NMR (CDCl$_3$, 300 MHz) δ 7.60–7.30 (5H, m), 4.30 (1H, m), 3.85 (2H, m), 3.50 (1H, m), 2.25 (1H, m), 2.05 (1H, m), 0.25 (9H, m).

Step 3

To a solution of (2R,5S)-2-phenyl-5-trimethylsilanyloxymethyl-pyrrolidine (0.98 g, 3.9 mmol) in ClCH$_2$CH$_2$Cl (5 mL) was added 1.9 mL (13.7 mmol, 3.5 eq) of Et$_3$N and 1.45 g (6.86 mmol, 1.8 eq) of 4-chlorobenzenesulfonyl chloride. The mixture was heated at 70° C. for 16 hr. After cooling to room temperature, the mixture was diluted with CH$_2$Cl$_2$ (20 mL), washed with water (10 mL), saturated brine (10 mL), dried (Na$_2$SO$_4$) and concentrated under vacuum. The crude product was chromatographed on silica gel (2% EtOAc/hexane) to give 0.78 g (46%) of (2R,5S)-1-(4-chloro-benzenesulfonyl)-2-phenyl-5-trimethylsilanyloxymethyl-pyrrolidine as a yellow gum.

1H NMR (CDCl$_3$, 300 MHz) δ 7.80 (2H, d), 7.55 (2H, d), 7.40 (5H, m), 4.72 (1H, t), 4.07 (2H, m), 3.85 (1H, m), 2.20–2.00 (3H, m), 1.82 (1H, m), 0.30 (9H, m).

Step 4

To a solution of (2R,5S)-1-(4-chloro-benzenesulfonyl)-2-phenyl-5-trimethylsilanyloxymethyl-pyrrolidine (0.76 g, 1.8 mmol) in 15 mL of MeOH at 0° C. was added K$_2$CO$_3$ (15 mg, 0.11 mmol, catalyst). After stirring at 0° C. for 30 min, the reaction mixture was partitioned between EtOAc (50 mL) and saturated brine (50 mL). The organic phase was separated, dried (Na$_2$SO$_4$) and concentrated under vacuum to give 0.63 g (100%) of (2R,5S)-[1-(4-chloro-benzenesulfonyl)-5-phenyl-pyrrolidin-2-yl]-methanol as a yellow gum. 1H NMR (CDCl$_3$, 300 MHz) δ 7.90 (1H, d), 7.60 (1H, d), 7.40 (5H, m), 4.87 (1H, t), 4.10–3.90 (3H, m), 2.90 (1H, m), 2.05 (2H, m), 1.85 (2H, m). HPLC analysis using an analytical chiracel OD column (hexane/isopropanol) showed an e.e. >99% for this compound (r.t. for (2R,5S)-eantiomer=9.9 min, r.t. for (2S,5R)-enantiomer=12.3 min).

Step 5

To a solution of (2R,5S)-[1-(4-chloro-benzenesulfonyl)-5-phenyl-pyrrolidin-2-yl]-methanol (0.040 g, 0.11 mmol) in 1 mL of CH$_2$Cl$_2$ was added 0.046 mL (0.33 mmol, 3 eq) of Et$_3$N followed by 0.022 g (0.11 mmol, 1 eq) of 4-nitrophenyl chloroformate. The mixture was stirred at room temperature for 16 hr. 4-Piperidinopiperidine (0.018 g, 0.11 mmol, 1 eq) was added and stirring continued for 6 hr. The mixture was diluted with 10 mL of CH$_2$Cl$_2$ and washed with 1 N NaOH (5 mL×2), water (5 mL×2), and saturated brine (5 mL). The organic layer was dried (Na$_2$SO$_4$) and concentrated under vacuum to give a yellow gum. Purification using reverse phase prep-HPLC gave 0.030 g (51%) of the desired product (2R,5S)-[1,4']bipiperidinyl-1'-carboxylic acid 1-(4-chloro-benzenesulfonyl)-5-phenyl-pyrrolidin-2-ylmethyl ester as a white solid. 1H NMR (CD$_3$OD, 300 MHz) δ 7.97 (2H, d), 7.75 (2H, d), 7.60–7.50 (5H, m), 4.80 (1H, t), 4.55–4.20 (3H, m), 3.65–3.40 (4H, m), 3.20–2.95 (4H, m), 2.30–1.60 (14H, m). MS(ESI): MH$^+$=546.2.

Example 176

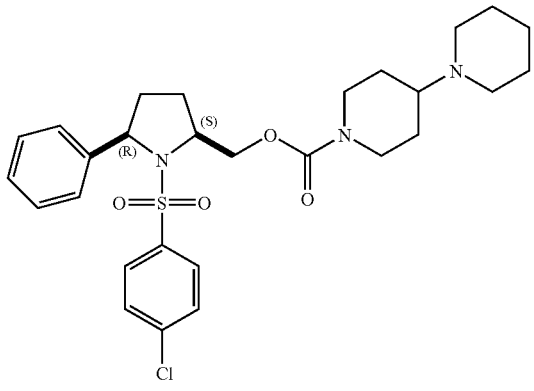

Following a similar procedure as in Example 175 except for using (2S,5R)-Boc-5-phenyl-pyrrolidine-2-carboxylic acid (1.3 g, 4.5 mmol, obtained from SNPE North America LLC, 5 Vaughn Drive—Suite 111, Princeton, N.J. 08540, USA) as the starting material, 0.035 g (59%) of (2S,5R)-[1,4']bipiperidinyl-1'-carboxylic acid 1-(4-chloro-benzenesulfonyl)-5-phenyl-pyrrolidin-2-ylmethyl ester was obtained as a white solid. MS(ESI): MH$^+$=546.2.

Following procedures similar to those in Example 175, the compounds in Table 23 were prepared.

TABLE 23

| Compound | Structure | Exact MS, calc. | MS (ESI) MH+ found |
|---|---|---|---|
| 176-A | 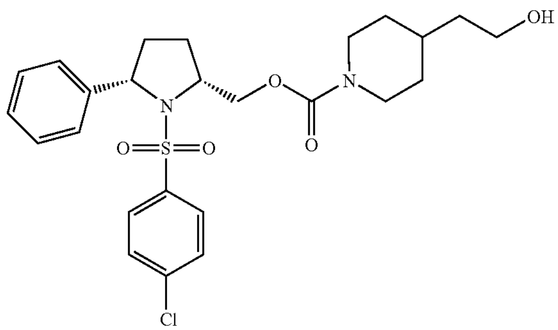 | 506.16 | 506.9 |
| 176-B | 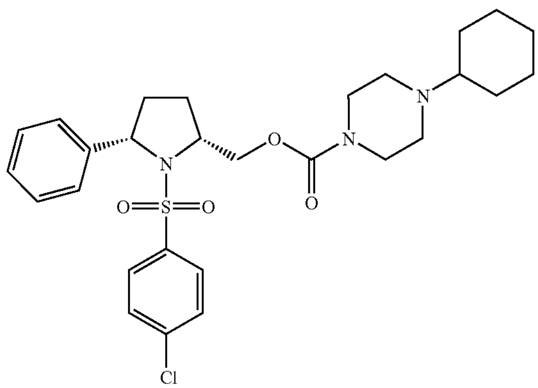 | 545.21 | 546.2 |
| 176-C | 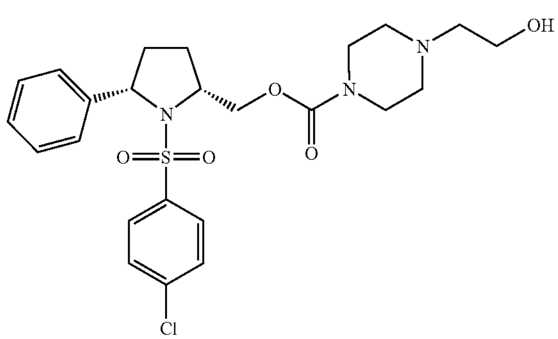 | 507.16 | 508.0 |
| 176-D | 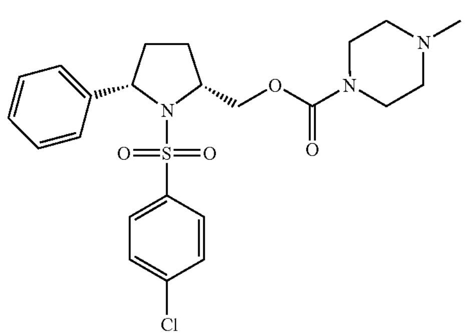 | 477.15 | 478.1 |

TABLE 23-continued

| Compound | Structure | Exact MS, calc. | MS (ESI) MH+ found |
|---|---|---|---|
| 176-E | 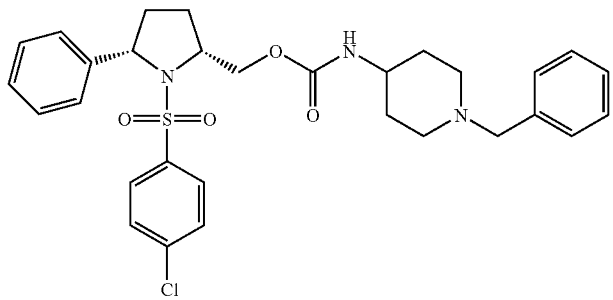 | 567.20 | 568.1 |
| 176-F | 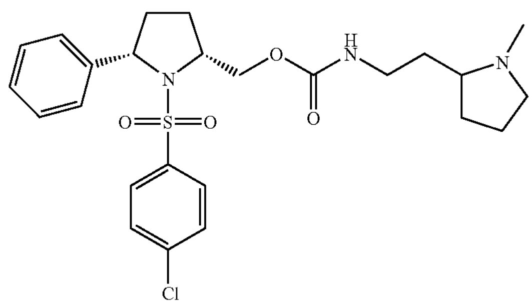 | 505.18 | 506.1 |
| 176-G | 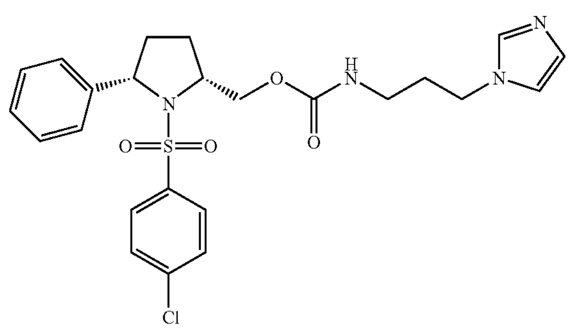 | 502.14 | 503.1 |
| 176-H | 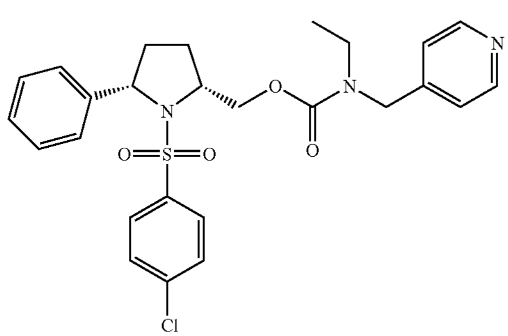 | 513.15 | 514.1 |

TABLE 23-continued

| Compound | Structure | Exact MS, calc. | MS (ESI) MH+ found |
|---|---|---|---|
| 176-I | 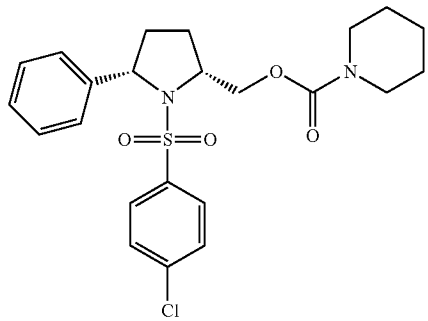 | 462.14 | 462.9 |
| 176-J | 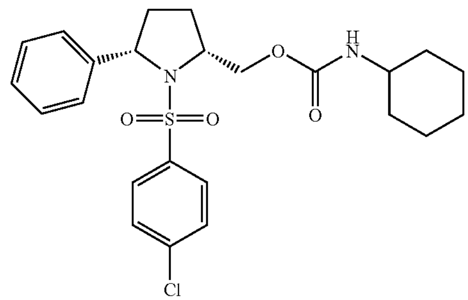 | 476.15 | 476.9 |

Example 177

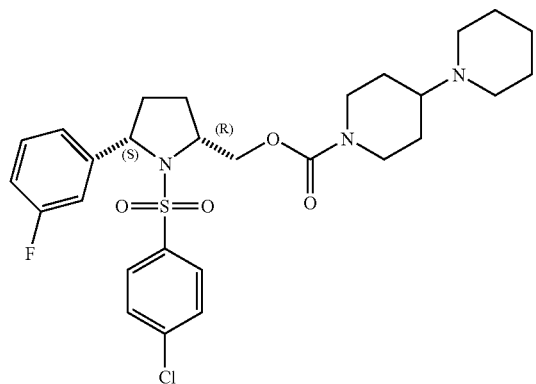

Step 1

Thionyl chloride (8.5 mL, 0.12 mol) was added dropwise into 40 mL of anhydrous MeOH at −20° C. D-Pyroglutamic acid (10 g, 0.077 mol, obtained from Aldrich, P.O. Box 2060, Milwaukee, Wis. 53201, USA) was added in one portion and the reaction mixture was stirred at to room temperature for 16 hr. The mixture was cooled to 0° C. and solid NaHCO$_3$ was added until pH reached about 9. The mixture was filtered through CELITE and the filtrate concentrated under vacuum. The crude product was chromatographed on silica gel (10–50% EtOAc/hexanes) to give 10.2 g (93%) of D-pyroglytamic acid methyl ester as a colorless oil. $^1$H NMR (CDCl$_3$, 300 MHz) δ 6.95 (1H, s), 4.35 (1H, dd), 3.85 (3H, s), 2.70–2.30 (4H, m).

Step 2

To a solution of D-pyroglutamic acid methyl ester (10.2 g, 71.2 mmol) in 240 mL of Et$_3$N/CH$_3$CN (3:1) was added DMAP (0.91 g, 7.4 mmol, 0.1 eq) followed by di-tert-butyl dicarbonate (31.7 g, 145 mmol, 2 eq). After stirring at room temperature for 3 hr, the reaction mixture was diluted with EtOAc (730 mL), washed with 3% HCl, saturated NaHCO$_3$, and brine, dried (Na$_2$SO$_4$), and concentrated under vacuum. The crude product was purified using silica gel chromatography (10–30% EtOAc/hexanes) to give 11.6 g (67%) of N-Boc-D-pyroglutamic acid methyl ester as a yellowish solid.

$^1$H NMR (CDCl$_3$, 300 MHz) δ 4.73 (1H, dd), 3.90 (3H, s), 2.80–2.20 (4H, m), 1.62 (9H, s).

Step 3

To a mixture of 1-bromo-3-fluorobenzene (0.79 g, 4.5 mmol) and magnesium turnings (0.12 g, 5.0 mmol) in anhydrous THF (8 mL) was added a small piece of iodine. The mixture was heated at reflux for 2 hr and no magnesium turnings left. The solution was cooled to 0° C. and transferred into a stirred solution of N-Boc-D-pyroglutamic acid methyl ester (0.80 g, 3.3 mmol) in anhydrous THF (4 mL) at −40° C. under argon atmosphere. After stirring at −40° C. for 1 hr and then at 0° C. for 1 hr, the reaction was quenched with 8 mL of 1:1 HOAc/MeOH and the mixture diluted with Et$_2$O (40 mL). The organic layers were washed with water and brine, dried (Na$_2$SO$_4$) and concentrated under vacuum. Purification by silica gel chromatography (10–20% EtOAc/hexanes) gave 0.57 g (51%) of (2R)-2-tert-butoxycarbonylamino-5-(3-fluoro-phenyl)-5-oxo-pentanoic acid methyl ester as a white solid. $^1$H NMR (CDCl$_3$, 300 MHz) δ 7.82 (1H, d), 7.75 (1H, d), 7.56 (1H, q), 7.38 (1H, t), 5.30 (1H, br.d), 4.50 (1H, br.s), 3.87 (3H, s), 3.20 (2H, m), 2.45 (1H, m), 2.20 (1H, m), 1.54 (9H, s).

Step 4

To a solution of (2R)-2-tert-butoxycarbonylamino-5-(3-fluoro-phenyl)-5-oxo-pentanoic acid methyl ester (0.57 g, 1.7 mmol) in 1.7 mL of $CH_2Cl_2$ at 0° C. was added dropwise 3.8 mL (49 mmol, 29 eq) of TFA. The mixture was stirred at 0° C. for 2 hr. After concentration under vacuum, the residue was dissolved in $CH_2Cl_2$ (30 mL), washed with 10% $NaHCO_3$, water, and brine, dried ($Na_2SO_4$) and concentrated under vacuum to give (2R)-5-(3-fluoro-phenyl)-3,4-dihydro-2H-pyrrole-2-carboxylic acid methyl ester as a colorless oil. $^1$H NMR ($CDCl_3$, 300 MHz) δ 7.77–7.70 (2H, m), 7.50 (1H, q), 7.27 (1H, tq), 5.05 (1H, tt), 3.90 (3H, s), 3.30–3.00 (2H, m), 2.55–2.30 (2H, m).

The oil was dissolved in 5 mL of absolute EtOH, and $PtO_2$ (5 mg, catalyst) was added. The mixture was hydrogenated at room temperature under a $H_2$ balloon for 16 hr. After filtration through CELITE, the filtrate was concentrated. Chromatography on silica gel (10–20% EtOAc/hexanes) gave 0.33 g (87%) of pure (2R,5S)-5-(3-fluoro-phenyl)-pyrrolidine-2-carboxylic acid methyl ester as a color less oil. 1H NMR ($CDCl_3$, 300 MHz) δ 7.43–7.27 (3H, m), 7.04 (1H, t), 4.33 (1H, q), 4.05 (1H, q), 3.90 (3H, s), 2.43 (1H, br.s), 2.38–2.17 (3H, m), 1.80 (1H, m).

Step 5

(2R,5S)-5-(3-fluoro-phenyl)-pyrrolidine-2-carboxylic acid methyl ester (0.33 g, 1.5 mmol) was dissolved in 1,2-dichloroethane (2 mL) and $Et_3N$ (1.0 mL, 7.4 mmol, 5 eq) was added followed by 4-chlorobenzenesulfonyl chloride (0.78 g, 3.7 mmol, 2.5 eq). The mixture was heated at 100° C. for 16 hr. Solvent was removed under vacuum and the residue was dissolved in EtOAc (10 mL), washed with 10% $NaHCO_3$ and brine, dried ($Na_2SO_4$) and concentrated under vacuum. Chromatography on silica gel (5–10% EtOAc/hexanes) yielded 0.45 g (75%) of pure (2R,5S)-1-(4-chloro-benzenesulfonyl)-5-(3-fluoro-phenyl)-pyrrolidine-2-carboxylic acid methyl ester as yellowish solid. $^1$H NMR ($CDCl_3$, 300 MHz) δ 7.67 (2H, d), 7.42 (2H, d), 7.24 (3H, m), 6.98 (1H, m), 4.95 (1H, t), 4.82 (1H, q), 3.94 (3H, s), 2.45–2.25 (3H, m), 2.05 (1H, m).

Step 6

To a solution of (2R,5S)-1-(4-chloro-benzenesulfonyl)-5-(3-fluoro-phenyl)-pyrrolidine-2-carboxylic acid methyl ester (0.45 g, 1.1 mmol) in anhydrous toluene (5 mL) at 0° C. was added dropwise diisobutylaluminum hydride (1M in hexane, 6.4 mL, 6.4 mmol). The mixture was allowed to warm to room temperature and stirred for 16 hr. The reaction was quenched by adding 1 N HCl (10 mL) and the mixture diluted with EtOAc (20 mL). The organic phase was separated, washed with 10% $NaHCO_3$ and brine, dried ($Na_2SO_4$) and concentrated under vacuum to give 0.40 g (99%) of (2R,5S)-[1-(4-chloro-benzenesulfonyl)-5-(3-fluoro-phenyl)-pyrrolidin-2-yl]-methanol as a yellowish solid. $^1$H NMR ($CDCl_3$, 300 MHz) δ 7.89 (2H, d), 7.62 (2H, d), 7.50–7.20 (3H, m), 7.06 (1H, td), 4.84 (1H, t), 4.05–3.85 (3H, m), 2.05 (2H, q), 1.95–1.80 (3H, m). The $^1$H NMR spectrum showed complete conversion of ester to alcohol and the material was used without further purification.

Step 7

To a solution of (2R,5S)-[1-(4-chloro-benzenesulfonyl)-5-(3-fluoro-phenyl)-pyrrolidin-2-yl]-methanol (0.027 g, 0.073 mmol) in 0.5 mL of $CH_2Cl_2$ was added 0.030 mL (0.22 mmol, 3 eq) of $Et_3N$ followed by 0.015 g (0.074 mmol, 1 eq) of 4-nitrophenyl chloroformate. The mixture was stirred at room temperature for 16 hr. 4-piperidinopiperidine (0.024 g, 0.14 mmol, 2 eq) was added and stirring continued for 16 hr. The mixture was diluted with 5 mL of $CH_2Cl_2$ and washed with 1 N NaOH (2 mL×2), water (2 mL×2), and saturated brine (2 mL). The organic layer was dried ($Na_2SO_4$) and concentrated under vacuum to give a yellow gum. Purification using reverse phase prep-HPLC gave 0.030 g (73%) of the desired product (2R,5S)-[1,4']bipiperidinyl-1'-carboxylic acid 1-(4-chloro-benzenesulfonyl)-5-(3-fluoro-phenyl)-pyrrolidin-2-ylmethyl ester as a white solid. 1H NMR ($CD_3OD$, 300 MHz) δ 7.98 (2H, d), 7.76 (2H, d), 7.46 (1H, q), 7.32 (2H, m), 7.10 (1H, t), 4.80 (1H, t), 4.50–4.35 (3H, m), 3.75–3.50 (4H, m), 3.00–2.95 (4H, m), 2.50–1.55 (14H, m). MS(ESI): $MH^+$=564.1.

Following procedures similar to those in Example 177, the compounds in Table 24 were prepared.

TABLE 24

| Compound | Structure | Exact MS, calc. | MS ESI) $MH^+$ found |
|---|---|---|---|
| 177-A | 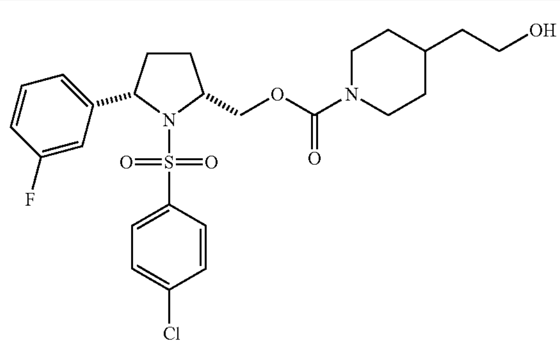 | 524.15 | 524.9 |

TABLE 24-continued

| Compound | Structure | Exact MS, calc. | MS ESI) MH+ found |
|---|---|---|---|
| 177-B | 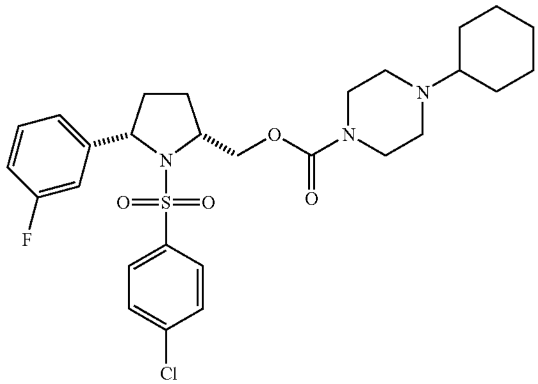 | 563.20 | 564.1 |
| 177-C | 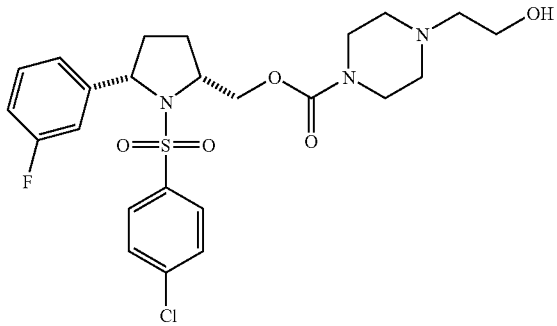 | 525.15 | 526.0 |
| 177-D | 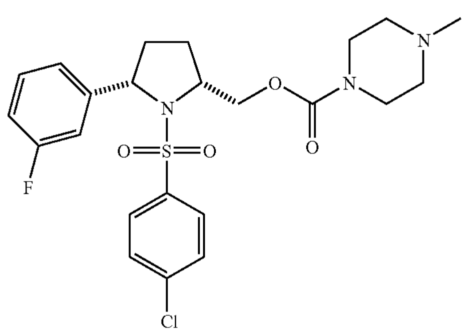 | 495.14 | 496.0 |
| 177-E | 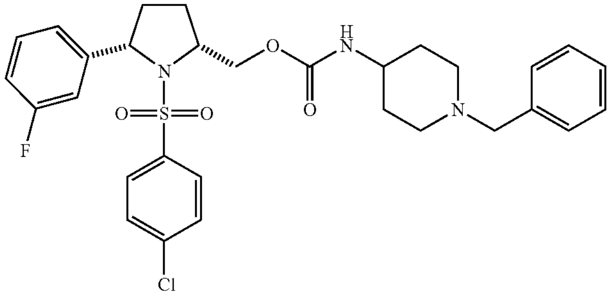 | 585.19 | 586.1 |

TABLE 24-continued
| Compound | Structure | Exact MS, calc. | MS ESI) MH+ found |
|---|---|---|---|
| 177-F | 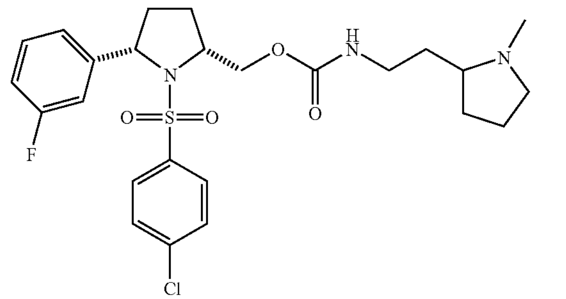 | 523.17 | 524.1 |
| 177-G | 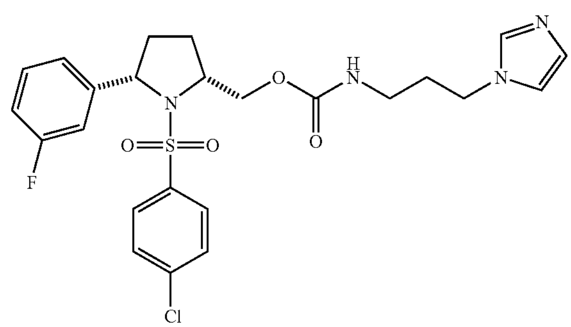 | 520.13 | 521.0 |
| 177-H | 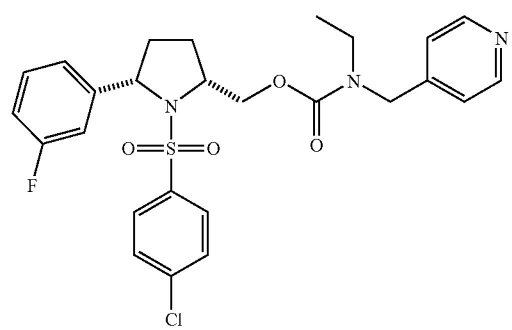 | 531.14 | 532.1 |
Example 178
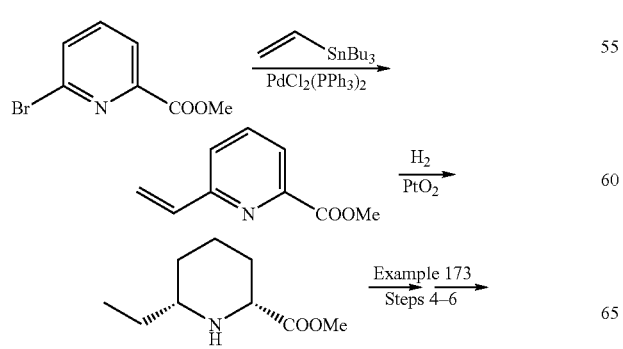
-continued
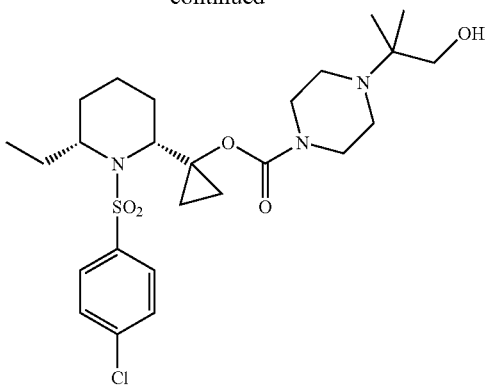

Step 1:

To a solution of 2-bromo-6-carbomethoxypyridine (30.7 g, 142 mmol) in anhydrous dioxane (600 mL) was added vinyltributyltin (53.7 g, 169 mmol) and dichlorobistriphenylphosphine palladium (10.4 g) and the reaction was heated to reflux at 110° C. overnight. The mixture was washed with 5% sodium carbonate solution, extracted with DCM, EtOAc and dried over sodium sulfate. The residue was then filtered over CELITE and concentrated. The residue was purified by flash-chromatography over silica gel (eluting with hexanes/EtOAc 100:0 to 80:20) to give 15.3 g (63%) of vinylpyridine ester.

Step 2:

A solution of vinylpyridine ester product of Step 1 (2.5 g, 14.6 mmol) and platinum oxide (215 mg) in MeOH (50 mL) and AcOH (17 mL) was reduced with hydrogen at 10 atm at RT overnight. The reaction was filtered over CELITE and concentrated. The residue was treated with saturated sodium carbonate solution, extracted with DCM, and the DCM layers were washed with brine, dried over sodium sulfate and concentrated to provide 1.5 g (60%) of ethylpiperidine ester.

Step 3:

The ethylpiperidine ester product of Step 2 was converted to 4-(2-hydroxy-1,1-dimethyl-ethyl)-piperazine-1-carboxylic acid 1-[1-(4-chloro-benzenesulfonyl)-6-ethyl-piperidin-2-yl]-cyclopropyl ester according to conditions similar to the ones described in Step 4–6 of Example 173, using 2-methyl-2-piperazin-1-yl-propan-1-ol at the last stage as the amine. $^1$H-NMR (300 MHz, CDCl$_3$) δ 7.73 (d, J=8.6 Hz, 2H), 7.42 (d, J=8.6 Hz, 2H), 4.53 (d, 1H), 3.73 (m, 1H), 3.25–3.60 (m, 7H), 2.15–2.70 (m, 6H), 1.92 (m, 1H), 1.60 (m, 1H), 1.30–1.50 (m, 3H), 1.10–1.30 (m, 2H), 0.90–1.10 (m, 12H); HRMS (MH$^+$) 528.2301.

Following procedures similar to those in Example 178, the compounds in Table 25 were prepared:

TABLE 25

| Compound | Structure | Mass Spec (M$^+$); retention time (min) |
|---|---|---|
| 178-A | 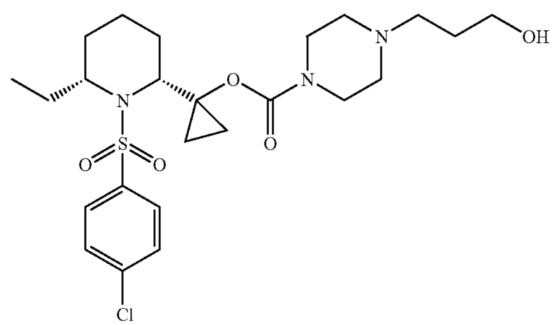 | 514.1; 4.29 |
| 178-B | 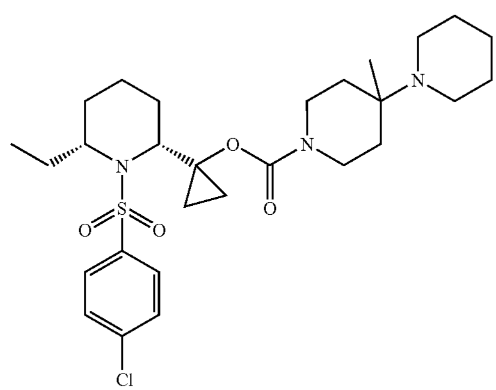 | 552.1; 5.08 |
| 178-C | 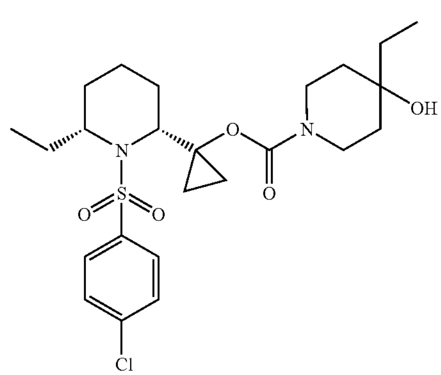 | 499.1; 4.85 |

TABLE 25-continued

| Compound | Structure | Mass Spec (M+); retention time (min) |
|---|---|---|
| 178-D | 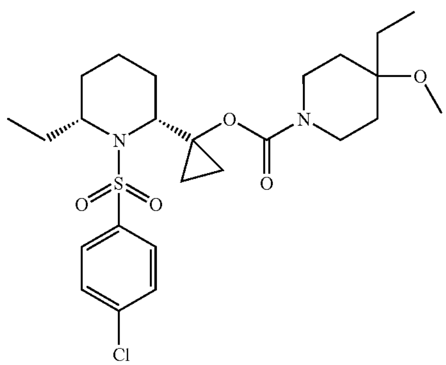 | 513.1; 5.73 |
| 178-E | 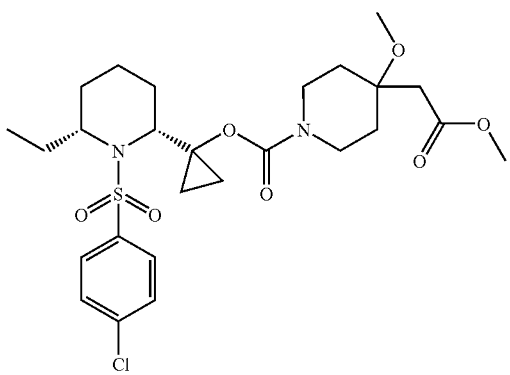 | 557.1; 5.75 |
| 178-F | 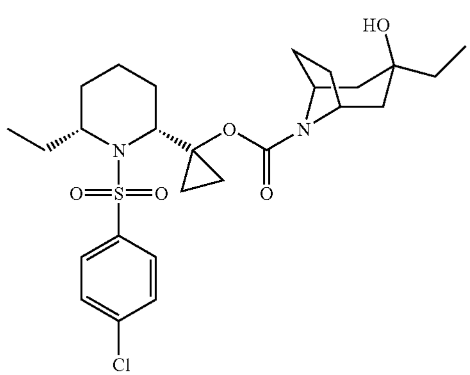 | 525.3; 4.74 |
| 178-G | 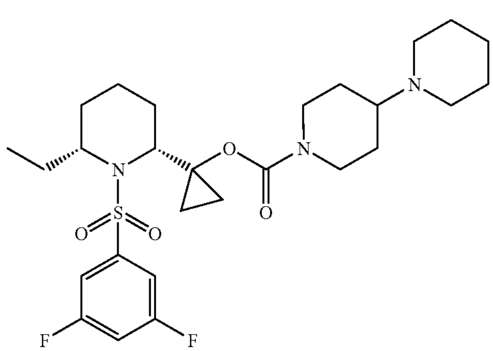 | 540.1; 3.66 |

TABLE 25-continued
| Compound | Structure | Mass Spec (M+); retention time (min) |
|---|---|---|
| 178-H | 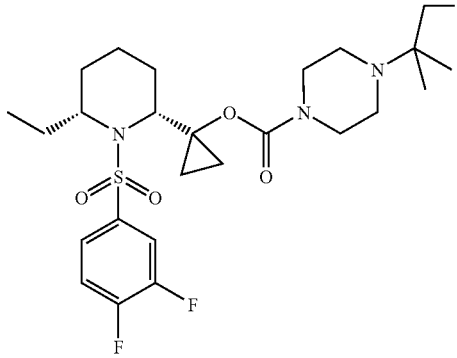 | 530.1; 3.47 |
| 178-I | 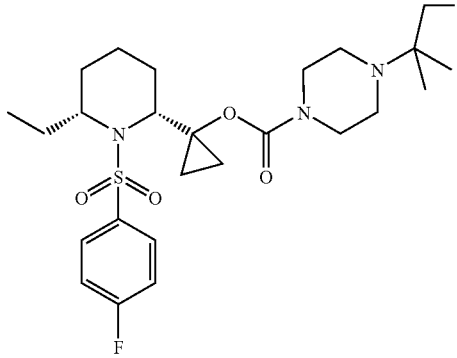 | 512.1; 3.39 |
| 178-J | 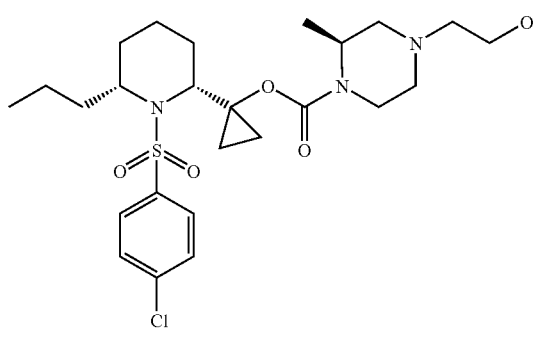 | 528.3; 3.42 |

TABLE 25-continued

| Compound | Structure | Mass Spec (M⁺); retention time (min) |
|---|---|---|
| 178-K | 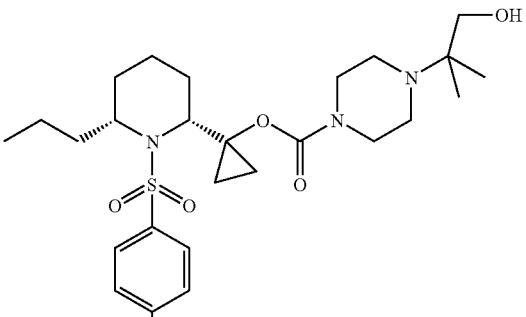 | 542.1; 3.80 |

Example 179

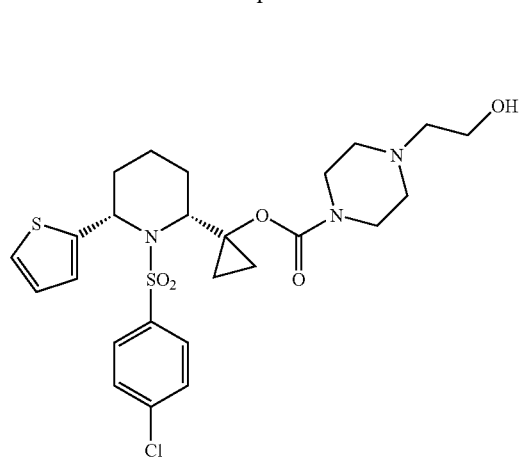

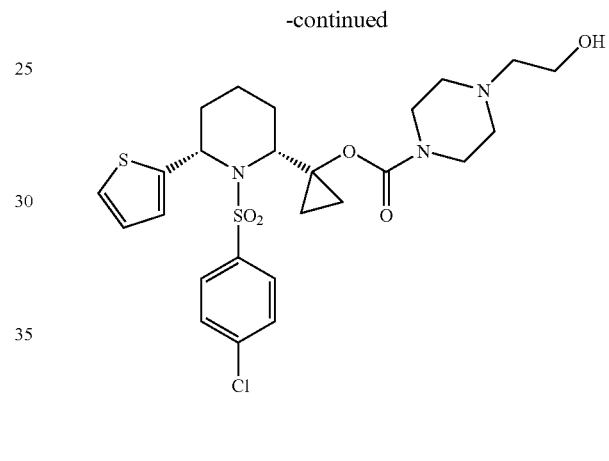

Step 1:

To a solution of methyl N-tert-butoxycarbonylpipecolate (52.6 g, 200 mmol) and sodium periodate (85.6 g, 400 mmol) in acetonitrile (300 mL) and water (1 L) in a water bath was added ruthenium oxide (530 mg, 4.00 mmol) and the reaction was stirred overnight at RT. The reaction was diluted with water and extracted with EtOAc. Isopropanol (100 mL) was then added and the solution was allowed to stand at RT for 30 min then filtered, dried over sodium sulfate, and concentrated. The residue was purified by flash-chromatography over silica gel (eluting with DCM/EtOAc 95:5 to 80:20) to afford 26.4 g (51%) of keto ester.

Step 2:

To a solution of keto ester product of Step 1 (7.72 g, 30.0 mmol) in THF at −78° C. was slowly added 2-thienylmagnesium bromide 1 N in THF (33 mL, 33 mmol) and the reaction was stirred 1 h at −78° C. then allowed to warm to −10° C. The reaction was poured into saturated ammonium chloride solution, extracted with DCM and EtOAc, dried over sodium sulfate and concentrated. The residue was purified by flash-chromatography over silica gel (eluting with hexanes/EtOAc 95:5 to 70:30) to give 5.83 g (57%) of thienylketone.

Step 3:

A solution of the thienylketone product of Step 2 (5.75 g, 16.8 mmol) and TFA (10 mL) in DCM (20 mL) was stirred 2 h at RT then concentrated. The residue was taken up in 1 N NaOH, extracted with DCM and AcOEt, dried over sodium sulfate and concentrated. The residue (3.46 g) and sodium sulfate (17 g) in DCE (100 mL) were treated with AcOH (1.7 mL) followed by sodium triacetoxyborohydride (3.47 g, 16.8 mmol), and the reaction was stirred overnight at RT. The crude product was diluted with water and 1 N NaOH, extracted with DCM and EtOAc, dried over sodium sulfate and concentrated. The residue was purified by flash-chromatography over silica gel (eluting with DCM to DCM/AcOEt 85:15) to provide 2.56 g (68%) of thienylpiperidine ester.

Step 4:

The thienylpiperidine ester product of Step 3 was converted to the title compound according to conditions similar to the ones described in Step 4–6 of Example 173, using N-(2-hydroxyethyl)piperazine at the last stage as the amine. $^1$H-NMR (300 MHz, CDCl$_3$) δ 7.82 (d, J=8.7 Hz, 2H), 7.50 (d, J=8.7 Hz, 2H), 7.26 (m, 1H), 7.12 (m, 1H), 6.97 (m, 1H), 5.26 (m, 1H), 4.70 (m, 1H), 3.30–3.70 (m, 3H), 3;18 (m, 1H), 2.30–2.70 (m, 4H), 2.09 (br d, 1H), 1.40–1.80 (m, 6H), 1.20–1.40 (m, 4H), 1.08 (m, 1H), 0.70–0.95 (m, 2H), 0.51 (m, 1H); HRMS (MH$^+$) 554.1550.

Following procedures similar to those in Example 179, the compounds in Table 25 were prepared:

TABLE 25

| Example No. | COMPOUND | Mass Spec (M$^+$); retention time (min) |
|---|---|---|
| 179-A | 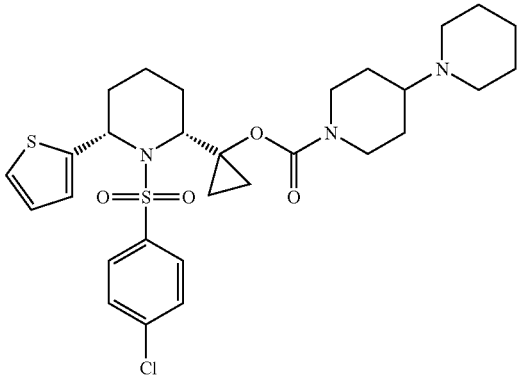 | 592.1; 5.26 |
| 179-B | 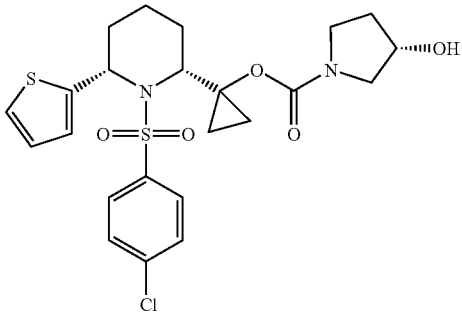 | 511.1; 4.57 |

Example 180

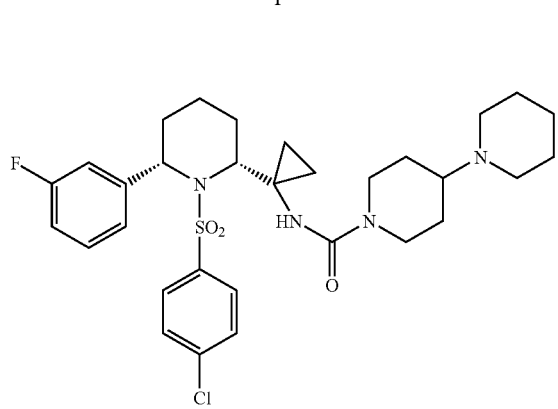

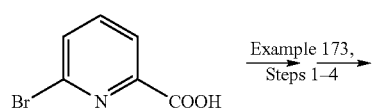

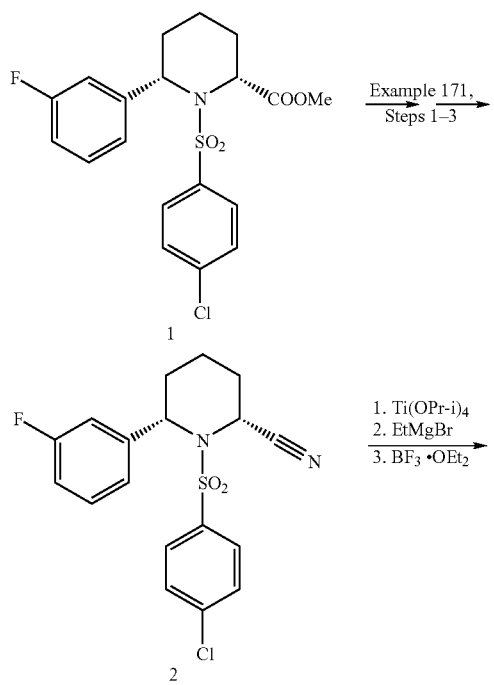

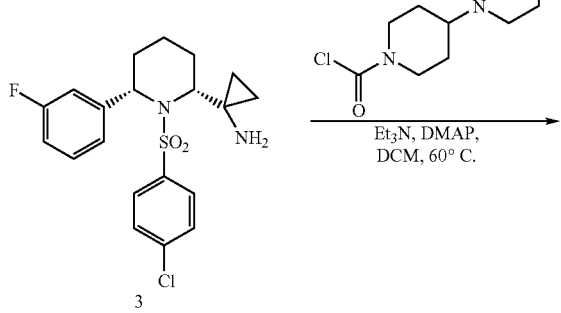

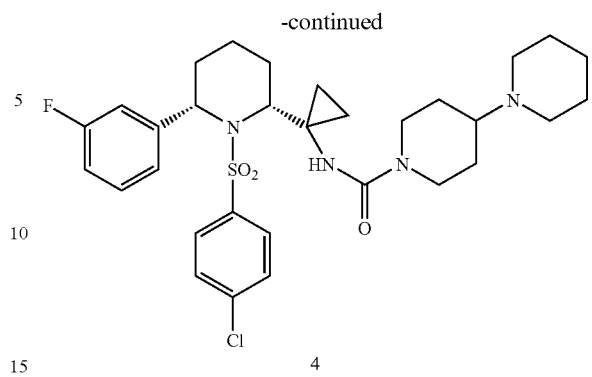

Step 1
Starting from 6-bromopicolinic acid, ester 1 was obtained by methods analogous to those described in Example 173, Steps 1–4.

Step 2
Ester 1 was converted to nitrile 3 as described in Example 171, Steps 1–3.

Step 3
To a solution of 314 mg (0.83 mmol) of nitrile 2 in 5.0 mL of THF at room temperature was added 0.25 mL (0.83 mmol) of Ti(OPr-i)$_4$, followed by slow addition of ethylmagnesium bromide. The mixture was stirred for 30 min and then 0.316 mL (2.5 mmol) of boron trifluoride etherate was added. The mixture was stirred for 30 min, quenched with 1 M NaOH, extracted with EtOAc, dried over Na$_2$SO$_4$, and concentrated. The residue was purified by prep. TLC (40% EtOAc in hexane as solvent) to furnish 64 mg of amine 3, LCMS m/z=409.1, ret. time 4.47 min.

Step 4
A mixture of 30 mg of cyclopropylamine 3, 40 mg of 1,4'-bipiperidinyl-1'-carbonyl chloride, 0.1 mL of triethylamine and 5 mg of DMAP in 2 mL of DCM was stirred overnight. Equal amounts of 1,4'-bipiperidinyl-1'-carbonyl chloride, triethylamine and DMAP were added and the mixture was heated for another overnight period at 60° C. in a sealed tube. The reaction mixture was cooled, diluted with DCM, washed with sat. NaHCO$_3$, dried over Na$_2$SO$_4$ and evaporated. The product was purified by prep. TLC using 6% MeOH in DCM as solvent to furnish 22 mg of product. LCMS m/z 603.3, ret. time 4.78 min. $^1$H NMR (CDCl$_3$ 400 MHz) δ 7.78 (2H, d, J=8.2 Hz), 7.50 (2H, d, J=8.2 Hz), 7.46–7.37 (3H, m), 7.01 (1H, t, J=8.2 Hz), 5.10 (1H, br), 3.77 (2H, m), 3.47 (1H, m), 3.12 (1H, m), 2.44 (6H, m), 2.26–2.10 (3H, ser. m.), 1.92–1.15 (15H, ser. m.), 0.08 (2H, m), 0.50 (1H, m).

Example 181

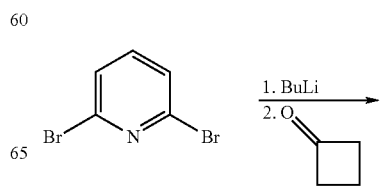

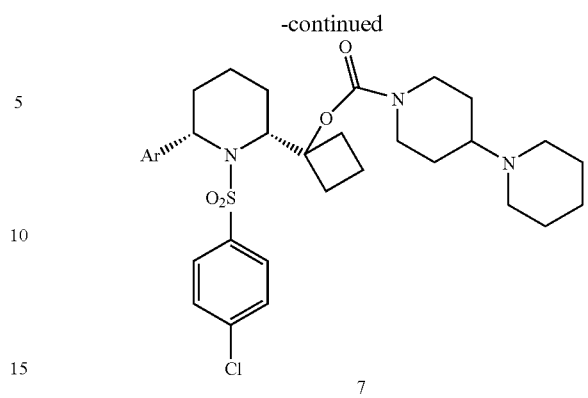

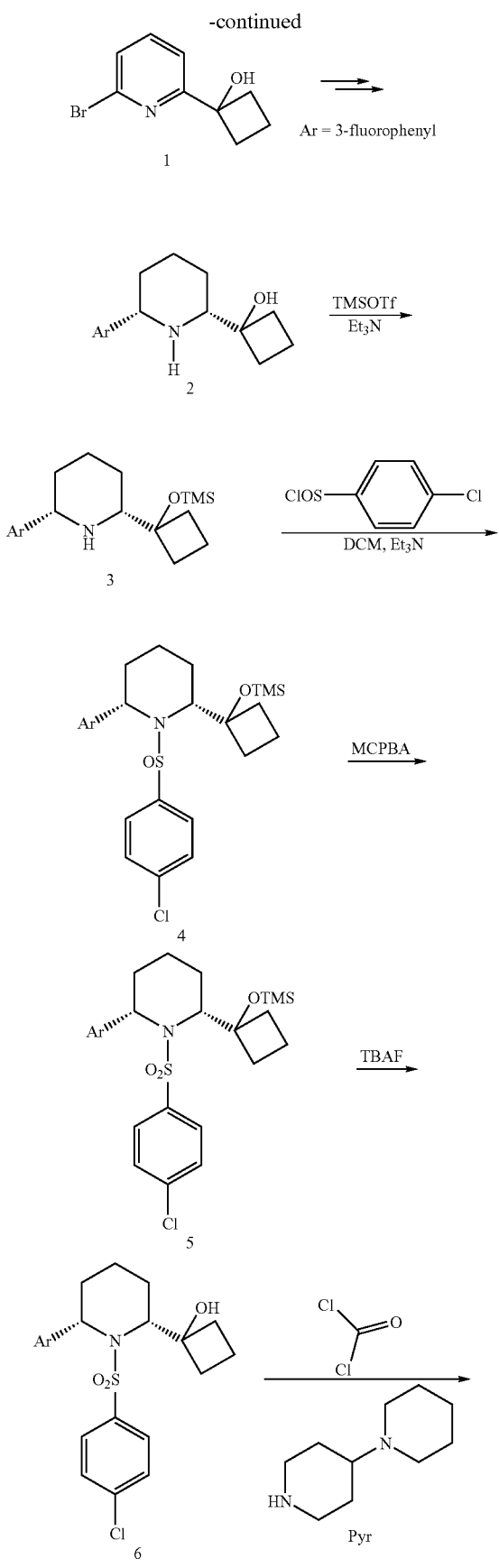

Step 1

To 40.0 mL of a 2.5 M solution of butyl lithium in hexanes (100 mmol) was added at −78° C. a solution of 23.6 g (100 mmol) of 2,6-dibromopyridine in 50.0 mL of THF, followed by drop-wise addition of 7.0 mL of cyclobutanone. The reaction was quenched with NaHCO₃ (sat), extracted with EtOAc, dried and concentrated to furnish 19.3 g. of alcohol 1.

Step 2

Alcohol 2 was obtained from alcohol 1 according to the method described in Example 173, Step 3

Step 3

To a solution of 1.4 g (5.62 mmol) of alcohol 2 in 30 ml DCM was added 2.4 mL (16.8 mmol) of triethylamine and 1.87 g (8.42 mmol) of trimethylsilyltrifluoromethanesulfonate. The mixture was stirred for 1 h, washed with sat. NaHCO₃, dried over Na₂SO₄, and concentrated to furnish 2.2 g of TMS ether 3.

Step 4

To a mixture of 500 mg (1.5 mmol) of TMS ether 3 and 500 mg (2.5 mmol) of 4-chloro-benzenesulfinyl chloride in 5.0 mL of DCM was added 0.5 mL of triethylamine. The mixture was stirred overnight, diluted with DCM and washed with sat. NaHCO₃. The organic phase was dried over Na₂SO₄ and concentrated. The residue was purified by chromatography using 10% of EtOAc in hexanes as solvent to furnish 330 mg of sulfinylamide 4.

Step 5

A mixture of 200 mg (0.42 mmol) of sulfinylamide 4 in 2.0 ml of DCM was treated with 174 mg of technical (77%) MCPBA (c.a. 0.64 mmol). After 1 h of stirring, the mixture was diluted with 20 mL of DCM and quenched with a solution of 600 mg of sodium thiosulfate in 10.0 mL of water. The organic phase was separated from the aqueous phase and washed with sat NaHCO₃ to furnish 200 mg of sulfonamide 5.

Step 6

TMS group of sulfonamide 5 was cleaved according to the method of Example 1, Step 3(b).

Step 7

To a mixture of 0.1 mL of 20% phosgene/toluene solution and 0.5 mL of DCM at 0° C. was added a solution of 41 mg (0.1 mmol) of alcohol 6 and 25 μL of pyridine in 0.5 mL of DCM. The mixture was stirred for 1 h and treated with a solution of 67 mg (0.4 mmol) of 4-piperidinopiperidine. The mixture was stirred for 1 h, diluted with DCM, and washed with sat. NaHCO₃. The product was isolated chromatographically (prep. TLC) using 5% of MeOH in DCM as solvent to furnish 21 mg of cyclobutylcarbamate 7. LCMS m/z=618.3, ret. time 3.92 min.

Example 182

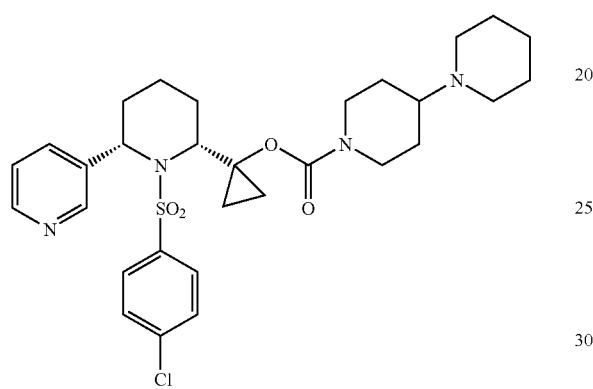

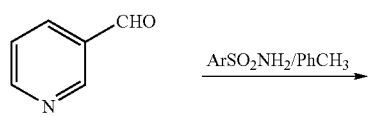

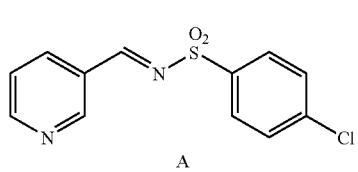

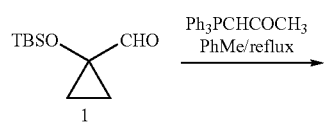

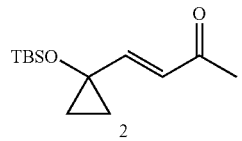

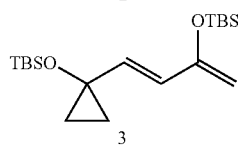

-continued

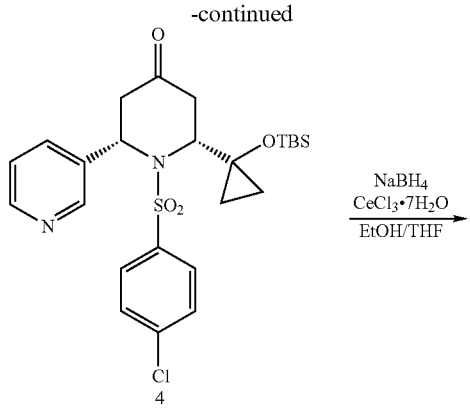

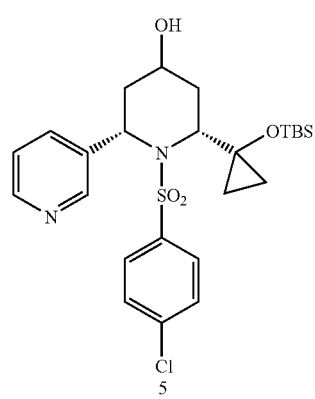

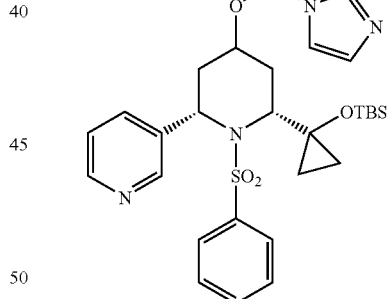

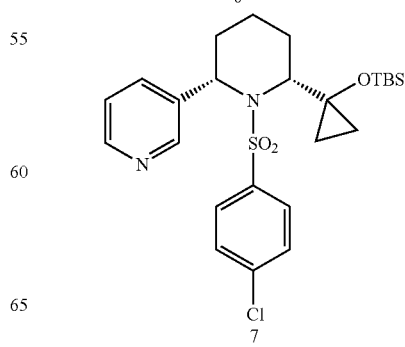

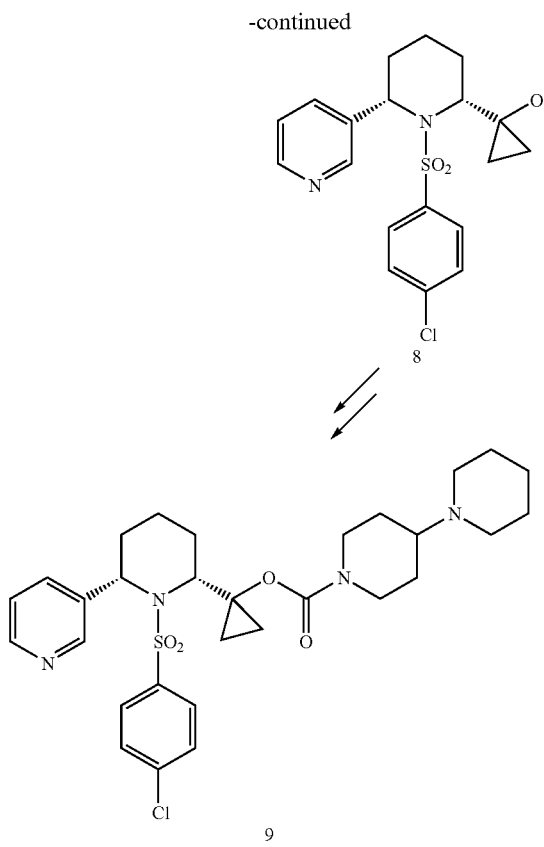

Step 1

1-(tert-Butyl-dimethylsilyloxy)-cycloprpopanecarboxaldehyde was obtained as described in J. Chem. Soc. Chem. Comm. 1985, (18), 1270–2, which is herein incorporated by reference in its entirety. A solution of this aldehyde (5.6 g, 27.9 mmol) in toluene (65 mL) was treated with 1-triphenyl phosphoranylidene-2-propanone (8.9 g, 27.9 mmol), and the reaction mixture was heated at reflux for 16 h. After cooling to room temperature, the solvent was removed under vacuum and the residue was purified by chromatography over silica gel (eluting with hexane/EtOAc 8:2) to give 4.2 g (63%) of a ketone product as an oil. $^1$H NMR (CDCl$_3$ 300 MHz) δ6.47 (1H, d), 6.30 (1H, d), 2.23 3H, s), 1.26 (2H, m), 0.95 (2H, m), 0.89 (9H, s), 0.01 (6H, s), MS (ES) m/e 240.4 (M)$^+$.

Step 2

To a solution of the ketone of Step 1 (4.25 g, 17.7 mmol) in THF 940 mL) cooled at –78° C. was slowly added NaHMDS (5.61 mmol, 11.3 mL, 0.5M in toluene). The reaction mixture was stirred at –30° C. for 1 h, cooled to –78° C. and then treated with a solution of TBSCI (3.0 g, 20.0 mmol) in THF (25 mL). The mixture was stirred at –78° C. for 2 h then allowed to warm to room temperature over 16 h. After quenching with sat. NH$_4$Cl, the mixture was extracted with EtOAc, dried over Na$_2$SO$_4$ and concentrated to yield 5.89 g (95%) of 1-(tert-butyl-dimethyl-silanyloxy)-1-[3-(tert-butyldimethylsilanyloxy)-buta-1,3-dienyl]-cyclopropane as an oil. $^1$H NMR (CDCl$_3$ 300 MHz) δ6.00 (1H, d), 5.81 (1H, d), 4.24 (2H, m), 1.02 (2H, m), 0.95 (9H, s), 0.75 (9H, s), 0.15 (6H, s), 0.11 (6H, s), MS (ES) m/e 368.7 (M)$^+$.

Step 3:

(a) 4-chloro-N-pyridin-3-ylmethylene-benzenesulfonamide

To a solution of 3-pyridine-carboxaldehyde (2.6 g, 24.2 mmol) and 4-chlorobenzenesulfonamide (5.0 g, 26.0 mmol) in toluene was added powdered molecular sieve 4A (2.5 g) and AMBERLYST H$^+$ (2.5 g). The reaction mixture was heated in a Dean-Stark apparatus for 16 h. After cooling to room temperature, the mixture was filtered through a pad of CELITE. The CELITE was washed with EtOAc, and the filtrate was concentrated to give 6.4 g (94%) of the title product as a white solid. $^1$H NMR (CDCl$_3$ 300 MHz) δ 9.12 (1H, s), 9.06 (1H, s), 8.83 (1H, m), 8.28 (1H, m), 7.95 (2H, d), 7.55 (2H, d), 7.47 (1H, m), MS (ES) m/e 280.5 (M)$^+$.

(b) 4-(tert-butyl-dimethyl-silanyloxy)-6-[1-(tert-butyl-dimethyl-silanyloxy)-cyclopropyl]-1-(4-chloro-benzenesulfonyl)-1,2,3,6-tetrahydro-[2,3']bipyridinyl To a solution of the diene of Step 2 (5.98 g, 16.9 mmol) in toluene (60 mL) was added the sulfonamide of Step 3a (4.7 g, 16.9 mmol) and the mixture was heated at 90° C. for 12 h. After cooling to room temperature the solvent was removed, and the residue was purified by chromatography over silica gel (eluting with hexane/EtOAc 8:2) to give 8.7 g (81%) of the title product as a solid. $^1$H NMR (CDCl$_3$ 300 MHz) δ8.56 (1H, s) 8.48 (1H, d), 7.90 (1H, d), 7.79 (2H, d), 7.50 (2H, d), 5.12 (1H, d), 4.84 (1H, m), 4.61 (1H, m), 2.39 (1H, m), 2.34 (1H, m), 1.85–1.78 (1H, m), 0.86 (9H, s), 0.79 (9H, s), 0.49–0.32 (3H, m), 0.10 (12H, m), MS (ES) m/e 635.4 (M)$^+$.

(c) 6-[1-(tert-Butyl-dimethyl-silanyloxy)-cyclopropyl]-1-(4-chloro-benzenesulfonyl)-2,3,5,6-tetrahydro-1H-[2,3']bipyridinyl-4-one To a solution of the sulfonamide of Step 3b (5.4 g, 8.50 mmol) in DCM (75 mL) cooled to 0° C. was added slowly con. HCl (4.5 mL). The reaction mixture was stirred at 0° C. for 2 h, then neutralized with sat NaHCO$_3$, the aqueous and organic layers separated, and the organic phase dried over Na$_2$SO$_4$ and concentrated. The residue was purified by chromatography over silica gel (eluting with hexane/EtOAc 7:3) to give 3.4 g (77%) of the title product as a white solid. $^1$H NMR (CDCl$_3$ 300 MHz) δ8.62 (1H, m), 8.50 (1H, m), 7.80 (1H, m), 7.67 (2H, d), 7.48 (2H, d), 7.25 (1H, m), 4.99 (1H, dd), 4.00 (1H, m), 3.30 (1H, m), 2.56 (1H, m), 2.44 (1H, dd), 2.19 (1H, dd), 1.20–0.92 (4H, m), 0.71 (9H, s), 0.06 (3H, s), 0.01 (6H, s), MS (ES) m/e 521 (M)$^+$.

Step 4: 6-[1-(tert-Butyl-dimethyl-silanyloxy)-cyclopropyl]-1-(4-chloro-benzenesulfonyl)-1,2,3,4,5,6-hexahydro-[2,3']bipyridinyl-4-ol To a solution of the ketone of Step 3 (3.41, 6.55 mmol) in a mixture of EtOH.THF (100 mL. 1:1) was added CeCl$_3$.7H$_2$O (0.5 g, 13.2 mmol) followed by NaBH$_4$ (2.7 g, 7.2 mmol). The cooling bath was removed and the reaction mixture was stirred at room temperature for 1 h. The mixture was diluted with water, extracted with EtOAc, dried over Na$_2$SO$_4$, and concentrated. The residue was purified by chromatography over silica gel (eluting with hexane-EtOAc 7:3) to give 1.7 g (50%) of the title product as a solid. $^1$H NMR (CDCl$_3$ 300 MHz) δ8.63 (1H, m), 8.45 (1H, m), 7.91

(1H, m), 7.72 (2H, d), 7.50 (2H, d), 4.65 (1H, m), 3.78 (1H, dd), 3.05 (1H, br. s) 2.26–2.10 (3H, m), 1.90–1.80 (1H, m) 1.70 (1H, m), 1.20–0.78 (4H, m), 0.71 (9H, s), 0.03 (6H, s), MS (ES) m/e 523 (M)$^+$.

Step 5: Imidazole-1-carbothioic Acid O-[6-[1-(tert-butyl-dimethyl-silanyloxy)-cyclopropyl]-1-(4-chloro-benzenesulfonyl)-1,2,3,4,5,6-hexahydro-[2,3']bipyridinyl-4-yl]Ester To a solution of the alcohol of Step 4 (1.86 g, 3.60 mmol) in THF (20 mL) was added 1,1-thiocarbonyldiimidazole (1.3 g, 7.10 mmol), and the mixture was heated at reflux for 3 h. The reaction mixture was then cooled to room temperature, the solvent was removed, and the residue was purified by chromatography over silica gel (eluting with hexane/EtOAc 1:9) to give 1.2 g (52) of the title product as a solid. $^1$H NMR (CDCl$_3$ 300 MHz) δ 8.69 (1H, m), 8.51 (1H, m), 8.20 (1H, s), 7.91 (1H, d) 7.79 (2H, d), 7.59 (2H, d), 7.29–7.26 (1H, m), 6.99 (1H, s), 4.95–4.90 (1H, m), 4.63–4.60 (1H, m), 3.82 (1H, d), 2.57–2.45 (3H, m), 2.17–2.14 (1H, m), 1.29–0.88 (4H, m), 0.71 (9H, s), 0.04 (6H, s), MS (ES) m/e 633 (M)$^+$.

Step 6: 6-[1-(tert-Butyl-dimethyl-silanyloxy)-cyclopropyl]-1-(4-chloro-benzenesulfonyl)-1,2,3,4,5,6-hexahydro-[2,3']bipyridinyl To a refluxing solution of tri-n-butyltin hydride (0.82 g, 2.80 mmol) in toluene (100 mL) was added slowly a solution of the thioimidazolide of Step 5 (1.19 g, 1.90 mmol) in a mixture of toluene:THF (60 mL, 2:4) over a period of 30 minutes. Reflux was continued for 16 h. After cooling to room temperature, the solvents were removed under vacuum, and the residue was purified by chromatography over silica gel (eluting with hexane/EtOAc 1:1) to give 0.79 g (88%) of the title product as an oil. $^1$H NMR (CDCl$_3$ 300 MHz) δ8.68 (1H, m), 8.45 (1H, m), 8.00 (1H, d), 7.78 (2H, d), 7.80 (2H, d), 7.23 (1H, m), 4.85 (1H, m), 3.75 (1H, m), 2.20–1.45 (6H, m), 1.02–0.89 (4H, m), 0.67 (9H, s), 0.06 (6H, m), MS (ES) m/e 507 (M)$^+$.

Step 7: 1-[1-(4-Chloro-benzenesulfonyl)-1,2,3,4,5,6-hexahydro-[2,3']bipyridinyl-6-yl]-cyclopropanol A solution of the silyl ether of Step 6 (79.2 mg, 1.56 mmol) in THF (20 mL) was treated with TBAF (2.0 mmol, 2.0 mL, 1M in THF). After stirring for 2 h at room temperature, the solvent was removed and the residue was purified by chromatography (eluting with EtOAc) to give 54.4 mg (89%) of the title compound as a white solid. $^1$H NMR (CDCl$_3$ 300 MHz) δ8.75 (1H, s) 8.50 (1H, s), 8.12 (1H, d), 7.80 (2H, d), 7.50 (2H, d), 7.35 (1H, m), 5.18 (1H, m), 3.60 (1H, d), 2.23 (1H, m), 1.97 (1H, m), 1.80 (1H, m), 1.48–1.23 (4H, m), 1.10 (1H, m), 0.64–0.45 (3H, m), MS (ES) m/e 393 (M)$^+$.

Step 8:

The product of step 7 was converted to the title compound according to Step 4 of Example 1, using 4-piperidinopiperidine at the last stages as the amine. $^1$H NMR (CDCl$_3$ 300 MHz) δ8.78 (1H, m), 8.51 (1H, m), 8.02 (1H, m), 7.82 (2H, m), 7.50 (2H, d), 7.30 (1H, m), 5.17 (1H, m), 4.65 (1H, dd), 4.18 (1H, dd), 3.75–3.45 (2H, m), 2.98 (1H, m), 2.80–0.080 (22H, m), 0.72 (1H, m), 0.41–0.15 (2H, m), MS (ES) m/e 587.3 (M)$^+$.

Following procedures similar to those of Example 182, the compounds in Table 26 were prepared:

TABLE 26

| Example No. | Structure | Retention Time (minutes) | Observed Mass |
|---|---|---|---|
| 182-A | 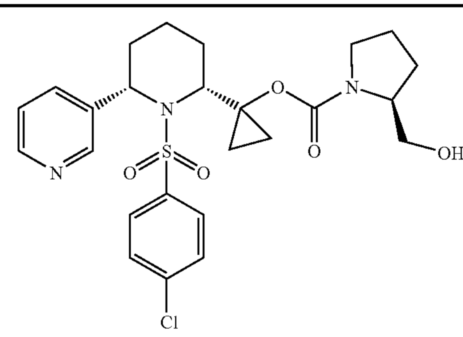 | 2.64 | 520.3 |
| 182-B | 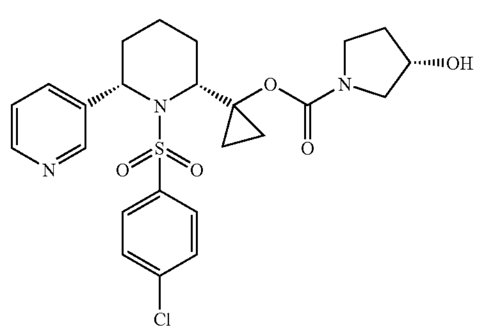 | 2.48 | 506.3 |

TABLE 26-continued

| Example No. | Structure | Retention Time (minutes) | Observed Mass |
|---|---|---|---|
| 182-C | 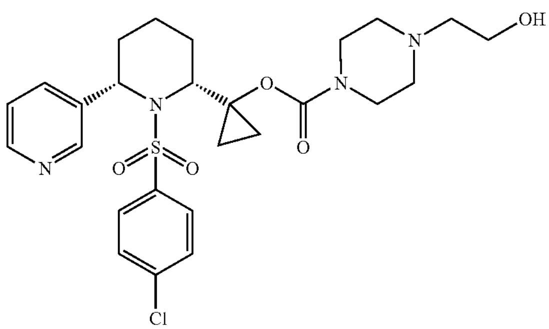 | 2.20 | 549.3 |
| 182-D | 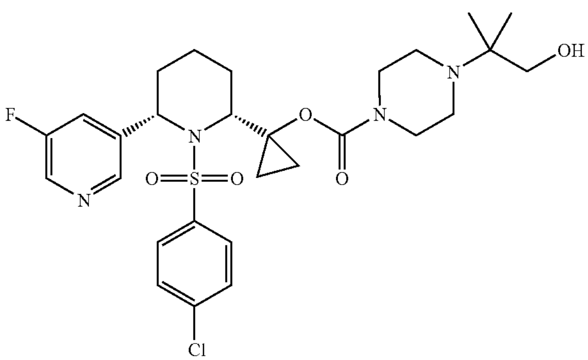 | 2.94 | 595.3 |
| 182-E | 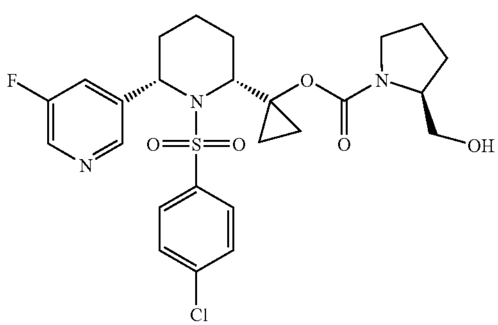 | 3.51 | 538.3 |
| 182-F | 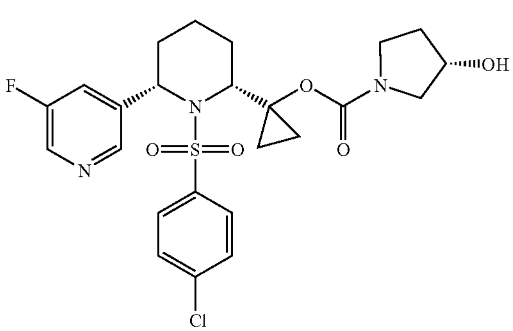 | 3.17 | 524.3 |

TABLE 26-continued

| Example No. | Structure | Retention Time (minutes) | Observed Mass |
|---|---|---|---|
| 182-G | 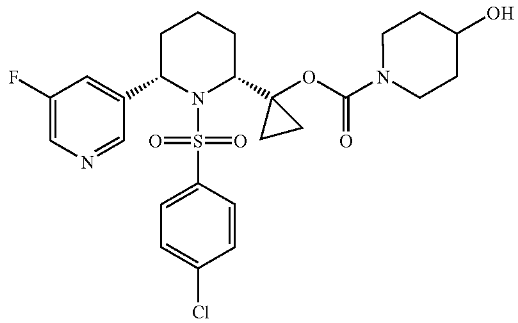 | 3.31 | 538.3 |
| 182-H | 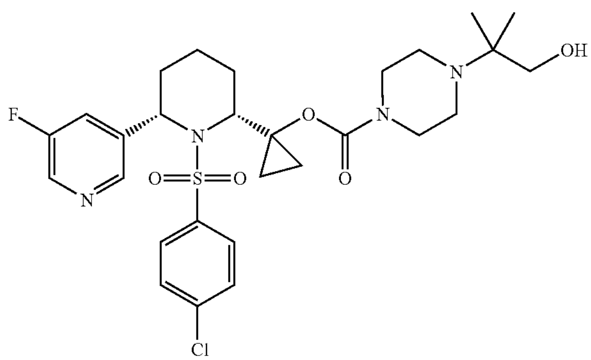 | 2.94 | 595.3 |
| 182-I | 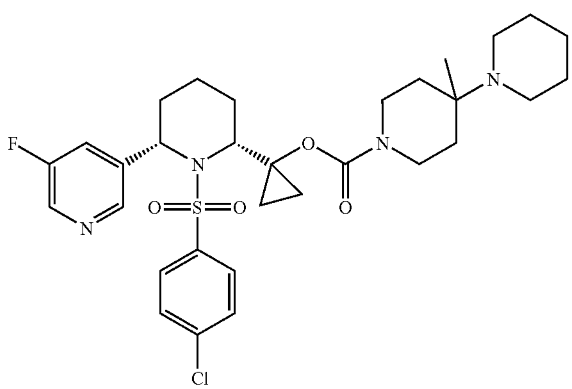 | 3.12 | 619.3 |
| 182-J | 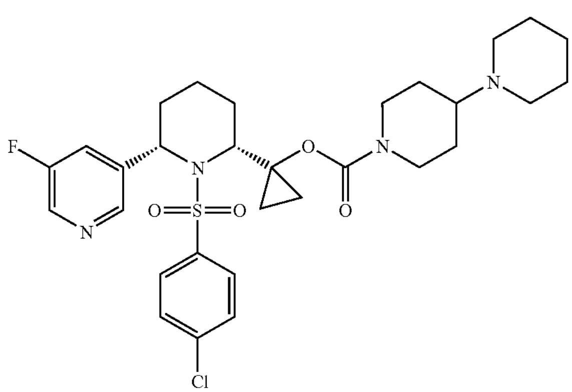 | 3.08 | 605.3 |

Example 183

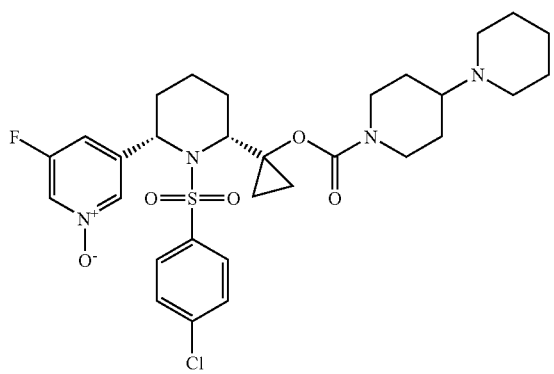

Step 1: Carbonic Acid 1-[1-(4-chloro-benzenesulfonyl)-5'-fluoro-1'-oxy-1,2,3,4,5,6-hexahydro-[2,3']bipyridinyl-6-yl]-cyclopropyl ester 4-nitro-phenyl Ester Carbonic acid 1-[1-(4-chloro-benzenesulfonyl)-5'-fluoro-1,2,3,4,5,6-hexahydro-[2,3']bipyridyl-6-yl]-cyclopropyl ester-4-nitro-phenyl ester was obtained according to Steps 1 to 6 in Example 182, using 5-fluoropyridin-3-carboxaldehyde as the starting material. A solution of this carbonate (359 mg, 0.62 mmol) in DCM (2.02 mL) was treated with a solution of MCPBA (168 mg, 0.75 mmol) in DCM (2.0 mL). After stirring for 16 h at room temperature, the reaction mixture was washed with 10% $NaHCO_3$, dried over $Na_2SO_4$, and concentrated at reduced pressure. The residue was purified by chromatography (eluting with EtOAc) to give 135 mg (37%) of the title compound.

$^1$H NMR ($CDCl_3$ 300 MHz) δ8.23 (2H, d), 8.17 (1H, s), 8.10 (1H, s), 7.80 (2H, d), 7.55 (3H, m), 7.45 (2H, d), 5.12 (1H, s), 4.79 (1H, s), 2.45–1.15 (6H, m), 1.05 (2H, m), 0.62 (2H, m), MS (ES) m/e 592 (M)$^+$.

Step 2: [1,4']Bipiperidinyl-1'-carboxylic acid 1-[1-(4-chloro-benzenesulfonyl)-5'-fluoro-1'-oxy-1,2,3,4,5,6-hexahydro-[2,3']bipyridinyl-6-yl]-cyclopropyl Ester The product of Step 1 was converted to the title compound (i.e., Example 183) according to Step 4 of Example 1, using 4-piperidinopiperidine at the last stages as the amine. $^1$H NMR ($CDCl_3$ 300 MHz) δ8.25 (1H, d), 8.06 (1H, s), 7.80 (2H, m), 7.50 (3H, m), 5.05 (1H, br. s), 4.85 (1H, m), 4.30–3.82 (2H, m), 3.00–1.00 (23H, m), 1.10–0.30 (4H, m), MS (ES) m/e 620.2 (M)$^+$.

Following procedures similar to those of Example 183, the compound in Table 27 was prepared:

TABLE 27

| Example No. | Structure | Retention Time (minutes) | Observed Mass |
|---|---|---|---|
| 183-A | 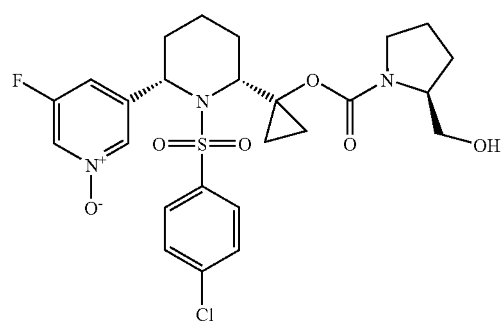 | 3.06 | 554.3 |

Assay:

Gamma secretase activity was determined as described by Zhang et al. (*Biochemistry*, 40 (16), 5049–5055, 2001). Activity is expressed either as a percent inhibition or as the concentration of compound producing 50% inhibition of enzyme activity.

Reagents

Antibodies WO2, G2–10, and G2–11 were obtained from Dr. Konrad Beyreuther (University of Heidelberg, Heidelberg, Germany). W02 recognizes residues 5–8 of Aβ peptide, while G2–10 and G2–11 recognize the specific C-terminal structure of Aβ 40 and Aδ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction

The construct SPC99-Lon, which contains the first 18 residues and the C-terminal 99 amino acids of APP carrying the London mutation, has been described (Zhang, L., Song, L., and Parker, E. (1999) *J. Biol. Chem.* 274, 8966–8972). Upon insertion into the membrane, the 17 amino acid signal peptide is processed, leaving an additional leucine at the N-terminus of Aβ. SPC99-lon was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aδ production by inducing C99 expression with 0.1 g/mL tetracycline for 16–20 h and analyzing conditioned media with a sandwich immunoassay (see below). One of the clones, designated as pTRE.15, was used in these studies.

Membrane Preparation

C99 expression in cells was induced with 0.1 g/mL tetracycline for 20 h. The cells were pretreated with 1 M phorbol 12-myristate 13-acetate (PMA) and 1 M brefeldin A (BFA) for 5–6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70 C.

γ-Secretase Reaction and Aβ Analysis

To measure γ-secretase activity, membranes were incubated at 37 C for 1 h in 50 L of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2–10 and biotin-W02, while Aβ 42 was identified with TAG-G2–11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

Using the above assay, the compounds of Examples 1–29, 31–33, 35–48, 50–61, 63–67, 67A–67BR, 68, 69, 71–74, 74A, 74B, 74C, 75, 76, 78–83, 85–99, 101–159, 159A, 159B, 160, 160A–160AA, 161, 161A–161G, 162, 162A, 162B, 164, 164A, 164B, 164C, 165–167, 167A, 167B, 167C, 168, 168A, 169, 169A–169D, 170, 170A–170AD, 171–173, 173A–173T, and 174 showed IC$_{50}$ within the range of about 0.0002 to about 15 μM. The compounds of Examples 67B, 67E, 67N, 67P, 67U, 67AG, 67AT, 67AW, 67AY, 67BA, 67BD, 67BE, 67BG, 67BH, 67BL, 160B, 160K, 161, 161A, 161E, 161F, 173, 173A, 173B, 173C, 173E, 173G, 173I, 173J, 173K, 173L and 173N showed IC$_{50}$ within the range of about 0.0002 to about 0.015 μM.

The γ-secretase inhibitory activity of some of the inventive compounds are shown below:

| Example | IC50 (μM) |
| --- | --- |
| 67-B | .0027 |
| 67-AT | .0038 |
| 67-BG | .0023 |
| 161-A | .0028 |
| 173 | .0002 |
| 173-A | .0007 |
| 173-C | .0018 |
| 173-E | .0027 |
| 173-J | .0008 |
| 173-N | .0024 |

Pharmaceutical compositions can comprise one or more of the compounds of formula I. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula

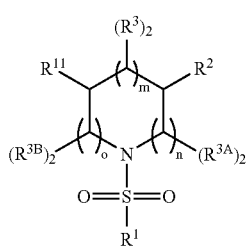

(I)

or a pharmaceutically acceptable salt, solvate or ester thereof, wherein:

(A) $R^1$ is selected from the group consisting of:
(1) unsubstituted aryl;
(2) aryl substituted with one or more $R^5$ groups;
(B) $R^2$ is selected from the group consisting of:
(1) alkyl;
(2) —XC(O)Y;
(3) —$(C_1-C_6)$alkylene-XC(O)Y;
(4) —$(C_0-C_6)$alkylene-$(C_3-C_6)$cycloalkylene-$(C_0-C_6)$alkylene-XC(O)Y;
(5) aryl;
(6) aryl substituted with one or more $R^5$ groups;
(7) heteroaryl;
(8) heteroaryl substituted with one or more $R^5$ groups;
(9) cycloalkylene-X—C(O)—Y;
(10) —$CH_2$—X—C(O)—$NR^3$—Y;
(11) —$CH_2$—X—C(O)—Y; and
(12) —$CH_2$—X—C(O)—$NR^3$—Y,
(C) Each $R^3$ is independently selected from the group consisting of:
(1) H;
(2) alkyl;
(3) —OH;
(4) —O—alkyl;
(5) Acyl;
(6) Aroyl;
(7) the moiety $(R^3)_2$, together with the ring carbon atom to which it is shown attached in formula I, defines a carbonyl group, —C(O)—, with the proviso that when m is an integer greater than 1, at most one carbonyl group is present in the ring shown in formula I;
(8) halo,
(D) Each $R^{3A}$ and $R^{3B}$ is independently selected from the group consisting of:
(1) H; and
(2) alkyl;
(E) $R^5$ is independently selected from the group consisting of:
(1) halo;
(2) —$CF_3$;
(3) —OH;
(4) —O-alkyl;
(5) —$OCF_3$;
(6) —CN;
(7) —$NH_2$;
(8) —$C(O)_2$alkyl;
(9) —$C(O)NR^6R^7$;
(10) -alkylene-$NR^6R^7$;
(11) —$NR^6C(O)$alkyl;
(12) —$NR^6C(O)$aryl;
(13) —$NR^6C(O)$heteroaryl; and
(14) —$NR^6C(O)NR^6R^7$;
(F) X is selected from the group consisting of:
(1) —O—;
(2) —NH—;
(3) —N-alkyl; and
(4) —O-alkylene;
(G) Y is selected from the group consisting of:
(1) —$NR^6R^7$;
(2) —$N(R^3)(CH_2)_b NR^6R^7$ wherein b is 2–6;
(3) unsubstituted aryl;
(4) unsubstituted heteroaryl;
(5) -alkyl;
(6) -cycloalkyl,
(7) unsubstituted arylalkyl;
(8) unsubstituted arylcycloalkyl;
(9) unsubstituted heteroarylalkyl;
(10) unsubstituted heteroarylcycloalkyl;
(11) unsubstituted arylheterocycloalkyl;
(12) substituted aryl;
(13) substituted heteroaryl;
(14) substituted arylalkyl;
(15) substituted arylcycloalkyl;
(16) substituted heteroarylalkyl;

(17) substituted heteroarylcycloalkyl; and
(18) substituted arylheterocycloalkyl;
(19) substituted heterocycloalkyl alkyl;
(20) unsubstituted heteroaryl alkyl;
(21) unsubstituted aryl alkyl heterocycloalkyl;
(22) unsubstituted heterocycloalkyl; and
(23) unsubstituted cycloalkyl, wherein the aryl moiety in said substituted groups (12), (14), (15), (18), and (21) of said Y group, and the heteroaryl moiety in said substituted groups (13), (16), (17) and (20) of said Y group, are substituted with one or more substituents independently selected from the group consisting of:

(a) halo;
(b) —CF$_3$;
(c) —OH;
(d) —O-alkyl;
(e) —OCF$_3$;
(f) —CN;
(g) —NH$_2$;
(h) —C(O)$_2$(C$_1$–C$_6$)alkyl;
(i) —C(O)NR$^6$R$^7$;
(j) —(C$_1$–C$_6$)alkylene-NR$^6$R$^7$;
(k) —NR$^6$C(O)alkyl;
(l) —NR$^6$C(O)aryl;
(m) —NR$^6$C(O)heteroaryl;
(n) —NR$^6$C(O)NR$^6$R$^7$; and
(o) alkyl, or Y is selected from the group consisting of:

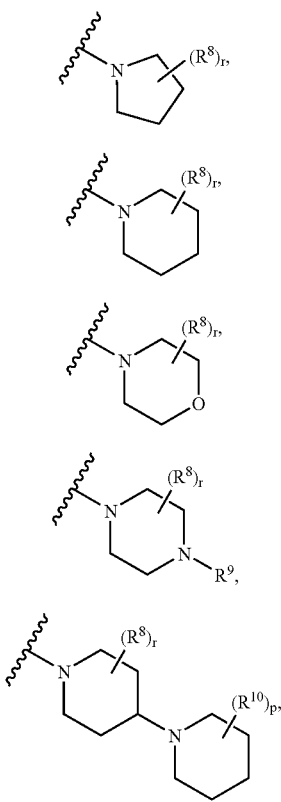

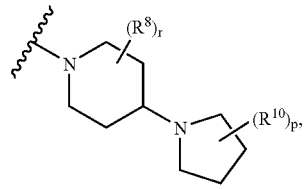

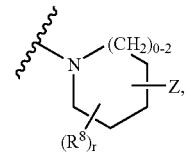

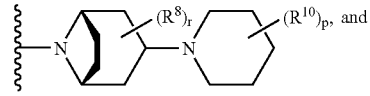

(H) R$^6$ and R$^7$ are independently selected from the group consisting of:
(1) H;
(2) alkyl;
(3) alkyl substituted with 1 to 4 hydroxy groups, with the proviso that one of the hydroxy groups are bonded to a carbon to which a nitrogen is also bonded;
(4) cycloalkyl;
(5) arylalkyl;
(6) heteroarylalkyl;
(7)

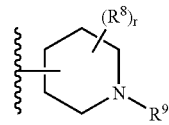

(8)

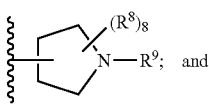

(9) heterocycloalkyl, (I) Each R$^8$ is independently selected from the group consisting of:
(1) H;
(2) alkyl;
(3) alkyl substituted with 1 to 4 hydroxy groups;
(4) aryl;
(5) —OH;
(6) —O-alkyl;
(7) —C(O)O-alkyl;

(8) if r is greater than 1, at least two R$^8$ groups, together with the ring carbon atom or atoms to which they are attached define a ring, wherein one or more carbon atoms of said ring may be replaced independently of each other by —O— or —C(O)O—, and said ring may be substituted with 1 to 4 hydroxy groups, (J) Each R$^9$ is independently selected from the group consisting of:
(1) H;
(2) alkyl;
(3) alkyl substituted with 1 to 4 hydroxy groups;
(4) cycloalkyl;
(5) cycloalkyl substituted with 1 to 4 hydroxy groups;
(6) arylalkyl;
(7) heteroarylalkyl;
(8) —C(O)O-alkyl;
(9) alkylene-O-alkylene-OH;
(10) aryl substituted with one or more R$^5$ groups;
(11) heteroaryl substituted with one or more R$^5$ groups;
(12) unsubstituted heteroaryl;
(13) unsubstituted aryl;
(14) -alkylene-C(O)O-alkyl; and
(15) hydroxyalkyl-O-alkyl, (K) Each R$^{10}$ is independently selected from the group consisting of:
(1) H; and
(2) alkyl, (L) R$^{11}$ is selected from the group consisting of:
(1) unsubstituted aryl;
(2) substituted aryl;
(3) unsubstituted heteroaryl,
(4) alkyl;
(5) cycloalkyl;
(6) unsubstituted arylalkyl;
(7) unsubstituted arylcycloalkyl,
(8) unsubstituted heteroarylalkyl;
(9) unsubstituted heteroarylcycloalkyl;
(10) unsubstituted arylheterocycloalkyl;
(11) alkoxyalkyl;
(12) substituted heteroaryl;
(13) substituted arylalkyl;
(14) substituted arylcycloalkyl;
(15) substituted heteroarylalkyl; and
(16) substituted arylheterocycloalkyl, wherein the aryl moiety in said substituted groups (2), (13), (14) and (16) of said R$^{11}$ group, and the heteroaryl moiety in said substituted groups (12) and (15) of said R$^{11}$ group, are substituted with one or more substituents independently selected from the group consisting of:
(a) halo;
(b) —CF$_3$;
(c) —OH;
(d) —O-alkyl;
(e) —OCF$_3$;
(f) —CN;
(g) —NH$_2$;
(h) —C(O)$_2$(C$_1$–C$_6$)alkyl;
(i) —C(O)NR$^6$R$^7$;
(j) —(C$_1$–C$_6$)alkylene-NR$^6$R$^7$;
(k) —NR$^6$C(O)alkyl;
(l) —NR$^6$C(O)aryl;
(m) —NR$^6$C(O)heteroaryl; and
(n) —NR$^6$C(O)NR$^6$R$^7$;

(M) (1) m is 0 to 3, and if m is greater than 1, m moieties can be the same or different from one another;
(2) n is 0 to 3, and if n is greater than 1, n moieties can be the same or different from one another;
(3) o is 0 to 3, and if o is greater than 1, o moieties can be the same or different from one another;
such that m+n+o is 1, 2, 3 or 4,
(N) p is 0 to 4, and if greater than 1, p moieties can be the same or different from one another;
(O) r is 0 to 4, and if greater than 1, r moieties can be the same or different from one another;
(P) s is 0 to 3, and if greater than 1, s moieties can be the same or different from one another; and
(Q) Z is selected from the group consisting of:
(1) unsubstituted heterocycloalkyl;
(2) substituted heterocycloalkyl;
(3) —NH$_2$;
(4) —NH(alkyl);
(5) —N(alkyl)$_2$ wherein each alkyl is the same or different;
(6) —NH(unsubstituted cycloalkyl);
(7) —NH(substituted cycloalkyl);
(8) —N(alkyl)(unsubstituted cycloalkyl);
(9) —N(alkyl)(substituted cycloalkyl);
(10) —NH(unsubstituted aralkyl);
(11) —NH(substituted aralkyl);
(12) —N(alkyl)(aralkyl);
(13) —NH(unsubstituted heterocycloalkyl);
(14) —NH(substituted heterocycloalkyl);
(15) —N(alkyl)(unsubstituted heterocycloalkyl),
(16) —N(alkyl)(substituted heterocycloalkyl);
(17) —NH(unsubstituted heteroaralkyl);
(18) —NH(substituted heteroaralkyl);
(19) —NH-alkylene-(unsubstituted cycloalkyl);
(20) —NH-alkylene-(substituted cycloalkyl);
(21) —N(alkyl)alkylene-(unsubstituted cycloalkyl);
(22) —N(alkyl)alkylene-(substituted cycloalkyl);
(23) —NHalkylene-(unsubstituted heterocycloalkyl);
(24) —NHalkylene-(substituted heterocycloalkyl);
(25) —N(alkyl)alkylene-(unsubstituted heterocycloalkyl);
(26) —N(alkyl)alkylene-(substituted heterocycloalkyl);
(27) unsubstituted benzofused heterocycloalkyl); and
(28) substituted benzofused heterocycloalkyl;
(29) H; and
(30) —N(hydroxyalkyl)$_2$, wherein each alkyl may be the same or different, wherein said substituted heterocycloalkyl moiety of substituents (2), (14), (16), (24), (26) and (27) of group Z, and said substituted cycloalkyl moiety of substituents (7), (9), (20) and (22) of group Z, and said substituted aryl moiety of substituent (11) of group Z, and said substituted heteroaryl moiety of substituent (18) of group Z, are substituted with 1 to 3 groups independently selected from the group consisting of:
(a) alkyl;
(b) —OH;
(c) -Oalkyl;
(d) —OC(O)alkyl;
(e) —OC(O)aryl;
(f) —NH$_2$;
(g) —NH(alkyl);
(h) —N(alkyl)$_2$ wherein each alkyl is the same or different;
(i) —NHC(O)alkyl;
(j) —N(alkyl)C(O)alkyl;
(k) —NHC(O)aryl;
(l) —N(alkyl)C(O)aryl;
(m) —C(O)alkyl;
(n) —C(O)aryl;

(o) —C(O)NH₂;
(p) —C(O)NH(alkyl);
(q) —C(O)N(alkyl)₂ wherein each alkyl is the same or different;
(r) —C(O)₂alkyl;
(s) -alkylene-C(O)Oalkyl;
(t) piperidinyl;
(u) pyrrolidinyl;
(v) 1,1-ethylenedioxy;
(w) aryl;
(x) heteroaryl; and
(y) —O—CH₂CH₂—O-wherein both oxygen atoms are bound to the same carbon atom, and provided that the aryl and heteroaryl moieties of said Z group are not substituted with said —O—CH₂CH₂—O— group.

2. The compound of claim 1 wherein:
(A) R¹ is aryl substituted with one or more R⁵ groups;
(B) n is 0 or 1 and m is 1, 2 or 3 such that m+n is 3;
(C) p is 0 or 1; and
(D) R² is —XC(O)Y, —(C₁–C₆)alkylene-XC(O)Y or —(C₀–C₆)alkylene-(C₃₋C₆)cycloalkylene-(C₀–C₆)alkylene-XC(O)Y.

3. The compound of claim 2 wherein:
(A) R¹ is phenyl substituted with one or more R⁵ groups; and
(B) n is 0 and m is 3.

4. The compound of claim 1, wherein R² is

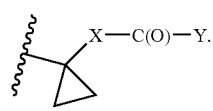

5. The compound of claim 3 wherein R¹ is phenyl substituted with one or more halo atoms.

6. The compound of claim 1 wherein:
(A) R¹ is aryl substituted with one or more R⁵ groups;
(B) n is 0 or 1 and m is 1, 2 or 3 such that m+n is 3;
(C) p is 0 or 1;
(D) R² is —XC(O)Y, —(C₁–C₆)alkylene-XC(O)Y or —(C₀–C₆)alkylene-(C₃₋C₆)cycloalkylene-(C₀–C₆)alkylene-XC(O)Y;
(E) X is O;
(F) Y is —NR⁶R⁷; or Y is selected from the group consisting of:

(c) 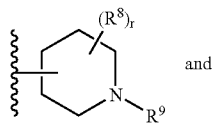

(d) 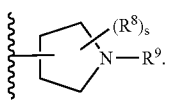

(e) 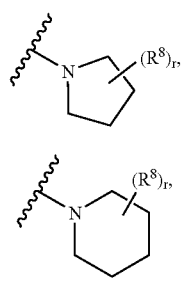

(f) 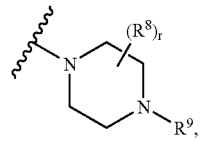

(g) 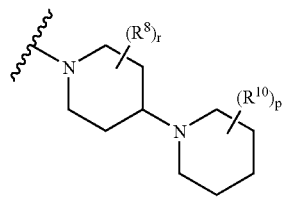

(h) 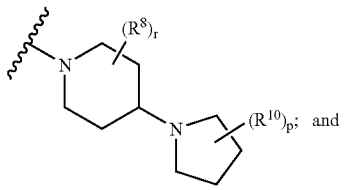

(G) R⁶ and R⁷ are independently selected from the group consisting of: H, methyl, ethyl, —(C₃–C₈)cycloalkyl, -aryl(C₁–C₆)alkyl, 4-pyridylmethyl, and (a) 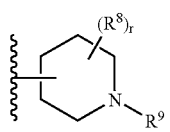

(b) 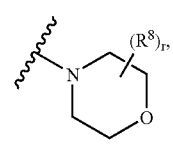

7. The compound of claim 6 wherein:
(A) R¹ is phenyl substituted with one or more R⁵ groups;
(B) n is 0 and m is 3;
(C) said group (a) 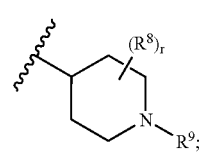

is a group of the formula:

(a1)

(D) said group

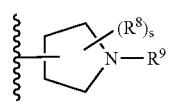

is a group of the formula:

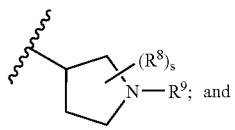

(E) R[11] is selected from the group consisting of: —($C_1$–$C_6$)alkyl, ($C_3$–$C_8$)-cycloalkyl, aryl, aryl($C_1$–$C_6$)alkyl and —($C_1$–$C_6$)alkoxyalkyl.

8. The compound of claim 7 wherein said R[11] is selected from the group consisting of: methyl, ethyl, cyclohexyl, phenyl, benzyl, —($CH_2$)$_2$phenyl, and —$CH_2OCH_3$.

9. The compound of claim 7 wherein R[1] is phenyl substituted with one or more halo atoms.

10. The compound of claim 8 wherein R[11] is phenyl substituted with one or more halo atoms.

11. The compound of claim 6 wherein Y is selected from the group consisting of:

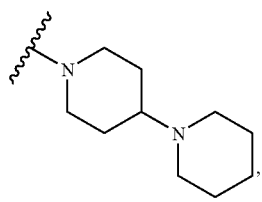

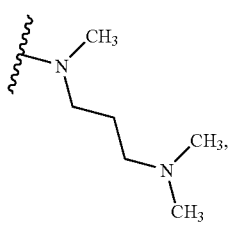

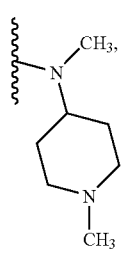

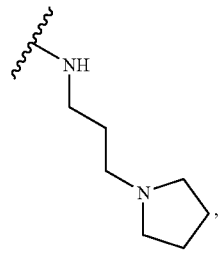

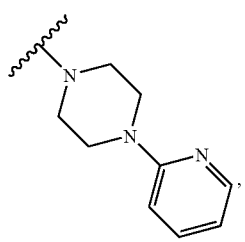

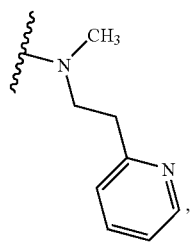

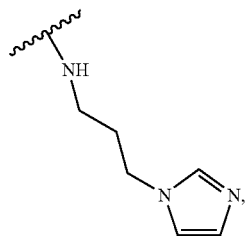

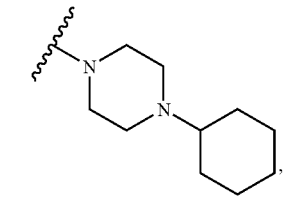

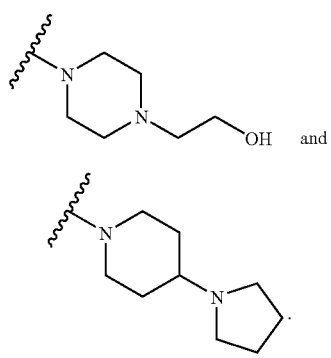

12. A pharmaceutical composition comprising at least one compound of claim 1 and at least one pharmaceutically acceptable carrier.

13. A compound selected from the group consisting of:

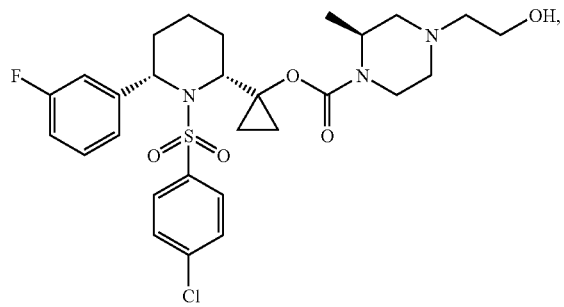

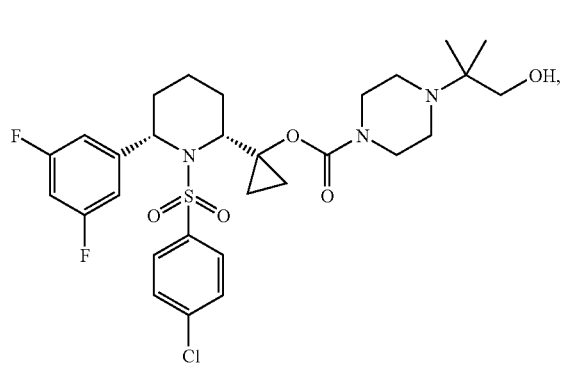

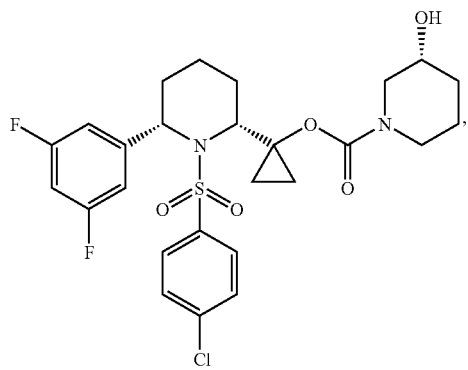

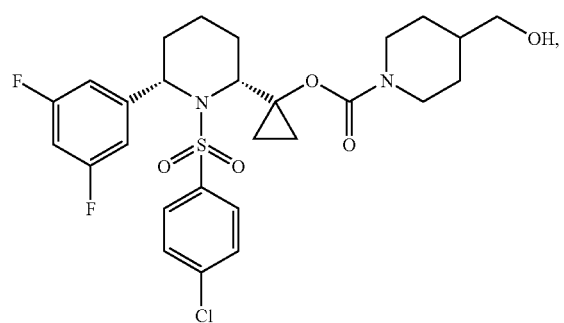

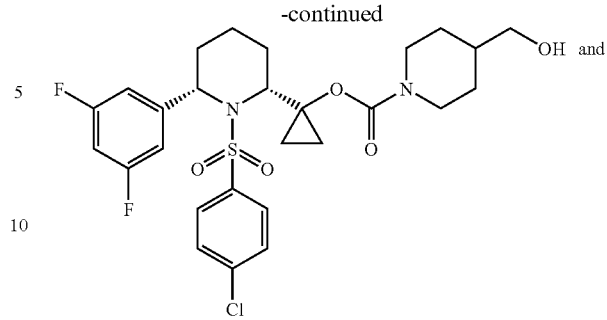

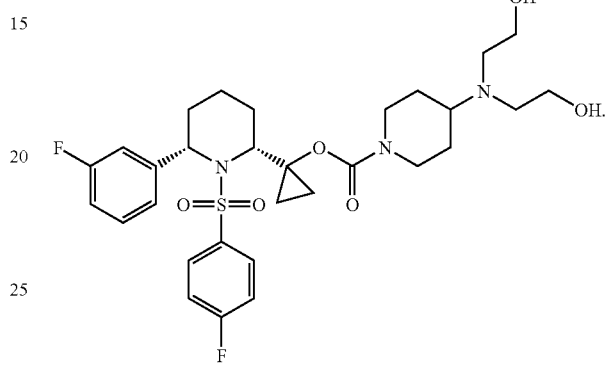

14. A pharmaceutical composition comprising a therapeutically effective amount of a compound of claim 13, or a pharmaceutically acceptable salt, ester or solvate thereof, together with a pharmaceutically acceptable excipient, diluent or carrier.

15. A compound of the following formula

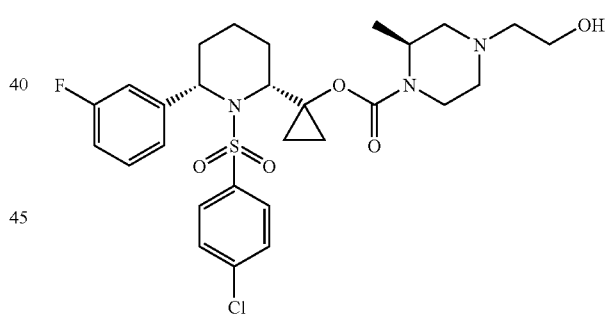

or a pharmaceutically acceptable salt, ester or solvate of said compound.

16. A compound of the following formula

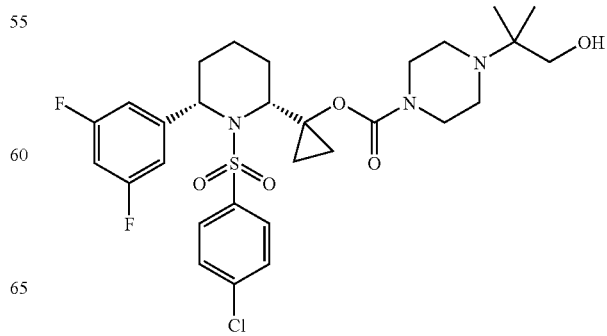

or a pharmaceutically acceptable salt, ester or solvate of said compound.

17. A compound of the following formula

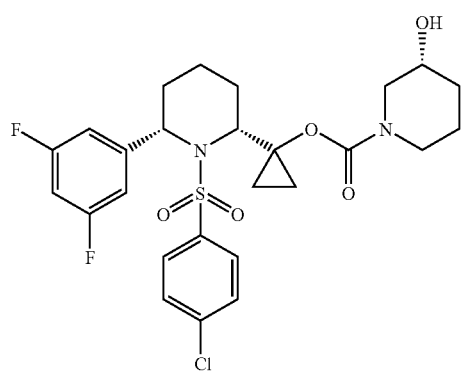

or a pharmaceutically acceptable salt, ester or solvate of said compound.

18. A compound of the following formula

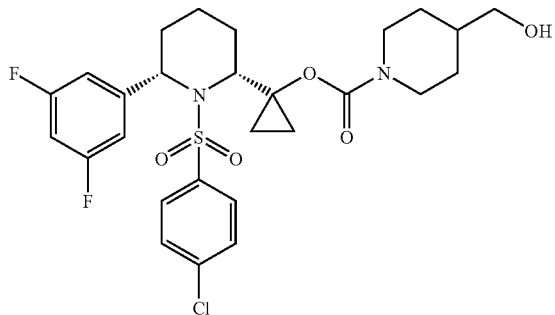

or a pharmaceutically acceptable salt, ester or solvate of said compound.

19. A compound of the following formula

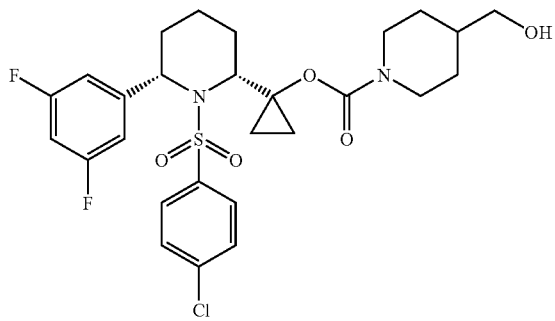

or a pharmaceutically acceptable salt, ester or solvate of said compound.

20. A compound of the following formula

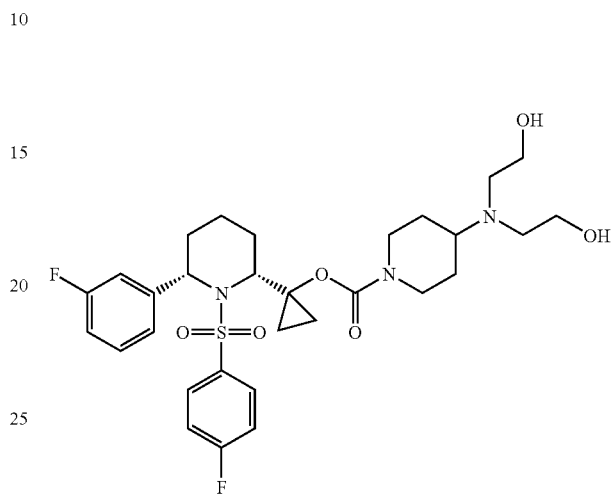

or a pharmaceutically acceptable salt, ester or solvate of said compound.

21. The compound of claim 1 selected from the group consisting of:

(Example 1)

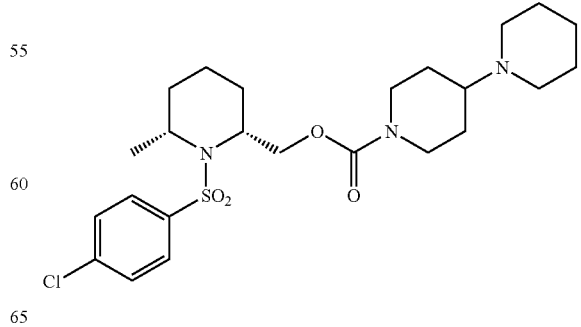

| EX. No. | COMPOUND |
|---|---|
| 2 | 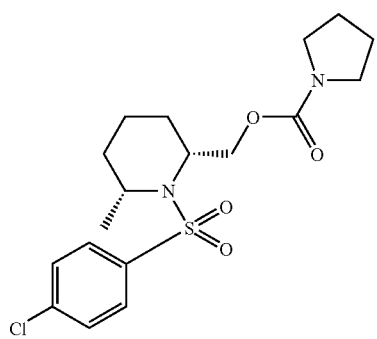 |
| 3 | 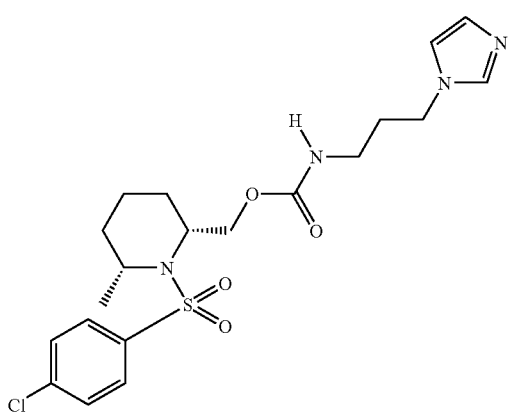 |
| 4 | 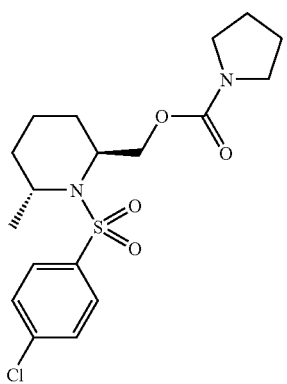 |
| 5 | 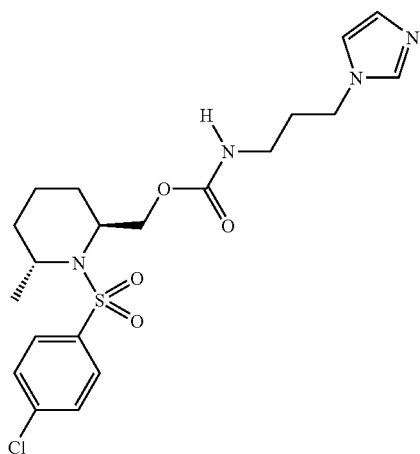 |

| EX. No. | COMPOUND |
|---|---|
| 6 | 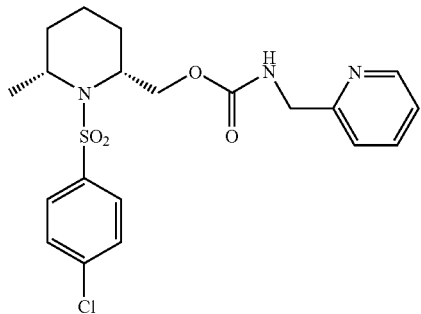 |
| 7 | 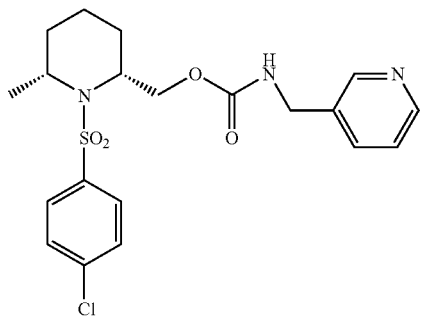 |
| 8 | 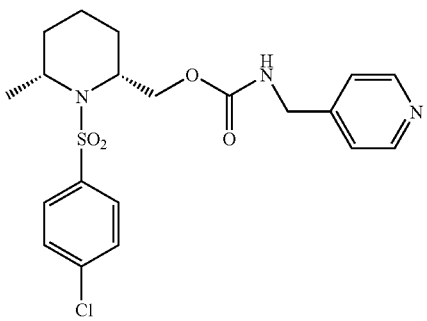 |
| 9 | 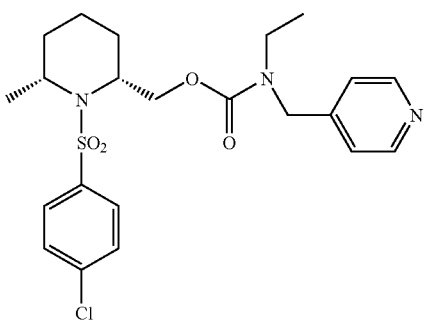 |

-continued
| EX. No. | COMPOUND |
|---|---|
| 10 | 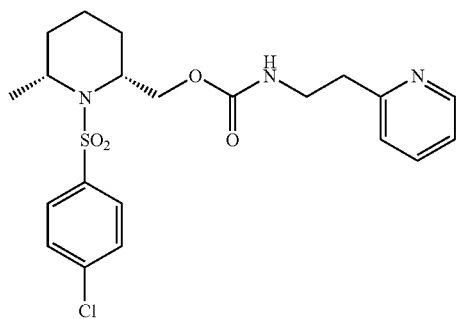 |
| 11 | 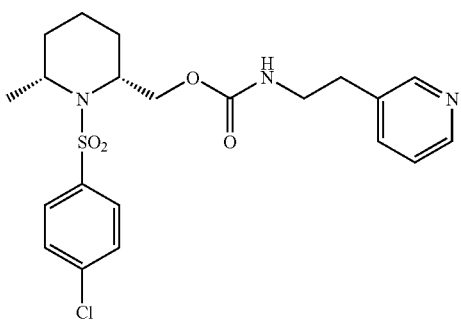 |
| 12 | 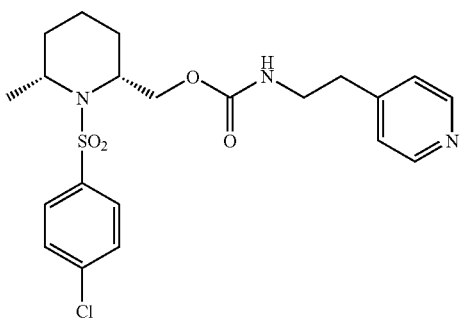 |
| 13 | 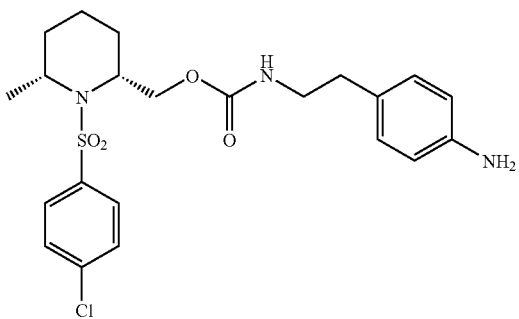 |

| EX. No. | COMPOUND |
|---|---|
| 14 | 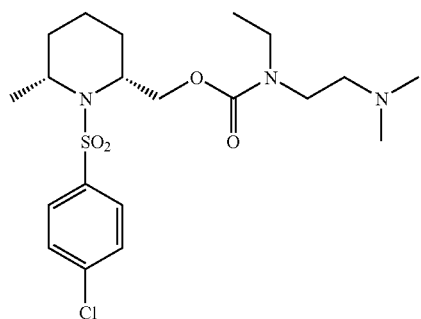 |
| 15 | 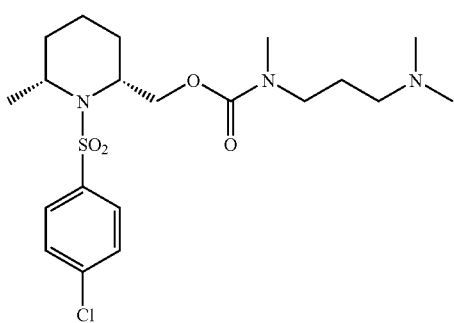 |
| 16 | 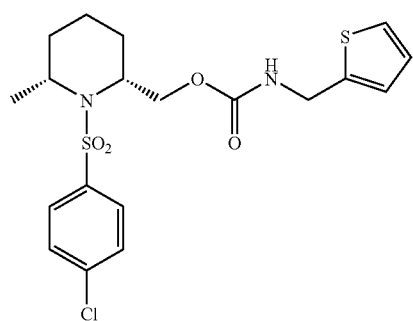 |
| 17 | 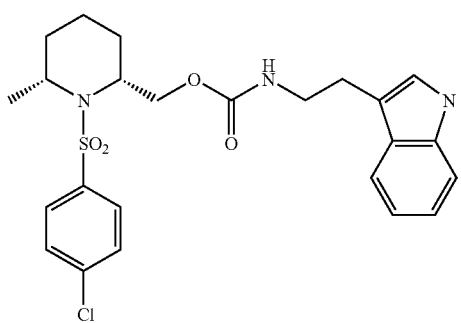 |

-continued
| EX. No. | COMPOUND |
|---|---|
| 18 | 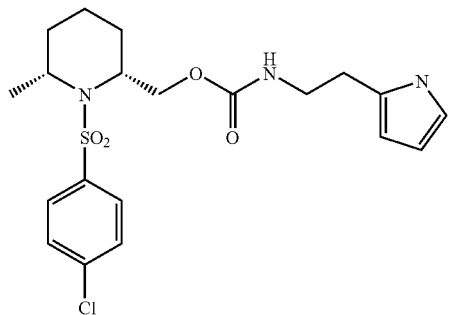 |
| 19 | 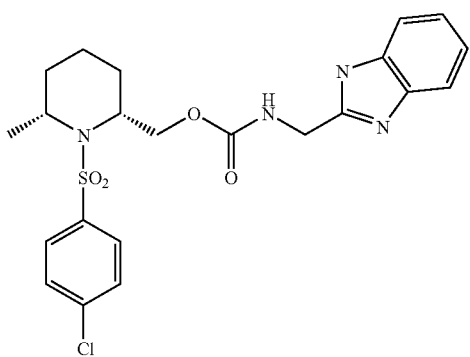 |
| 20 | 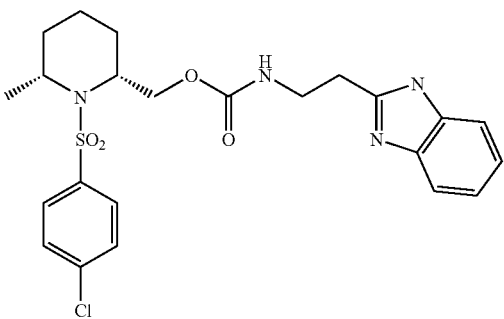 |
| 21 | 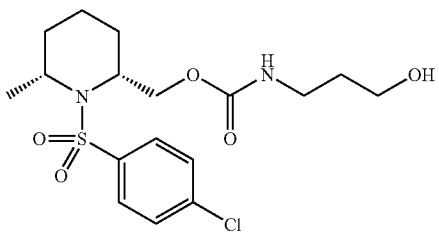 |
| 22 | 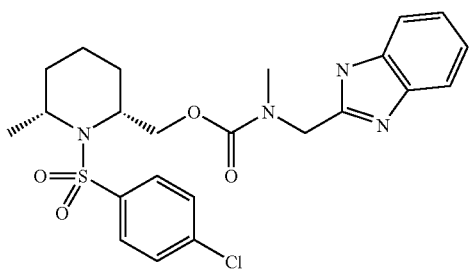 |

| EX. No. | COMPOUND |
|---|---|
| 23 | 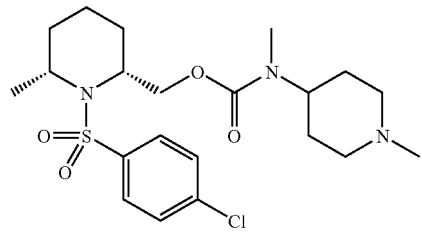 |
| 24 | 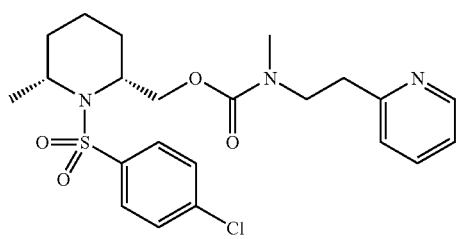 |
| 25 | 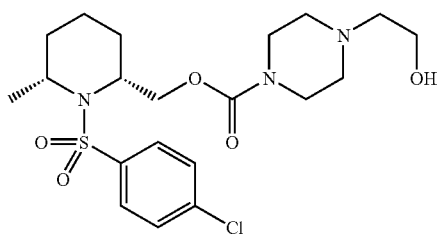 |
| 26 | 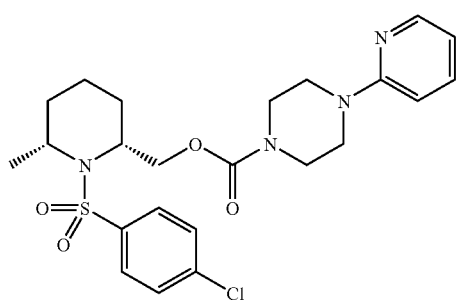 |
| 27 | 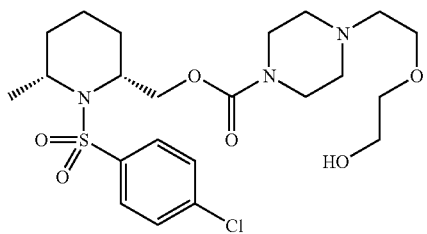 |

-continued
| EX. No. | COMPOUND |
|---|---|
| 28 | 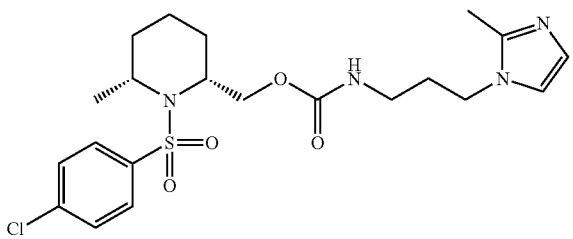 |
| 29 | 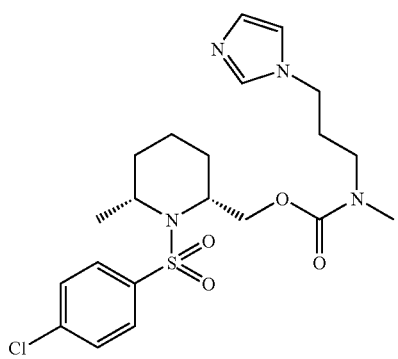 |
(Example 31)
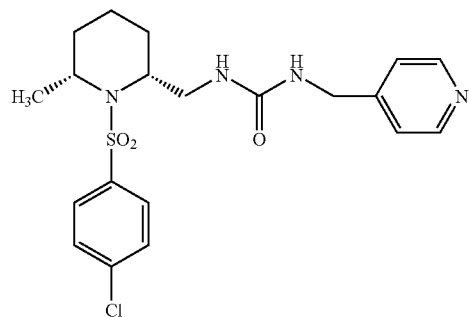
| EX. No. | COMPOUND |
|---|---|
| 32 | 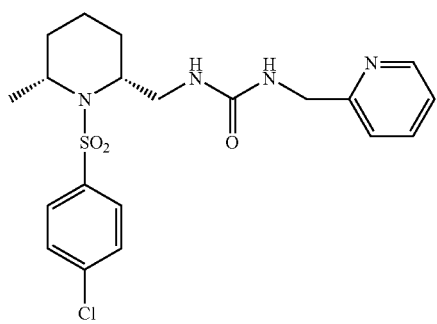 |
-continued
| EX. No. | COMPOUND |
|---|---|
| 33 | 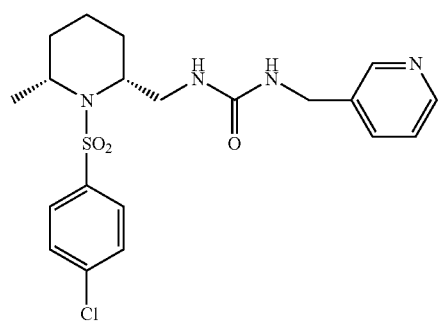 |
| 35 | 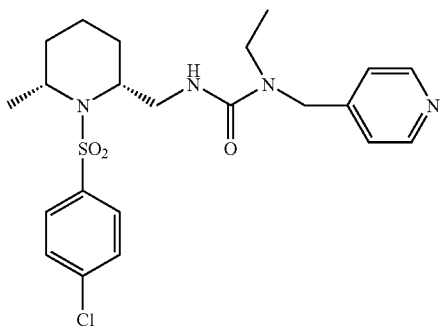 |

-continued
| EX. No. | COMPOUND |
|---|---|
| 36 | 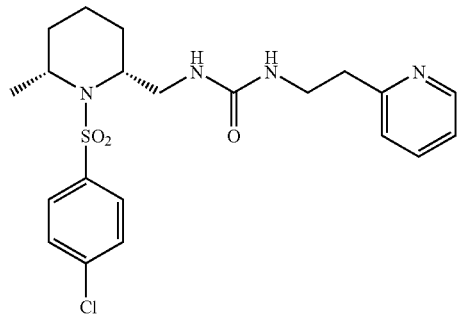 |
| 37 | 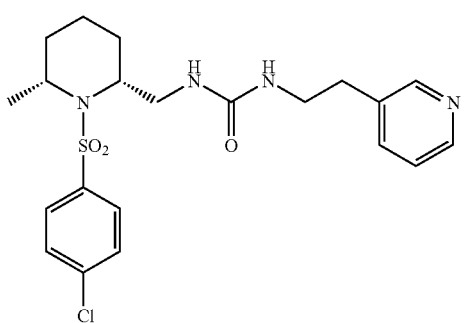 |
| 38 | 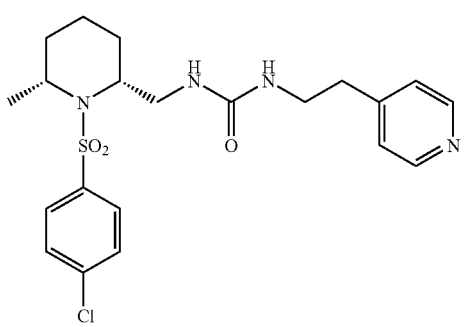 |
| 39 | 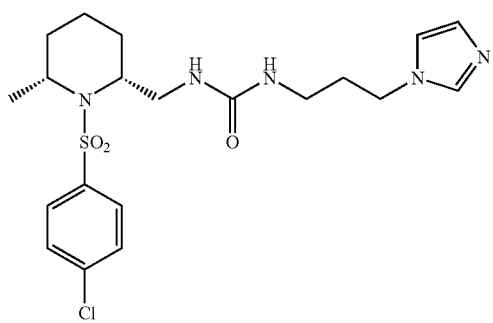 |
-continued
| EX. No. | COMPOUND |
|---|---|
| 40 | 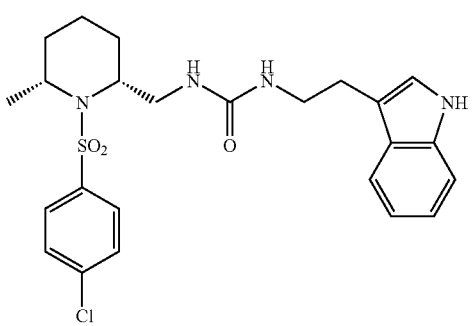 |
| 41 | |
| 42 | |

| EX. No. | COMPOUND |
|---|---|
| 43 | 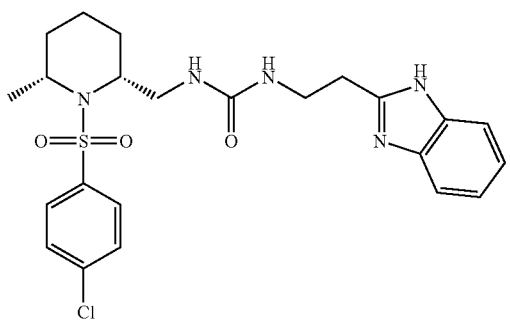 |
| | (Example 44) 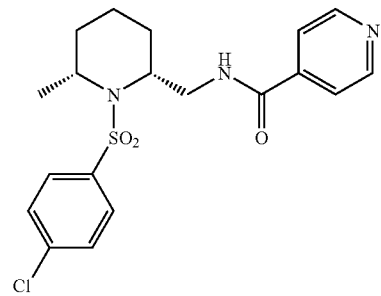 |
| EX. No. | COMPOUND |
|---|---|
| 45 | 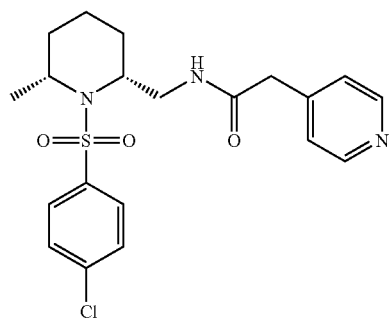 |
| 46 | 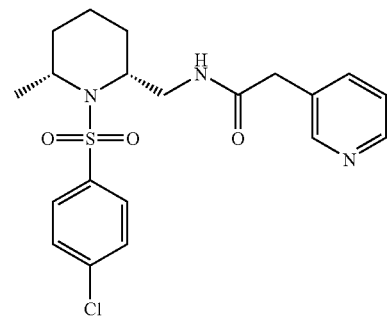 |
| 47 | 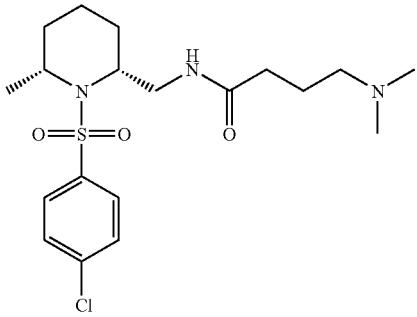 |

-continued
| | |
|---|---|
| 48 | 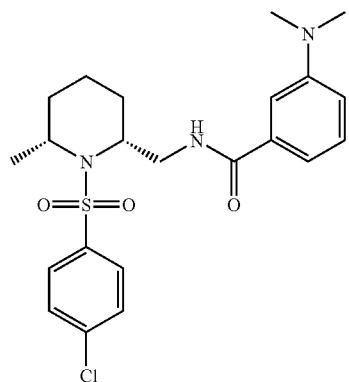 |
| 50 | 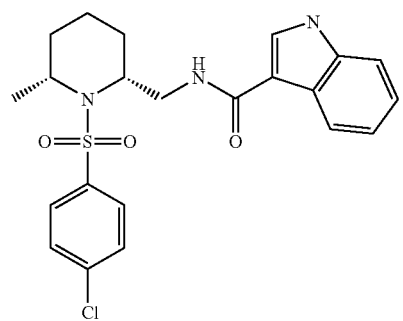 |
| 51 | 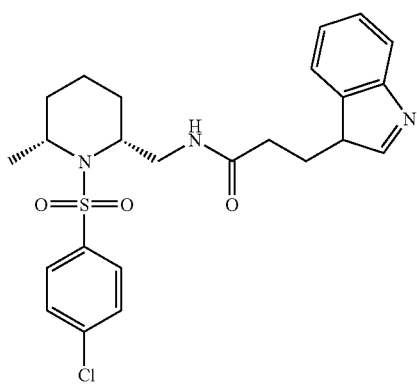 |
| 52 | 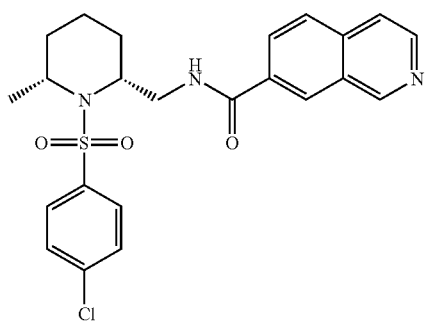 |

(Example 53)
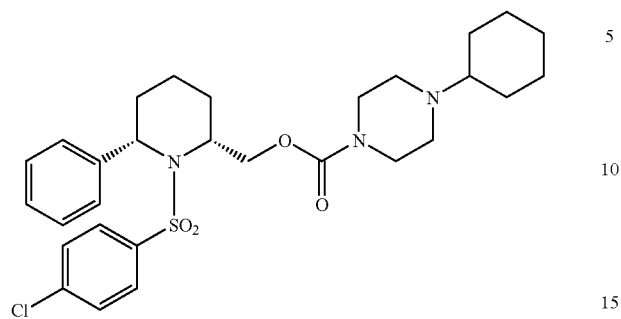
| Compound No. | Structure |
|---|---|
| 54 | 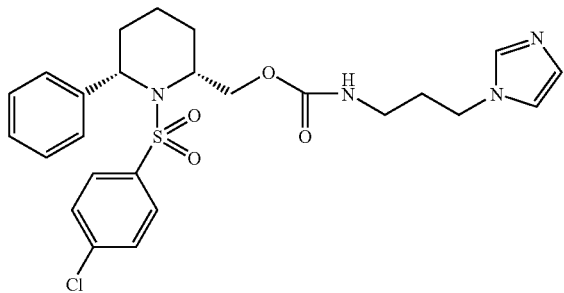 |
| 55 | 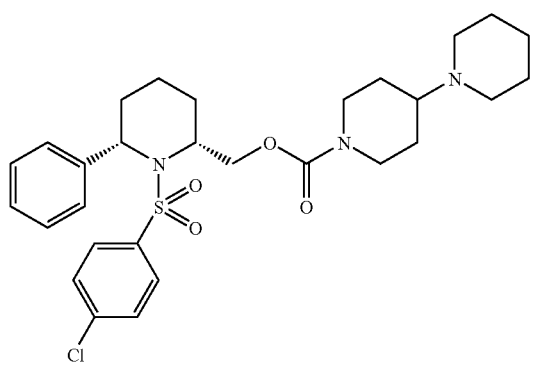 |
| 56 | 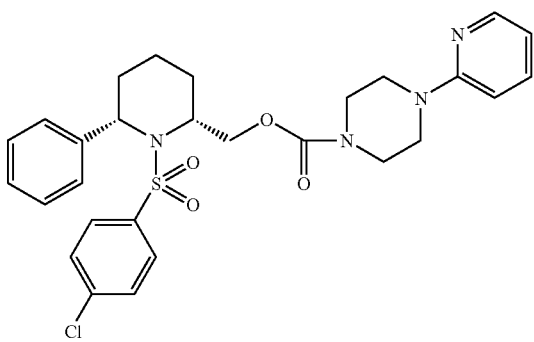 |

-continued
| Compound No. | Structure |
|---|---|
| 57 | 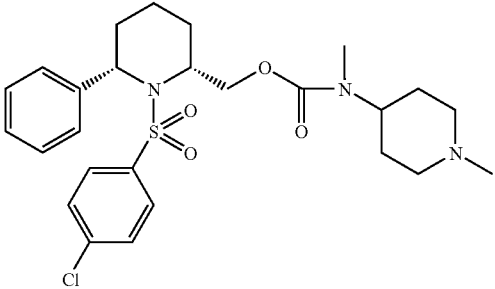 |
| 58 | 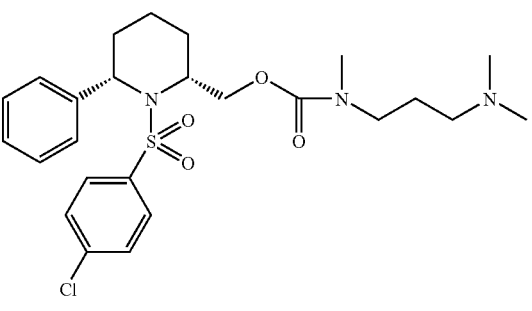 |
| 59 | 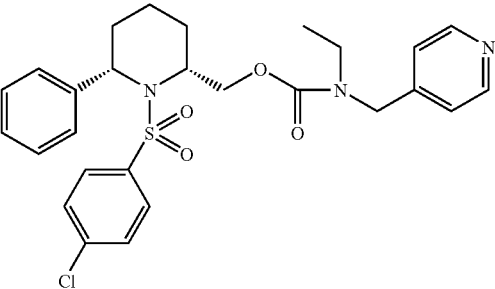 |
| 60 | 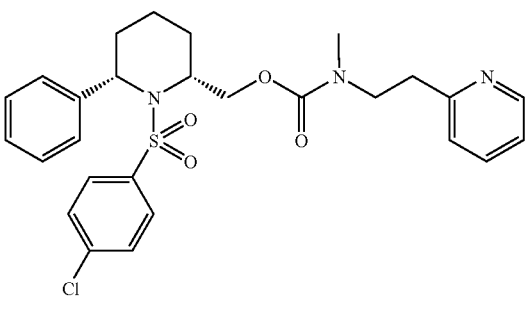 |
| 61 | 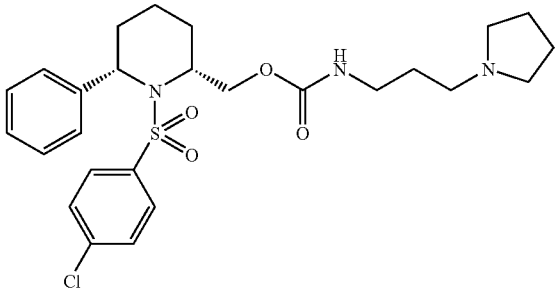 |

-continued
| Compound No. | Structure |
|---|---|
| 63 | 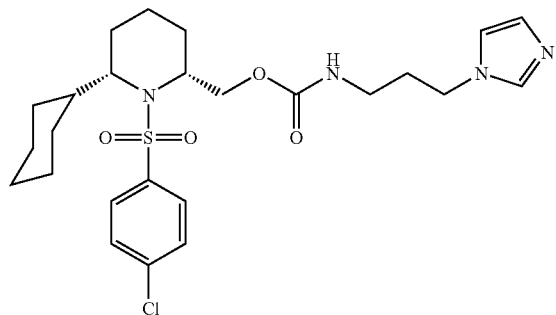 |
| 64 | 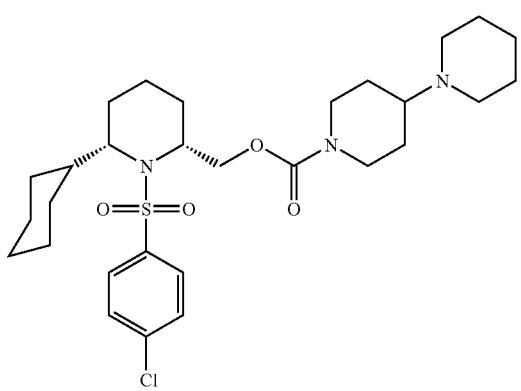 |
| 65 | 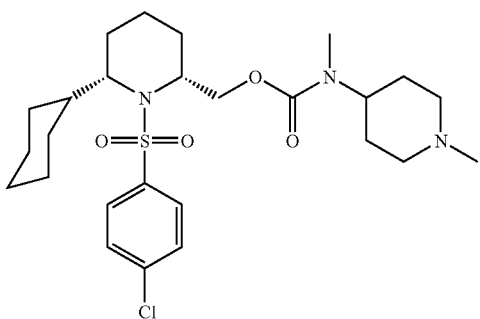 |
| 66 | 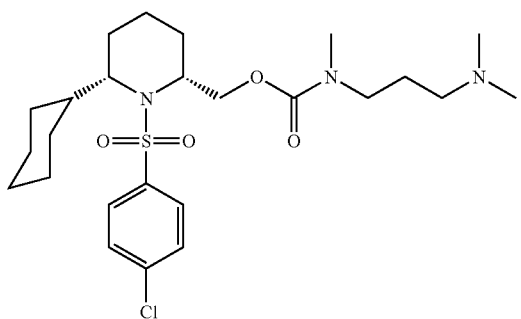 |

-continued
| Compound No. | Structure |
|---|---|
| 67 | 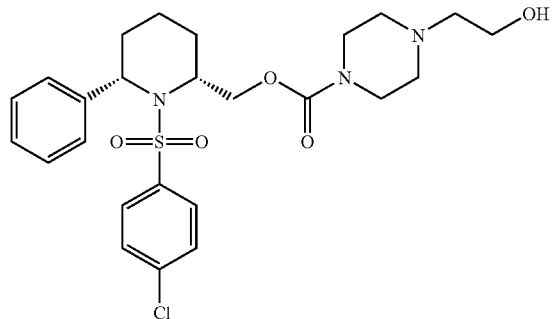 |
| 67-A | 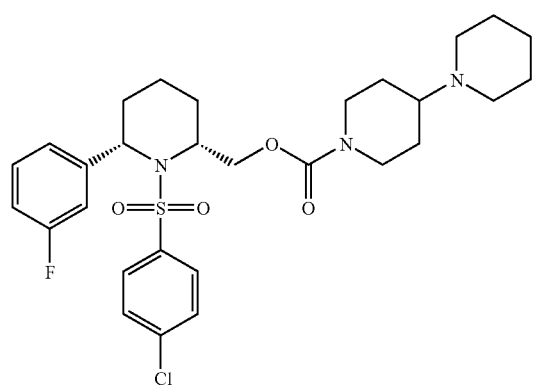
$[Alpha]_D^{20} = +51.40$ |
| 67-B | 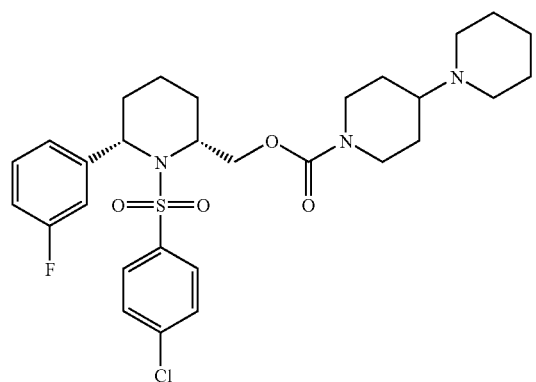
$[Alpha]_D^{20} = -56.95$ |
| 67-C | 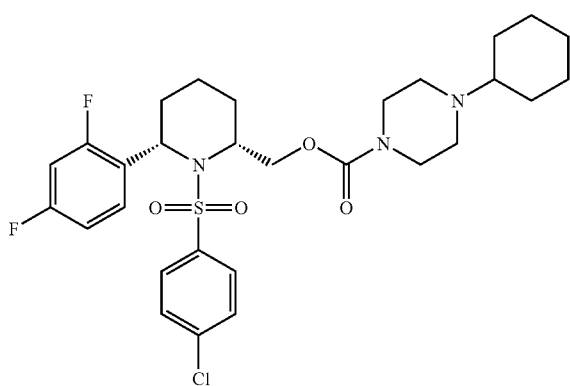 |

| Compound No. | Structure |
|---|---|
| 67-D | 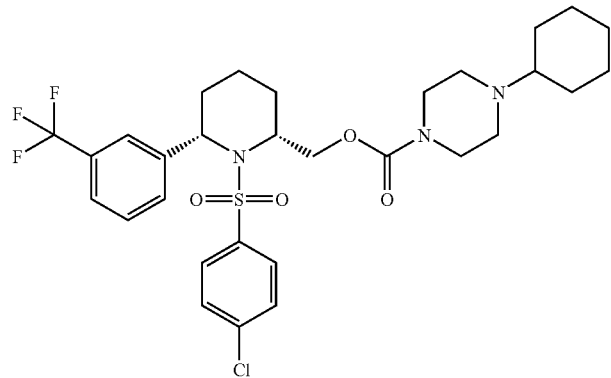 |
| 67-E | 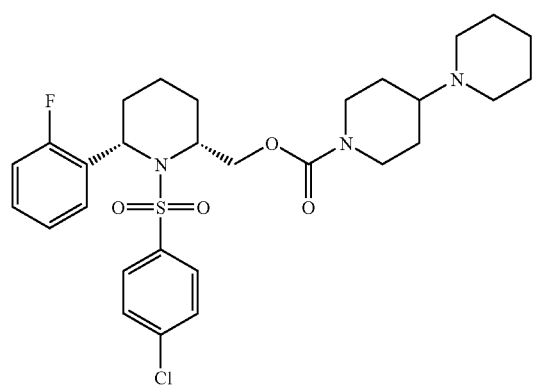 |
| 67-F | 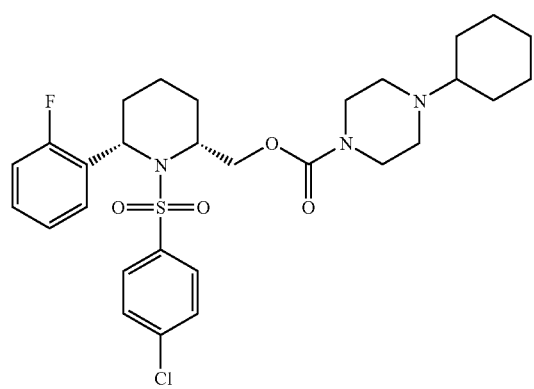 |
| 67-G | 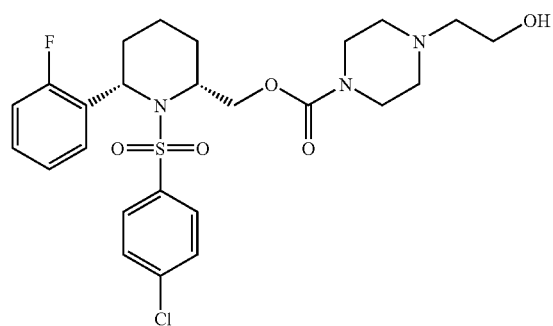 |

| Compound No. | Structure |
|---|---|
| 67-H | 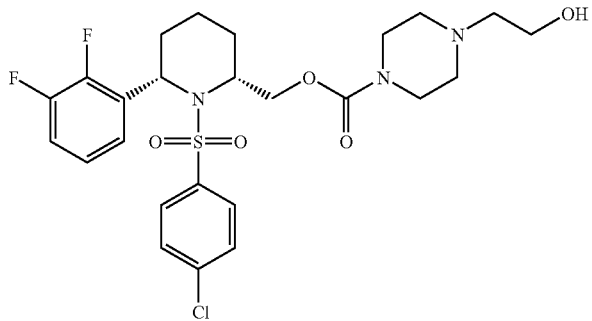 |
| 67-I | 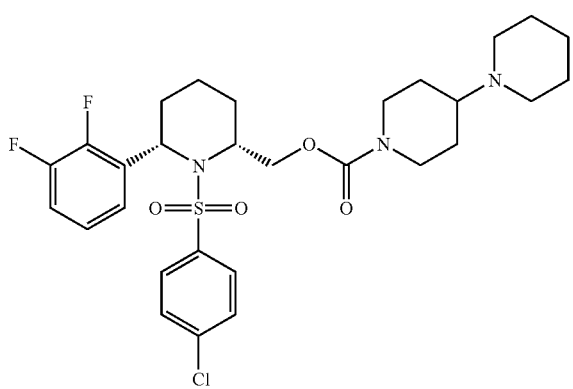 |
| 67-J | 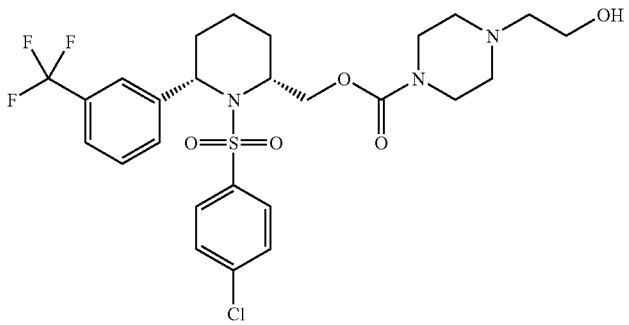 |
| 67-K | 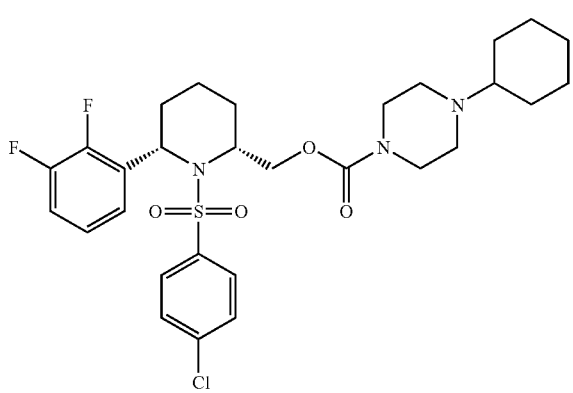 |

-continued
| Compound No. | Structure |
|---|---|
| 67-L | 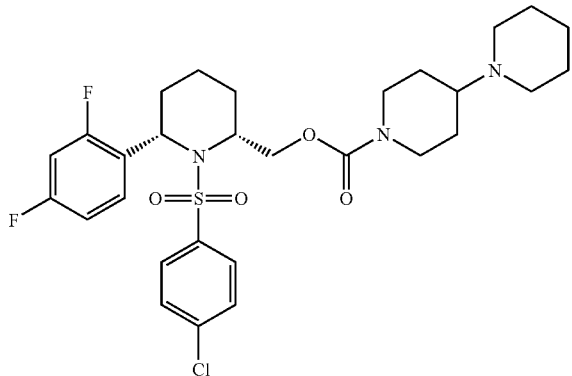 |
| 67-M | 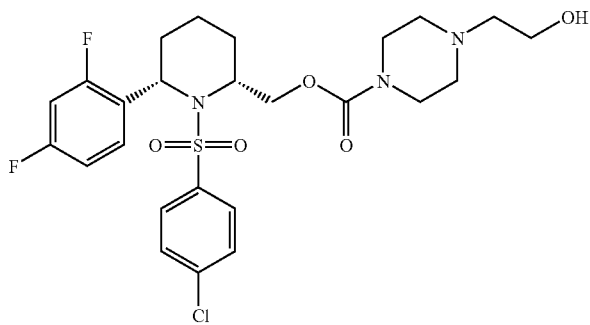 |
| 67-Q | 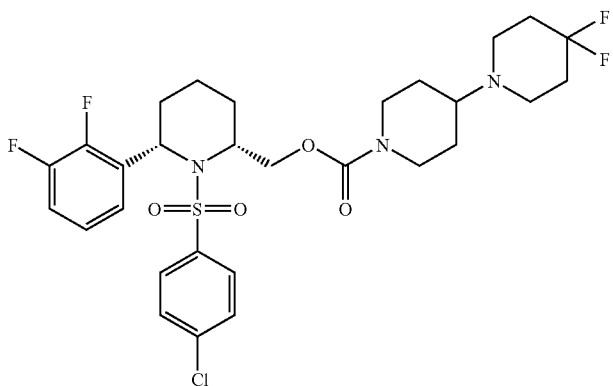 |
| 67-R | 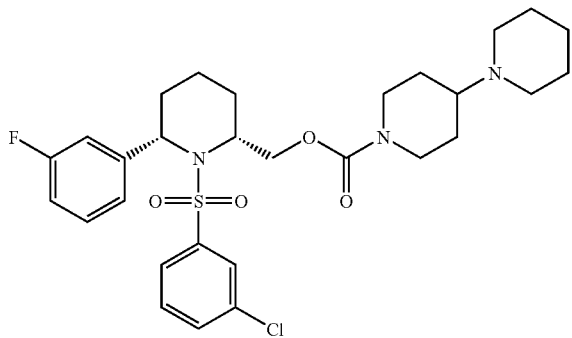 |

| Compound No. | Structure |
|---|---|
| 67-S | 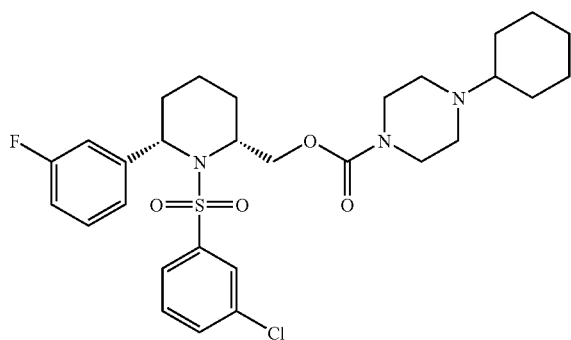 |
| 67-T | 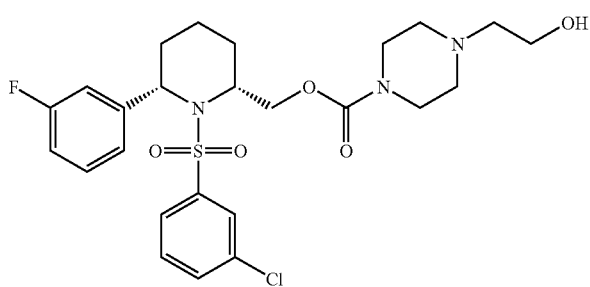 |
| 67-U | 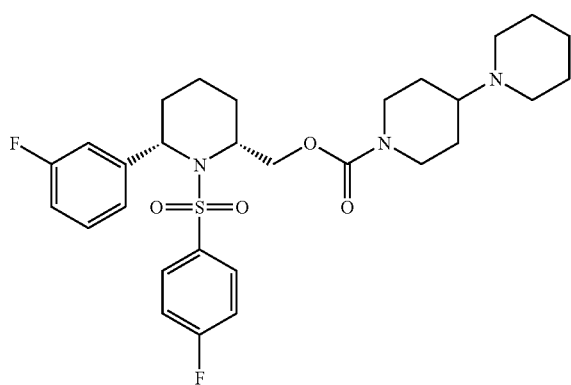 |
| 67-V | 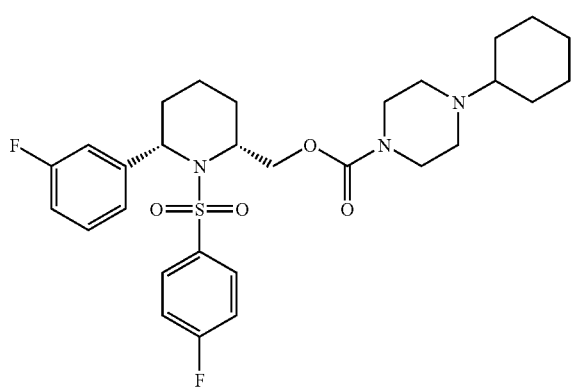 |

| Compound No. | Structure |
|---|---|
| 67-W | 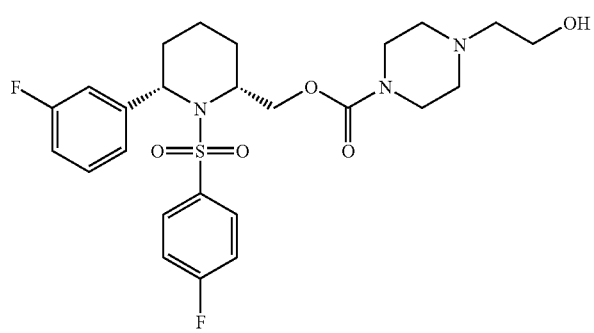 |
| 67-X | 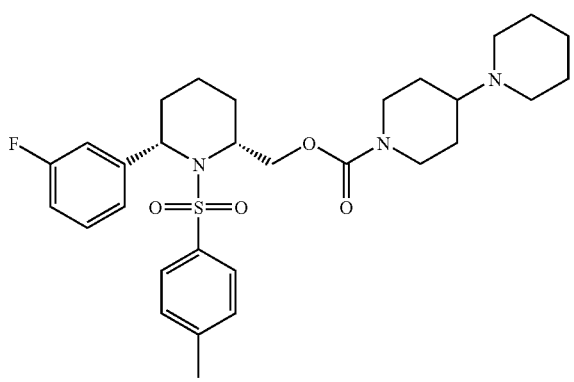 |
| 67-Y | 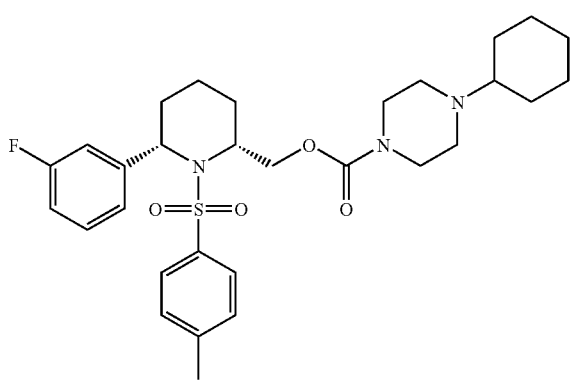 |
| 67-Z | 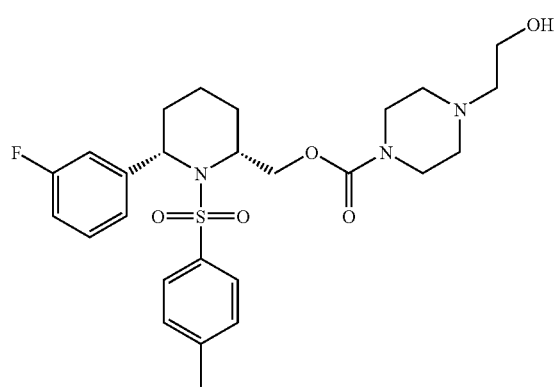 |

-continued
| Compound No. | Structure |
|---|---|
| 67-AA | 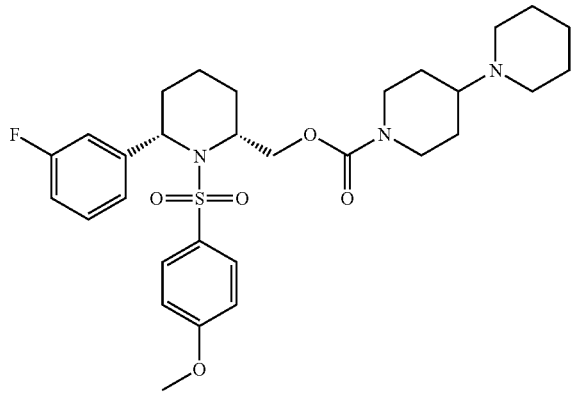 |
| 67-AB | 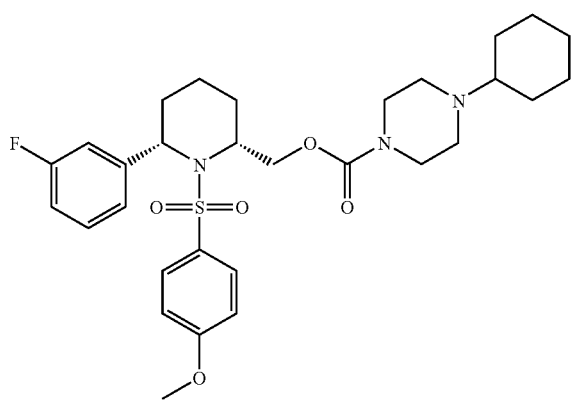 |
| 67-AC | 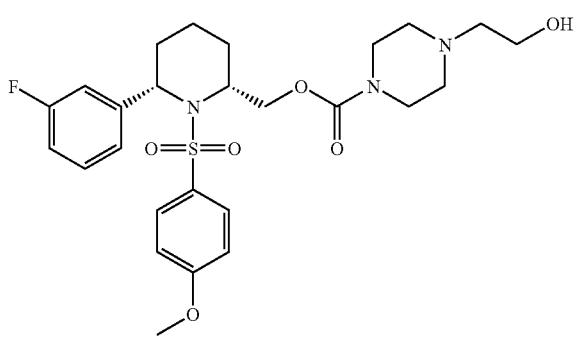 |
| 67-AD | 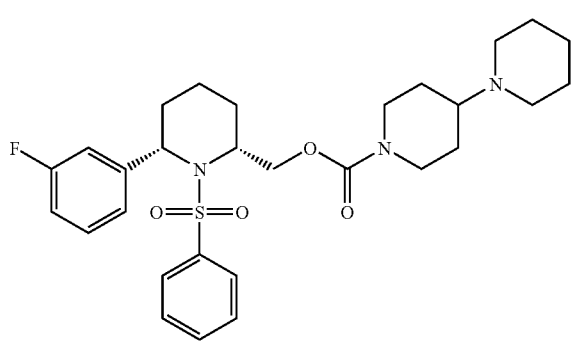 |

-continued

| Compound No. | Structure |
|---|---|
| 67-AE | 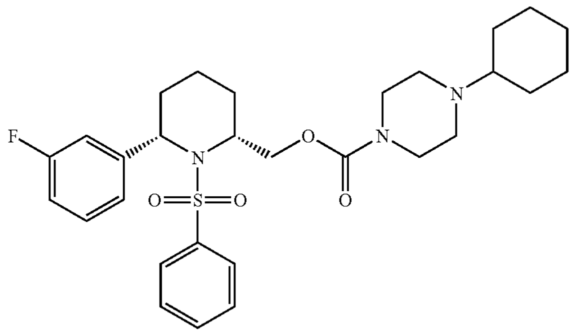 |
| 67-AF | 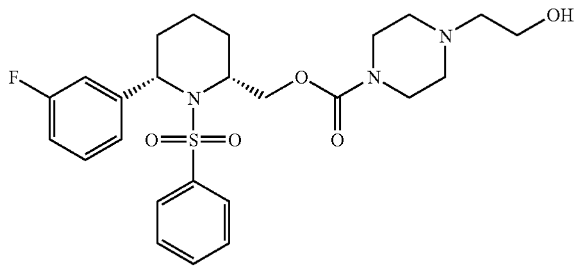 |
| 67-AG | 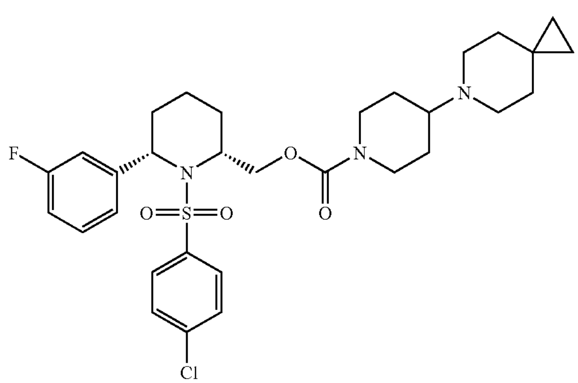 |
| 67-AH | 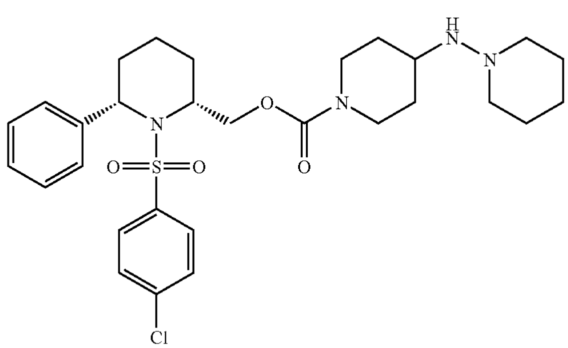 |

-continued

| Compound No. | Structure |
|---|---|
| 67-AI | 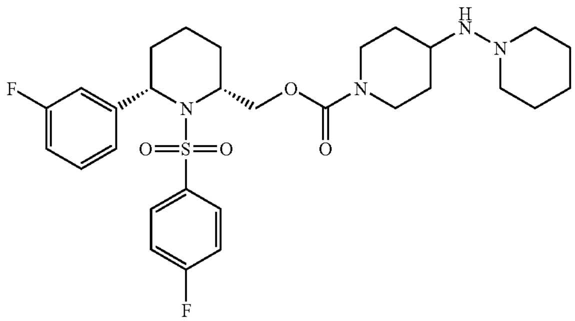 |
| 67-AJ | 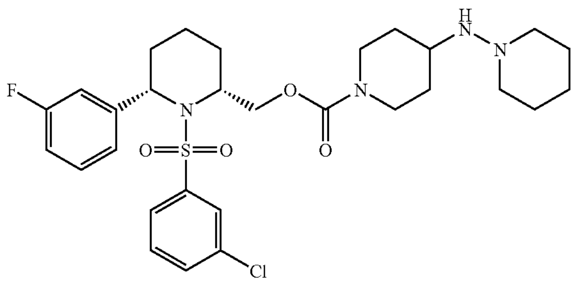 |
| 67-AK | 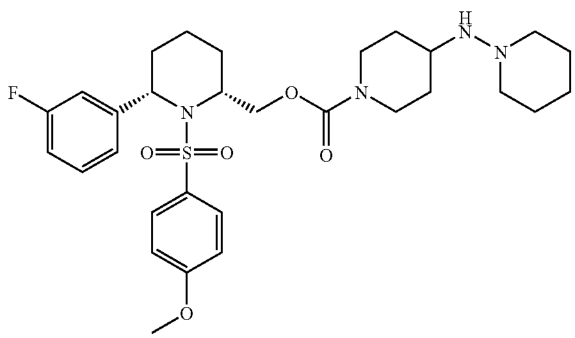 |
| 67-AL | 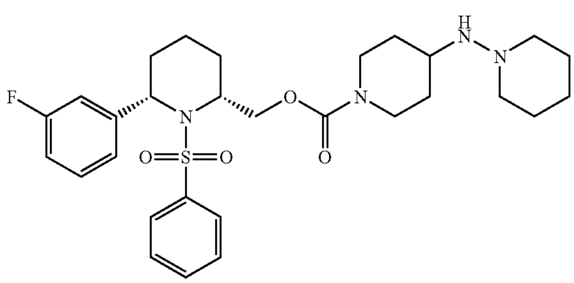 |
| 67-AM | 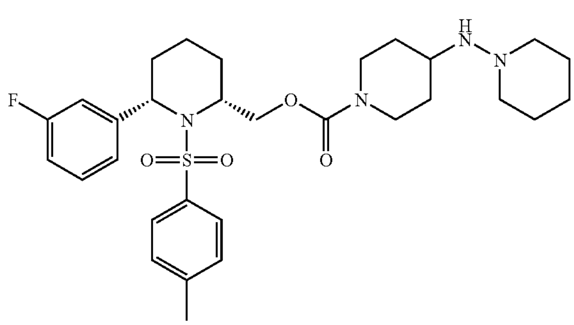 |

| Compound No. | Structure |
|---|---|
| 67-AN | 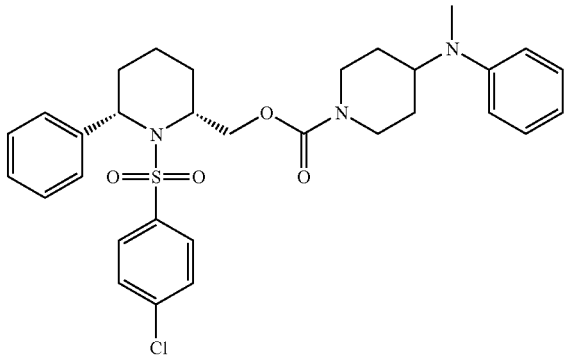 |
| 67-AO | 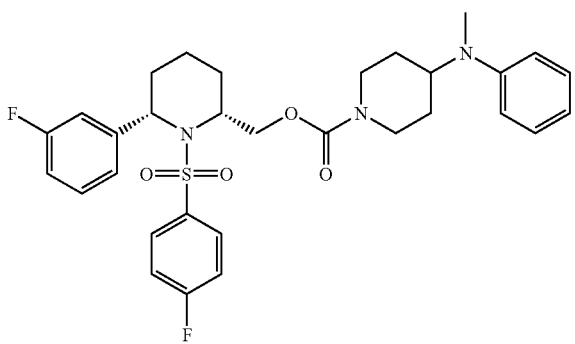 |
| 67-AP | 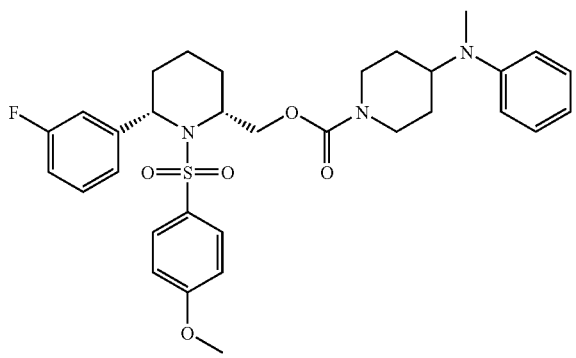 |
| 67-AQ | 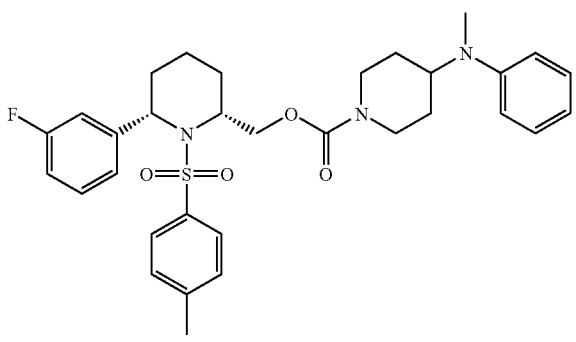 |

| Compound No. | Structure |
|---|---|
| 67-AR | 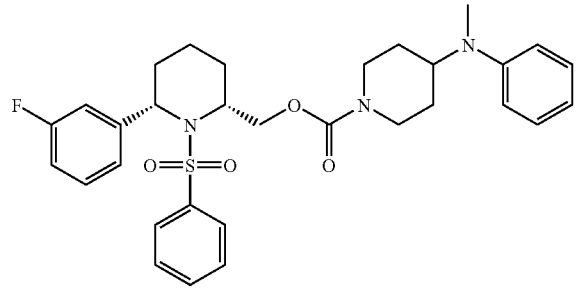 |
| 67-AS | 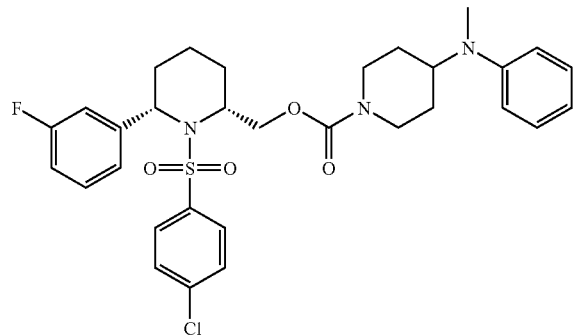 |
| 67-AT | 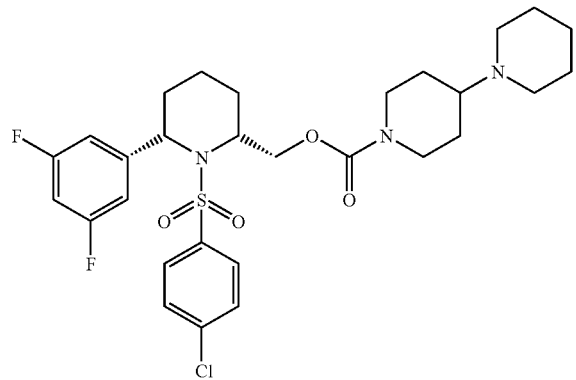 |
| 67-AV | 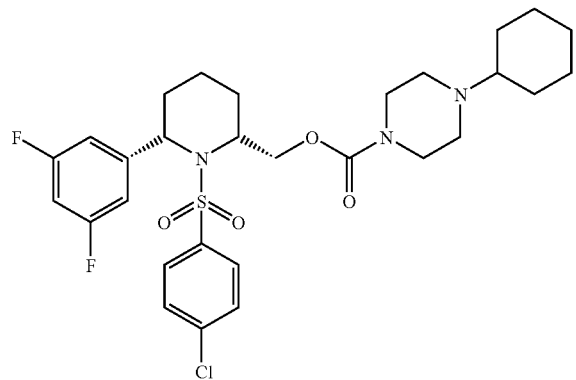 |

-continued
| Compound No. | Structure |
|---|---|
| 67-AW | 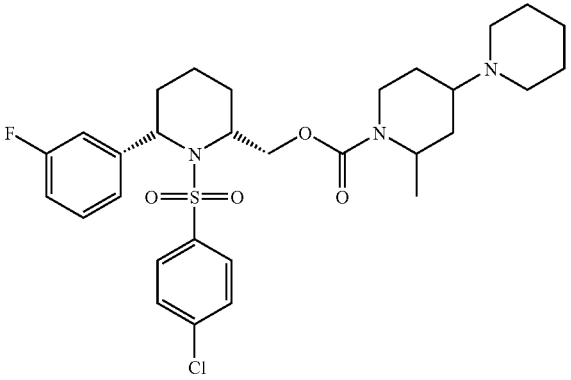 |
| 67-AX | 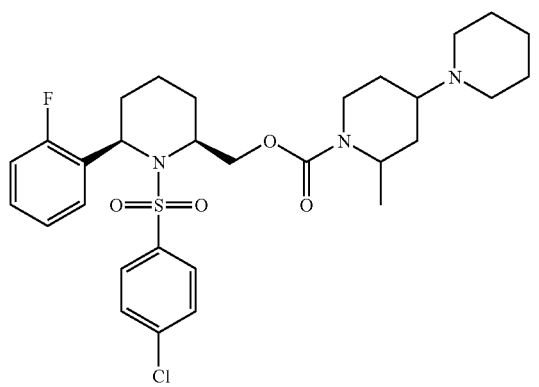 |
| 67-AY | 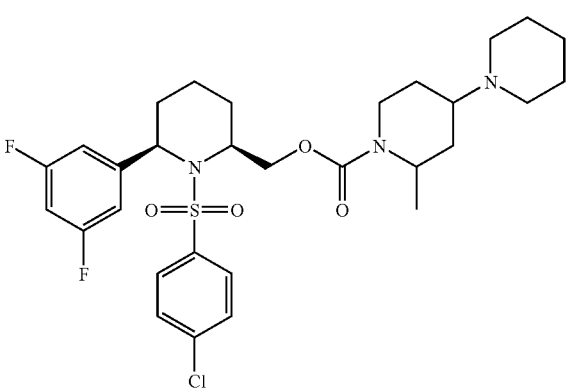 |
| 67-AZ | 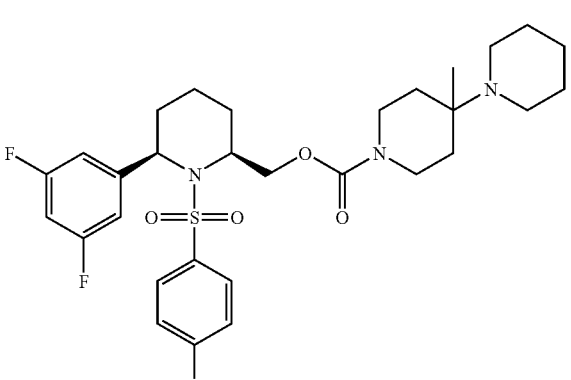 |

| Compound No. | Structure |
|---|---|
| 67-BA | 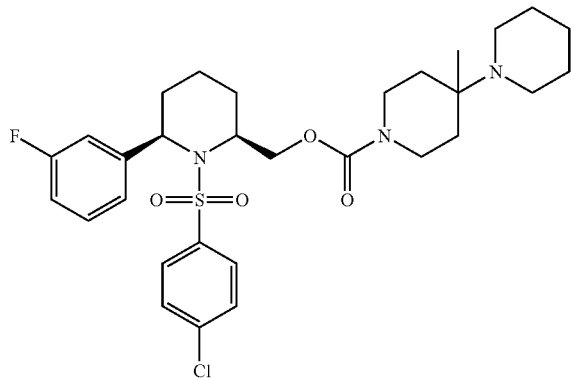 |
| 67-BB | 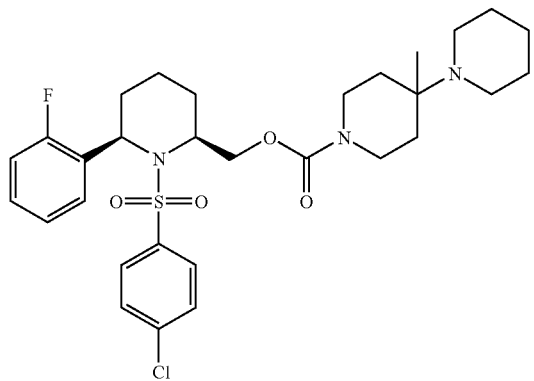 |
| 67-BC | 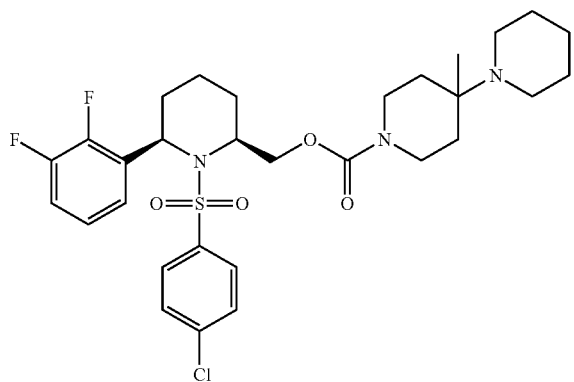 |
| 67-BD | 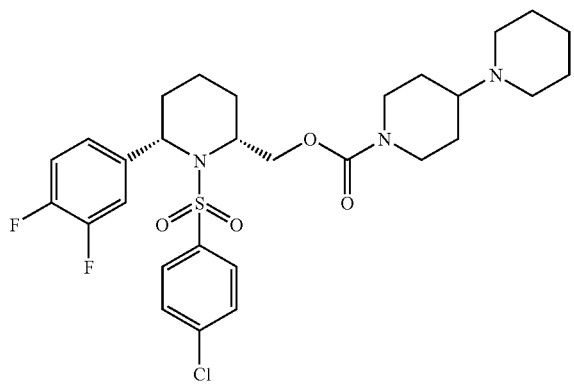 |

| Compound No. | Structure |
|---|---|
| 67-BE | 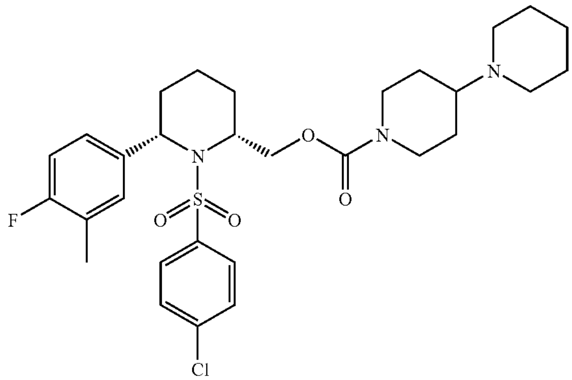 |
| 67-BF | 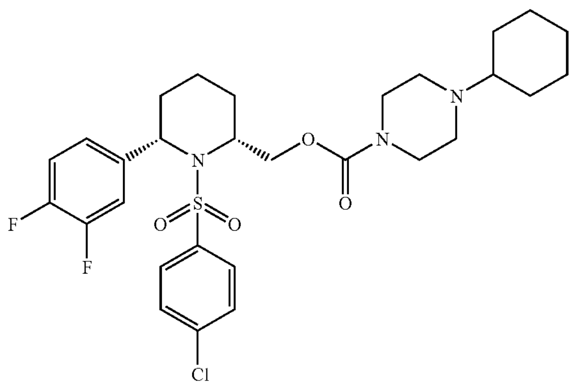 |
| 67-BG | 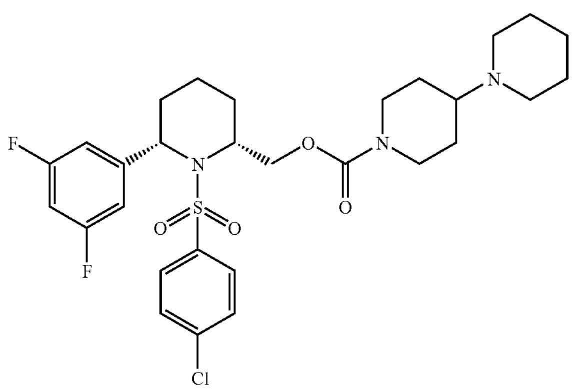 |
| 67-BH | 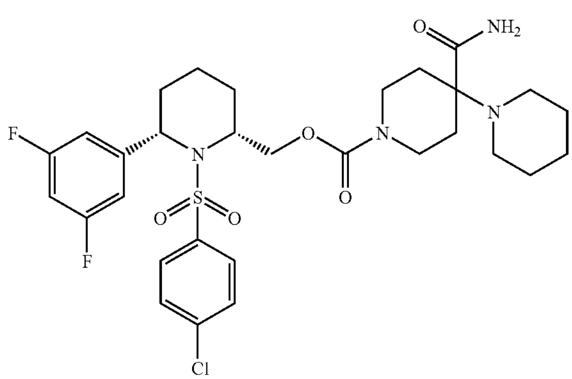 |

-continued
| Compound No. | Structure |
|---|---|
| 67-BI | 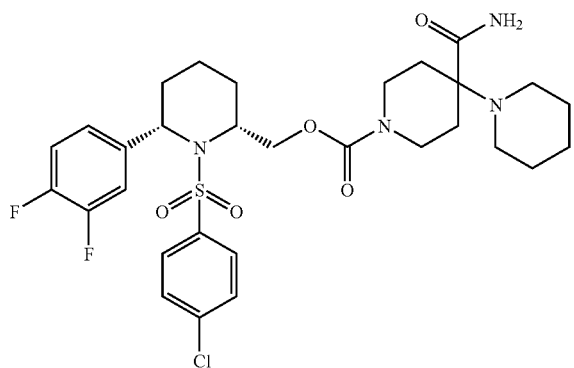 |
| 67-BJ | 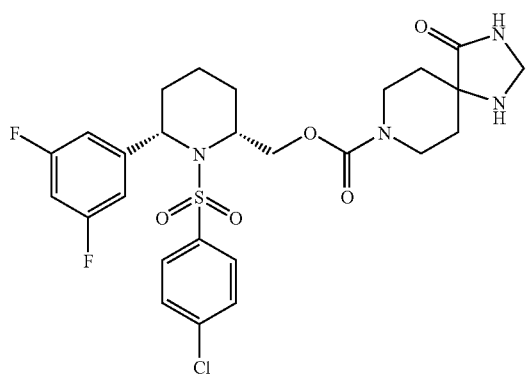 |
| 67-BK | 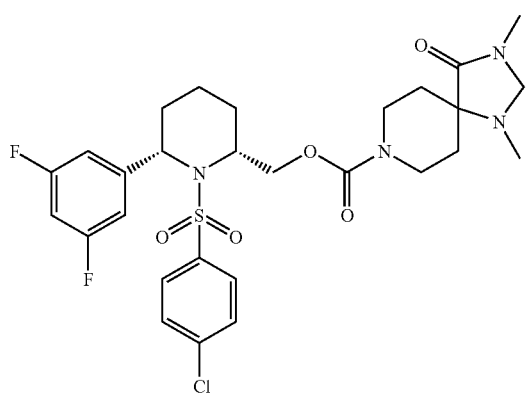 |
| 67-BL | 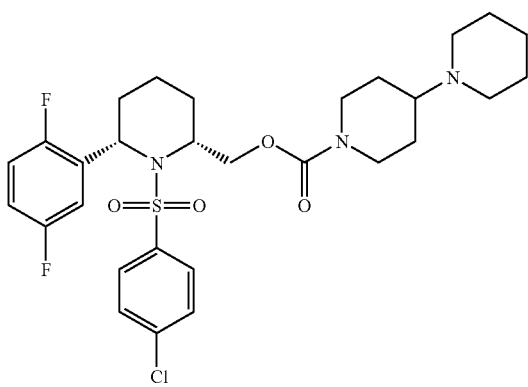 |

-continued
| Compound No. | Structure |
|---|---|
| 67-BM | 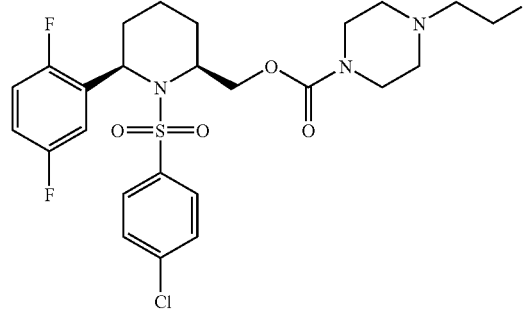 |
| 67-BN | 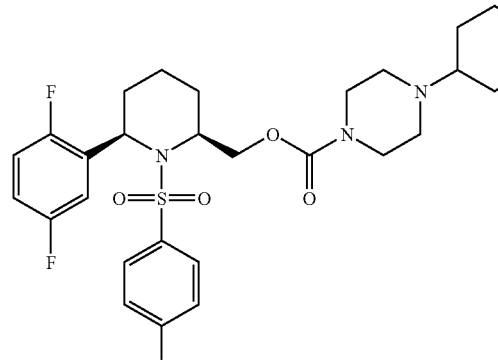 |
| 67-BO | 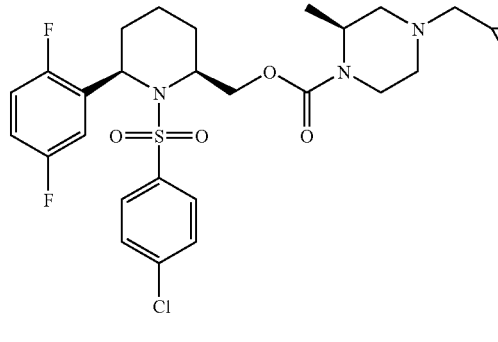 |
| 67-BP | 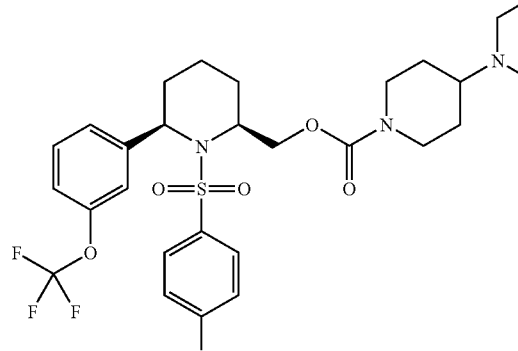 |

-continued
| Compound No. | Structure |
|---|---|
| 67-BQ | 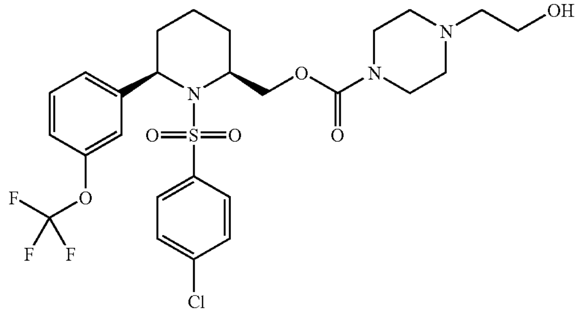 |
| 67-BR | 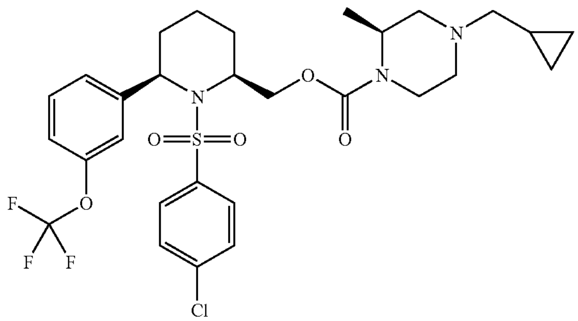 |
(Example 68)
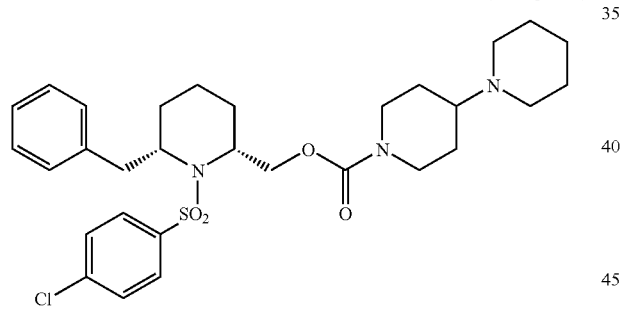
| EX No. | COMPOUND |
|---|---|
| 69 | |

| EX No. | COMPOUND |
|---|---|
| 71 | 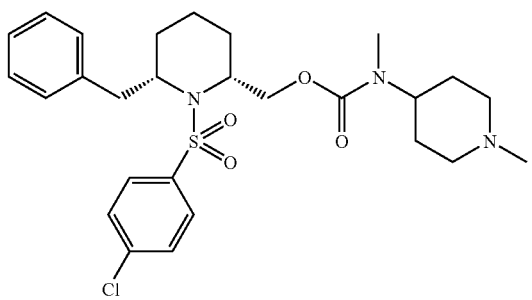 |
| 72 | 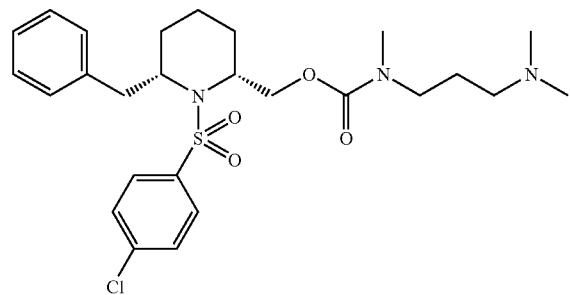 |
| 73 | 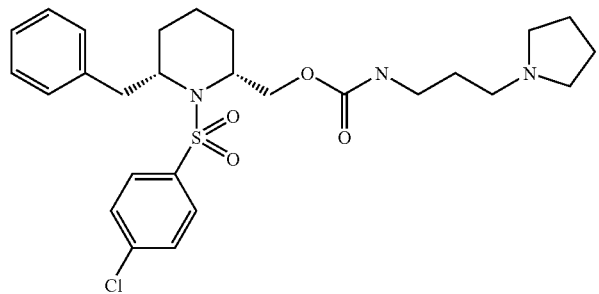 |
| 74 | 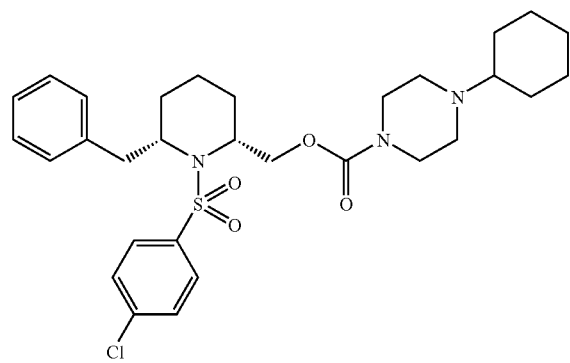 |

| EXAMPLE NO. | STRUCTURE |
|---|---|
| 74-A | 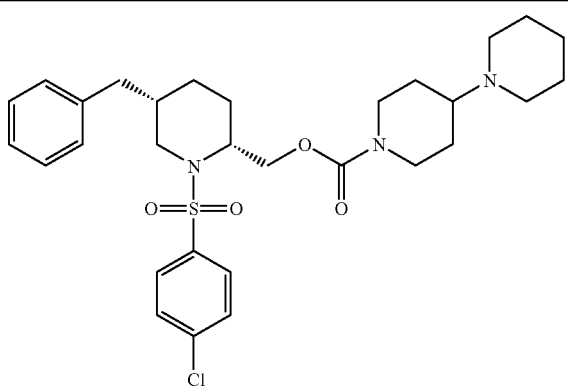 |
| 74-B | 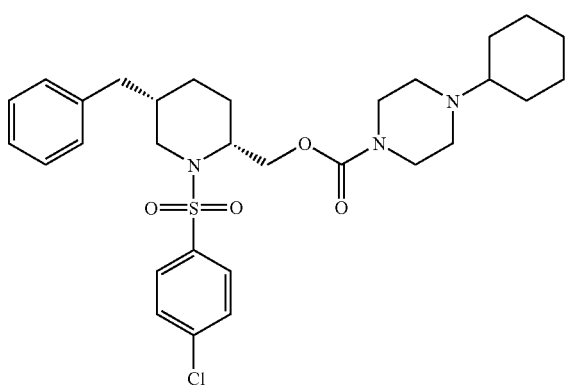 |
| 74-C | 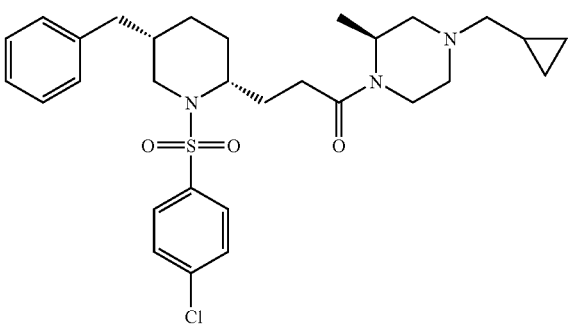 |
(Example 75)
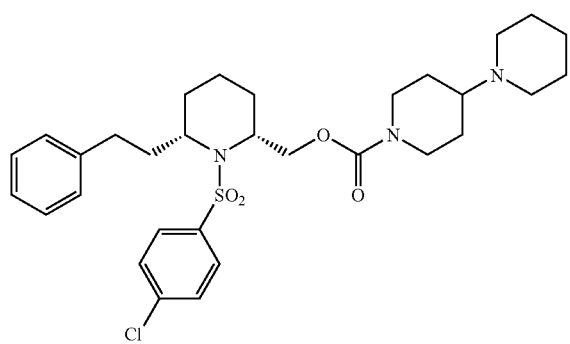

| EX No. | COMPOUND |
|---|---|
| 76 | 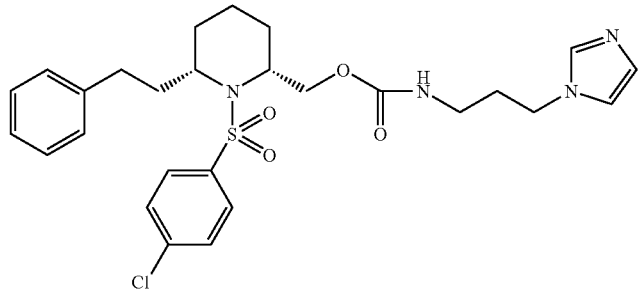 |
| 78 | 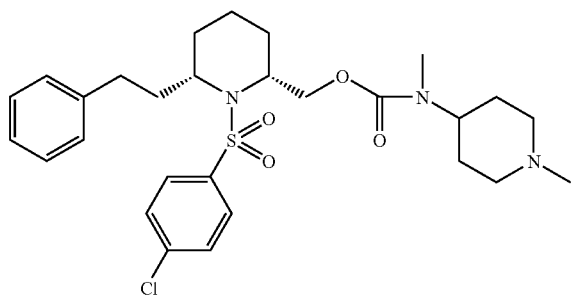 |
| 79 | 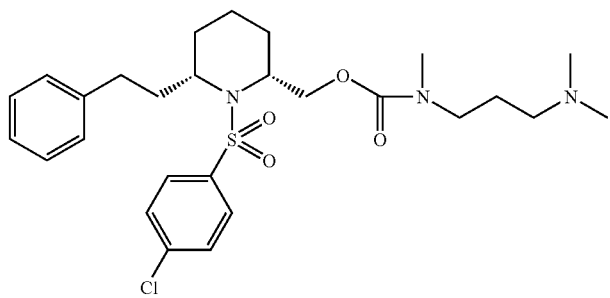 |
| 80 | 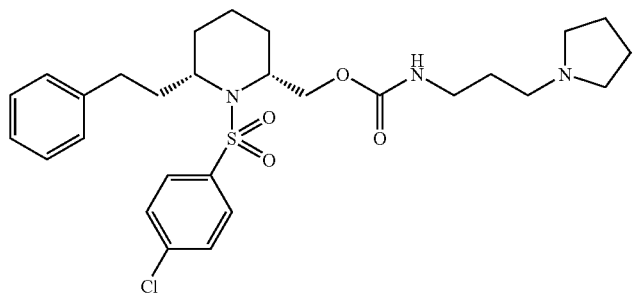 |

-continued
| EX No. | COMPOUND |
|---|---|
| 81 | 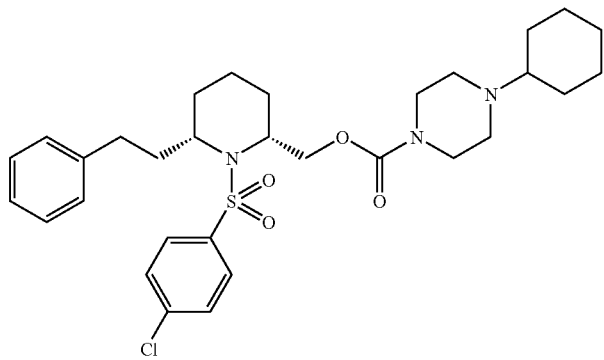 |
(Example 82)
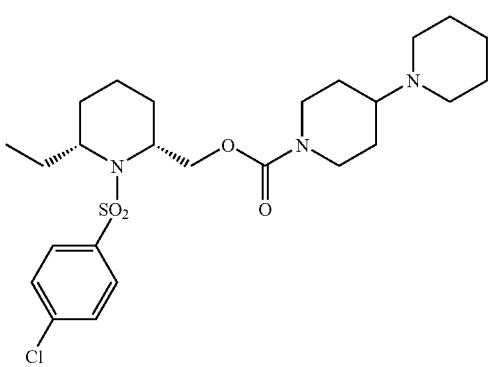
-continued
| EX No. | COMPOUND |
|---|---|
| 86 | 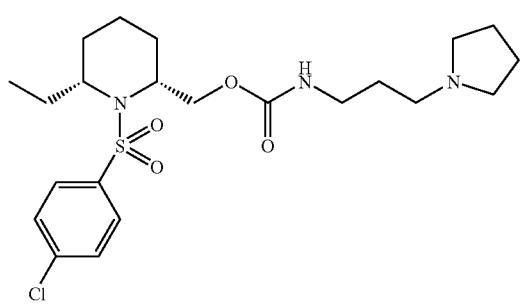 |
| EX No. | COMPOUND |
|---|---|
| 83 | 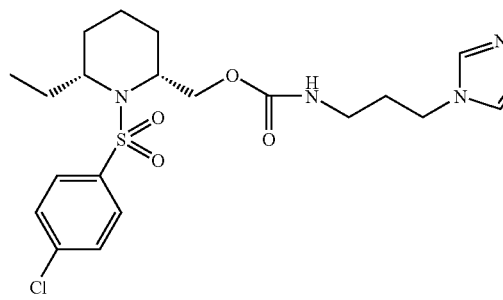 |
| 85 | 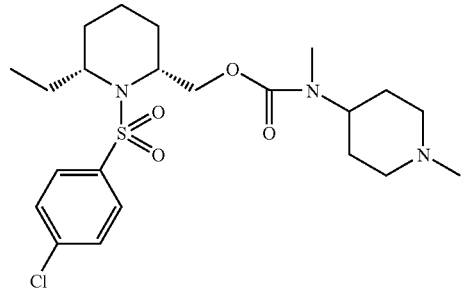 |
| 87 | 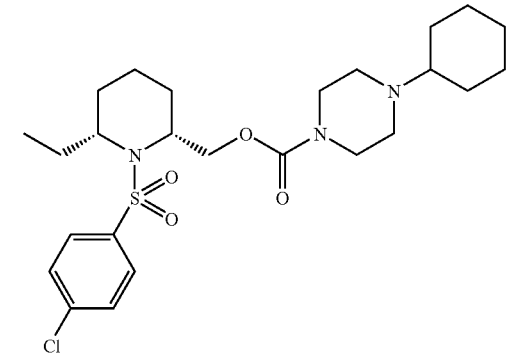 |

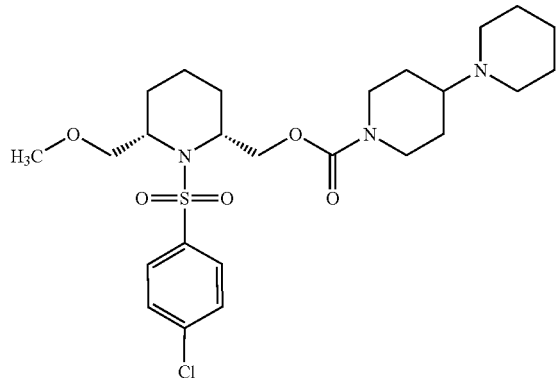
(Example 88)
| EX No. | COMPOUND |
|---|---|
| 89 | 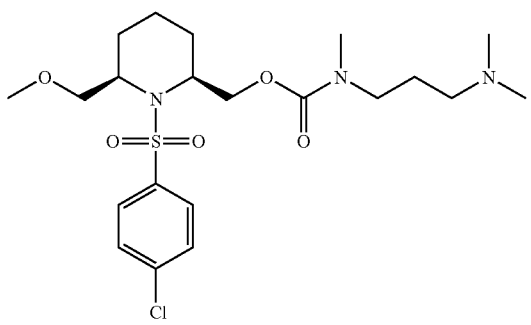 |
| 90 | 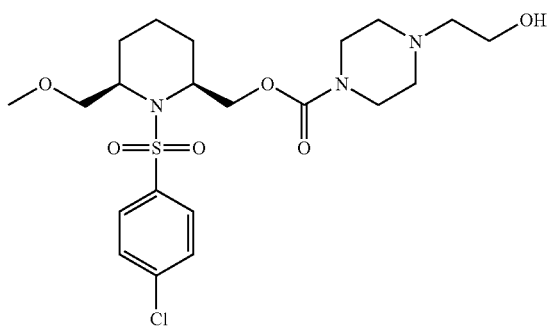 |
| 91 | 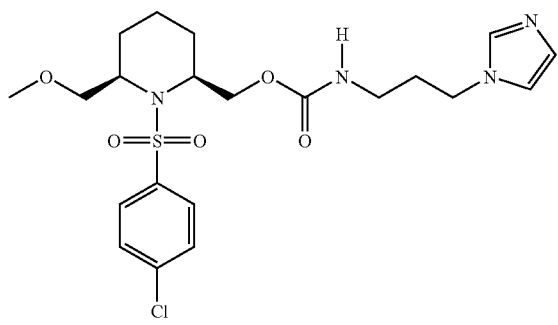 |

-continued
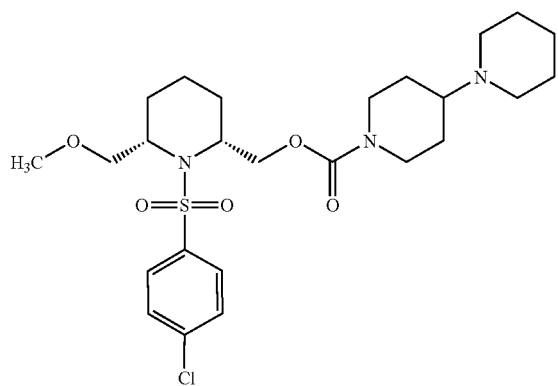
(Example 88)
| EX No. | COMPOUND |
|---|---|
| 92 | 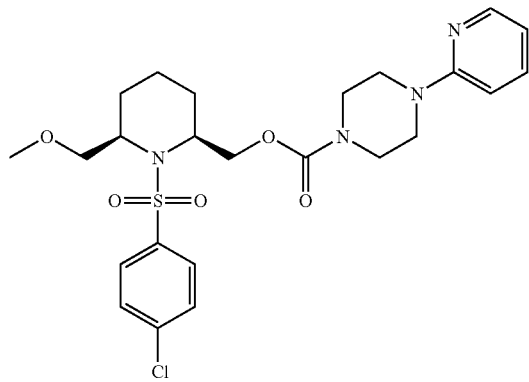 |
| 93 | 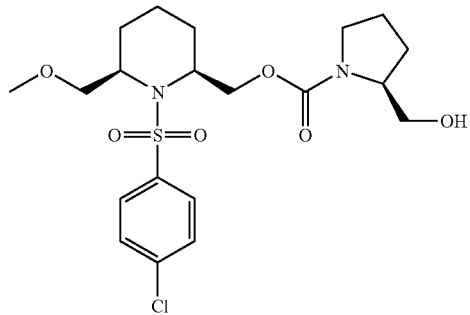 |
| 94 | 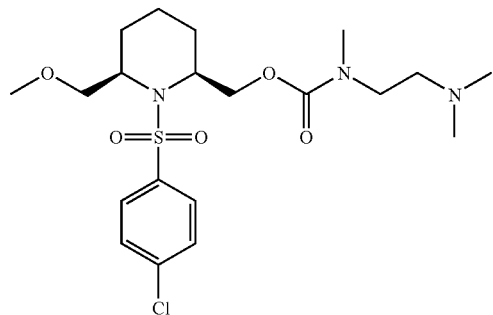 |

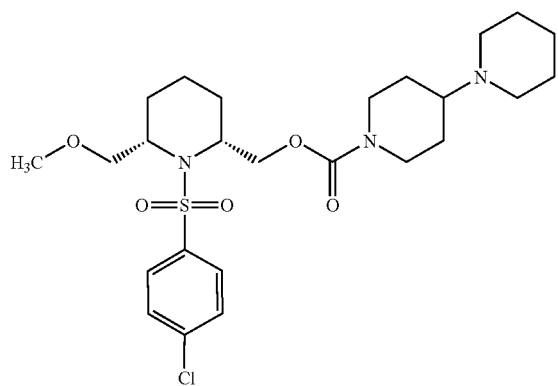
(Example 88)
| EX No. | COMPOUND |
|---|---|
| 95 | 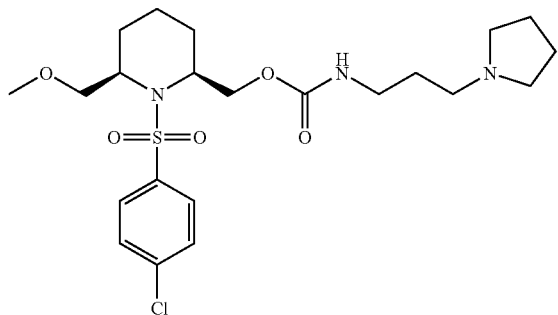 |
| 96 | 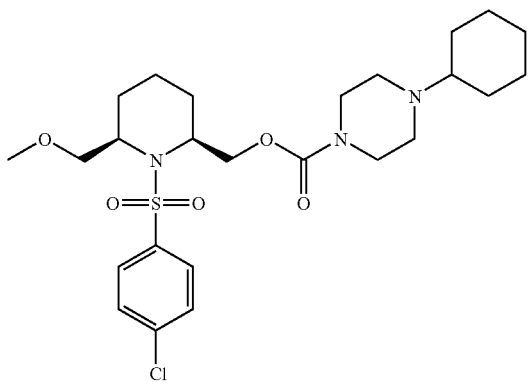 |
| 97 | 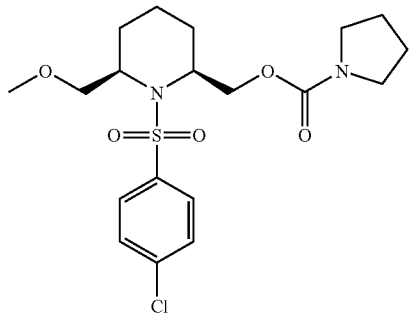 |

-continued
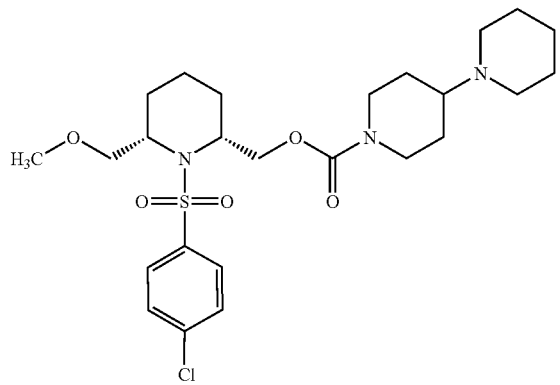
(Example 88)
| EX No. | COMPOUND |
|---|---|
| 98 | 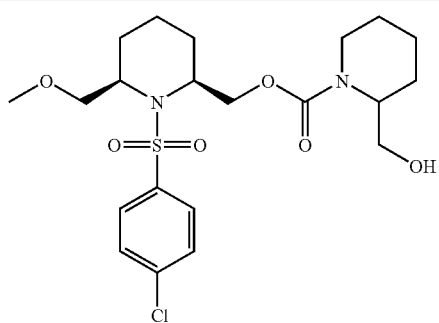 |
| 99 | 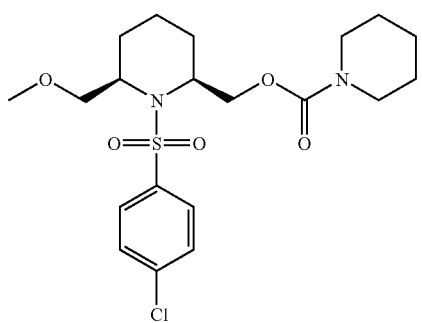 |
| 101 | 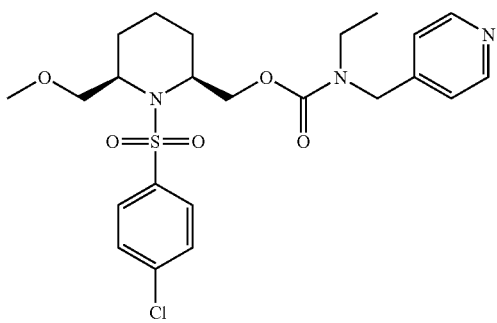 |

-continued
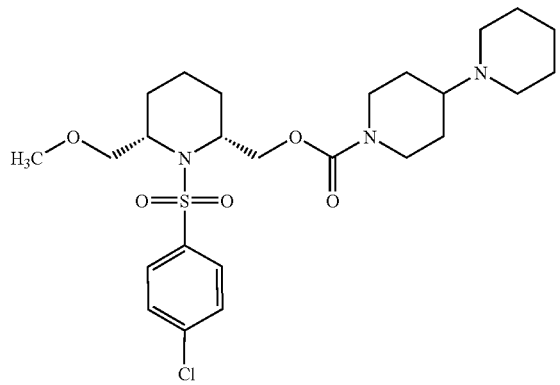
(Example 88)
| EX No. | COMPOUND |
|---|---|
| 102 | 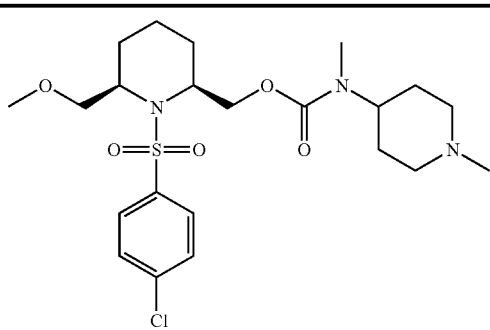 |
| 103 | 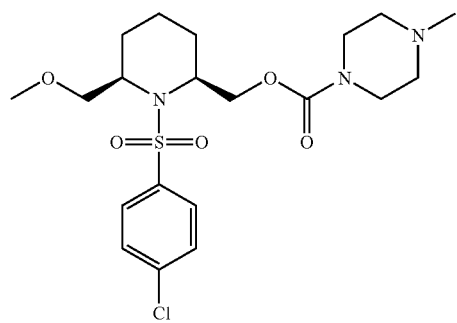 |
| 104 | 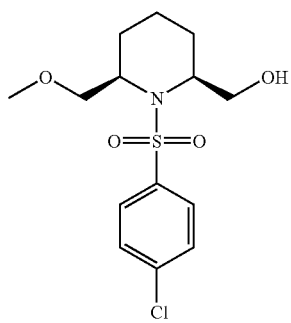 |

| | |
|---|---|
| 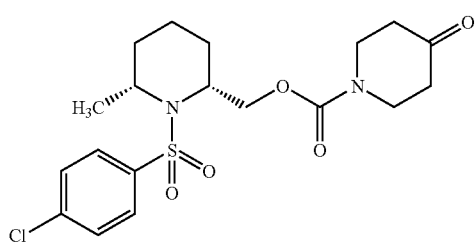<br>(Example 105) | 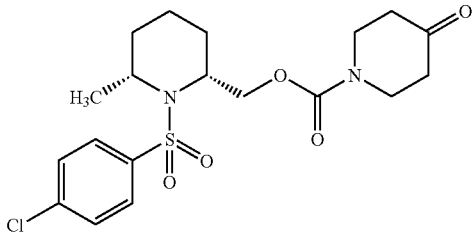<br>(Example 105) |
| EX No. | COMPOUND |
|---|---|
| 106 | 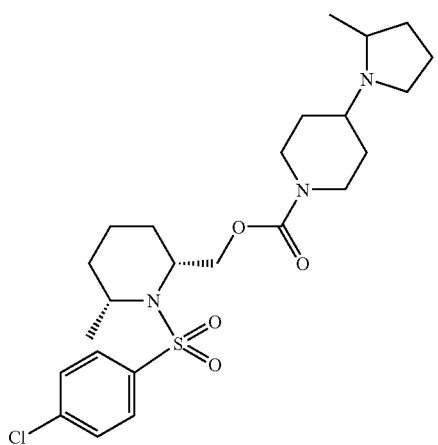 |
| 107 | 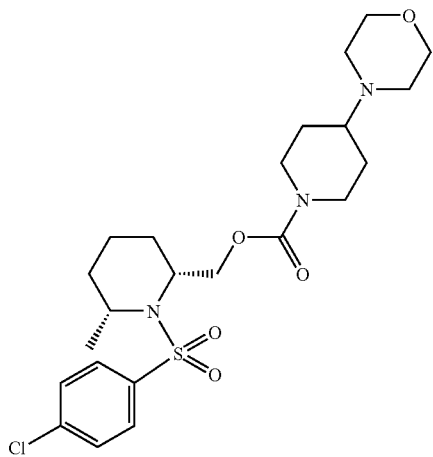 |
| EX No. | COMPOUND |
|---|---|
| 108 | 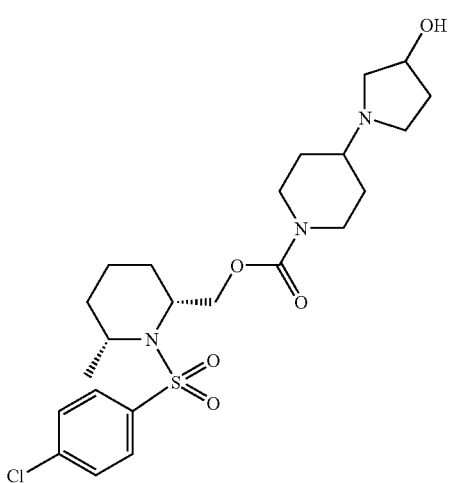 |
| 109 | 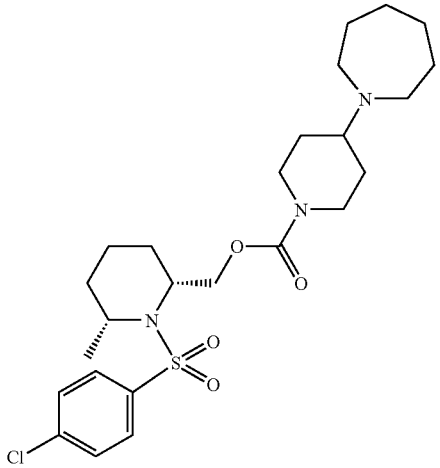 |

| 401 | 402 |
|---|---|
| -continued | -continued |
| 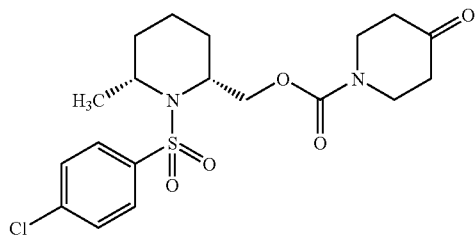 | 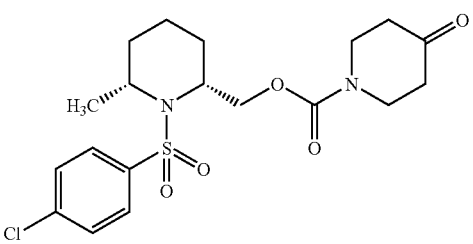 |
| (Example 105) | (Example 105) |
| EX No. | COMPOUND | EX No. | COMPOUND |
|---|---|---|---|
| 110 | 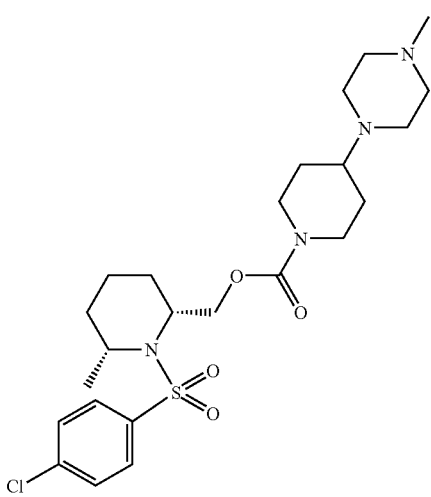 | 112 | 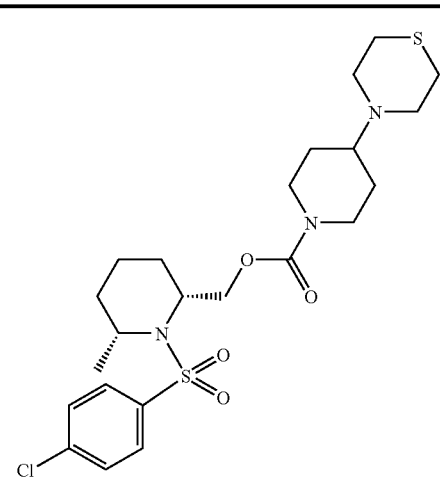 |
| 111 | 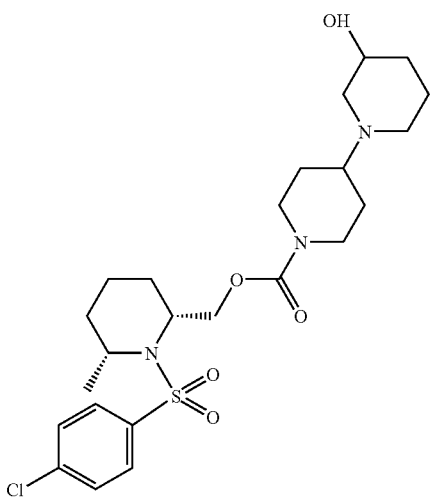 | 113 | 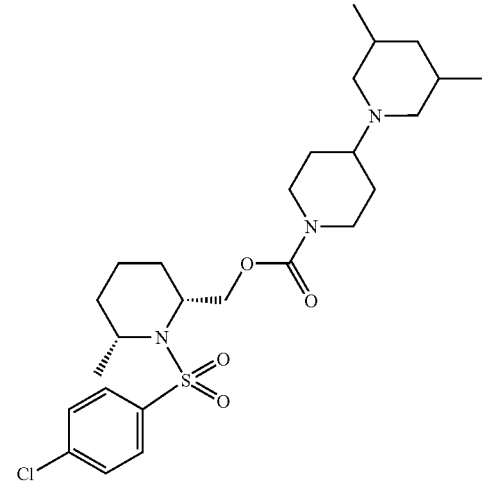 |

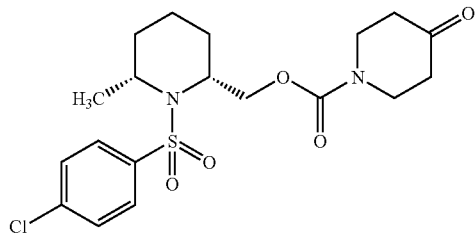
(Example 105)
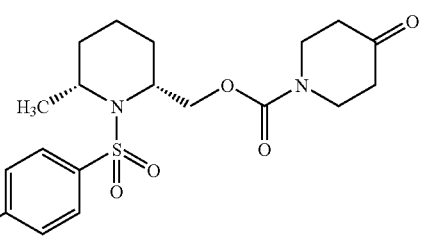
(Example 105)
| EX No. | COMPOUND |
|---|---|
| 114 | 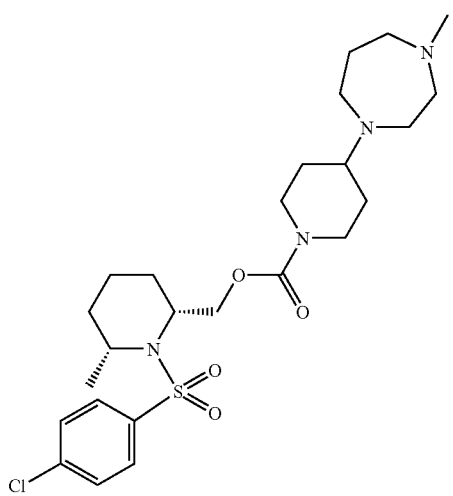 |
| 115 | 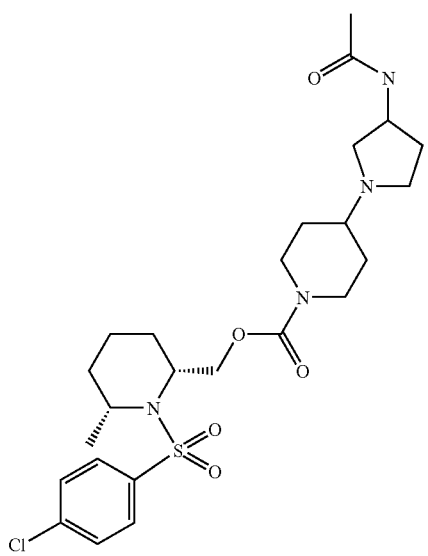 |
| EX No. | COMPOUND |
|---|---|
| 116 | 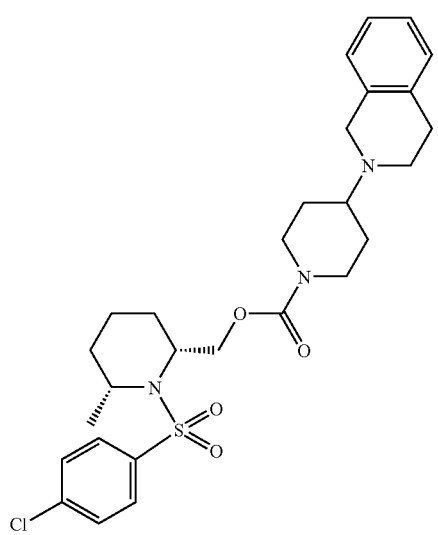 |
| 117 | 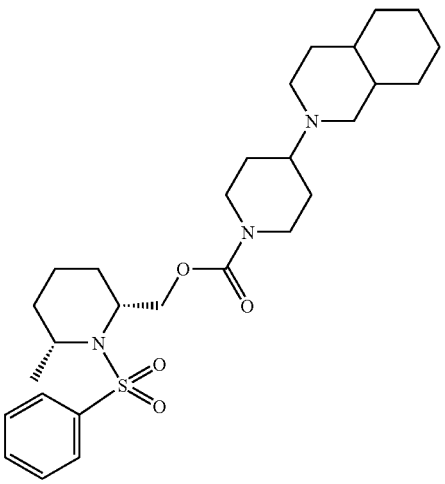 |

| 405 | 406 |
|---|---|
| -continued | -continued |
| 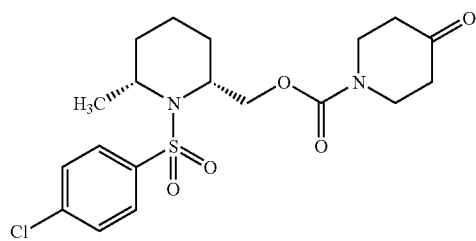 | 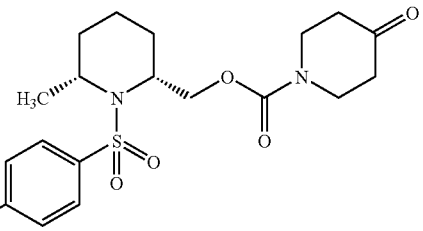 |
| (Example 105) | (Example 105) |
| EX No. | COMPOUND | EX No. | COMPOUND |
|---|---|---|---|
| 118 | 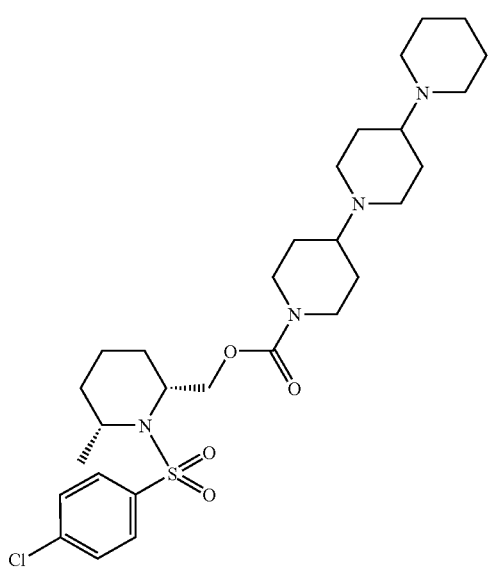 | 120 | 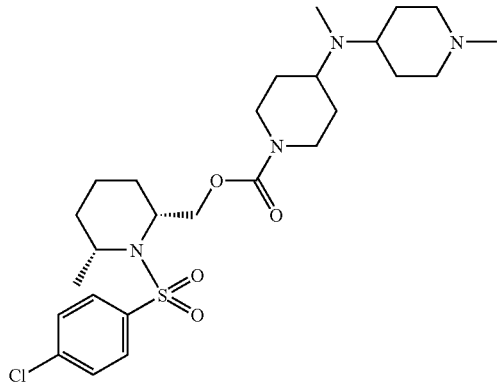 |
| 119 | 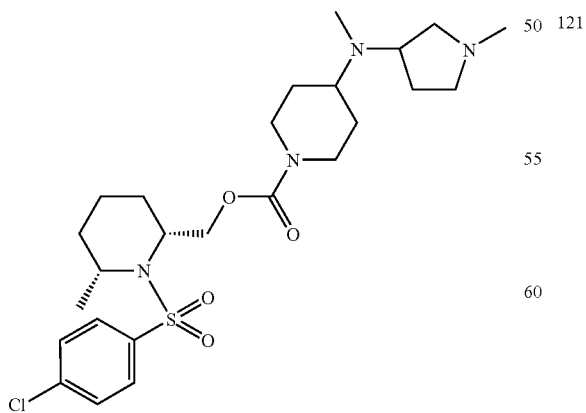 | 121 | 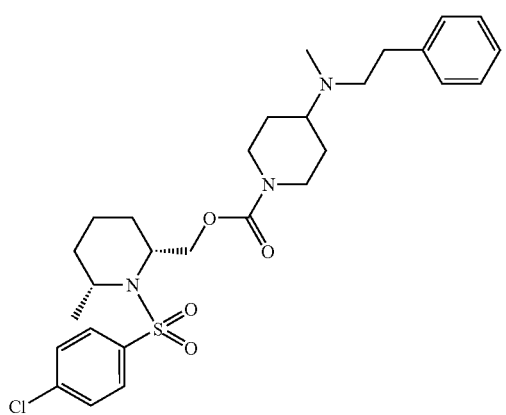 |

| | |
|---|---|
| | -continued |
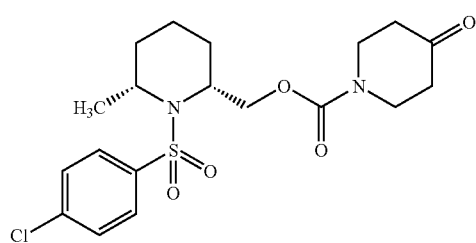
(Example 105)
| EX No. | COMPOUND |
|---|---|
122
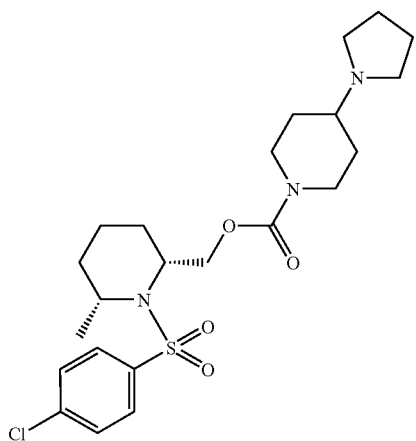
123
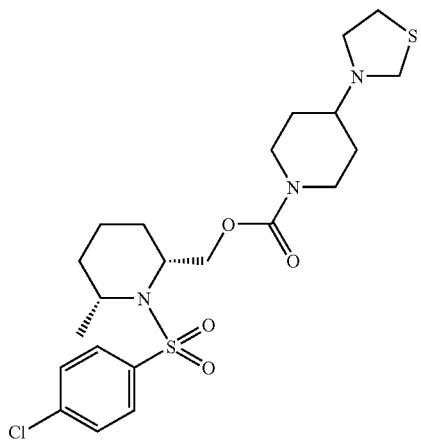
| | |
|---|---|
| | -continued |
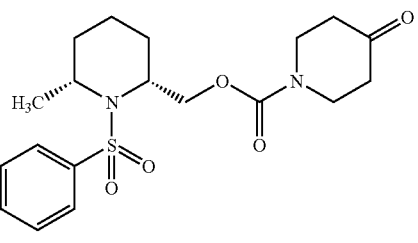
(Example 105)
| EX No. | COMPOUND |
|---|---|
124
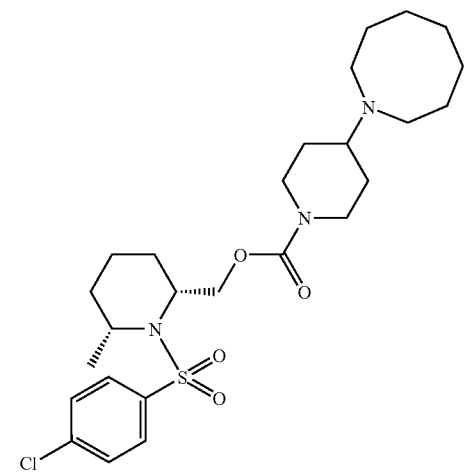
125
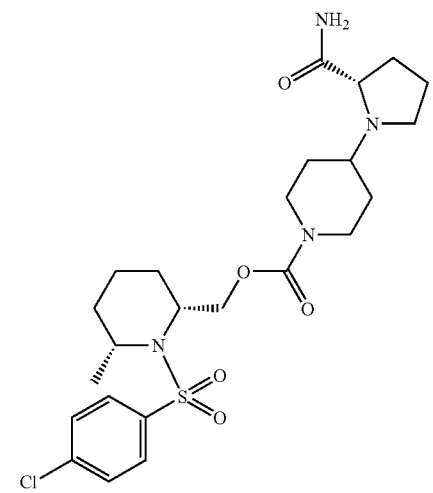

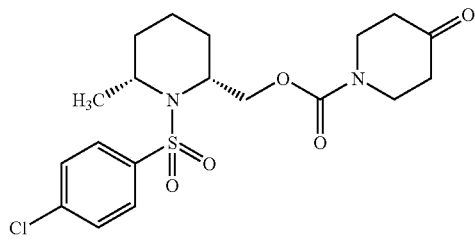
(Example 105)
(Example 105)
| EX No. | COMPOUND |
|---|---|
| 126 | 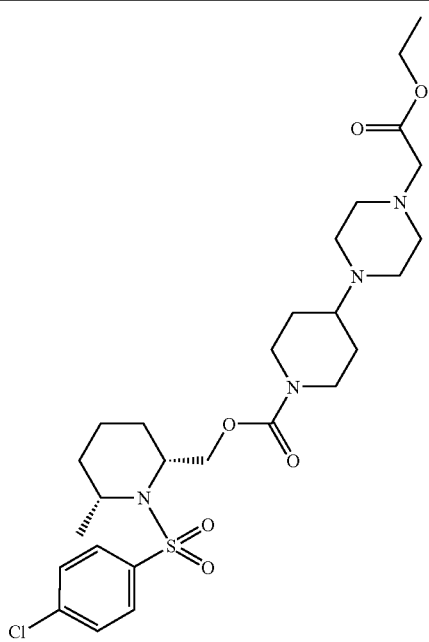 |
| 127 | 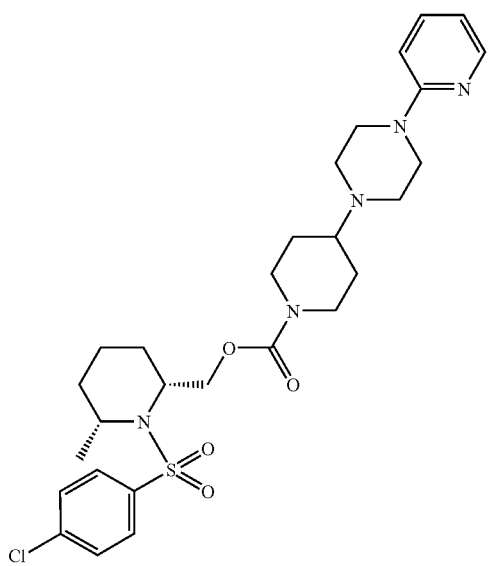 |
| EX No. | COMPOUND |
|---|---|
| 128 | 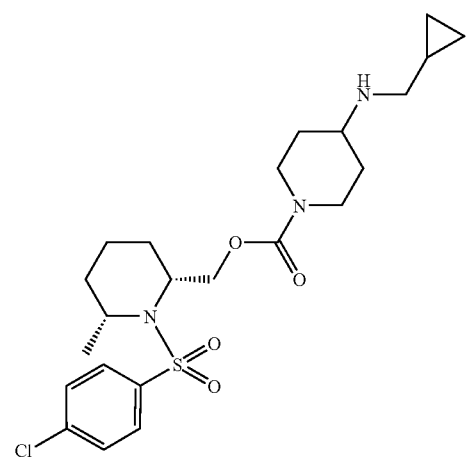 |
| 129 | 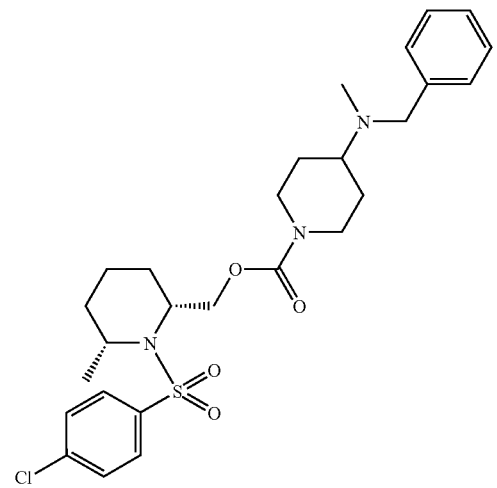 |

-continued
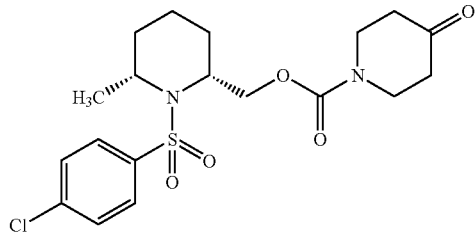
(Example 105)
| EX No. | COMPOUND |
|---|---|
| 130 | 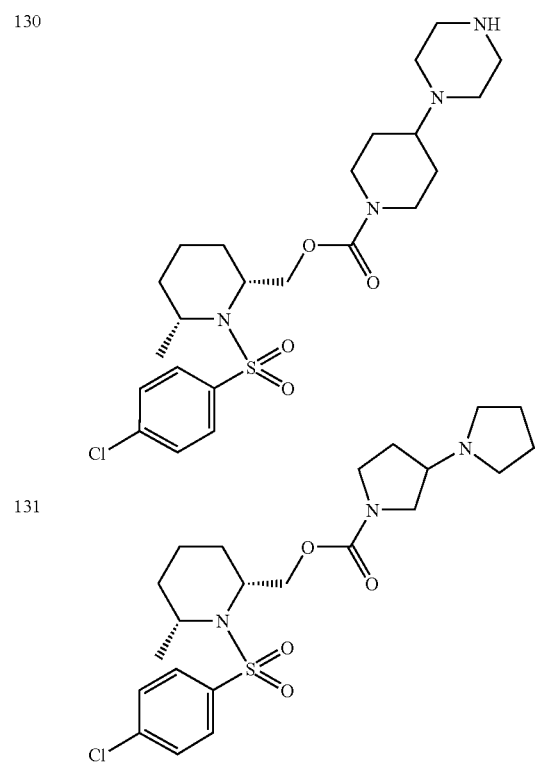 |
| 131 | |
| 132 | 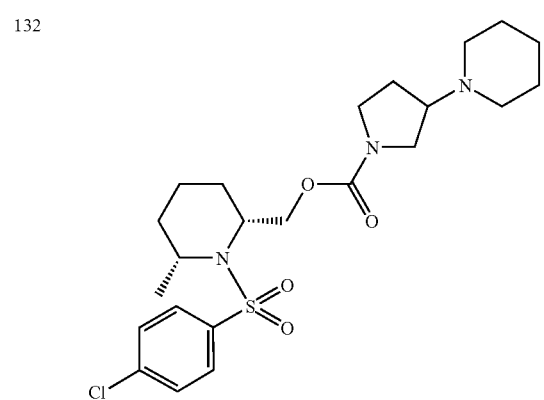 |
-continued
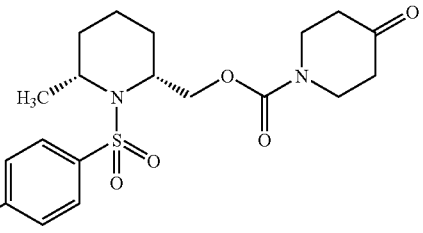
(Example 105)
| EX No. | COMPOUND |
|---|---|
| 133 | 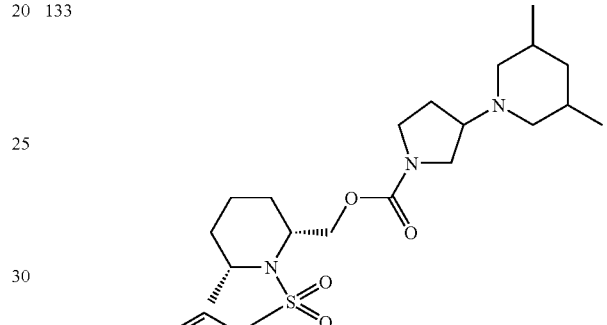 |
| 134 | 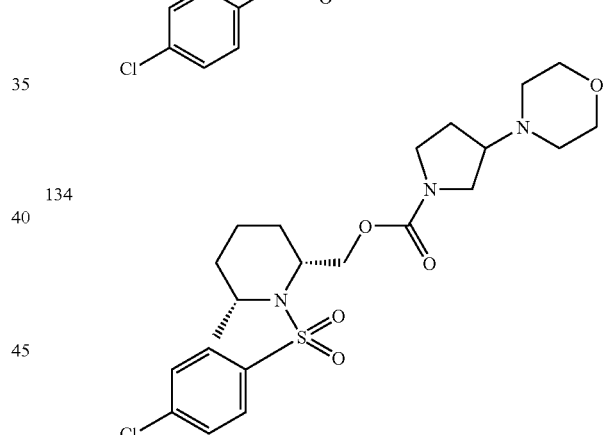 |
| 135 | 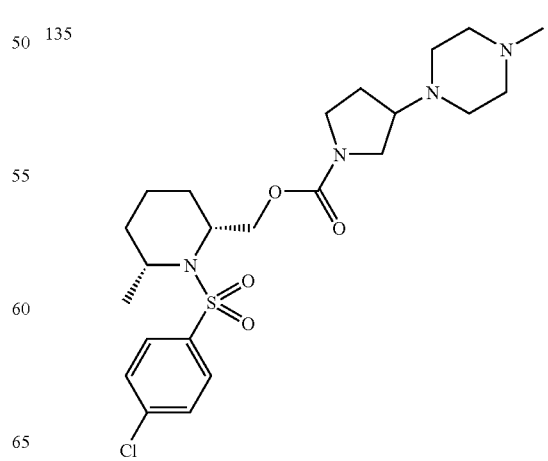 |

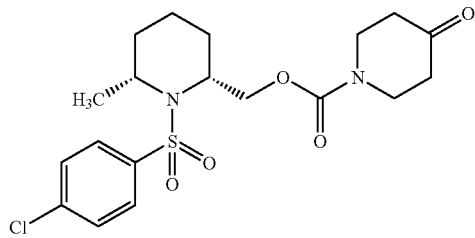
(Example 105)
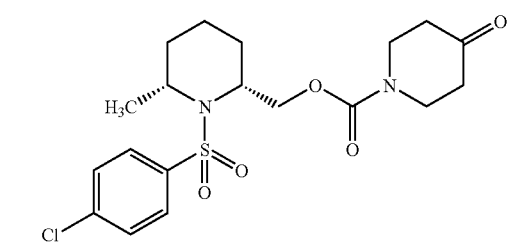
(Example 105)
| EX No. | COMPOUND |
|---|---|
| 136 | 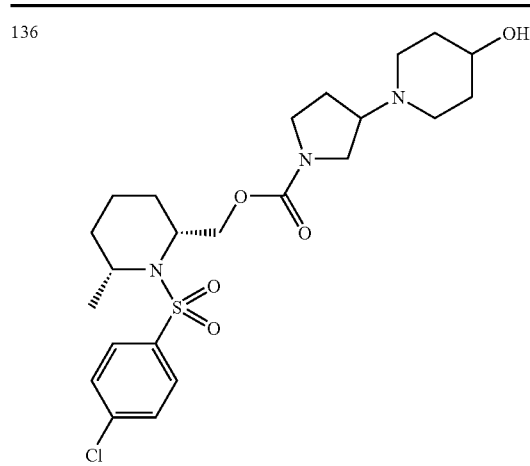 |
| 137 | 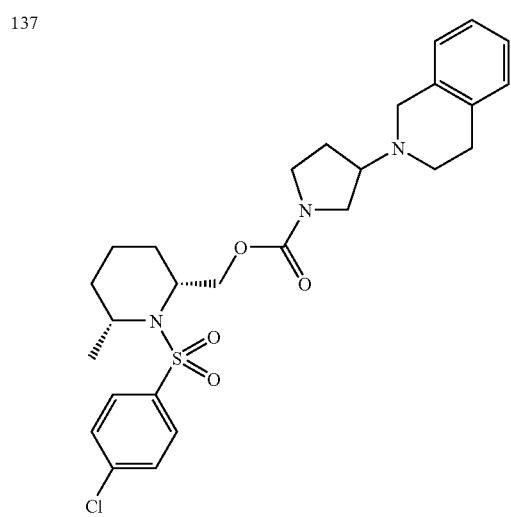 |
| EX No. | COMPOUND |
|---|---|
| 138 | 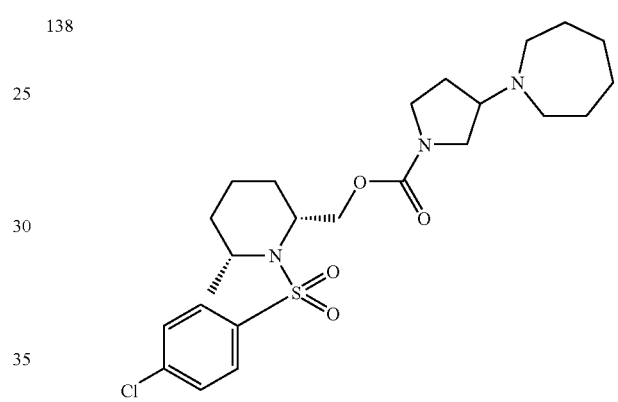 |
| 139 | 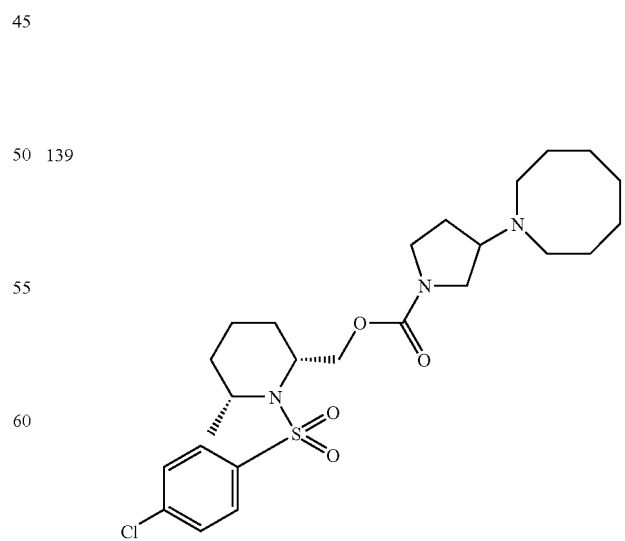 |

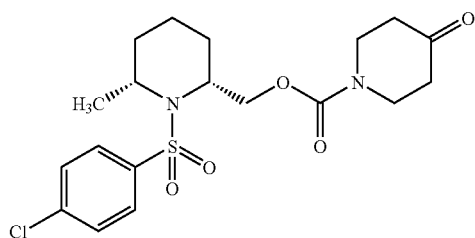
(Example 105)
| EX No. | COMPOUND |
|---|---|
| 140 | 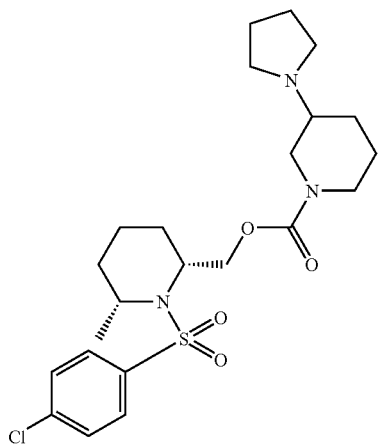 |
| 141 | 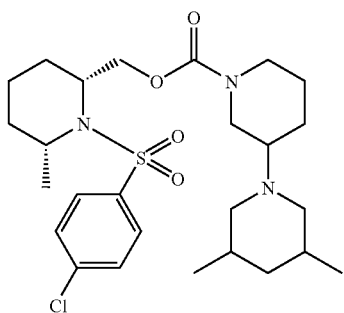 |
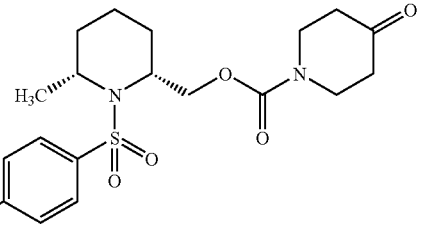
(Example 105)
| EX No. | COMPOUND |
|---|---|
| 142 | 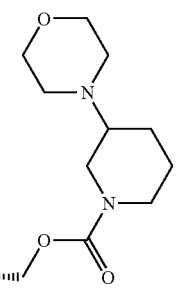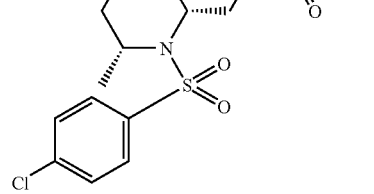 |
| 143 | 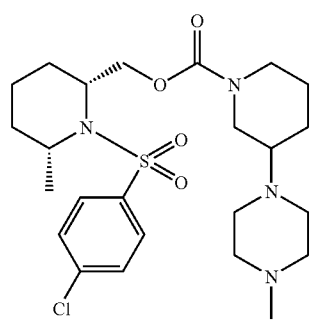 |
| 144 | 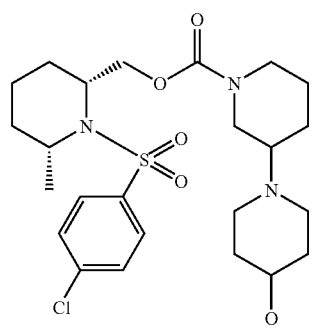 |

-continued
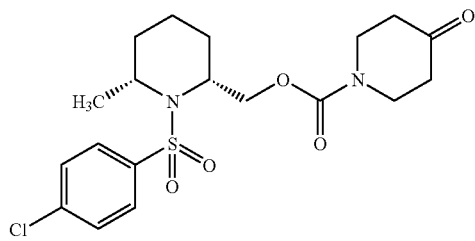
(Example 105)
| EX No. | COMPOUND |
|---|---|
| 145 | 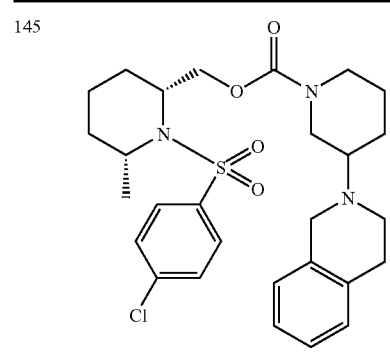 |
| 146 | 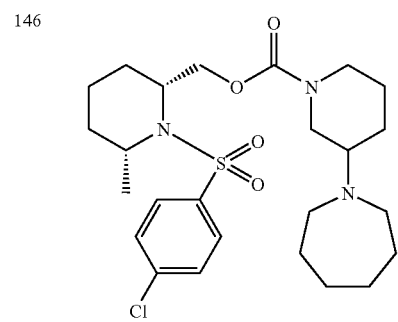 |
| 147 | 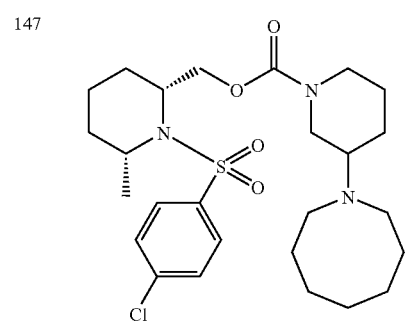 |
-continued
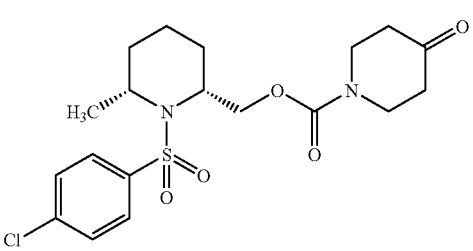
(Example 105)
| EX No. | COMPOUND |
|---|---|
| 148 | 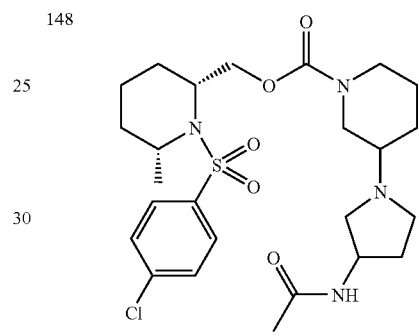 |
| 149 | 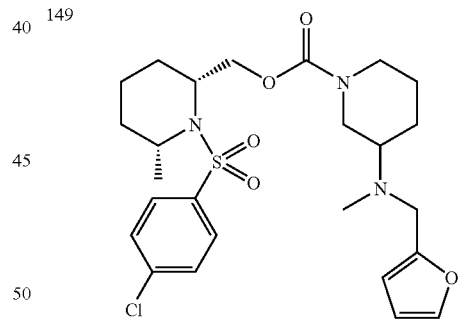 |
| 150 | 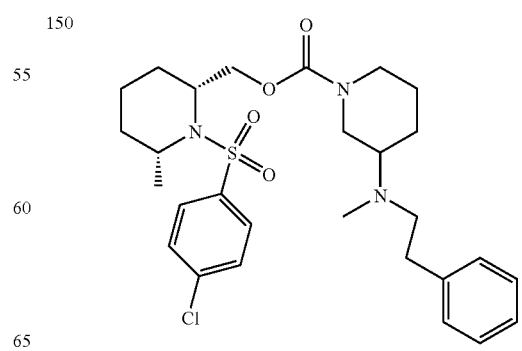 |

| 419 | 420 |
|---|---|
| -continued | -continued |
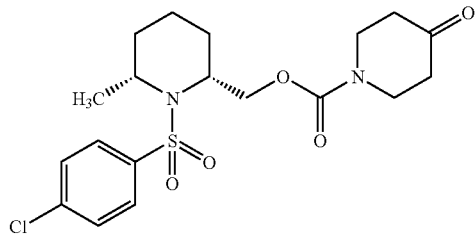
(Example 105)
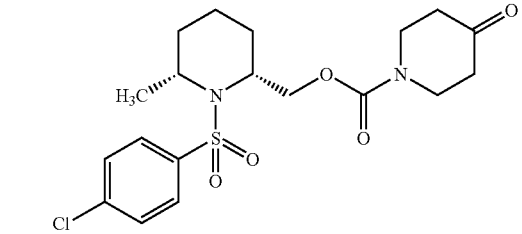
(Example 105)
| EX No. | COMPOUND |
|---|---|
| 151 | 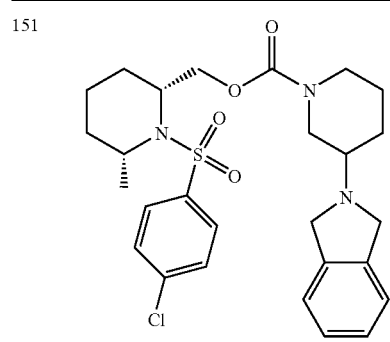 |
| 152 | 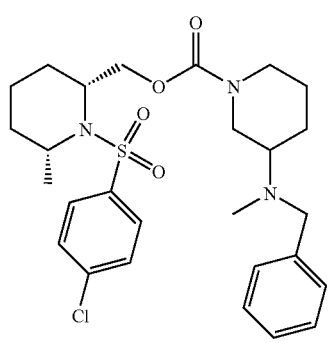 |
| 153 | 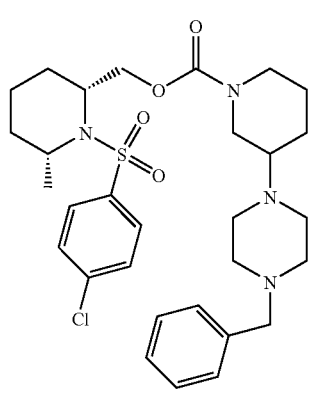 |
| EX No. | COMPOUND |
|---|---|
| 154 | 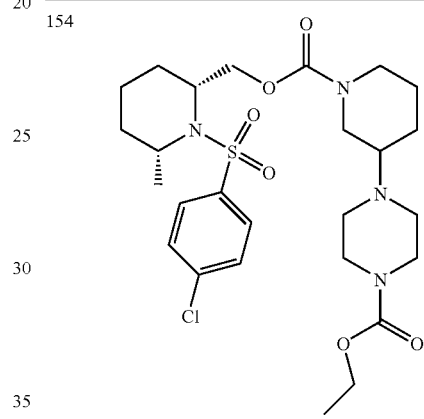 |
| 155 | 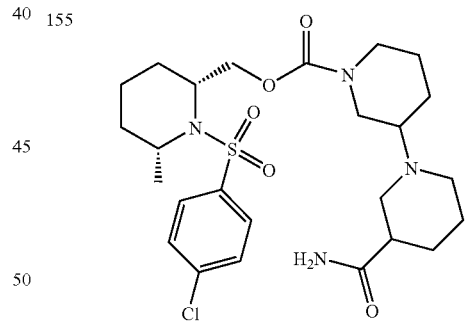 |
| 156 | 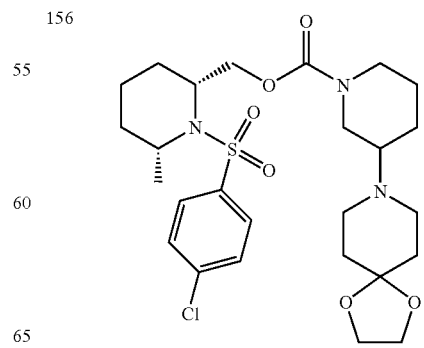 |

421
-continued
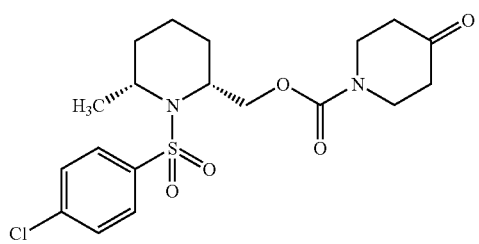
(Example 105)
| EX No. | COMPOUND |
|---|---|
| 157 | 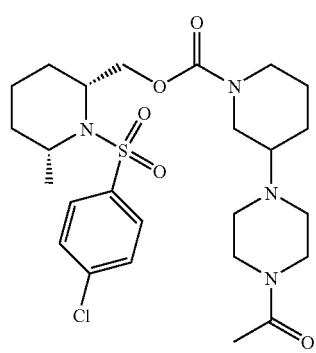 |
| 158 | 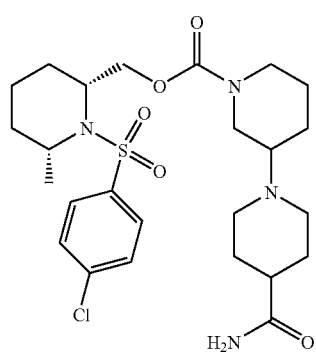 |
422
-continued
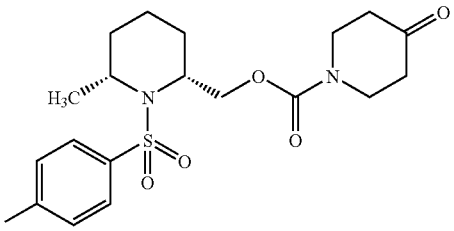
(Example 105)
| EX No. | COMPOUND |
|---|---|
| 159-A | 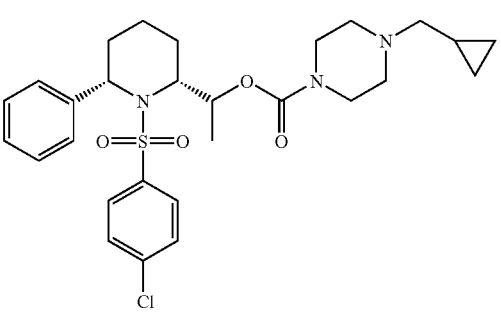<br>isomer A |
| 159-B | 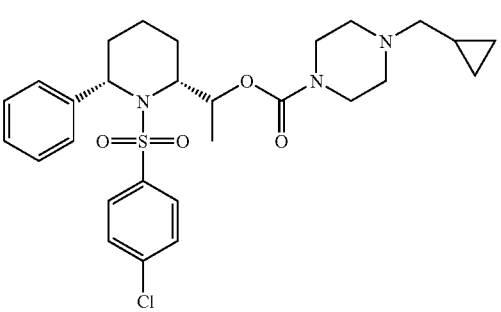<br>isomer B |

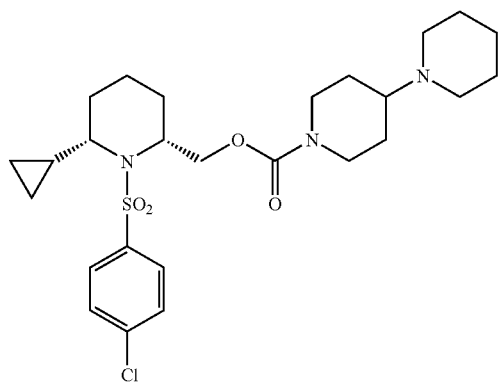
(Example 160)
| Compound No. | Structure |
|---|---|
| 160-A | 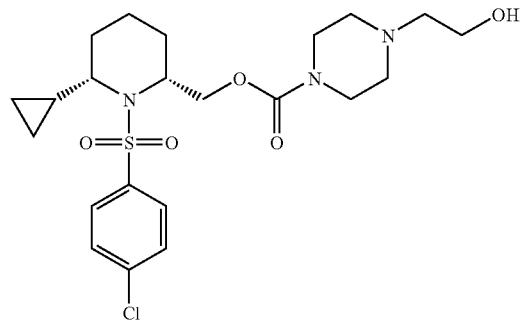 |
| 160-B | 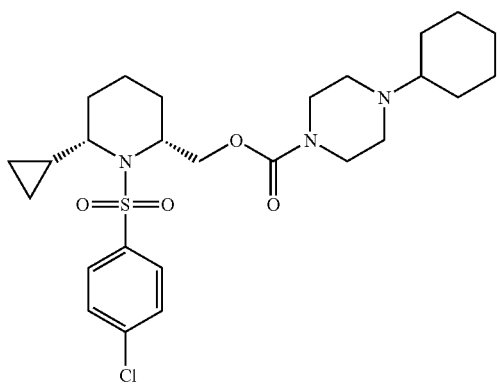 |
| 160-C | 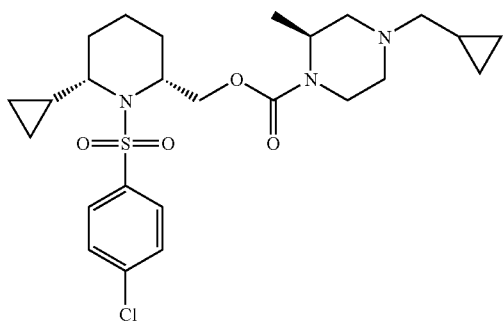 |

-continued
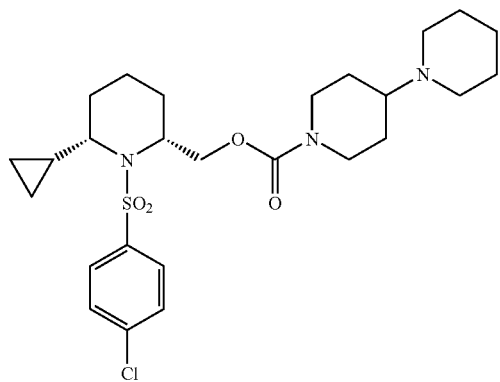
(Example 160)
| Compound No. | Structure |
|---|---|
| 160-D | 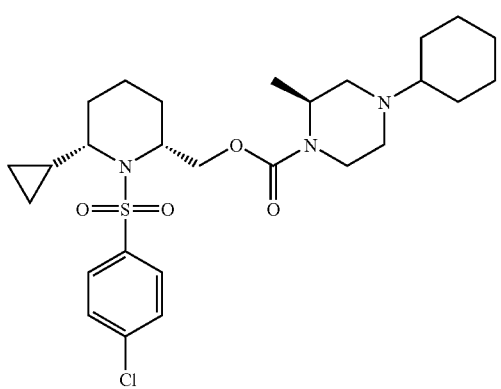 |
| 160-E | 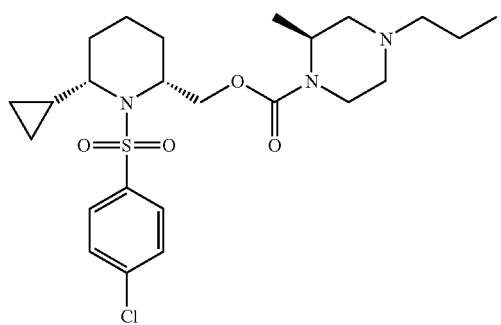 |

-continued
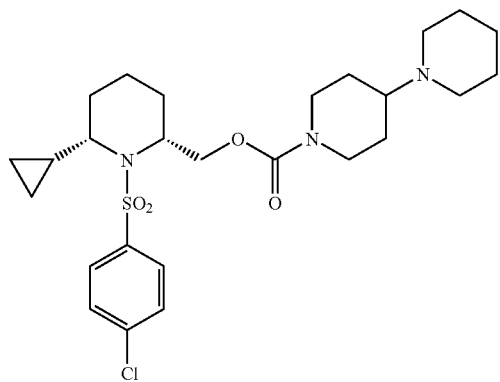
(Example 160)
| Compound No. | Structure |
|---|---|
| 160-F | 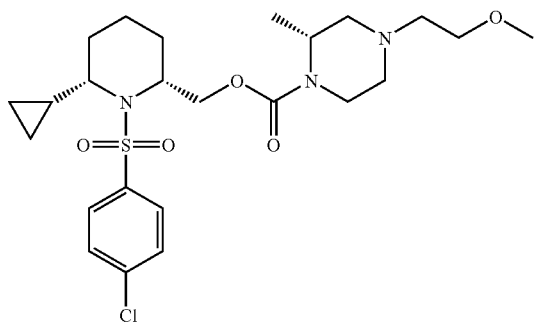 |
| 160-G | 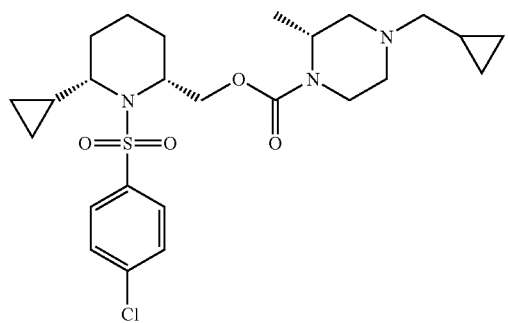 |

-continued
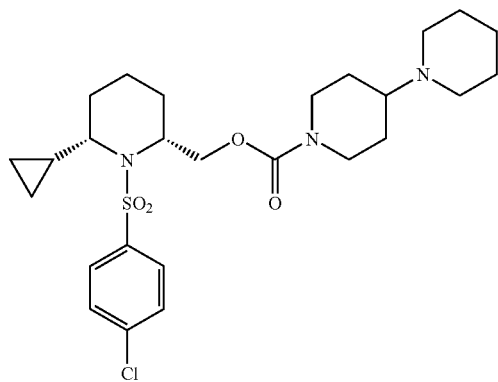
(Example 160)
| Compound No. | Structure |
|---|---|
160-H
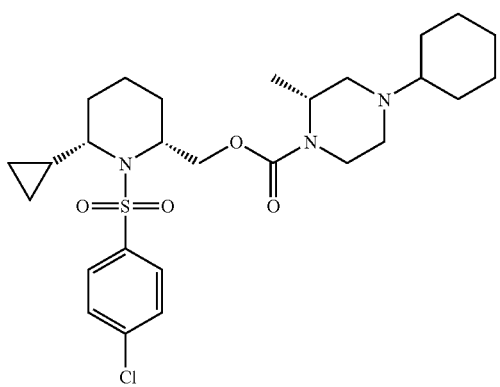
160-I
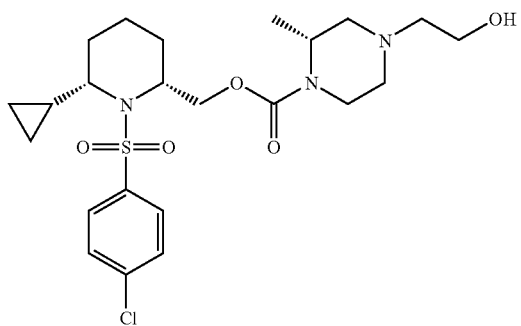

-continued
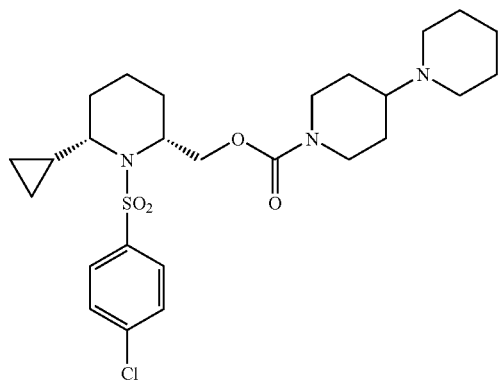
(Example 160)
| Compound No. | Structure |
|---|---|
| 160-J | 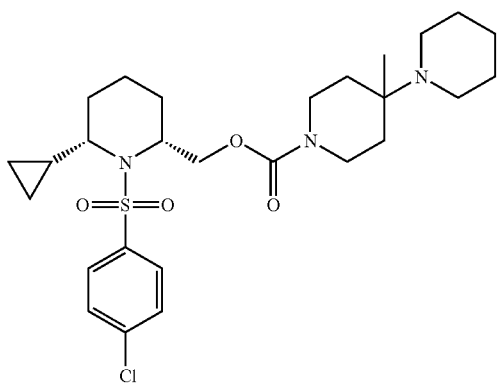 |
| 160-K | 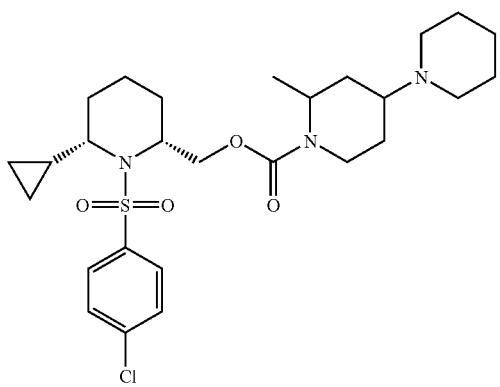 |

-continued
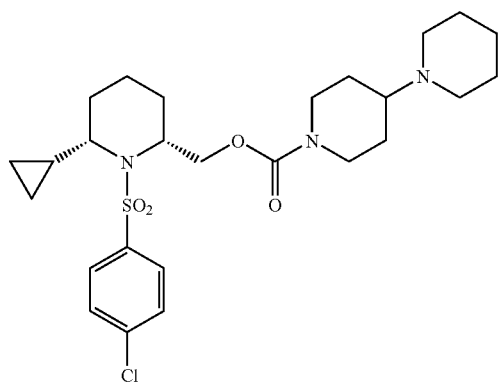
(Example 160)
| Compound No. | Structure |
|---|---|
| 160-L | 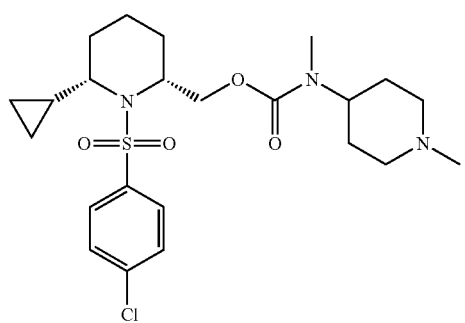 |
| 160-M | 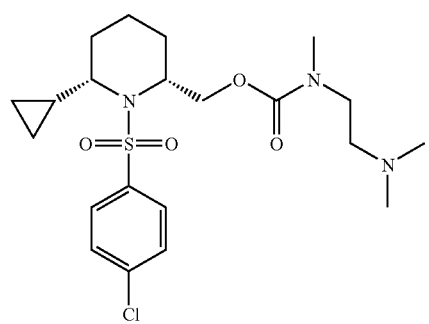 |

-continued
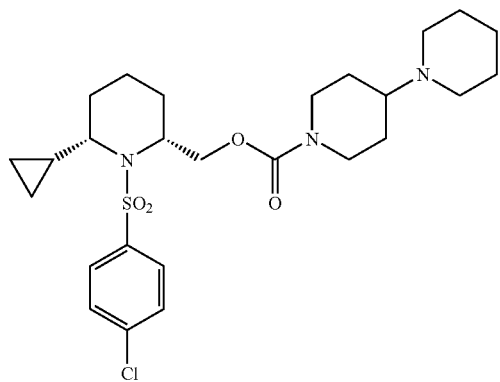
(Example 160)
| Compound No. | Structure |
|---|---|
| 160-N | 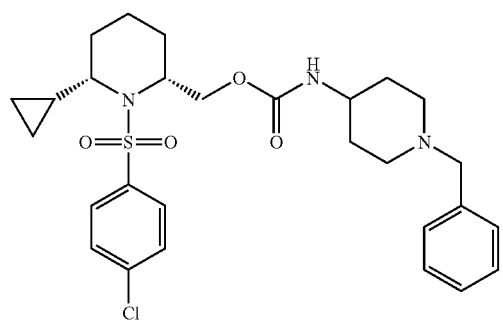 |
| 160-O | 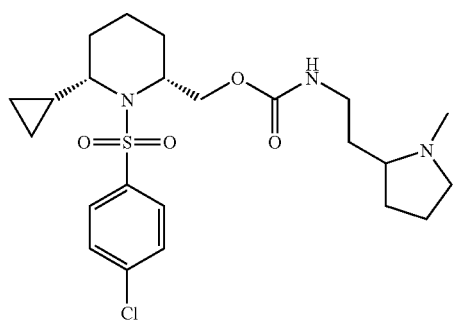 |
| 160-P | 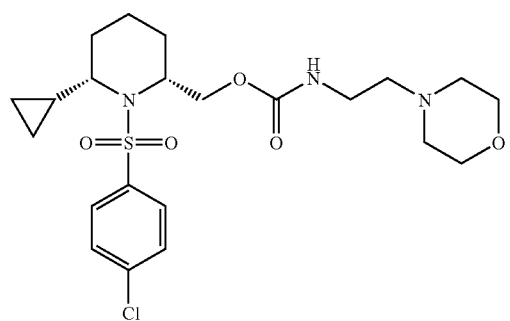 |

-continued
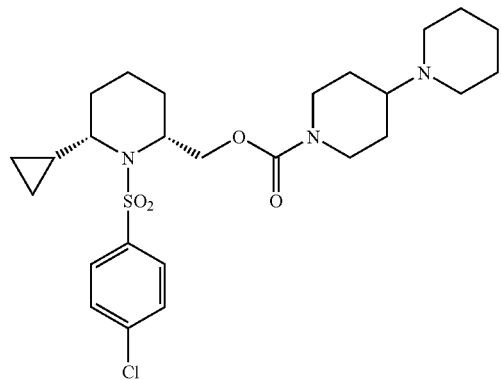
(Example 160)
| Compound No. | Structure |
|---|---|
| 160-Q | 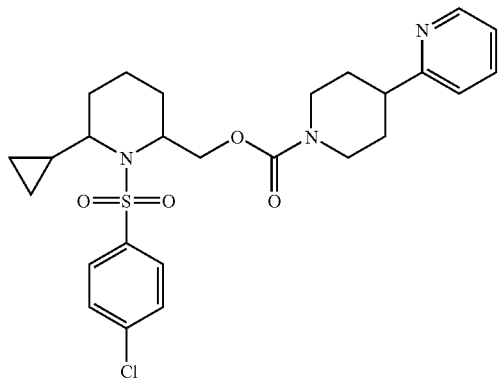 |
| 160-R | 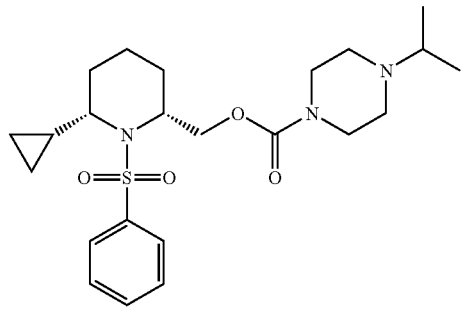 |
| 160-S | 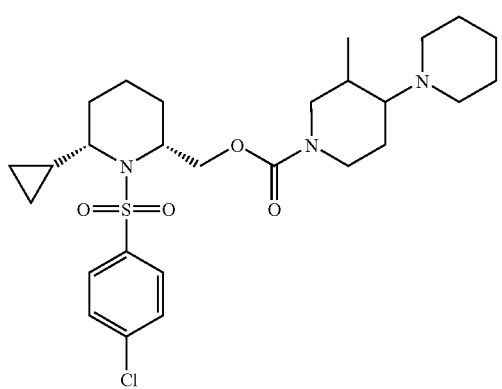 |

-continued
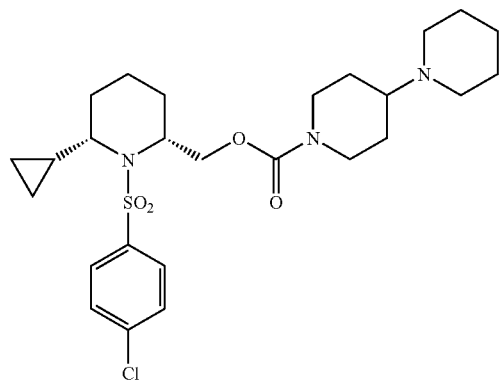
(Example 160)
| Compound No. | Structure |
| --- | --- |
| 160-T | 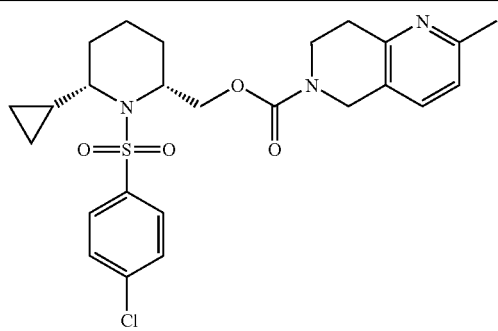 |
| 160-U | 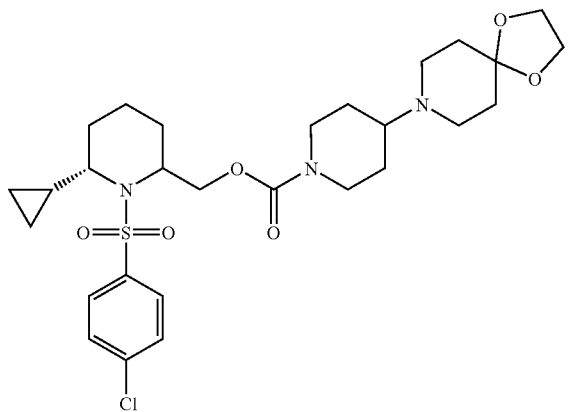 |
| 160-V | 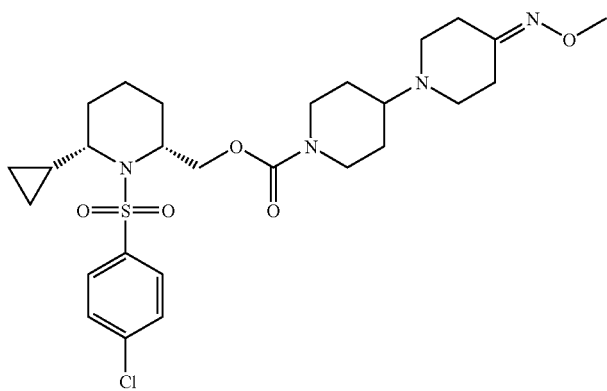 |

-continued
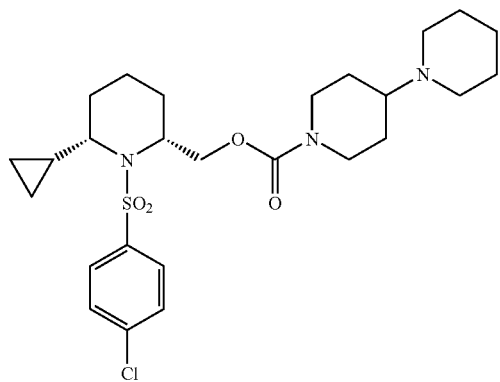
(Example 160)
| Compound No. | Structure |
|---|---|
| 160-W | 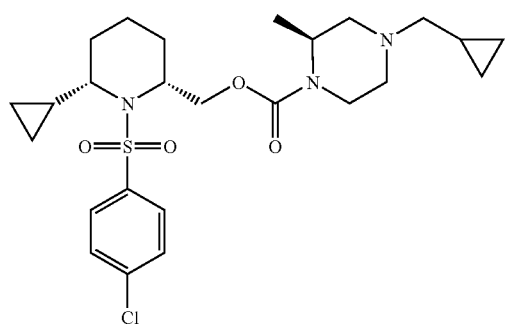 |
| 160-X | 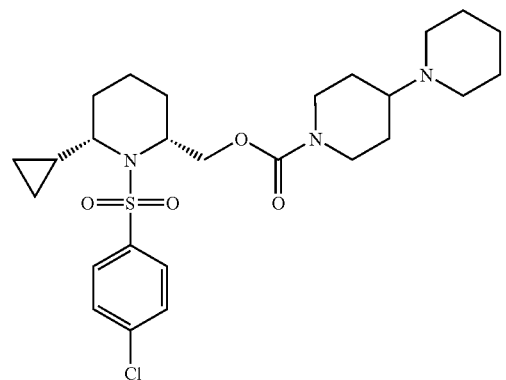 |

-continued
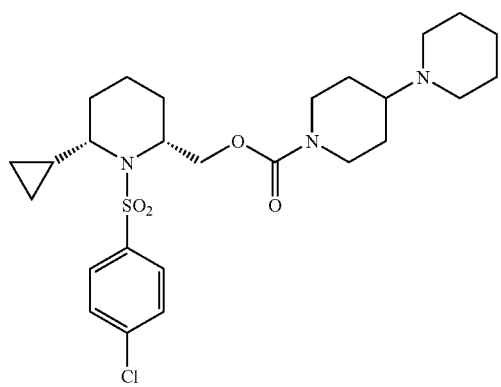
(Example 160)
| Compound No. | Structure |
|---|---|
| 160-Y | 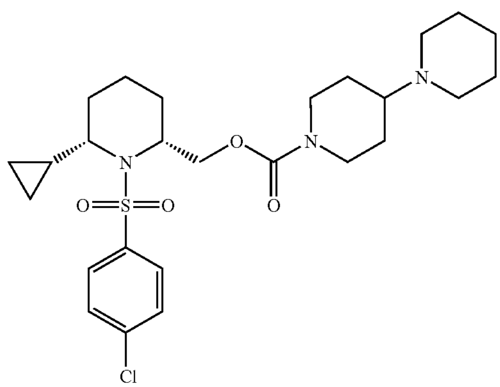 |
| 160-Z | 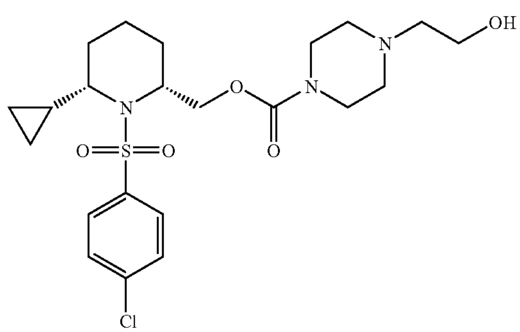 |
| 160-AA | 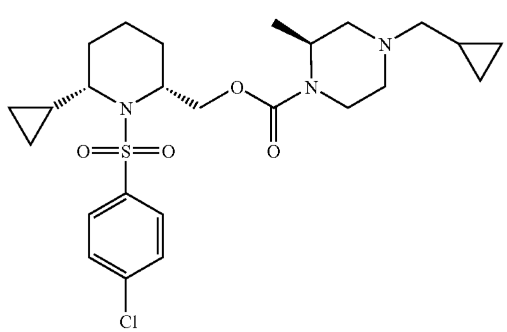 |

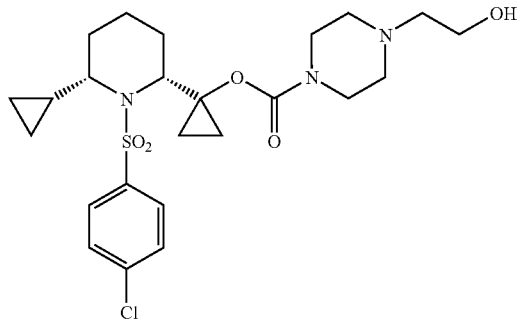
(Example 161)
| Compound No. | Structure |
|---|---|
| 161-A | 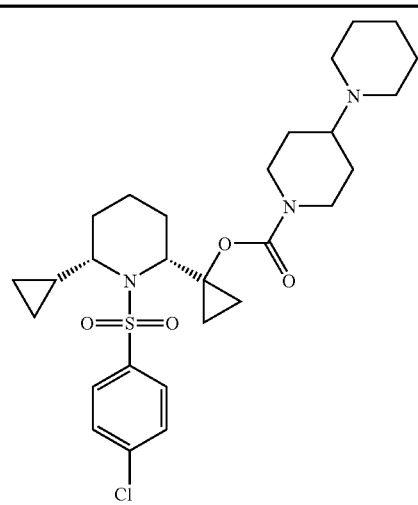 |
| 161-B | 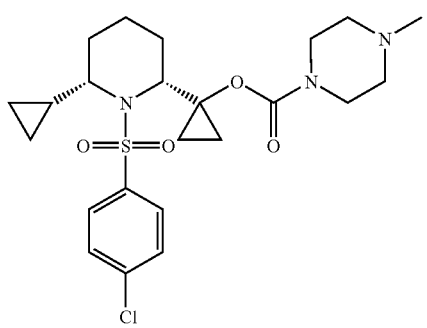 |
-continued
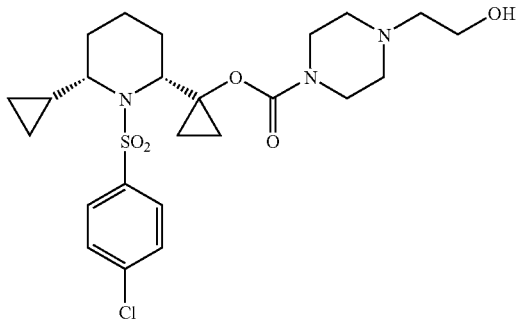
(Example 161)
| Compound No. | Structure |
|---|---|
| 161-C | 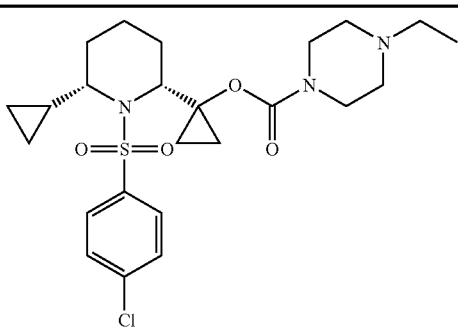 |
| 161-D | 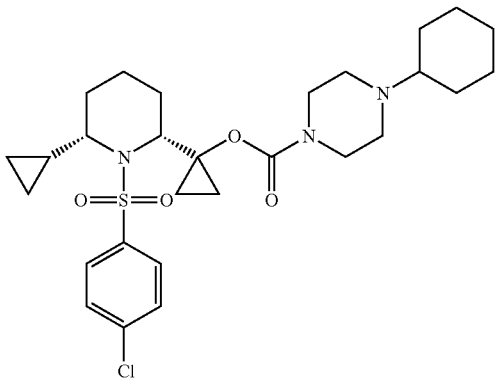 |
| 161-E | 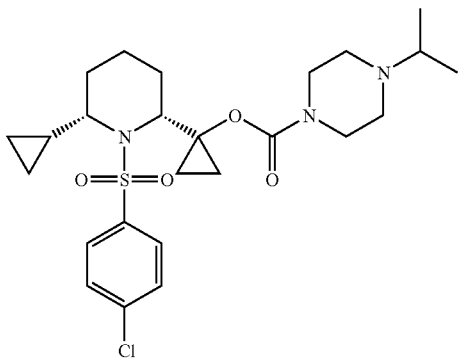 |

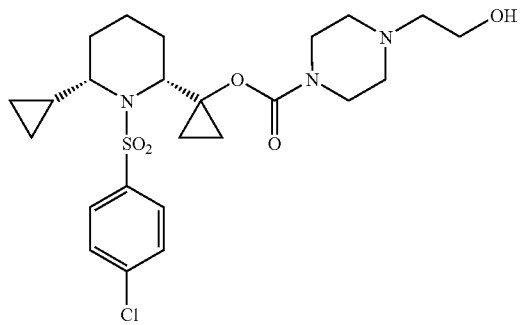
(Example 161)
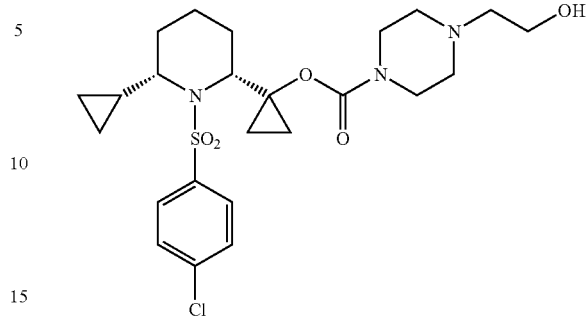
(Example 161)
| Compound No. | Structure |
|---|---|
| 161-F | 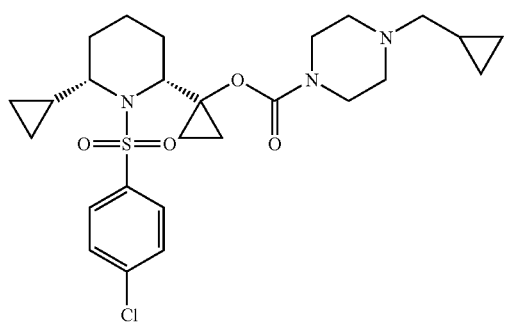 |
| 161-G | 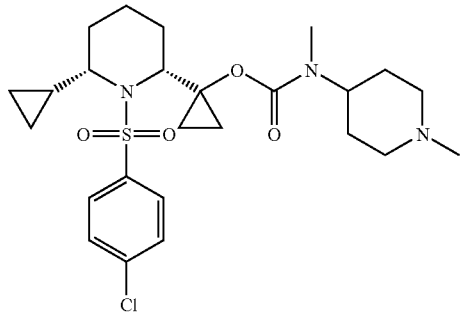 |

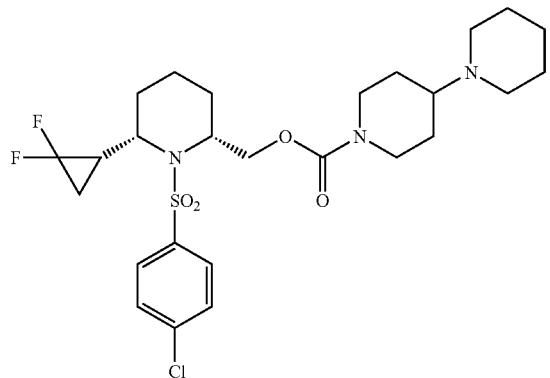
(Example 162)
| Compound No. | Structure |
|---|---|
| 162-A | 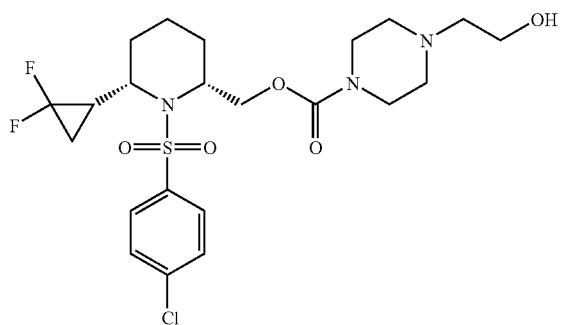 |
| 162-B | 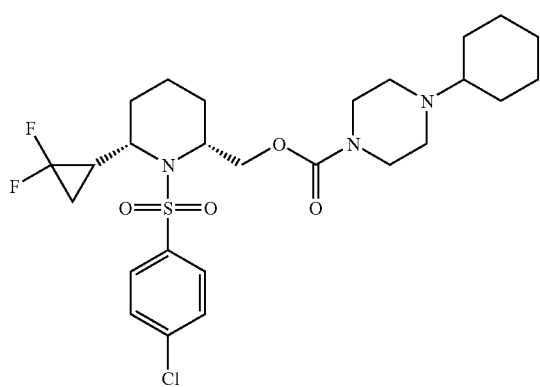 |

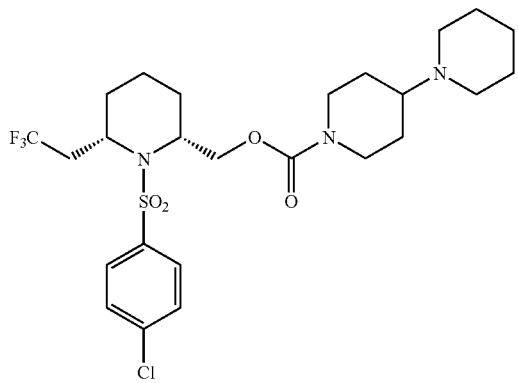
(Example 164)
| Compound No. | Structure |
|---|---|
| 164-A | 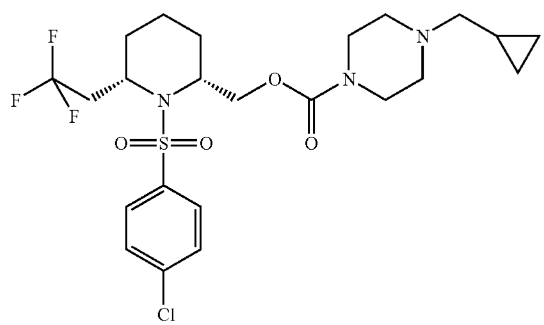 |
| 164-B | 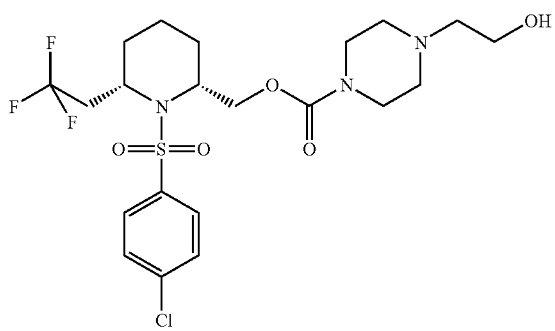 |
| 164-C | 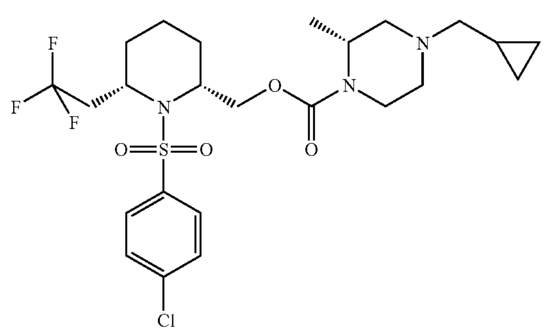 |

(Example 165)
(Example 166)
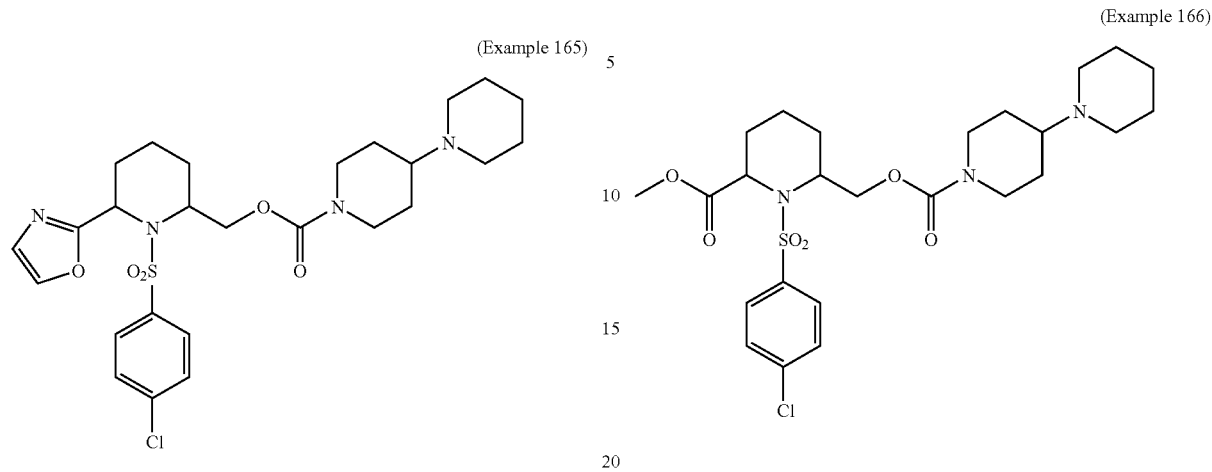
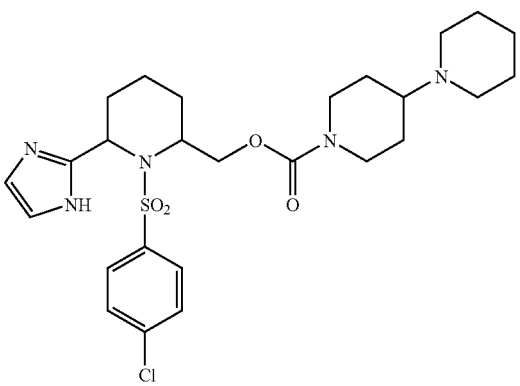
(Example 167)
| Compound No. | Structure |
|---|---|
| 167-A | 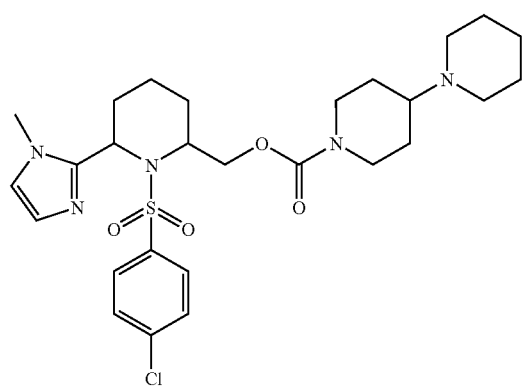 |

-continued
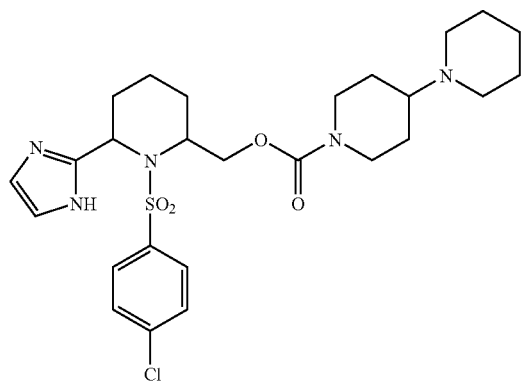
(Example 167)
| Compound No. | Structure |
|---|---|
| 167-B | 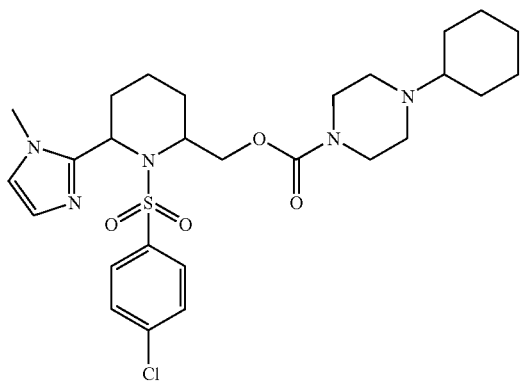 |
| 197-C | 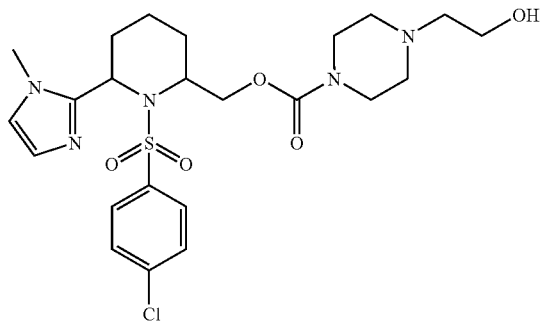 |

(Example 168)
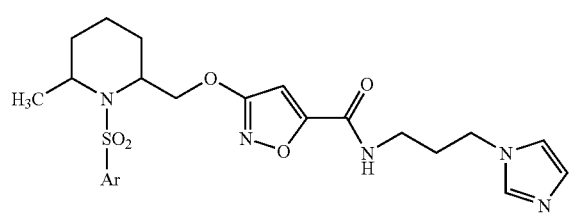
(Compound No. 168-A)
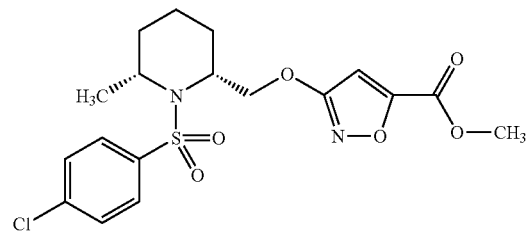
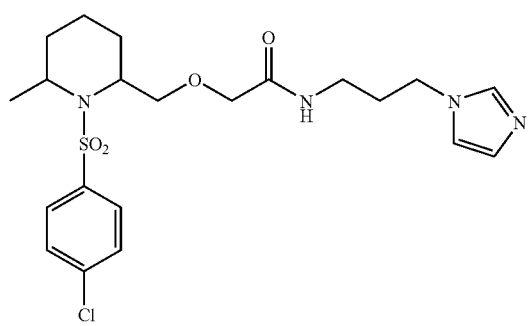
(Example 169)
| Compound No. | Structure |
|---|---|
| 169-A | 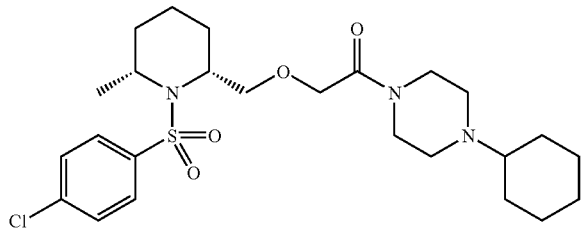 |
| 169-B | 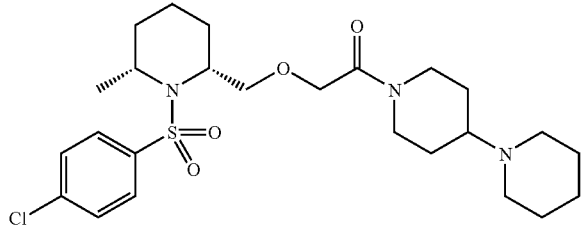 |
| 169-C | 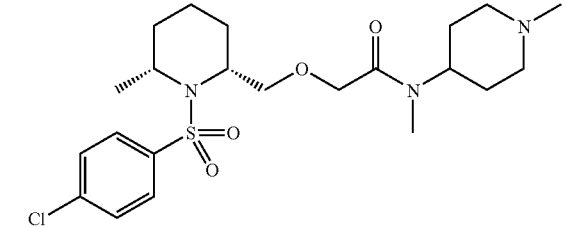 |

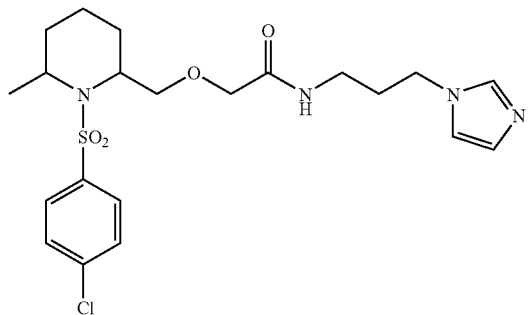
(Example 169)
| Compound No. | Structure |
|---|---|
| 169-D | 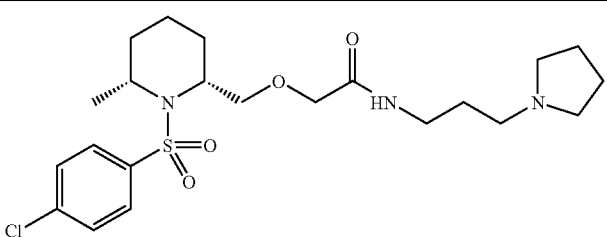 |
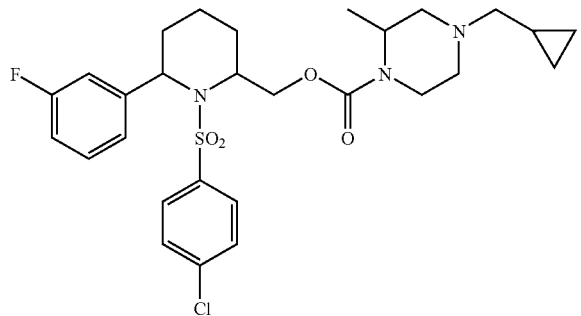
(Example 170)
| Compound No. | Structure |
|---|---|
| 170-A | 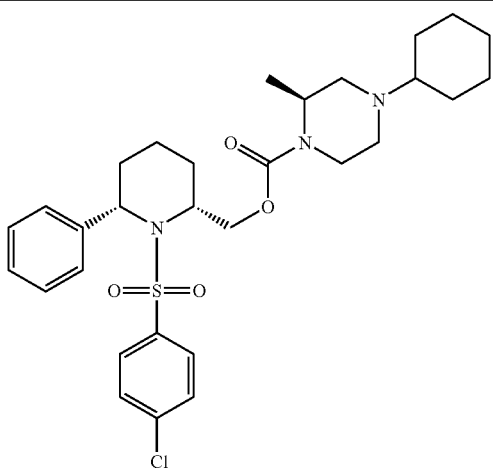 |

-continued
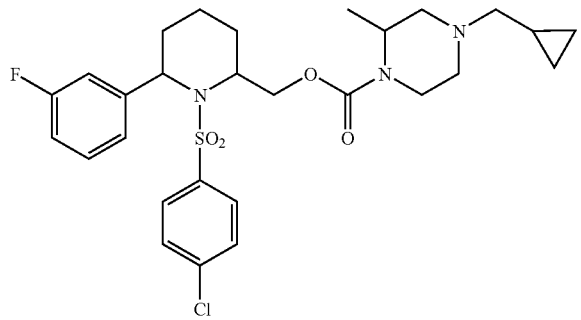
(Example 170)
| Compound No. | Structure |
|---|---|
| 170-B | 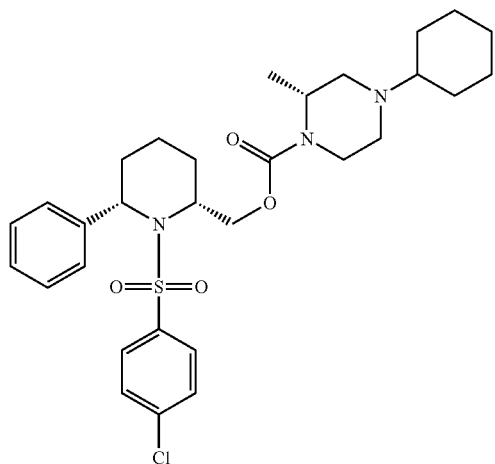 |
| 170-C | 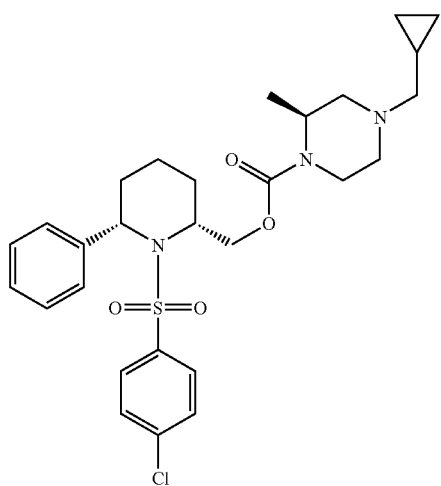 |
| 170-D | 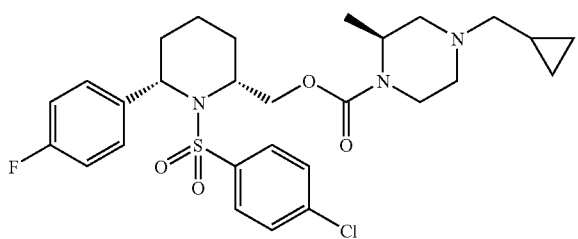 |

-continued
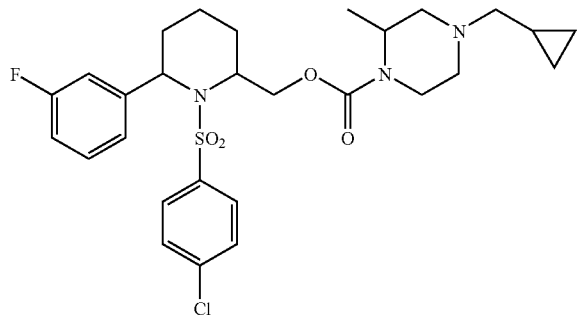
(Example 170)
| Compound No. | Structure |
|---|---|
| 170-E | 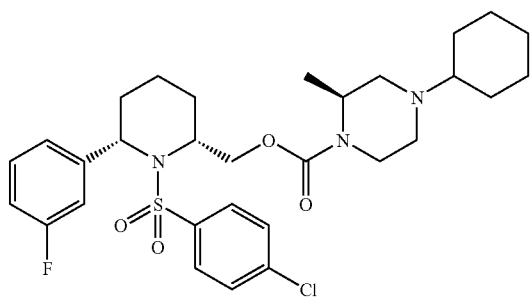 |
| 170-F | 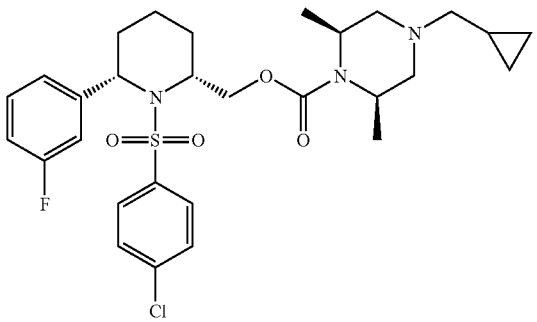 |
| 170-G | 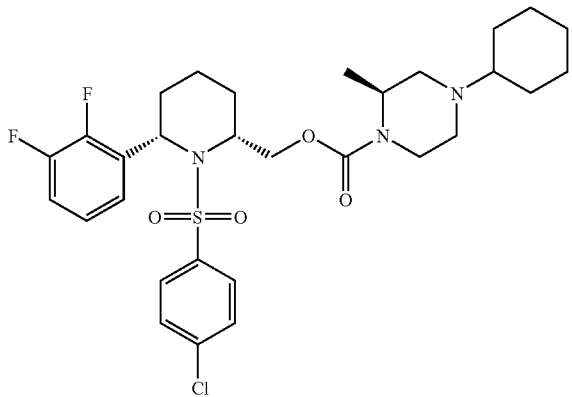 |

-continued
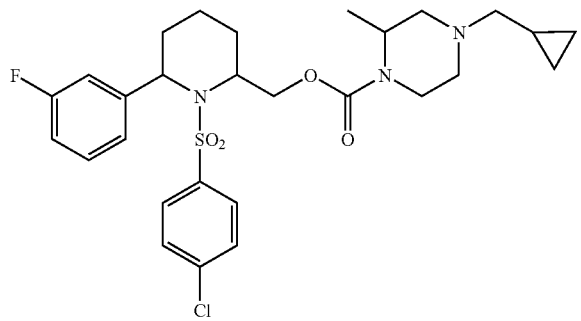
(Example 170)
| Compound No. | Structure |
|---|---|
| 170-H | 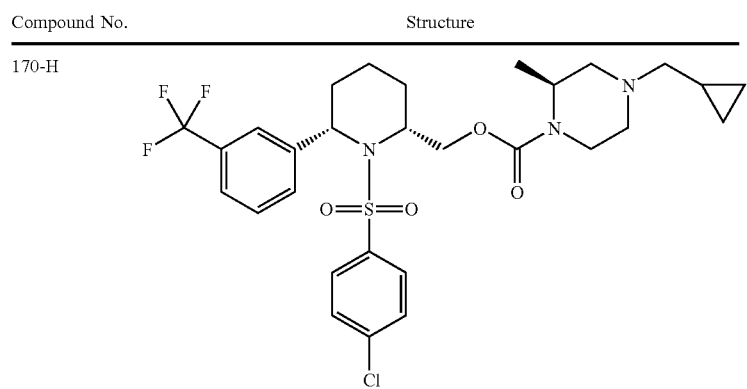 |
| 170-I | 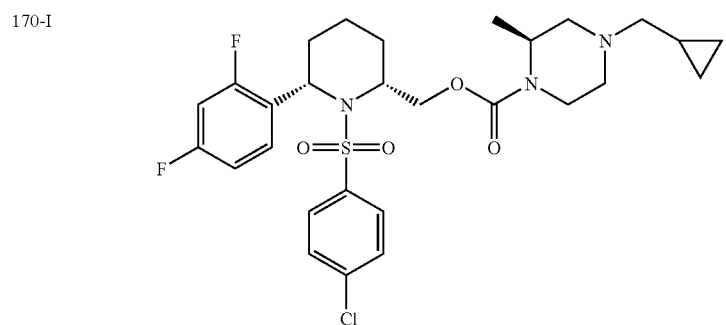 |
| 170-J | 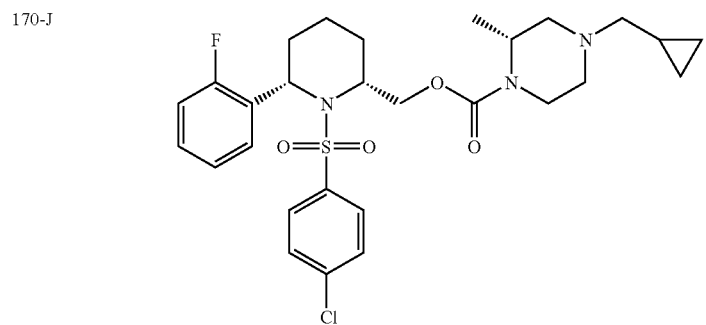 |

-continued
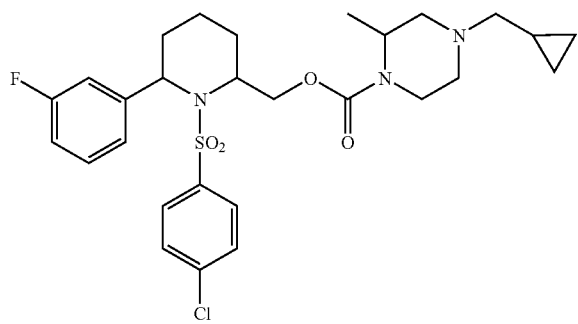
(Example 170)
| Compound No. | Structure |
|---|---|
| 170-K | 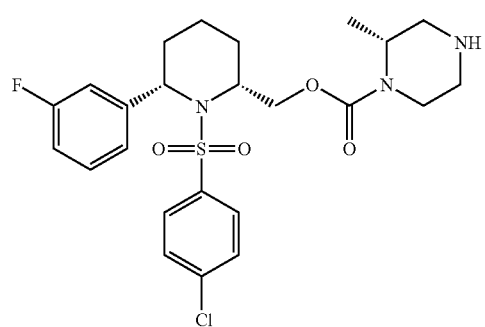 |
| 170-L | 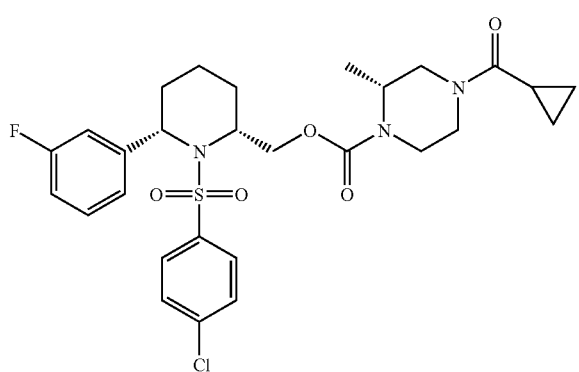 |
| 170-M | 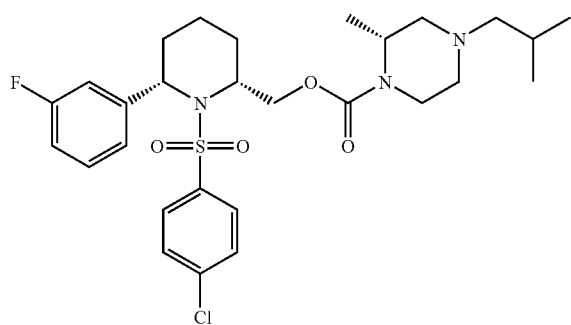 |

-continued
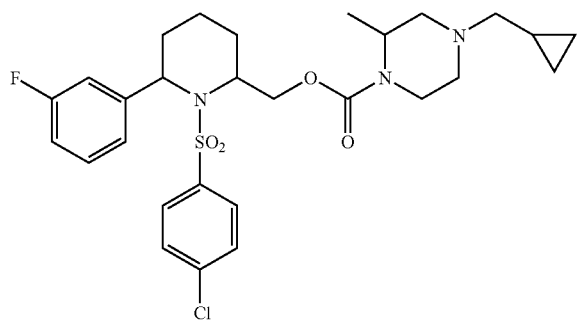
(Example 170)
| Compound No. | Structure |
|---|---|
| 170-N | 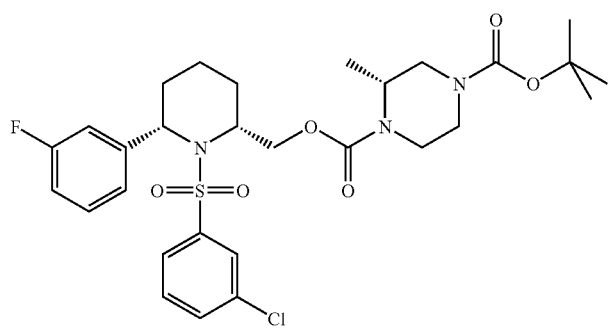 |
| 170-O | 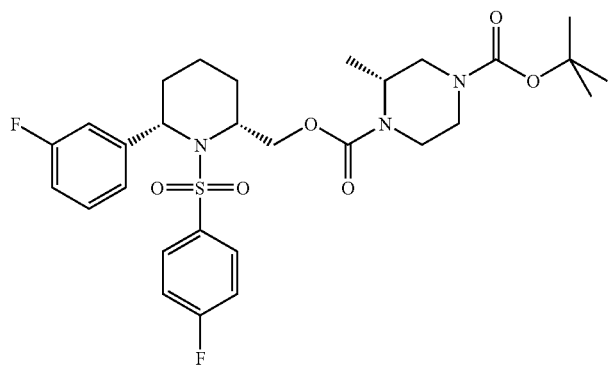 |
| 170-P | 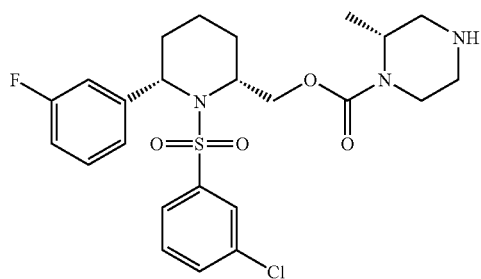 |

-continued
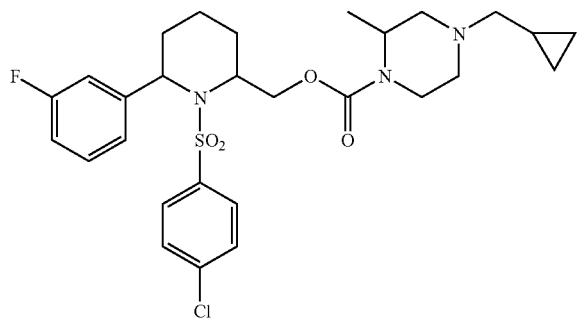
(Example 170)
| Compound No. | Structure |
|---|---|
| 170-Q | 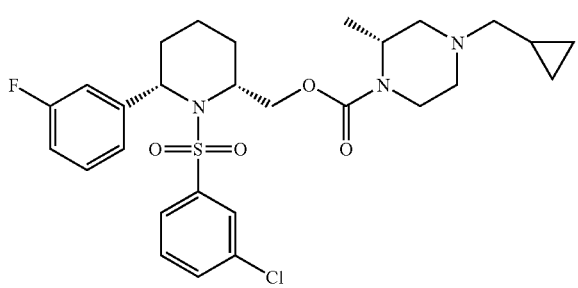 |
| 170-R | 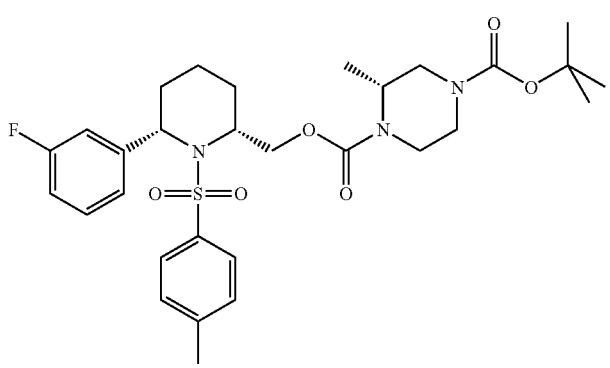 |
| 170-S | 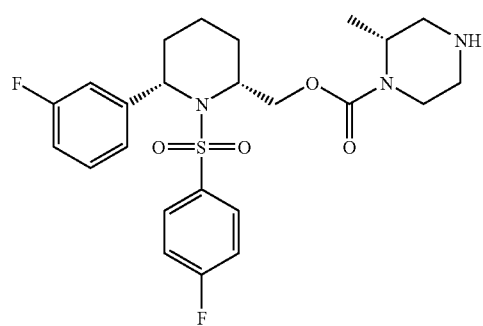 |

-continued
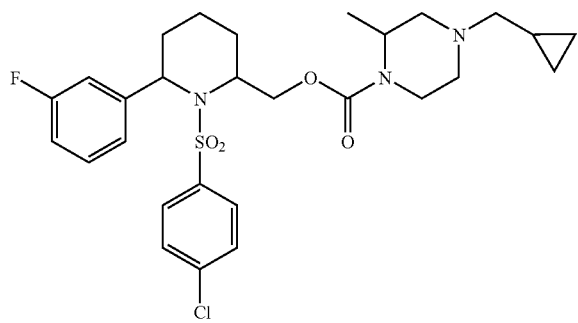
(Example 170)
| Compound No. | Structure |
|---|---|
| 170-T | 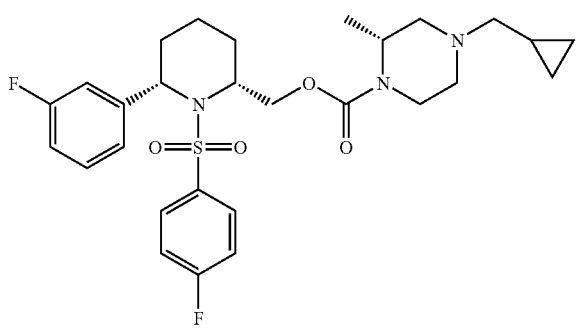 |
| 170-U | 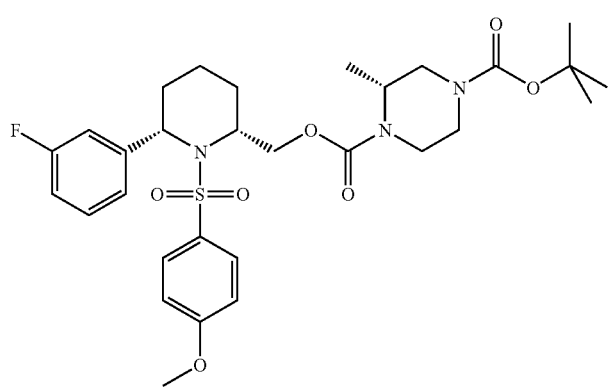 |
| 170-V | 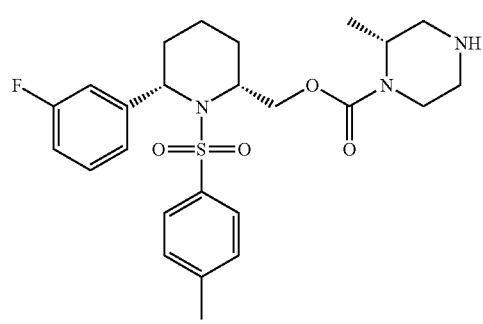 |

-continued
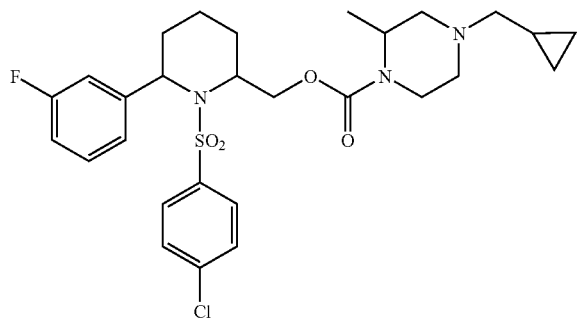
(Example 170)
| Compound No. | Structure |
|---|---|
| 170-W | 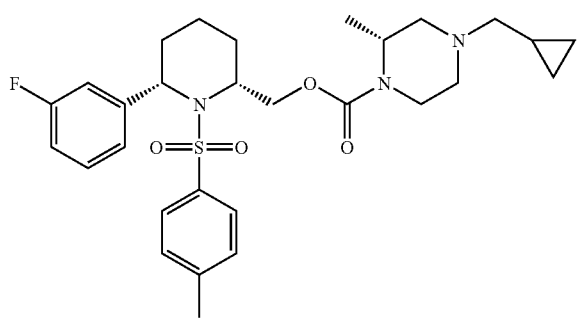 |
| 170-X | 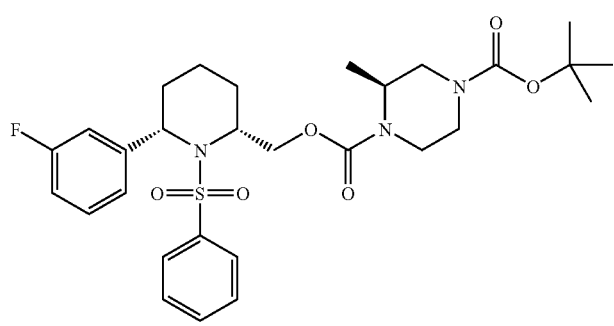 |
| 170-Y | 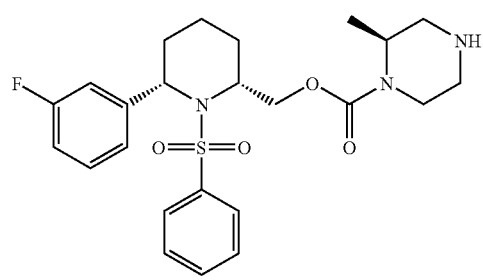 |

-continued
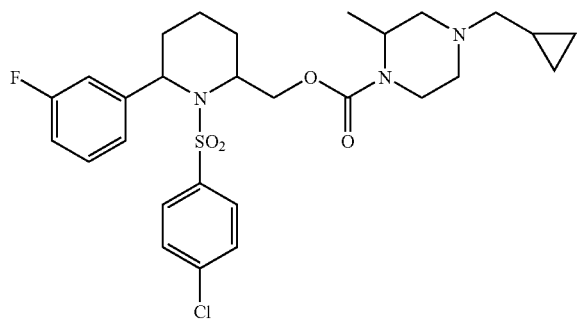
(Example 170)
| Compound No. | Structure |
|---|---|
| 170-Z | 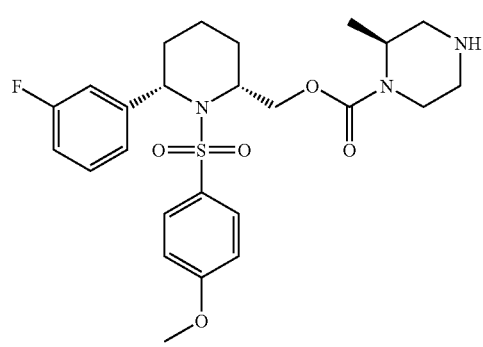 |
| 170-AA | 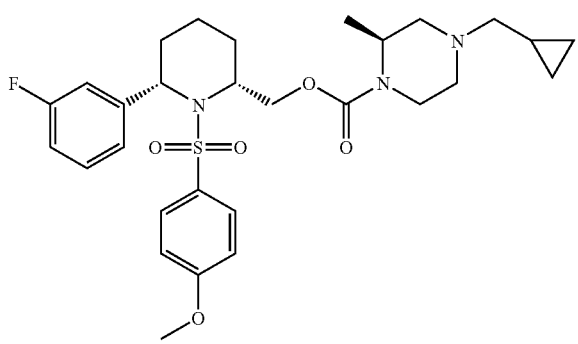 |
| 170-AB | 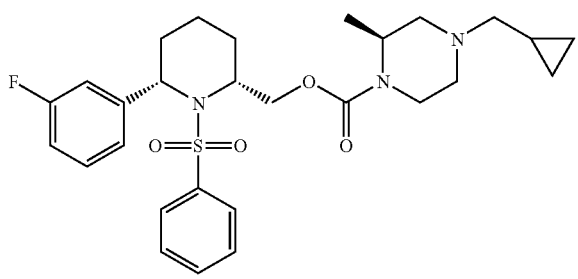 |

-continued
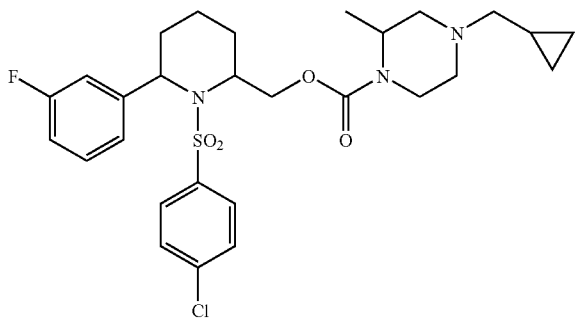
(Example 170)
| Compound No. | Structure |
|---|---|
| 170-AC | 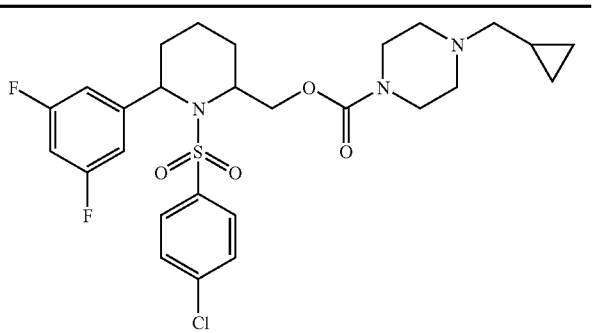 |
| 170-AD | 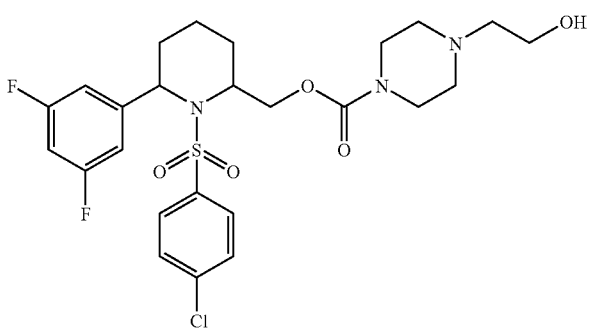 |
(Example 171)
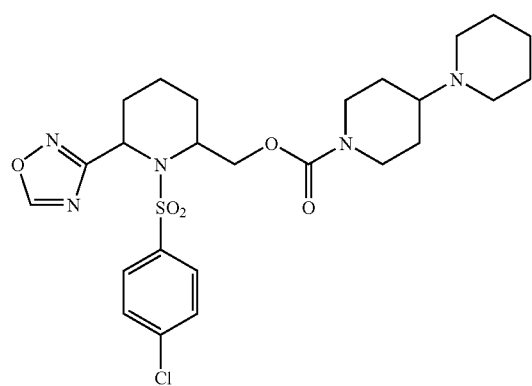
(Example 172)
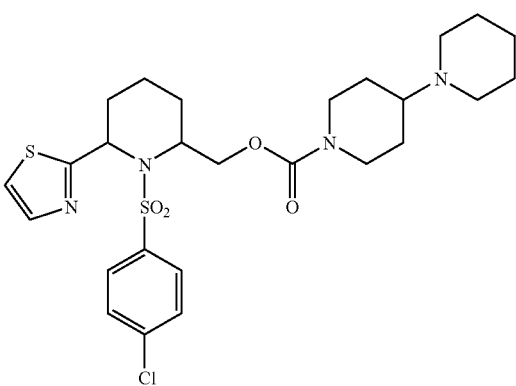

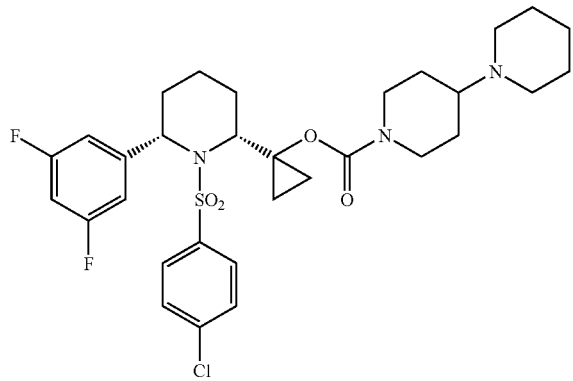
(Example 173)
| Compound No. | Structure |
|---|---|
| 173-A | 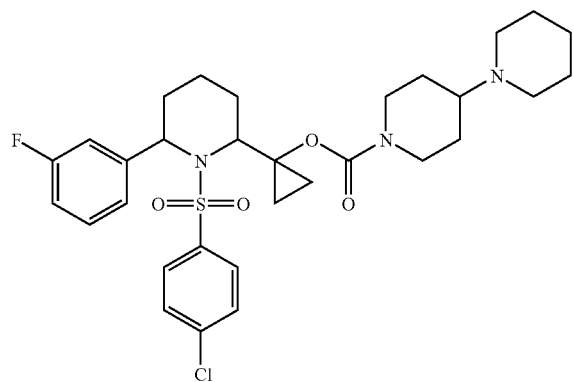 |
| 173-B | 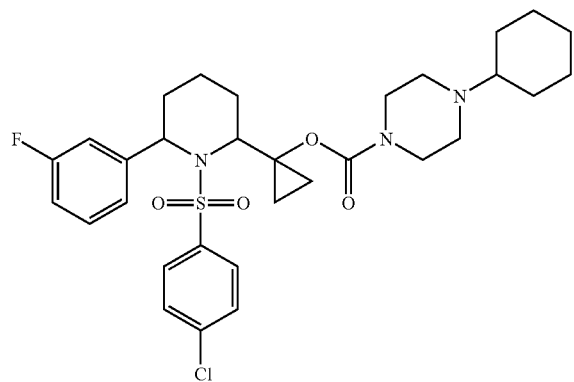 |
| 173-C | 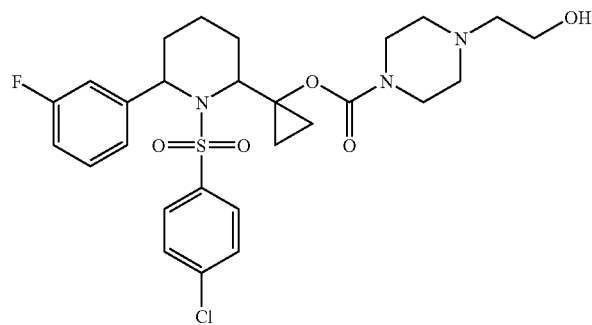 |

-continued
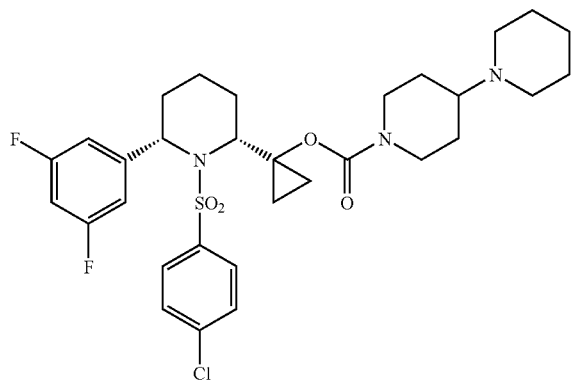
(Example 173)
| Compound No. | Structure |
|---|---|
| 173-D | 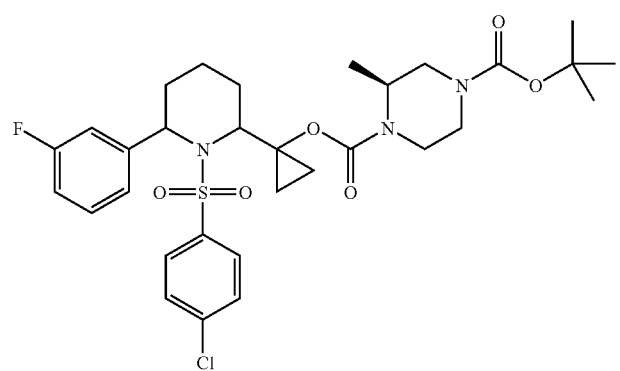 |
| 173-E | 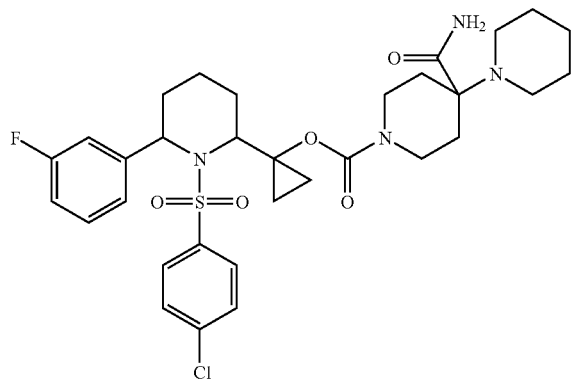 |
| 173-F | 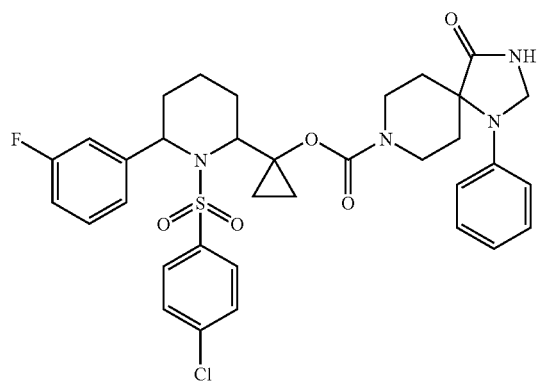 |

-continued
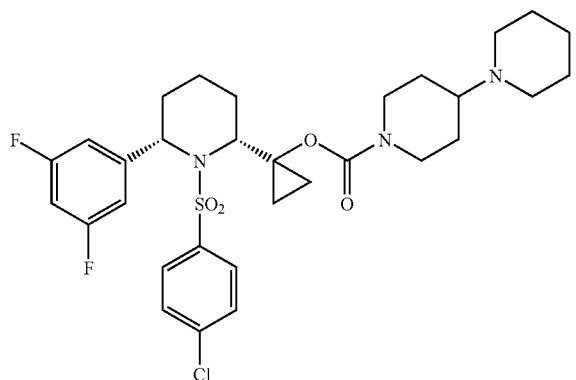
(Example 173)
| Compound No. | Structure |
| --- | --- |
| 173-G | 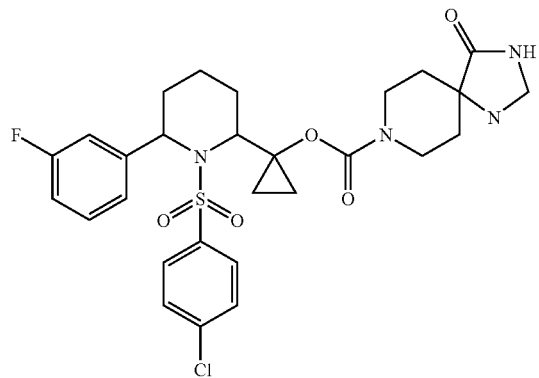 |
| 173-I | 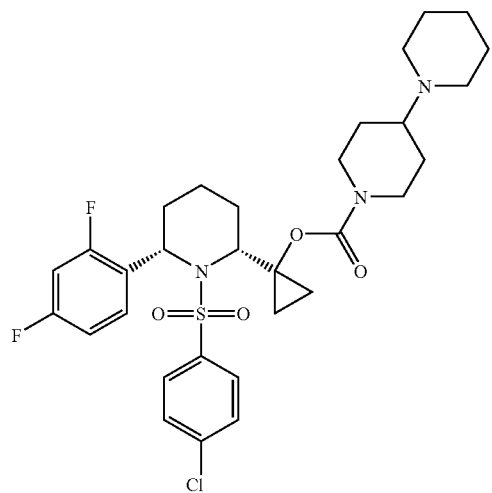 |

-continued
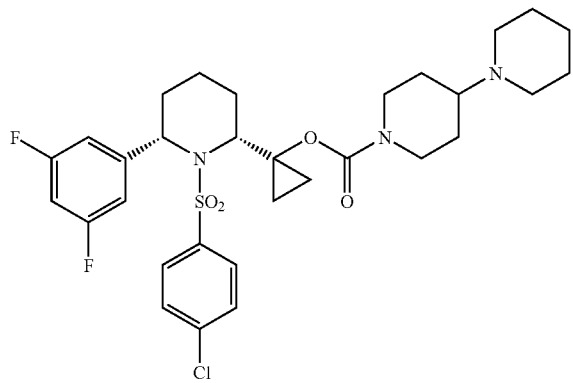
(Example 173)
| Compound No. | Structure |
|---|---|
| 173-J | 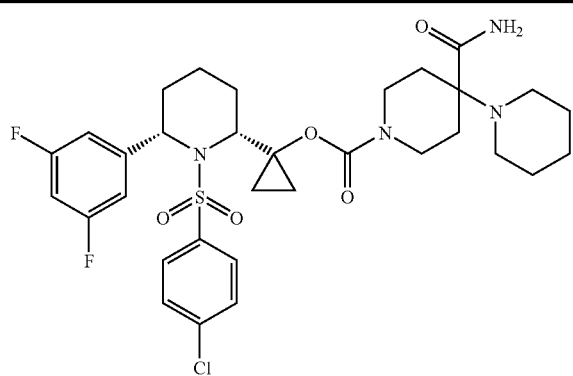 |
| 173-K | 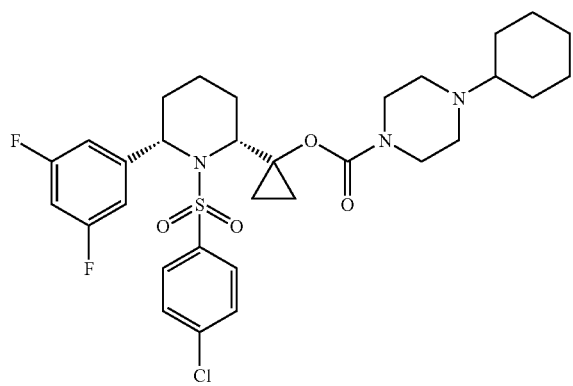 |
| 173-L | 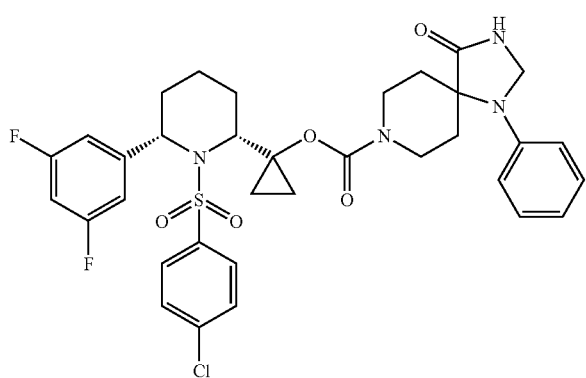 |

-continued
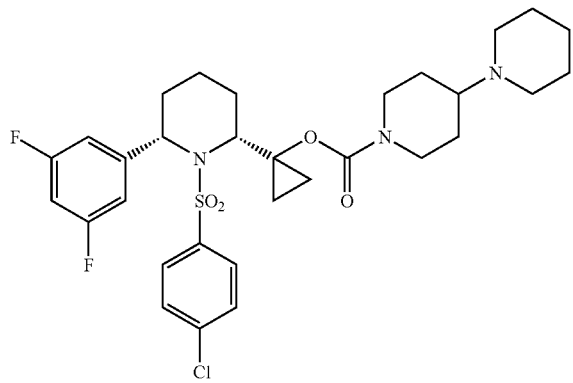
(Example 173)
| Compound No. | Structure |
| --- | --- |
| 173-M | 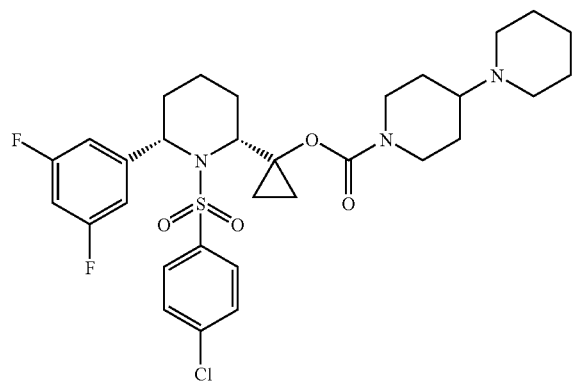 |
| 173-N | 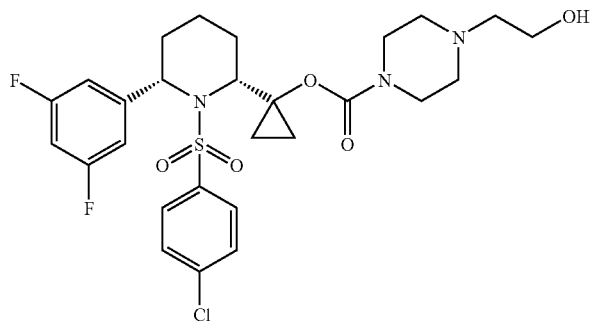 |
| 173-O | 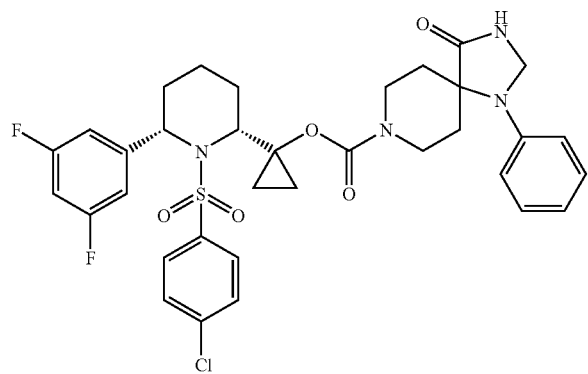 |

-continued
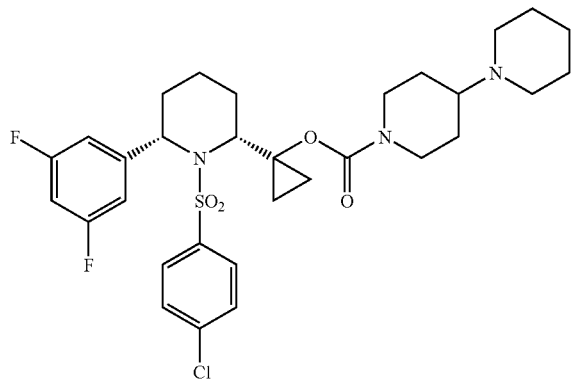
(Example 173)
| Compound No. | Structure |
| --- | --- |
| 173-P | 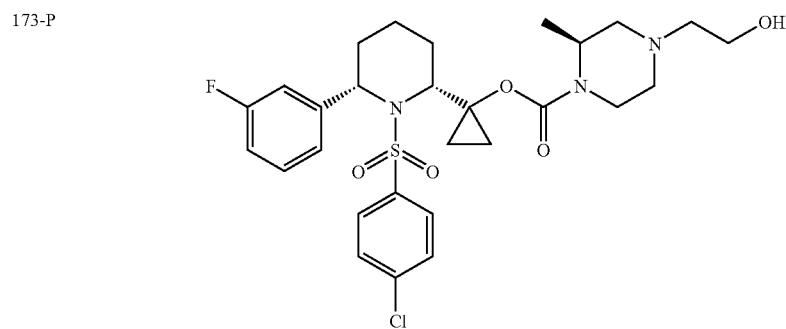 |
| 173-Q | 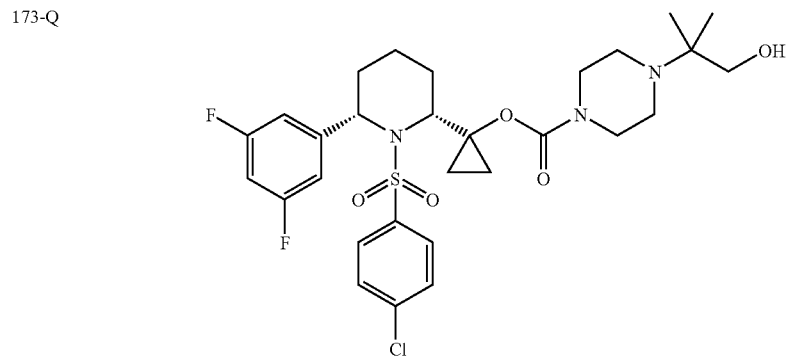 |

-continued
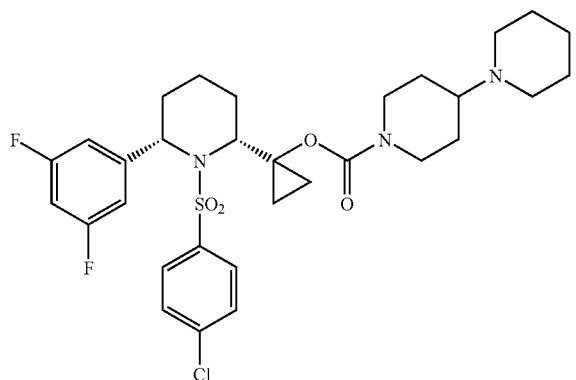
(Example 173)
| Compound No. | Structure |
|---|---|
| 173-R | 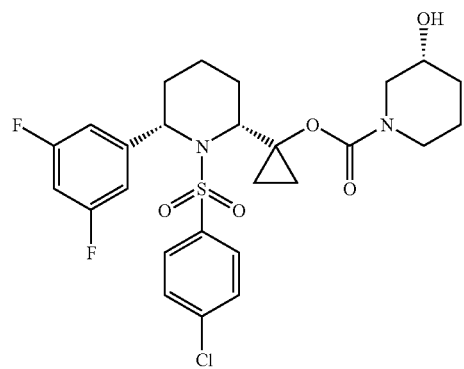 |
| 173-S | 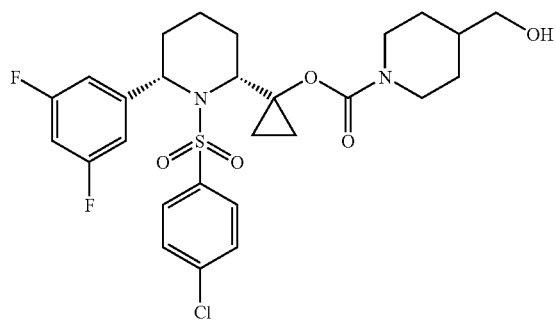 |
| | and |
| 173-T | 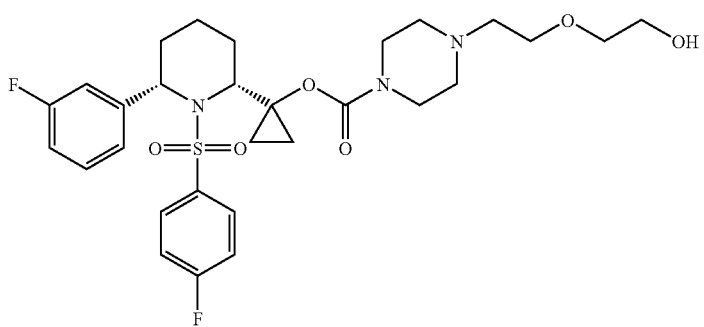 |

(Example 174)
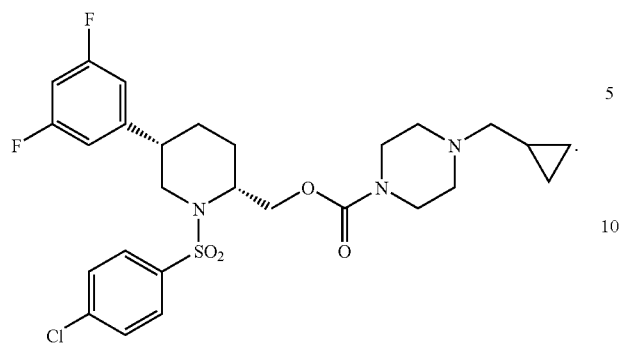
22. The compound of claim 1 selected from the group consisting of:
| Compound No. | Structure |
|---|---|
| 67-B | 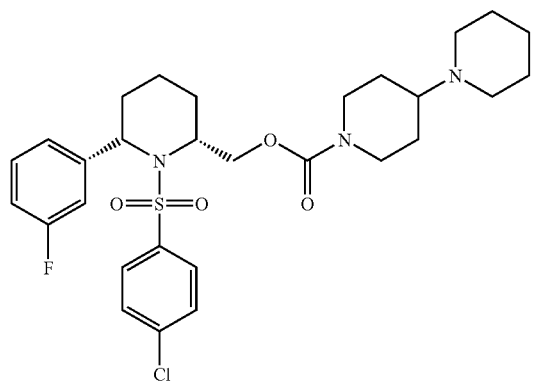<br>$[Alpha]_D^{20} = -56.95$ |
| 67-E | 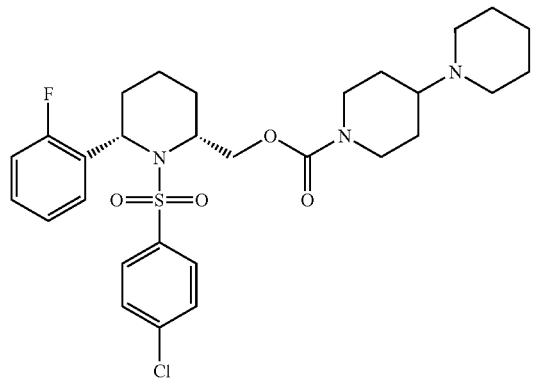 |

| Compound No. | Structure |
|---|---|
| 67-N | 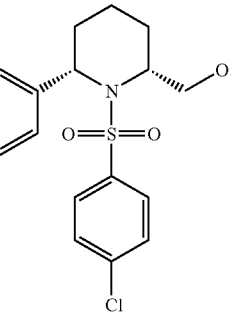 |
| 67-P | 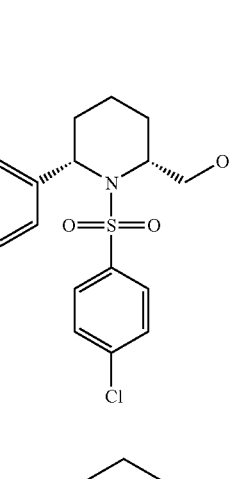 |
| 67-T | 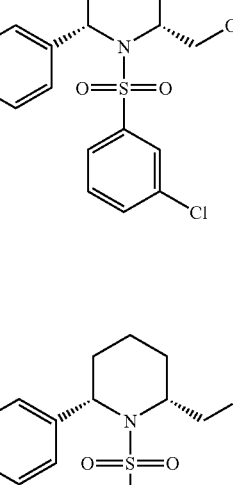 |
| 67-U | 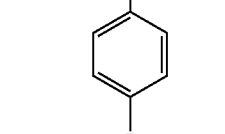 |

-continued
| Compound No. | Structure |
|---|---|
| 67-AG | 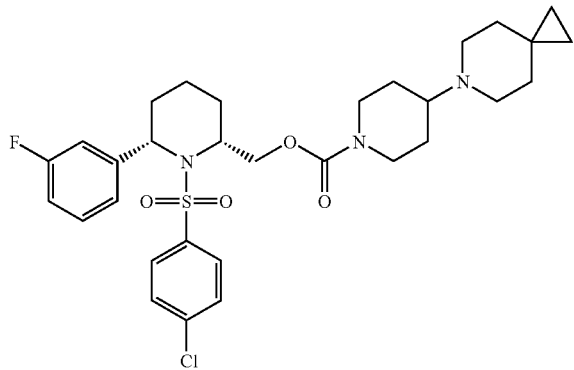 |
| 67-AT | 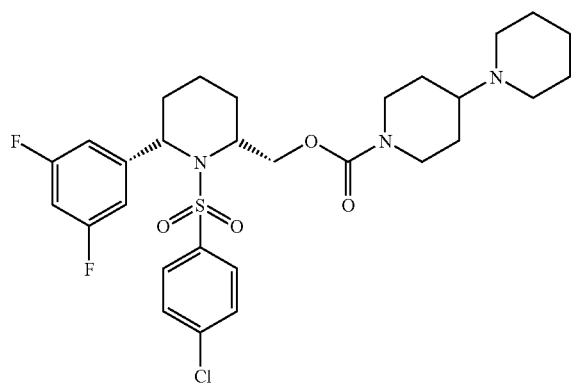 |
| 67-AW | 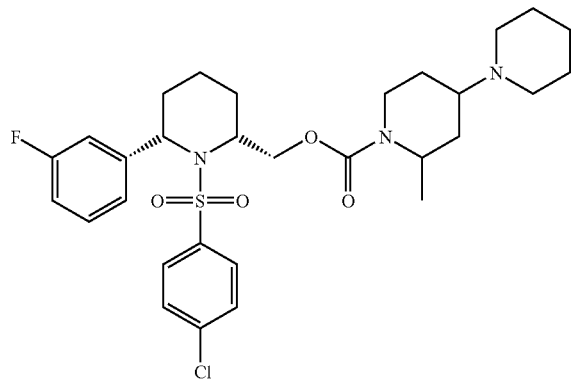 |
| 67-AY | 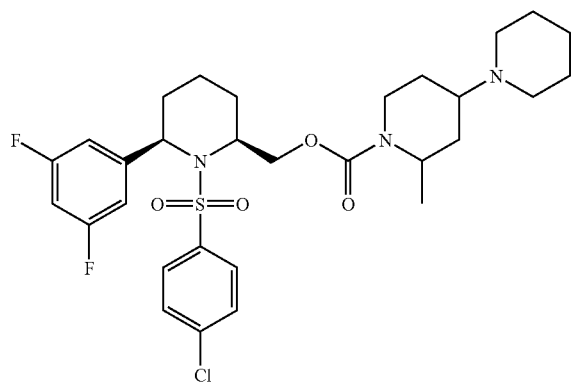 |

-continued
| Compound No. | Structure |
|---|---|
| 67-BA | 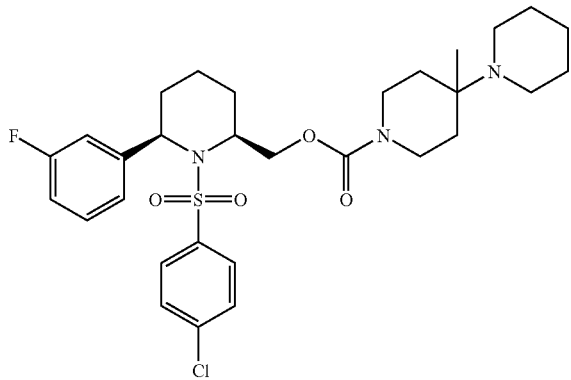 |
| 67-BD | 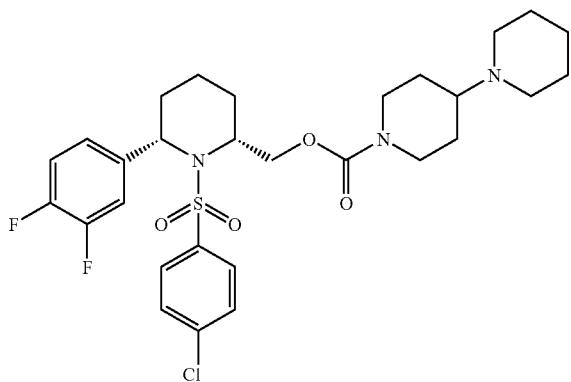 |
| 67-BE | 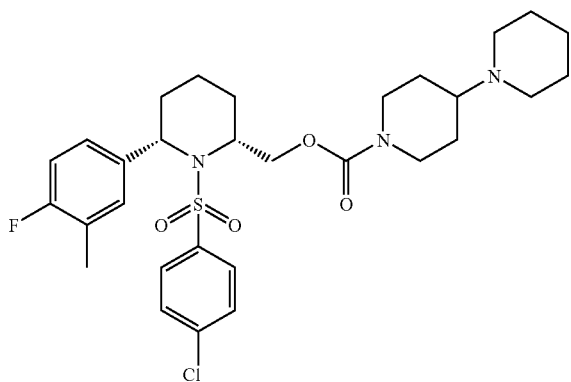 |

| Compound No. | Structure |
|---|---|
| 67-BG | 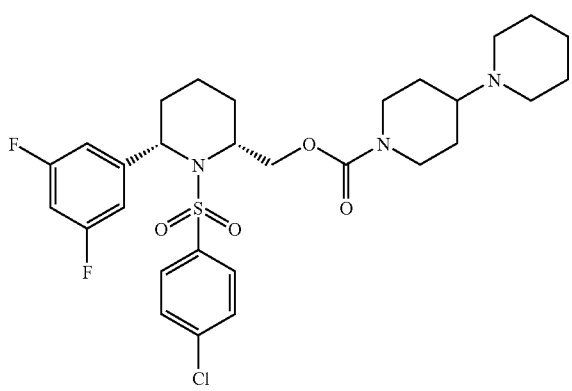 |
| 67-BH | 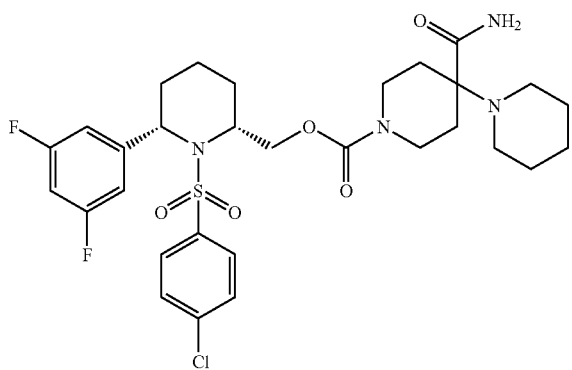 |

-continued
| Compound No. | Structure |
|---|---|
| 67-BL | 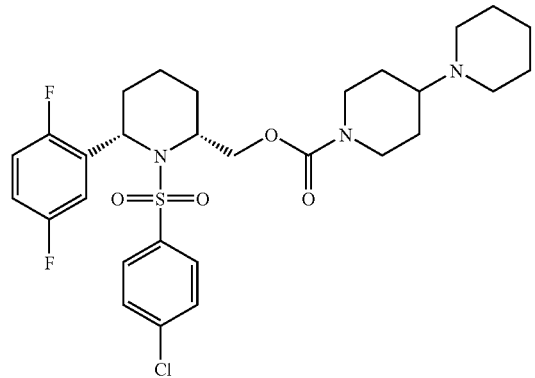 |
| Compound No. | Structure |
|---|---|
| 160-B | 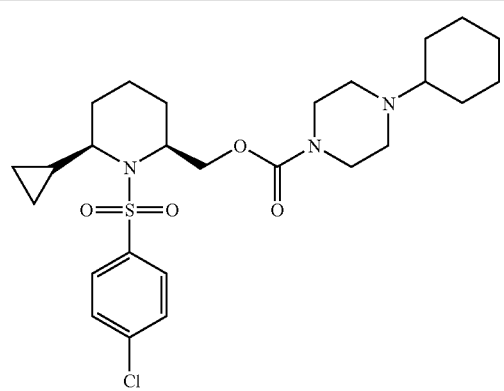 |
| 160-K | 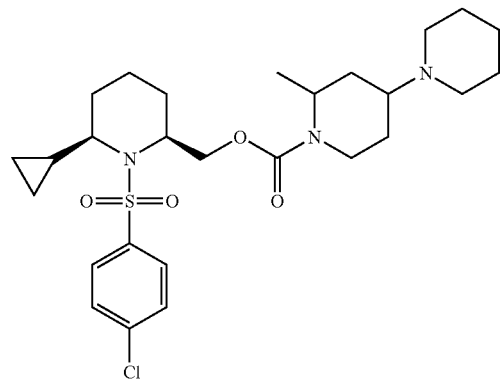 |
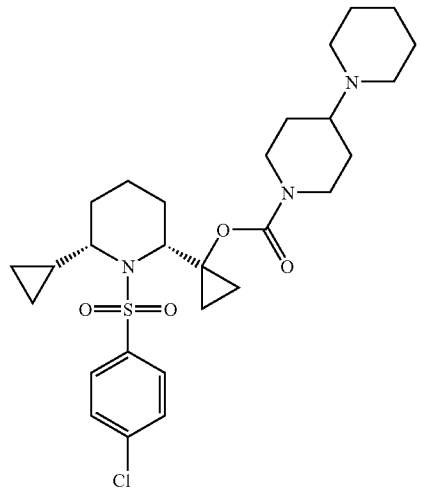
(Example 161)
| Compound No. | Structure |
|---|---|
| 161-A | |

161-E
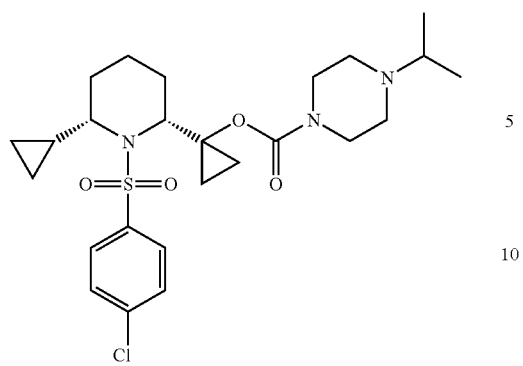
161-F
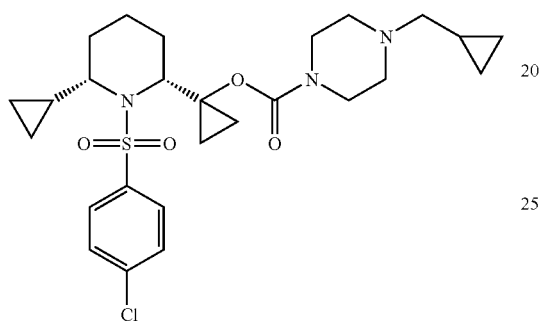
(Example 173)
| Compound No. | Structure |
|---|---|
| 173-A | 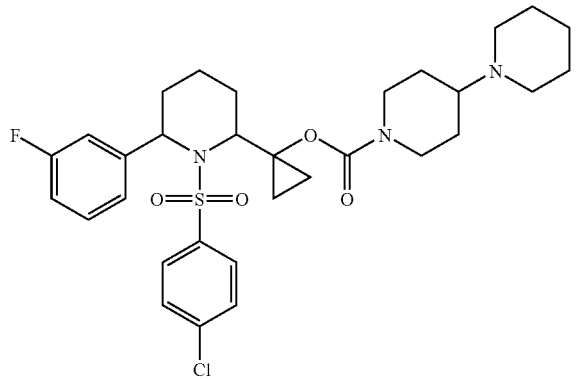 |

-continued
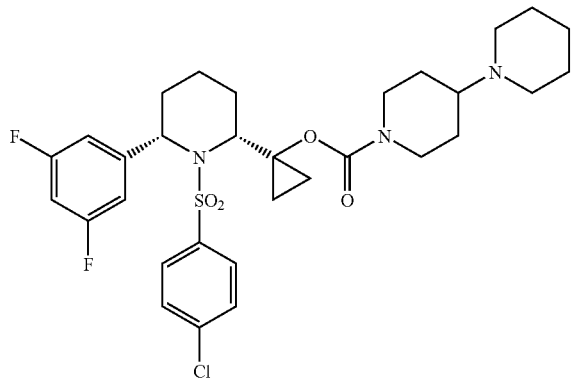
(Example 173)
| Compound No. | Structure |
|---|---|
| 173-B | 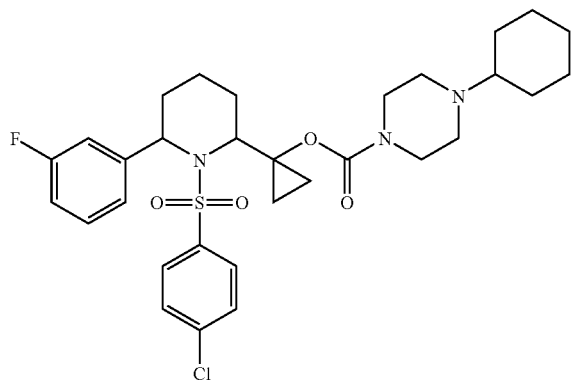 |
| 173-C | 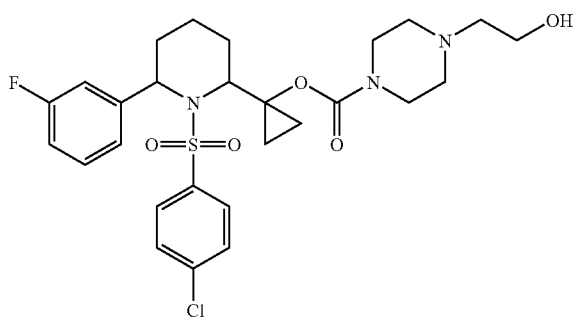 |
| 173-E | 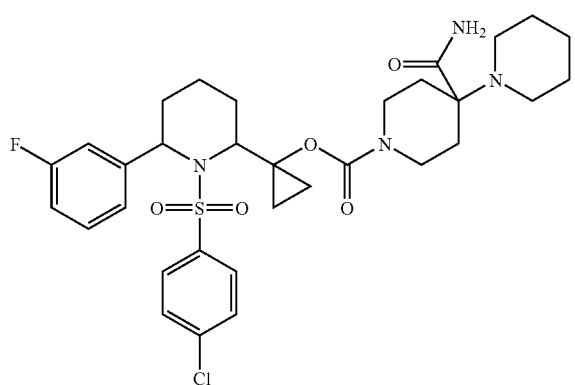 |

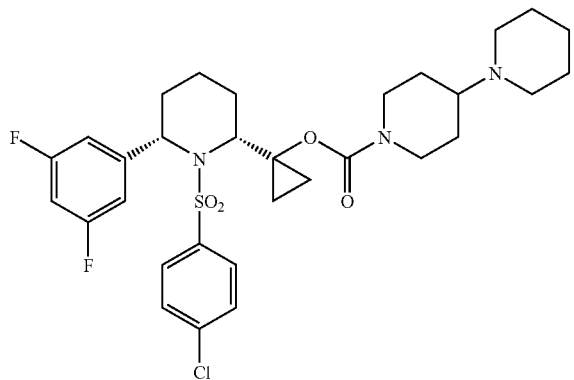
(Example 173)
| Compound No. | Structure |
|---|---|
| 173-G | 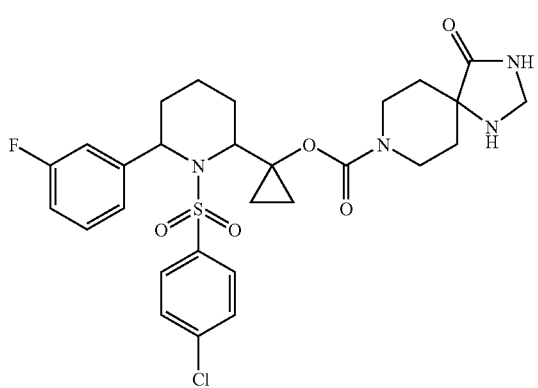 |
| 173-I | 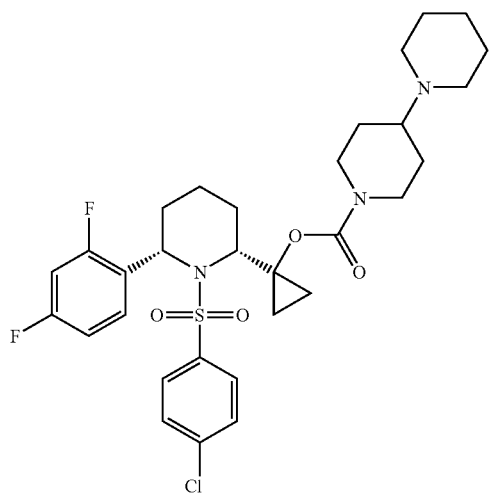 |

-continued
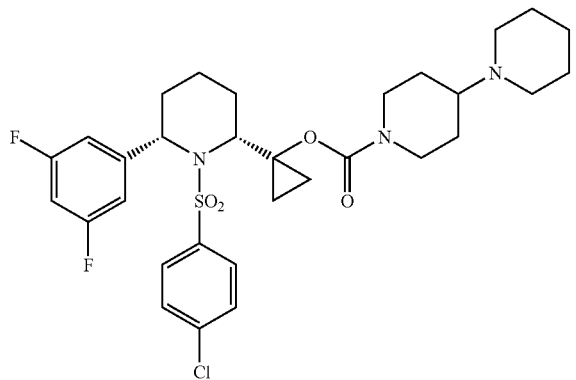
(Example 173)
| Compound No. | Structure |
|---|---|
| 173-J | 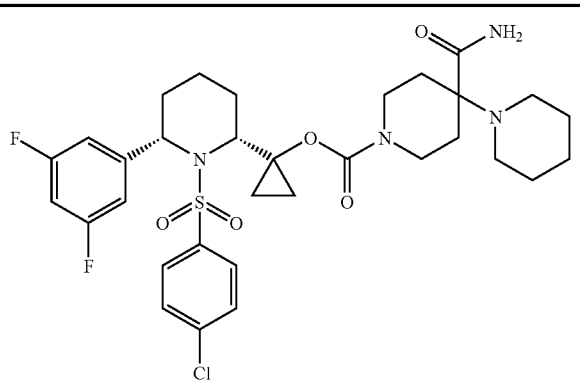 |
| 173-K | 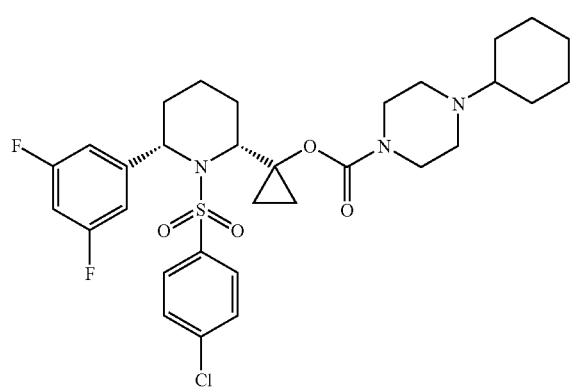 |
| 173-L | 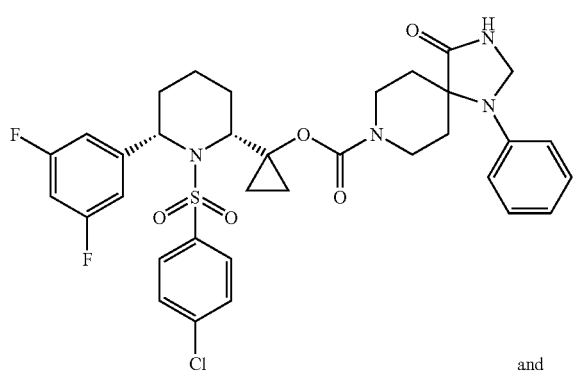 and |

(Example 173)
| Compound No. | Structure |
|---|---|
| 173-N | 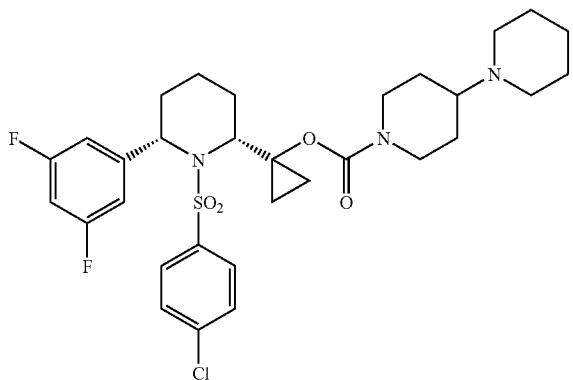 OH. |
23. The compound of claim 1 selected from the group consisting of:
| Compound No. | Structure |
|---|---|
| 67-B | 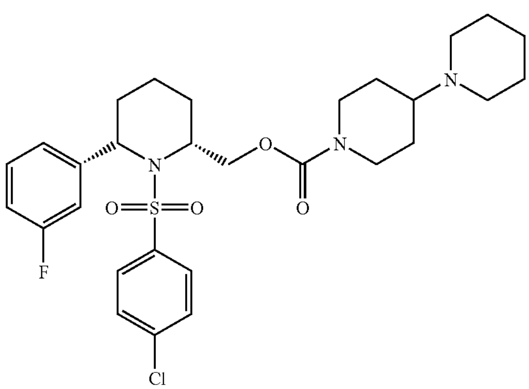 |
[Alpha]$_D^{20}$ = -56.95

| Compound No. | Structure |
|---|---|
| 67-AT | 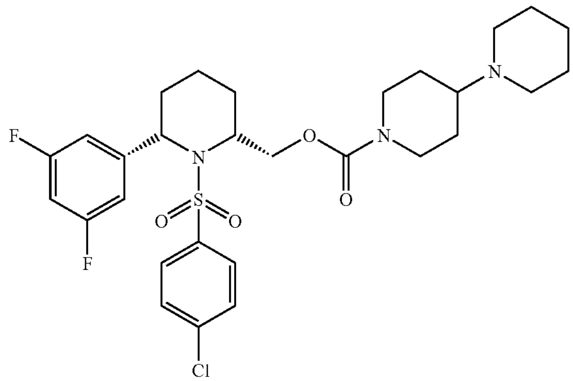 |
| 67-BG | 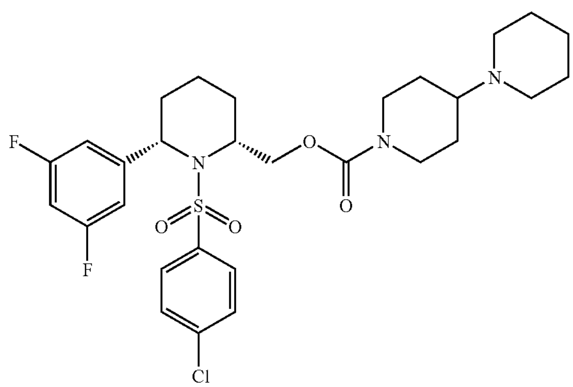 |

| Compound No. | Structure |
|---|---|
| 161-A | |

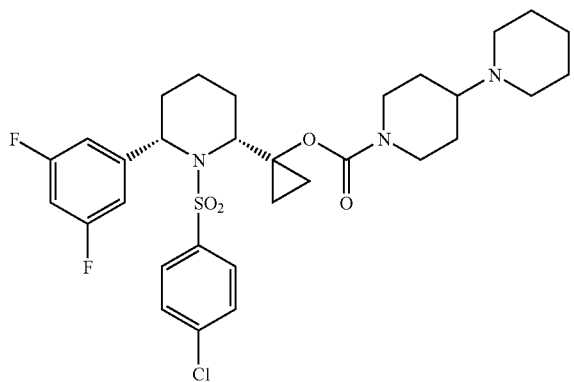
(Example 173)
| Compound No. | Structure |
|---|---|
| 173-A | 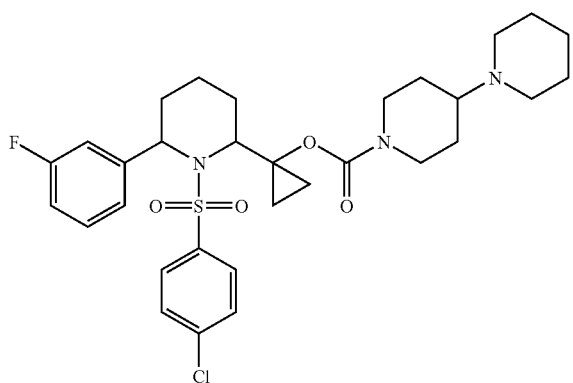 |
| 173-C | 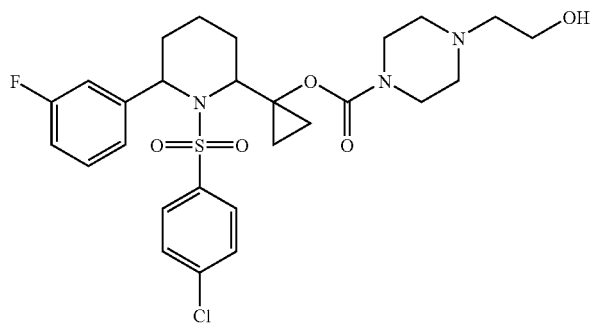 |

-continued
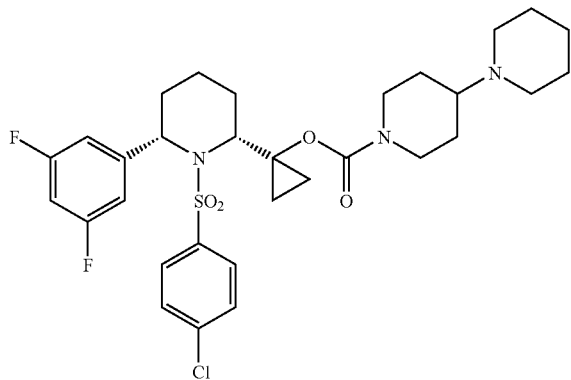
(Example 173)
| Compound No. | Structure |
|---|---|
| 173-E | 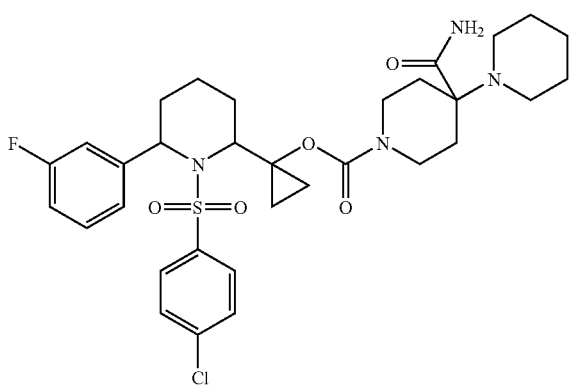 |
| 173-J | 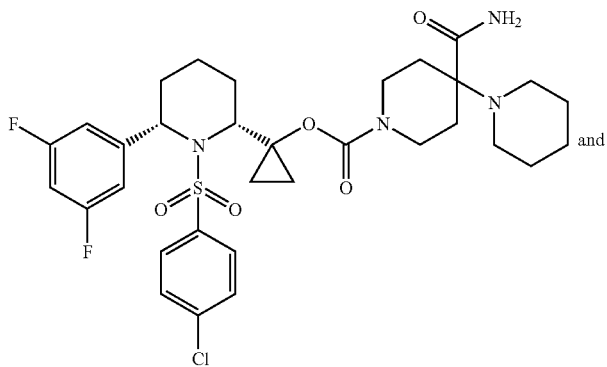 and |

-continued
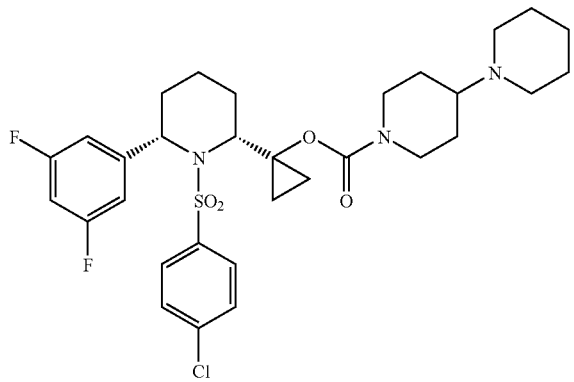
(Example 173)
| Compound No. | Structure |
|---|---|
| 173-N | 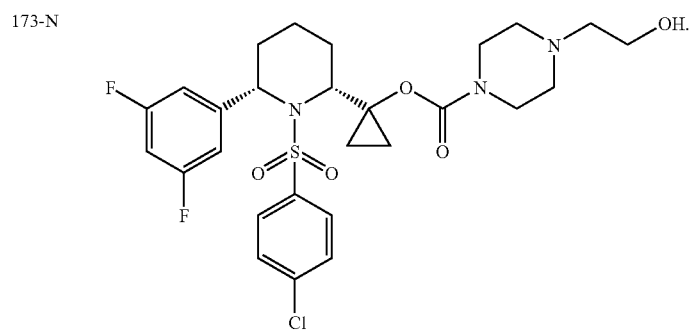 |
24. The compound of claim 1 selected from the group consisting of:
| Compound No. | COMPOUND |
|---|---|
| 67-BS | 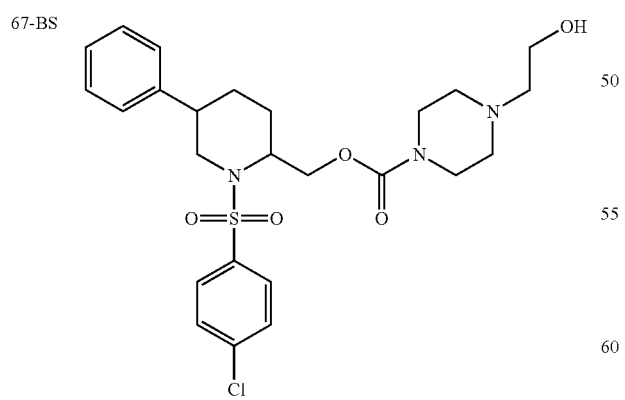 |

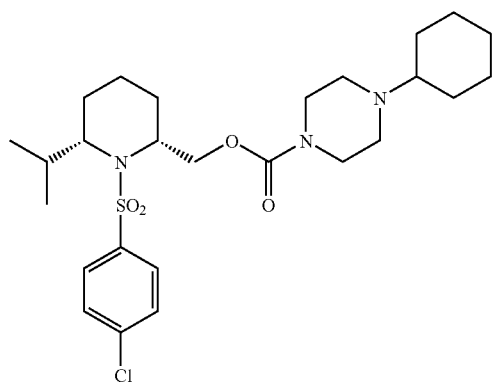
(Example 163)
| Compound No. | Structure |
|---|---|
| 163-A | 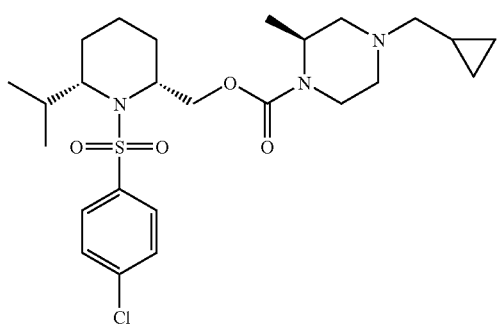 |
| 163-B | 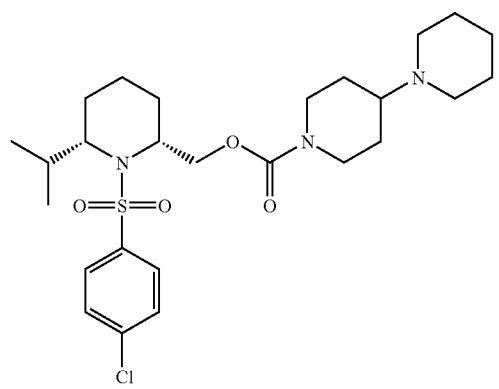 |
| 163-C | 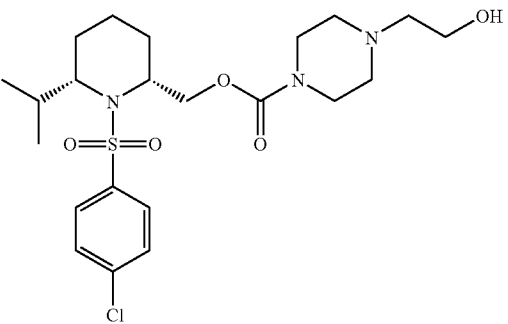 |

-continued
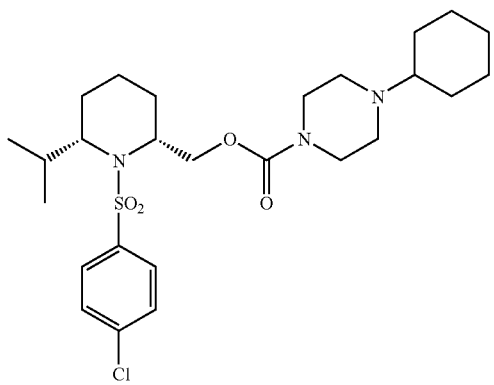
(Example 163)
| Compound No. | Structure |
|---|---|
| 173-U | 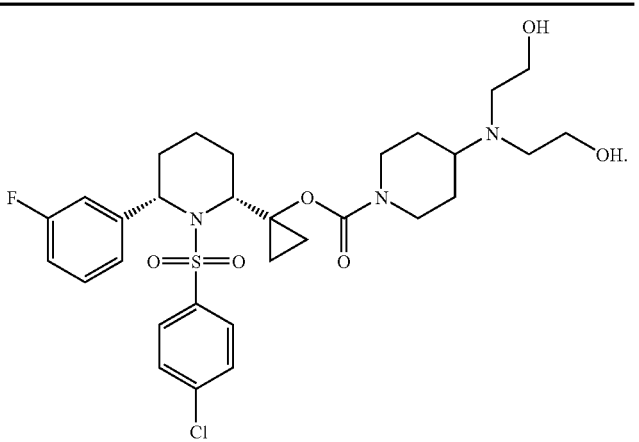 |
* * * * *